United States Patent
Formica et al.

(10) Patent No.: US 11,517,699 B2
(45) Date of Patent: Dec. 6, 2022

(54) MASK SYSTEM

(71) Applicant: ResMed Pty Ltd, Bella Vista (AU)

(72) Inventors: Justin John Formica, Sydney (AU);
Jose Ignacio Romagnoli, Sydney (AU);
Philip Rodney Kwok, Sydney (AU);
Joel Edward Gibson, Sydney (AU);
David Anthony Pidcock, Sydnet (AU);
Christopher Scott Skipper, Sydney (AU); Stephen Gray, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 17/586,303

(22) Filed: Jan. 27, 2022

(65) Prior Publication Data
US 2022/0143348 A1    May 12, 2022

Related U.S. Application Data

(63) Continuation of application No. 16/987,520, filed on Aug. 7, 2020, which is a continuation of application
(Continued)

(51) Int. Cl.
*A61M 16/06*        (2006.01)
*A61M 16/08*        (2006.01)
(Continued)

(52) U.S. Cl.
CPC .... *A61M 16/0666* (2013.01); *A61M 16/0057* (2013.01); *A61M 16/06* (2013.01);
(Continued)

(58) Field of Classification Search
CPC .............. A61M 16/06; A61M 16/0605; A61M 16/0611; A61M 16/0616; A61M 16/0622; A61M 16/0666; A61M 16/0683
See application file for complete search history.

(56) References Cited

U.S. PATENT DOCUMENTS

| 122,905 A | 1/1872 | O'Dell |
|---|---|---|
| 1,192,186 A | 7/1916 | Greene |

(Continued)

FOREIGN PATENT DOCUMENTS

| AU | 2 385 533 | 8/2003 |
|---|---|---|
| AU | 2008906390 | 12/2008 |

(Continued)

OTHER PUBLICATIONS

U.S. Appl. No. 16/922,398, filed Jul. 7, 2020 of Formica et al., for "Mask System," 316 pages.
(Continued)

*Primary Examiner* — Joseph D. Boecker
(74) *Attorney, Agent, or Firm* — Nixon & Vanderhye P.C.

(57) ABSTRACT

A patient interface assembly includes a flexible cushion with a nares sealing portion configured to sealingly engage the patient's nares and a mouth sealing portion configured to seal around the patient's mouth. A cushion clip is attached to the flexible cushion, forms at least part of a plenum chamber with the flexible cushion, and is more rigid than the flexible cushion. A frame is attached to the cushion clip, is more rigid than the flexible cushion. A superior portion of the frame extends beyond the mouth sealing portion in the superior direction to overlap at least a part of the pair of lateral nares engagement portions of the nares sealing portion. At least a part of the nares sealing portion of the flexible cushion is decoupled from both the cushion clip and the superior portion of the frame that overlaps the nares sealing portion so that the lateral nares engagement portions are movable independently of the frame and the cushion clip.

29 Claims, 108 Drawing Sheets

Related U.S. Application Data

No. 15/652,671, filed on Jul. 18, 2017, now Pat. No. 10,744,290, which is a continuation of application No. 13/876,606, filed as application No. PCT/AU2011/001259 on Sep. 30, 2011, now Pat. No. 9,737,678.

(60) Provisional application No. 61/528,524, filed on Aug. 29, 2011, provisional application No. 61/457,981, filed on Jul. 27, 2011, provisional application No. 61/443,623, filed on Feb. 16, 2011, provisional application No. 61/388,357, filed on Sep. 30, 2010.

(51) Int. Cl.
*A61M 16/00* (2006.01)
*A61M 16/20* (2006.01)

(52) U.S. Cl.
CPC .... *A61M 16/0611* (2014.02); *A61M 16/0616* (2014.02); *A61M 16/0622* (2014.02); *A61M 16/0683* (2013.01); *A61M 16/0816* (2013.01); *A61M 16/0825* (2014.02); *A61M 16/0875* (2013.01); *A61M 16/20* (2013.01); *A61M 16/208* (2013.01); *A61M 2202/0225* (2013.01); *A61M 2205/0216* (2013.01); *A61M 2210/0618* (2013.01); *A61M 2210/0625* (2013.01)

(56) References Cited

U.S. PATENT DOCUMENTS

| | | |
|---|---|---|
| 1,229,050 A | 6/1917 | Donald |
| 1,362,766 A | 12/1920 | McGargill |
| 1,445,010 A | 2/1923 | Feinberg |
| 1,710,160 A | 2/1925 | Gibbs |
| 2,126,755 A | 8/1938 | Dreyfus |
| 2,130,555 A | 9/1938 | Malcom |
| 2,228,218 A | 1/1941 | Schwartz |
| 2,578,621 A | 12/1951 | Yant |
| 2,706,983 A | 4/1955 | Matheson et al. |
| 3,330,273 A | 7/1967 | Bennett |
| 3,424,633 A | 1/1969 | Corrigall et al. |
| 4,126,131 A | 11/1978 | Davis |
| 4,248,218 A | 2/1981 | Fischer |
| 4,263,908 A | 4/1981 | Mizerak |
| 4,537,192 A | 8/1985 | Foster |
| 4,676,236 A | 6/1987 | Piorkowski et al. |
| 4,676,241 A | 6/1987 | Webb et al. |
| 4,782,832 A | 11/1988 | Trimble et al. |
| 4,919,128 A | 4/1990 | Kopala et al. |
| 4,944,310 A | 7/1990 | Sullivan |
| 4,989,596 A | 2/1991 | Macris et al. |
| 5,005,571 A | 4/1991 | Dietz |
| 5,018,519 A | 5/1991 | Brown |
| 5,042,478 A | 8/1991 | Kopala et al. |
| 5,062,421 A | 11/1991 | Burns et al. |
| D322,318 S | 12/1991 | Sullivan |
| 5,243,971 A | 9/1993 | Sullivan et al. |
| 5,265,595 A | 11/1993 | Rudolph |
| 5,375,593 A | 12/1994 | Press |
| 5,513,634 A | 5/1996 | Jackson |
| 5,560,354 A | 10/1996 | Berthon-Jones |
| 5,657,752 A | 8/1997 | Landis et al. |
| 5,662,101 A | 9/1997 | Ogden et al. |
| 5,724,965 A | 3/1998 | Handke |
| 5,746,201 A | 5/1998 | Kidd |
| 5,921,239 A | 7/1999 | McCall et al. |
| 6,016,804 A | 1/2000 | Gleason et al. |
| 6,119,694 A | 9/2000 | Correa |
| 6,123,071 A * | 9/2000 | Berthon-Jones ............ A61M 16/0616 128/205.25 |
| 6,192,886 B1 | 2/2001 | Rudolph |
| 6,263,874 B1 | 7/2001 | Ledez et al. |
| 6,412,488 B1 | 7/2002 | Barnett et al. |
| 6,418,928 B1 | 7/2002 | Bordewick et al. |
| 6,431,172 B1 | 8/2002 | Bordewick |
| 6,435,181 B1 | 8/2002 | Jones, Jr. et al. |
| 6,457,473 B1 | 10/2002 | Brostrom et al. |
| 6,467,483 B1 | 10/2002 | Kopacko et al. |
| 6,478,026 B1 | 11/2002 | Wood |
| 6,530,373 B1 | 3/2003 | Patron et al. |
| 6,561,190 B1 | 5/2003 | Kwok |
| 6,581,594 B1 | 6/2003 | Drew et al. |
| 6,584,975 B1 | 7/2003 | Taylor |
| 6,631,718 B1 | 10/2003 | Lovell |
| 6,644,315 B2 | 11/2003 | Ziaee |
| 6,691,707 B1 | 2/2004 | Gunaratnam et al. |
| 6,796,308 B2 | 9/2004 | Gunaratnam et al. |
| 6,823,869 B2 | 11/2004 | Raje et al. |
| 6,851,425 B2 | 2/2005 | Jaffre et al. |
| 6,860,270 B2 | 3/2005 | Sniadach |
| 6,907,882 B2 | 6/2005 | Ging et al. |
| 7,007,696 B2 | 3/2006 | Palkon et al. |
| 7,152,602 B2 | 12/2006 | Bateman et al. |
| 7,178,525 B2 | 2/2007 | Matula, Jr. et al. |
| 7,178,528 B2 | 2/2007 | Lau et al. |
| 7,210,481 B1 | 5/2007 | Lovell |
| 7,219,669 B1 | 5/2007 | Lovell et al. |
| 7,243,650 B2 | 7/2007 | Thornton |
| 7,353,827 B2 | 4/2008 | Geist |
| 7,357,136 B2 | 4/2008 | Ho et al. |
| 7,448,386 B2 | 11/2008 | Ho et al. |
| 7,658,189 B2 | 2/2010 | Davidson et al. |
| 7,708,017 B2 | 5/2010 | Davidson et al. |
| 7,827,990 B1 | 11/2010 | Melidis et al. |
| 7,909,035 B2 | 3/2011 | Thornton |
| 7,942,148 B2 | 5/2011 | Davidson et al. |
| 8,042,539 B2 | 10/2011 | Chandran et al. |
| 8,297,285 B2 | 10/2012 | Henry et al. |
| 8,402,971 B2 | 3/2013 | Scheiner et al. |
| 8,443,807 B2 | 5/2013 | McAuley et al. |
| 8,479,741 B2 | 7/2013 | McAuley et al. |
| 8,714,157 B2 | 5/2014 | McAuley et al. |
| 8,887,725 B2 | 11/2014 | Hernandez et al. |
| 8,944,061 B2 | 2/2015 | D'Souza et al. |
| 8,950,404 B2 | 2/2015 | Formica et al. |
| 8,960,196 B2 | 2/2015 | Henry |
| 9,027,556 B2 | 5/2015 | Ng et al. |
| 9,095,673 B2 | 8/2015 | Barlow et al. |
| 9,119,931 B2 | 9/2015 | D'Souza et al. |
| 9,242,062 B2 | 1/2016 | Melidis et al. |
| 9,333,315 B2 | 5/2016 | McAuley et al. |
| 9,339,624 B2 | 5/2016 | McAuley et al. |
| 9,381,316 B2 | 7/2016 | Ng et al. |
| 9,517,317 B2 | 12/2016 | McAuley et al. |
| 9,539,405 B2 | 1/2017 | McAuley et al. |
| 9,737,678 B2 | 8/2017 | Formica et al. |
| 10,441,738 B2 | 10/2019 | Formica et al. |
| 10,744,290 B2 | 8/2020 | Formica et al. |
| 2002/0020416 A1 | 2/2002 | Namey |
| 2002/0029780 A1 | 3/2002 | Frater et al. |
| 2002/0096173 A1 | 7/2002 | Berthon-Jones et al. |
| 2003/0029454 A1 | 2/2003 | Gelinas et al. |
| 2003/0196655 A1 | 10/2003 | Ging et al. |
| 2003/0196658 A1 | 10/2003 | Ging et al. |
| 2004/0025882 A1 | 2/2004 | Madaus et al. |
| 2004/0041342 A1 | 3/2004 | Frieman |
| 2004/0067333 A1 | 4/2004 | Amarasinghe |
| 2004/0112384 A1 | 6/2004 | Lithgow et al. |
| 2004/0118406 A1 | 6/2004 | Lithgow et al. |
| 2004/0182398 A1 | 9/2004 | Sprinkle et al. |
| 2004/0211428 A1 | 10/2004 | Jones, Jr. et al. |
| 2004/0221850 A1 | 11/2004 | Ging et al. |
| 2004/0226566 A1 | 11/2004 | Gunaratnam et al. |
| 2004/0255949 A1 | 12/2004 | Lang et al. |
| 2005/0001152 A1 | 1/2005 | Stewart et al. |
| 2005/0011524 A1 | 1/2005 | Thomlinson et al. |
| 2005/0016544 A1 | 1/2005 | Thornton |
| 2005/0028822 A1 | 2/2005 | Sleeper et al. |
| 2005/0121030 A1 * | 6/2005 | Bateman ............ A61M 16/0683 128/201.25 |
| 2005/0155604 A1 | 7/2005 | Ging et al. |

(56) References Cited

U.S. PATENT DOCUMENTS

| | | |
|---|---|---|
| 2005/0199242 A1 | 9/2005 | Matula, Jr. et al. |
| 2005/0205096 A1 | 9/2005 | Matula, Jr. et al. |
| 2006/0042629 A1 | 3/2006 | Geist |
| 2006/0060200 A1 | 3/2006 | Ho et al. |
| 2006/0118117 A1 | 6/2006 | Berthon-Jones et al. |
| 2006/0124131 A1 | 6/2006 | Chandran et al. |
| 2006/0201514 A1 | 9/2006 | Jones |
| 2006/0207597 A1 | 9/2006 | Wright |
| 2006/0237017 A1 | 10/2006 | Davidson |
| 2006/0272646 A1 | 12/2006 | Ho et al. |
| 2006/0283461 A1 | 12/2006 | Lubke et al. |
| 2007/0006879 A1 | 1/2007 | Thornton |
| 2007/0044804 A1 | 3/2007 | Matula, Jr. et al. |
| 2007/0062539 A1 | 3/2007 | Gunaratnam |
| 2007/0125385 A1* | 6/2007 | Ho .............. A61M 16/0683 128/206.26 |
| 2007/0144525 A1 | 6/2007 | Davidson et al. |
| 2007/0163594 A1 | 7/2007 | Ho |
| 2007/0175480 A1 | 8/2007 | Gradon et al. |
| 2007/0186930 A1 | 8/2007 | Davidson et al. |
| 2007/0272249 A1* | 11/2007 | Chandran .............. A61M 16/20 128/206.28 |
| 2008/0006277 A1 | 1/2008 | Worboys et al. |
| 2008/0110464 A1 | 5/2008 | Davidson et al. |
| 2008/0110466 A1 | 5/2008 | Armitstead |
| 2008/0257354 A1 | 10/2008 | Davidson et al. |
| 2009/0032026 A1 | 2/2009 | Price et al. |
| 2009/0044808 A1 | 2/2009 | Guney |
| 2009/0078259 A1 | 3/2009 | Kooij et al. |
| 2009/0095303 A1 | 4/2009 | Sher |
| 2009/0114229 A1* | 5/2009 | Frater .............. A61M 16/0694 128/205.25 |
| 2009/0126739 A1 | 5/2009 | Ng |
| 2009/0133696 A1 | 5/2009 | Remmers |
| 2009/0159084 A1 | 6/2009 | Sher et al. |
| 2009/0241961 A1* | 10/2009 | McAuley .............. A61M 16/0825 128/207.18 |
| 2009/0277452 A1 | 11/2009 | Lubke et al. |
| 2010/0000534 A1 | 1/2010 | Kooij et al. |
| 2010/0006101 A1 | 1/2010 | McAuley |
| 2010/0018534 A1 | 1/2010 | Veliss et al. |
| 2010/0132717 A1 | 6/2010 | Davidson et al. |
| 2010/0199992 A1 | 8/2010 | Ho et al. |
| 2010/0229868 A1 | 9/2010 | Rummery |
| 2010/0313891 A1 | 12/2010 | Veliss et al. |
| 2011/0056497 A1* | 3/2011 | Scheiner .............. A61M 16/06 128/206.24 |
| 2011/0072553 A1 | 3/2011 | Ho |
| 2011/0146685 A1 | 6/2011 | Allan |
| 2011/0209709 A1 | 9/2011 | Davidson et al. |
| 2011/0232647 A1 | 9/2011 | Ho |
| 2012/0204870 A1 | 8/2012 | McAuley |
| 2012/0204880 A1 | 8/2012 | Smith |
| 2013/0037030 A1 | 2/2013 | Matula, Jr. |
| 2013/0112206 A1 | 5/2013 | Buddharaju |
| 2013/0199537 A1 | 8/2013 | Formica et al. |
| 2014/0083430 A1 | 3/2014 | Matula, Jr. et al. |
| 2014/0174446 A1 | 6/2014 | Prentice |
| 2017/0312468 A1 | 11/2017 | Formica et al. |
| 2018/0318540 A1 | 11/2018 | Barlow et al. |
| 2019/0091431 A1 | 3/2019 | Formica |
| 2019/0091432 A1 | 3/2019 | Barlow et al. |
| 2019/0091433 A1 | 3/2019 | Barlow et al. |
| 2020/0330715 A1 | 10/2020 | Formica et al. |
| 2020/0345964 A1 | 11/2020 | Formica et al. |
| 2020/0360639 A1 | 11/2020 | Formica et al. |
| 2020/0360640 A1 | 11/2020 | Formica et al. |

FOREIGN PATENT DOCUMENTS

| | | | | |
|---|---|---|---|---|
| AU | 2009900327 | 1/2009 | | |
| AU | 2009902524 | 6/2009 | | |
| AU | 2009902731 | 6/2009 | | |
| AU | 2009904236 | 9/2009 | | |
| AU | 2009906101 | 12/2009 | | |
| AU | 2010902359 | 5/2010 | | |
| CN | 2721141 | 8/2005 | | |
| CN | 1901961 | 1/2007 | | |
| CN | 101237902 | 8/2008 | | |
| DE | 4004157 | 4/1991 | | |
| EP | 1020201 A2 | 7/2000 | | |
| EP | 2 022 528 A2 | 2/2009 | | |
| GB | 01085 | 12/1909 | | |
| GB | 2385533 | 8/2003 | | |
| GB | 2385533 A * | 8/2003 | ............ | A61M 16/06 |
| JP | 2007-516750 | 6/2007 | | |
| JP | 2008-501438 | 1/2008 | | |
| JP | 2008-541955 | 11/2008 | | |
| JP | 2009-527260 | 7/2009 | | |
| WO | WO 00/50122 A1 | 8/2000 | | |
| WO | WO 02/47749 A1 | 6/2002 | | |
| WO | WO 03/076020 | 9/2003 | | |
| WO | 03/090827 A1 | 11/2003 | | |
| WO | WO 2004/022147 A1 | 3/2004 | | |
| WO | 2004/041341 A1 | 5/2004 | | |
| WO | WO 2004/041342 A1 | 5/2004 | | |
| WO | WO 2004/052438 | 6/2004 | | |
| WO | 2004/078231 | 9/2004 | | |
| WO | WO 2004/073778 A1 | 9/2004 | | |
| WO | 2004/096332 A1 | 11/2004 | | |
| WO | WO 2005/021075 A1 | 3/2005 | | |
| WO | 2005/046776 A1 | 5/2005 | | |
| WO | WO 2005/051468 A1 | 6/2005 | | |
| WO | 2005/063328 | 7/2005 | | |
| WO | 2005/063328 A1 | 7/2005 | | |
| WO | WO 2005/063328 | 7/2005 | | |
| WO | WO 2005/079726 A1 | 9/2005 | | |
| WO | 2005/118042 | 12/2005 | | |
| WO | WO 2005/123166 A1 | 12/2005 | | |
| WO | WO 2006/000046 A1 | 1/2006 | | |
| WO | WO 2006/000770 A1 | 1/2006 | | |
| WO | WO 2006/074515 A1 | 7/2006 | | |
| WO | 2006/130903 | 12/2006 | | |
| WO | 2007/008725 | 1/2007 | | |
| WO | WO 2007/006089 A1 | 1/2007 | | |
| WO | WO 2007/008725 | 1/2007 | | |
| WO | WO 2007/014088 A2 | 2/2007 | | |
| WO | WO 2007/041751 A1 | 4/2007 | | |
| WO | WO 2007/045008 A1 | 4/2007 | | |
| WO | WO 2007/048174 A1 | 5/2007 | | |
| WO | 2007/064665 | 6/2007 | | |
| WO | WO 2007/130067 | 11/2007 | | |
| WO | WO 2007/139531 | 12/2007 | | |
| WO | WO 2007/147088 A2 | 12/2007 | | |
| WO | WO 2008/007985 | 1/2008 | | |
| WO | WO 2008/030831 A2 | 3/2008 | | |
| WO | WO 2008/068966 A1 | 6/2008 | | |
| WO | WO 2009/026627 A1 | 3/2009 | | |
| WO | WO 2009/052560 | 4/2009 | | |
| WO | WO 2009/059353 A1 | 5/2009 | | |
| WO | WO 2009/151344 A1 | 12/2009 | | |
| WO | 2010/059592 | 5/2010 | | |
| WO | 2010/066004 | 6/2010 | | |
| WO | 2010/067235 | 6/2010 | | |
| WO | WO 2010/135785 | 12/2010 | | |
| WO | WO 2010/139014 | 12/2010 | | |
| WO | WO 2010/139014 A1 | 12/2010 | | |
| WO | WO 2012/040791 | 4/2012 | | |
| WO | WO 2013/066195 A1 | 5/2013 | | |

OTHER PUBLICATIONS

ACP Composites—Large Stock of Ready to Use Composite Plate, Tube, Sheet, Fabrics and Core Materials, https://www.acpsakes.com/Core-Materials-nd-Foam.html, dated Oct. 5, 2015, 4 pages.

Flexifit instructions, http://web.archive.org/web/1 9970126045828/ http:/www.archive.org/ dated Jan. 26, 1997, Affidavit of Christopher Butler dated Sep. 6, 2016, 23 pages.

Guidelines for Sandwich Core Materials, http://fibreglast.com/product/guidelines-for-sandwich-core-materials/Learning_Center, dated Oct. 5, 2015, 3 pages.

(56) References Cited

OTHER PUBLICATIONS http://pdf.medicalexpo.com [online], "Opus Brochure," Fisher & Paykel Healthcare, available on or before Apr. 25, 2015, via Internet Archive: Wayback Machine URL <https://web.archive.org/web/20150425003833/http://pdf.medicalexpo.com/pdf/fisher-paykel-healthcare/opus-specification-sheet/70844-126507.html> [retrieved on Apr. 30, 2019], retrieved from: URL <www.fphcare.com>, 18 pages.
Malloy, Plastic Part Design for Injection Molding, New York: Hanser Publishers, 1994, 34 pages.
ResMed Mask Frames, Nasal Cushions and Headgear, http://web.archive.org/web/19970126045828/http://www.archive.org/ dated Jan. 26, 1997, Affidavit of Christopher Butler dated Jul. 6, 2017, 8 pages.
ResMed Mirage Swift Nasal Pillows System, www.resmed.com, 2004, 6 pages.
ResMed Mirage Vista Nasal Mask-Component Cards, www.resmed.com Reference No. 1010279/30502, dated 2005, 1 page.
ResMed Origins Brochure dated Apr. 17, 2016, 64 pages.
Ultra Mirage Full Face Mask brochure, http://web.archive.org/web/19970 1 26045828/http://www.archive.org/ dated Jan. 26, 1997, Affidavit of Christopher Butler dated Sep. 6, 2016, 9 pages.
Users Guide ResMed Mirage Swift Nasal Pillows System, www.myresmed.com dated May 6, 2004, 11 pages.
Office Action dated May 2, 2017 issued in Chinese Application No. 201510757297.0 with English translation (22 pages).
Office Action dated Nov. 2, 2016 issued in Chinese Application No. 201410650331.X with English translation (6 pages).
Further Examination Report dated Oct. 13, 2016 issued in related New Zealand Application No. 713055 (3 pages).
Second Office Action issued in Japanese Application No. 2013-530494 dated Feb. 29, 2016, with English translation.
First Office Action issued in Japanese Application No. 2015-191227 dated Jul. 15, 2016, with English translation.
Third Office Action issued in Chinese Application No. 201180047592.7 dated Mar. 4, 2016 with English translation.
International Preliminary Report on Patentability issued in Application No. PCT/AU2011/001259 dated Apr. 2, 2013.
First Examination Report issued in corresponding New Zealand Application No. 713055 dated Oct. 27, 2015.
Further Examination Report dated Aug. 8, 2014 in New Zealand Application No. 607879 (2 pages).
First Examination Report dated Sep. 19, 2013 in New Zealand Application No. 607879 (2 pages).
First Examination Report dated Nov. 19, 2014 issued in New Zealand Application No. 701501 (3 pages).
Notification of the First Office Action dated Dec. 15, 2014 issued in Chinese Application No. 201180047592.7 with English translation (17 pages).
Extended European Search Report dated May 4, 2015 issued in European Application No. 11827829.0 (7 pages).
Patent Examination Report No. 1 dated Jun. 5, 2015 issued in Australian Application No. 2014224136 (8 pages).
Notice of Reasons for Rejection dated Jun. 29, 2015 issued in Japanese Application No. 2013-530494 with English translation (15 pages).
Notification of Second Office Action dated Aug. 24, 2015 issued in Chinese Application No. 201180047592.7 with English translation (19 pages).
First Examination Report dated Nov. 5, 2014 in New Zealand Application No. 701074 (3 pages).
International Search Report for PCT/AU2011/001259, dated Dec. 13, 2011.
Extended European Search Report dated Aug. 17, 2017 issued in European Application No. 16205363.1 (9 pages).
Second Office Action dated Jan. 19, 2018 issued in Chinese Application No. 201510757297.0 with English translation (23 pages).
First Examination Report dated Nov. 7, 2018 in New Zealand Application No. 747496, 3 pages.
Decision of Rejection dated Feb. 28, 2019 in Chinese Application No. 201510757297.0, with English translation, 11 pages.
File History of U.S. Appl. No. 16/198,518, filed Nov. 21, 2018 of Justin John Formica et al., entitled "Mask System," 2370 pages.
Further Examination Report dated May 10, 2022 issued in New Zealand Application No. 763697 (4 pages).
Examination Report dated May 10, 2022 issued in New Zealand Application No. 763697 (4 pages).

\* cited by examiner

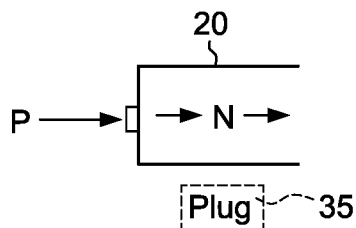
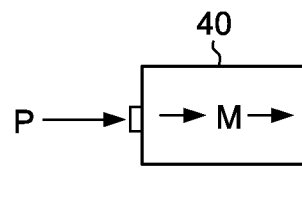
FIG. 32(a)     FIG. 32(b)
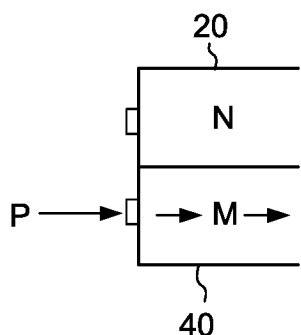
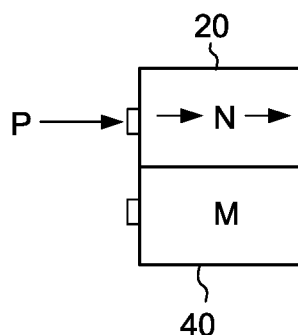
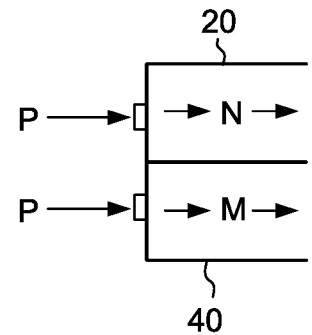
FIG. 32(c)     FIG. 32(d)     FIG. 32(e)
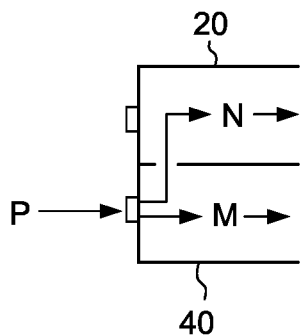
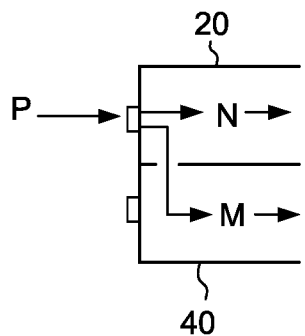
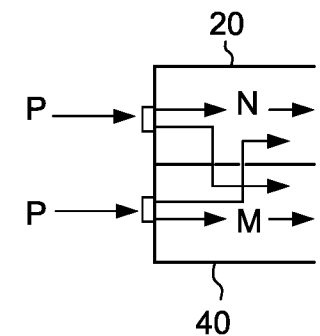
FIG. 32(f)     FIG. 32(g)     FIG. 32(h)
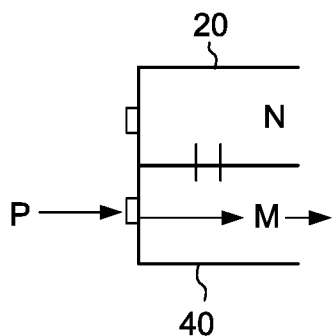
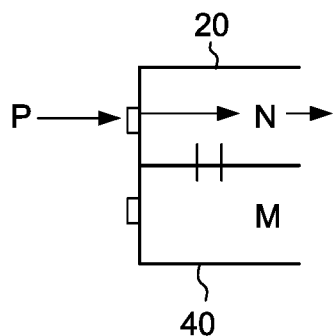
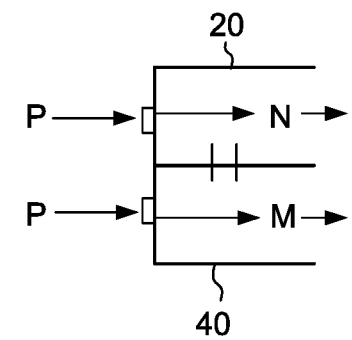
FIG. 32(i)     FIG. 32(j)     FIG. 32(k)

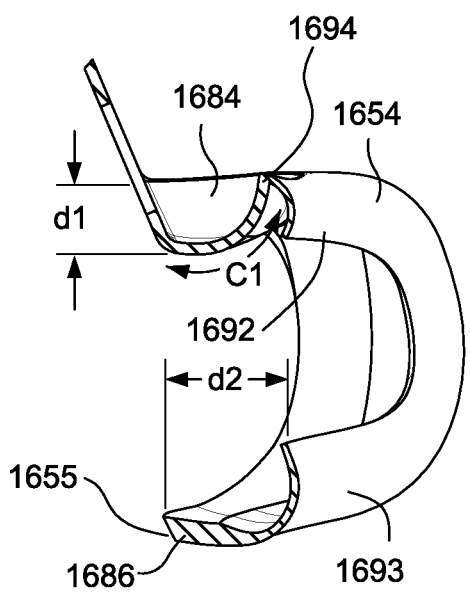
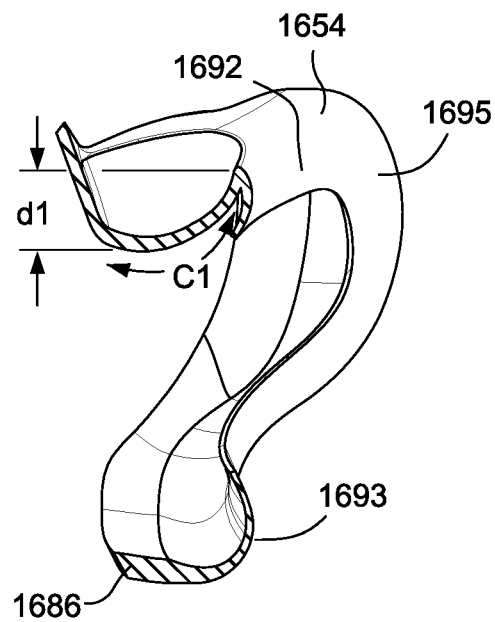
FIG. 80      FIG. 81
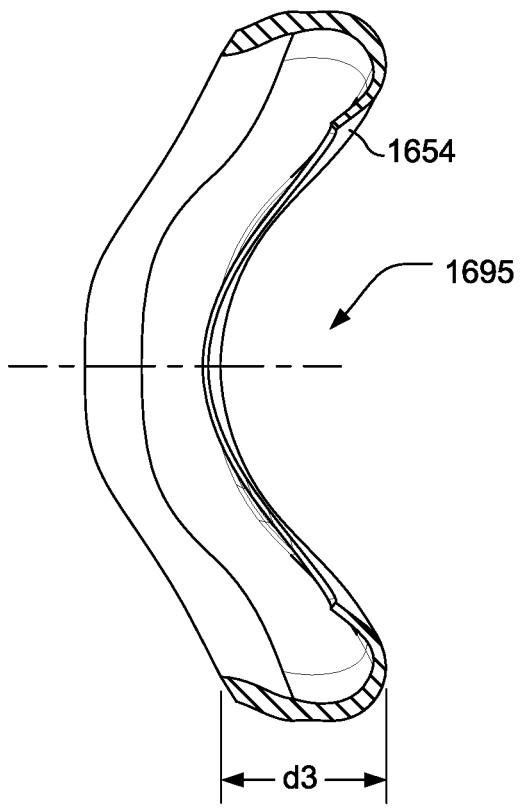
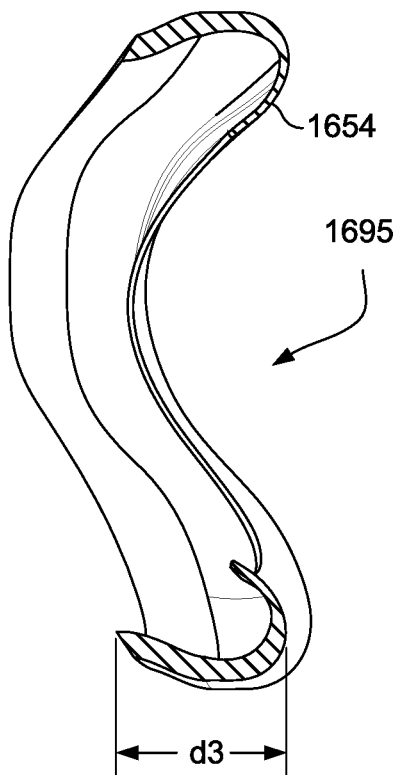
FIG. 82      FIG. 83

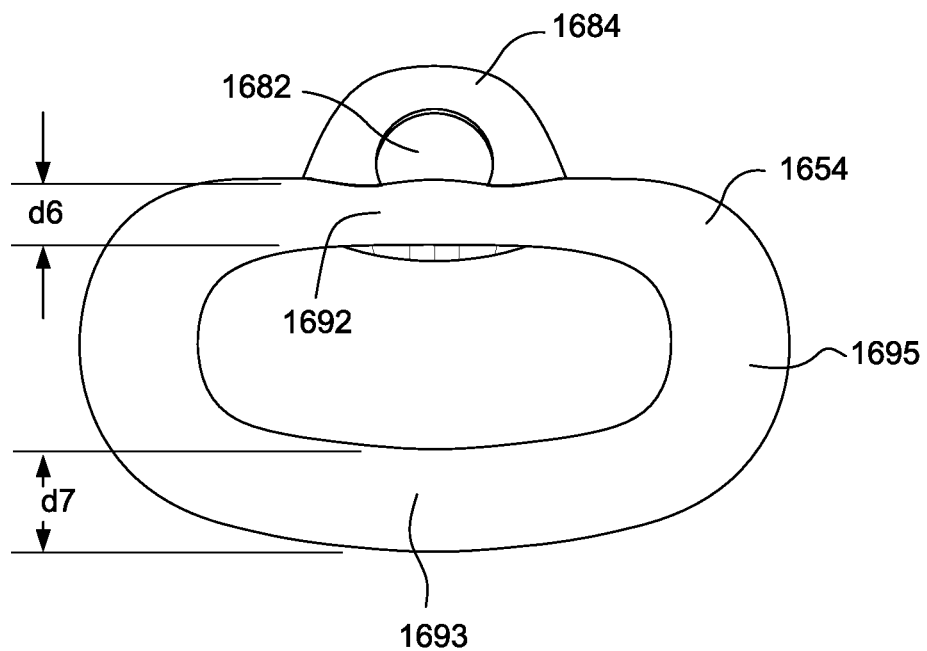
FIG. 86
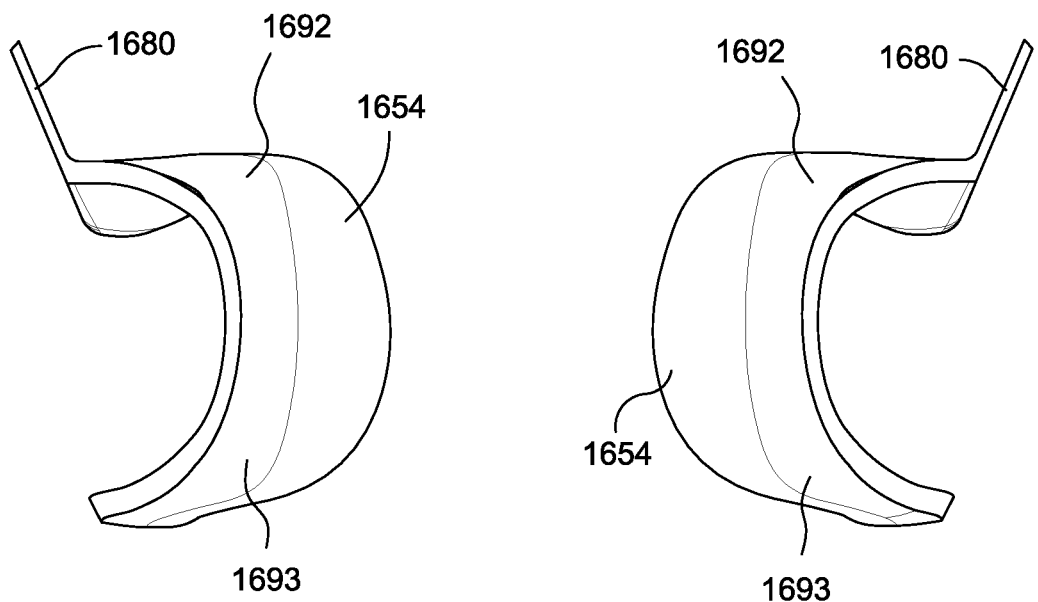
FIG. 87
FIG. 88

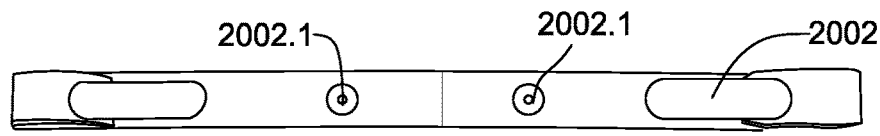
FIG. 91A
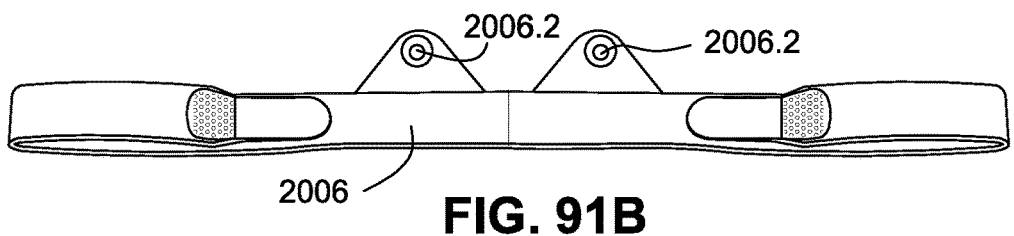
FIG. 91B
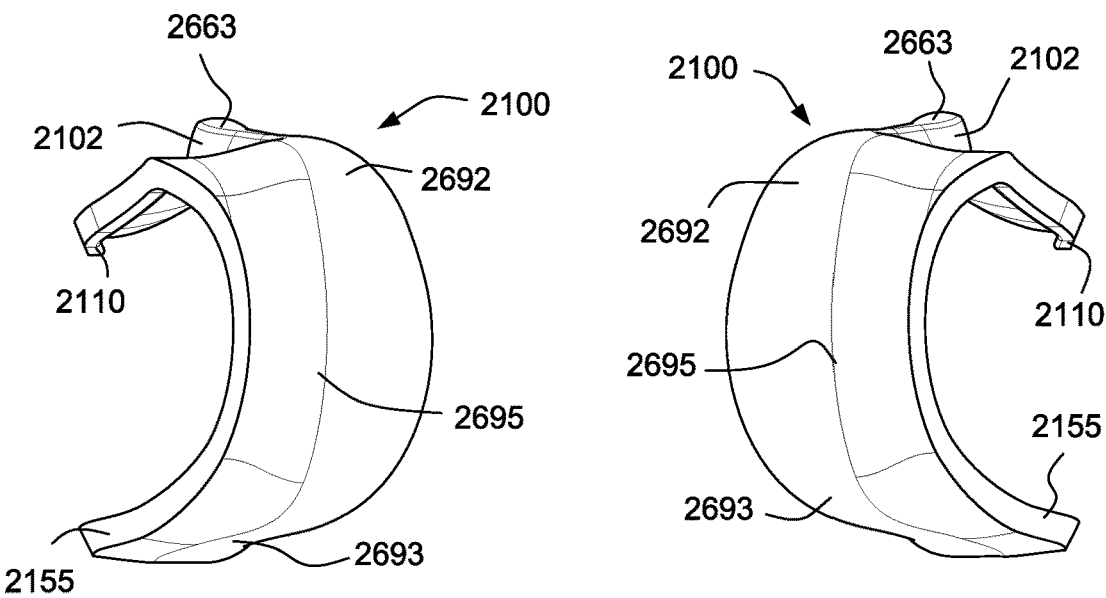
FIG. 92A  FIG. 92B
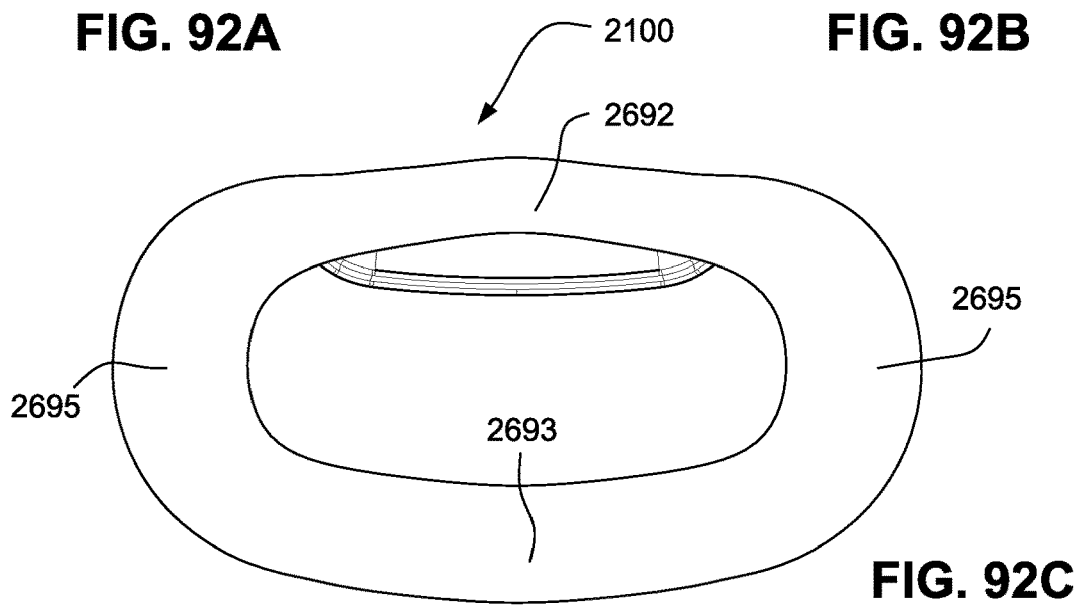
FIG. 92C

2104

2104

2104

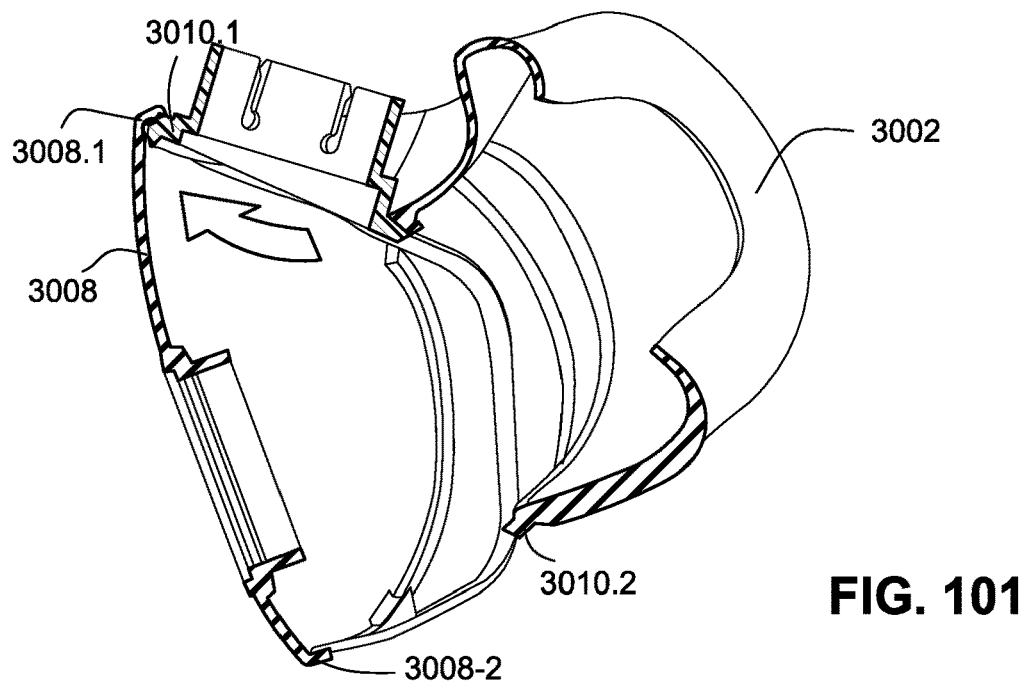
FIG. 101
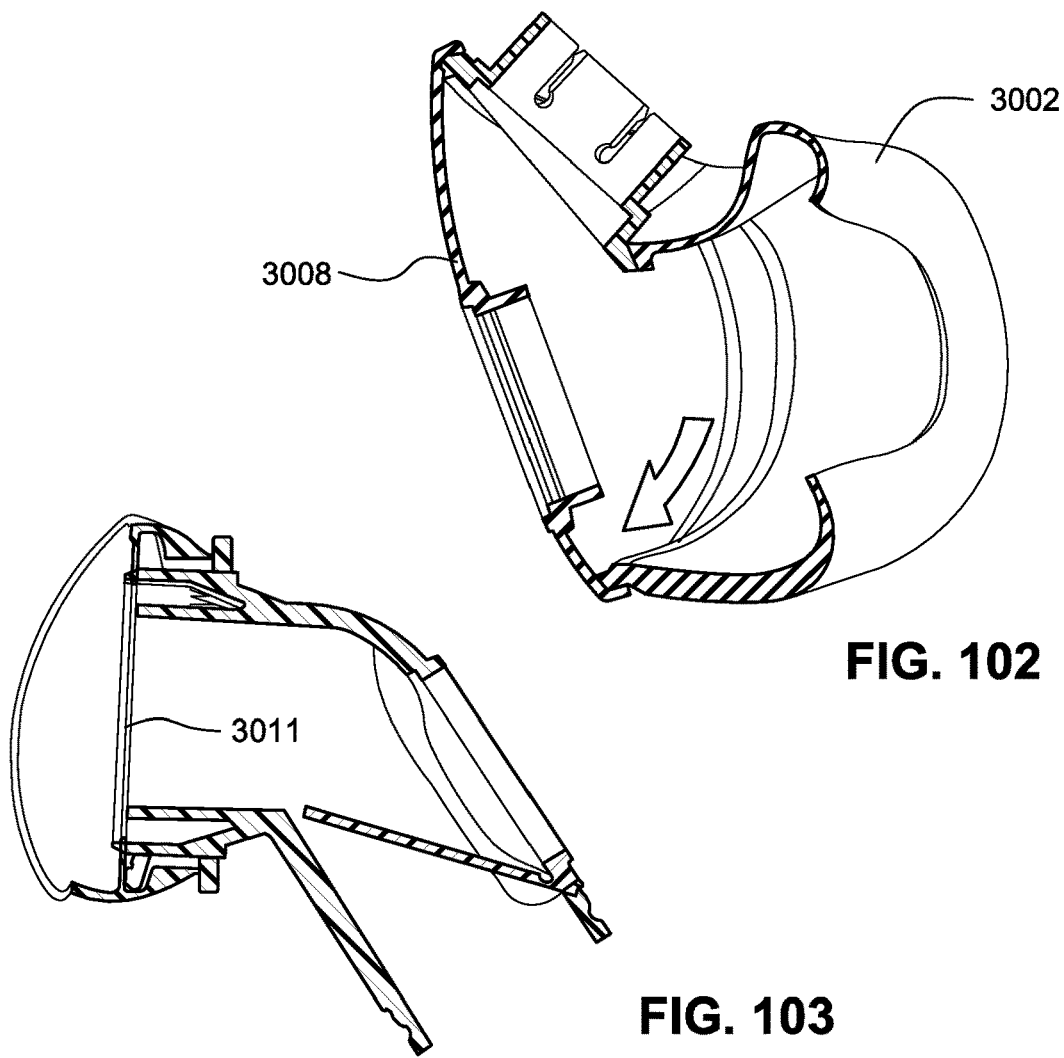
FIG. 102
FIG. 103

MASK SYSTEM

CROSS-REFERENCE TO APPLICATIONS

This application is a continuation of U.S. application Ser. No. 16/987,520, filed Aug. 7, 2020, which is a continuation of U.S. application Ser. No. 15/652,671, filed Jul. 18, 2017, now U.S. Pat. No. 10,744,290, which is a continuation of U.S. application Ser. No. 13/876,606, filed Mar. 28, 2013, now U.S. Pat. No. 9,737,678, which is the U.S. national phase of International Application No. PCT/AU2011/001259, filed Sep. 30, 2011, which designated the U.S. and claims the benefit of U.S. Provisional Application Nos. 61/388,357, filed Sep. 30, 2010, 61/443,623, filed Feb. 16, 2011, 61/457,981, filed Jul. 27, 2011, and 61/528,524, filed Aug. 29, 2011, each of which is incorporated herein by reference in its entirety.

FIELD OF THE TECHNOLOGY

The present technology relates to a mask system used for Non-invasive Positive Pressure Ventilation (NPPV) and for continuous positive airway pressure (CPAP) therapy of sleep disordered breathing (SDB) conditions such as obstructive sleep apnea (OSA).

BACKGROUND OF THE TECHNOLOGY

Treatment of sleep disordered breathing (SDB), such as obstructive sleep apnea (OSA), by continuous positive airway pressure (CPAP) flow generator systems involves the continuous delivery of air (or other breathable gas) pressurized above atmospheric pressure to the airways of a human or other mammalian patient via a conduit and a mask. Typically, the mask fits over or in the mouth and/or nose of the patient. Pressurized air flows to the mask and to the airways of the patient via the nose and/or mouth. Pressurized air is delivered to the mask by a conduit connected to the CPAP device and the mask.

The mask should be comfortable and unobtrusive so that a patient may tolerate their therapy and maintain usage. Some patients may prefer a pillows or prongs type mask (as known in the art), or a nasal mask or a full face mask. Some patient's may prefer to use one or a combination of these masks interchangeably. However, this would require the purchase of a number of different mask systems, which may be expensive and/or may not be covered by insurance.

In addition, masks including oro-nasal masks typically include a rigid frame. Patients may not find this comfortable. The frame may also dislodge the sealing portion of the mask away from the face of the patient if it is contacted or forced by bed clothing, pillows, etc.

SUMMARY OF THE TECHNOLOGY

One aspect of the present technology relates to a mask system that is able to be used as either a nasal only type mask or an oro-nasal mask.

Another aspect of the present technology relates to an oro-nasal mask that is substantially comprised of flexible components.

Another aspect of the present technology relates to an oro-nasal mask that is stabilised at the nose sealing portion separately to the mouth sealing portion.

Another aspect of the present technology relates to an oro-nasal mask having at least a first headgear connection on the nasal portion of the mask and at least a second headgear connection on the mouth portion of the mask.

Another aspect of the present technology relates to a modular mask system that is adapted to be used in a nares only configuration, or in a nares and mouth configuration.

Another aspect of the present technology relates to a modular mask system that is adapted to be used in a nares only configuration, in a mouth only configuration, or in a nares and mouth configuration.

In one form of the present technology, the mask system is provided with a nares portion and a mouth portion that are useable at the option of the patient with the nares portion and the mouth portion, or with just the nares portion. The mouth portion when used with the nares portion may be used to deliver respiratory therapy to the patient's mouth, or may be used as a mouth seal.

In one form of the present technology, the mask system is provided with a nares portion and a mouth portion that are useable at the option of the patient with the nares portion and the mouth portion, with just the nares portion, or with just the mouth portion.

In one form of the present technology, the mask system is provided with a nares portion and a mouth portion, where the nares portion includes a nares sealing portion adapted to form a seal with the patient's nares, where the nares sealing portion is structured to extend or curve outwardly from a supporting wall defining an air path into the nares sealing portion.

Another aspect of the present technology relates to a mask system that includes a nares portion and a mouth portion, and the mouth portion is adapted to be used in both a first configuration where at least a portion of the pressurized, breathable gas is delivered to the patient's mouth and in a second configuration where the mouth portion functions as a mouth seal that prevents any of the pressurized, breathable gas from being delivered to the patient's mouth.

Another aspect of the present technology relates to a method of providing a mask system kit for delivering respiratory therapy to a patient, where a nares portion and a mouth portion are useable at the option of the patient with the nares portion and the mouth portion, with just the nares portion, or with just the mouth portion.

Another aspect of the present technology relates to a method of providing a mask system kit for delivering respiratory therapy to a patient, where a nares portion and a mouth portion are useable at the option of the patient with the nares portion and the mouth portion, with just the nares portion, or with just the mouth portion, where the when the nares portion and the mouth portion are both utilized, the nares portion and the mouth portion may both be utilized to deliver pressurized air to the nares and mouth of the patient, respectively, or one of the nares portion and the mouth portion may be utilized to deliver pressurized air to the nares or mouth of the patient, while the other of the nares portion and the mouth portion is utilized as a nares or mouth seal.

Another aspect of the present technology relates to a method of converting a mask system having a nares portion and a mouth portion between first and second modes, where in the first mode the mask system is useable with the nares portion and the mouth portion, and in the second mode the mask system is useable with only the nares portion.

Another aspect of the present technology relates to a kit providing a nares only portion for delivering respiratory therapy to a patient's nares, the nares portion adapted to function with a mouth portion.

Another aspect of the present technology relates to a kit providing a mouth portion for delivering respiratory therapy to a patient's mouth, the mouth portion adapted to function with a nares portion.

Another aspect of the present technology relates to a method of providing respiratory therapy to one of a patient's nares only, a patient's mouth only, or to both a patient's nares and mouth, and periodically changing the respiratory therapy to another of the patient's nares only, the patient's mouth only, or to both the patient's nares and mouth.

Another aspect of the present technology relates to a method of respiratory therapy treatment, where a first mask with a first footprint is applied to a patient for a period of time, then the first mask is removed, and a second mask with a second footprint different from the first footprint is applied to the patient for a second period of time.

Another aspect of the present technology relates to a mouth portion for delivering respiratory therapy to a patient's mouth, the mouth portion including a docking station adapted to receive a nares portion, wherein the nares portion is capable of functioning as a nares only device for delivering pressurized gas to the nares of a patient.

Another aspect of the present technology relates to a mask system for delivery of respiratory therapy to a patient, the mask system including a nares portion adapted to form a seal with the patient's nares, a mouth portion including a mouth chamber and a mouth sealing portion adapted to form a seal with the patient's mouth, the mouth chamber including an opening adapted to selectively receive pressurized, breathable gas, an inlet conduit connected to at least one of the nares portion and the mouth portion to deliver the pressurized, breathable gas, wherein the mask system is adapted to selectively utilize the nares portion and/or the mouth portion in a first mode utilizing both the nares portion and the mouth portion, and in a second mode utilizing the nares portion and not utilizing the mouth portion.

Another aspect of the present technology relates to a mask system for delivery of respiratory therapy to a patient, the mask system including a nares portion adapted to form a seal with the patient's nares, a mouth portion including a mouth chamber and a mouth sealing portion adapted to form a seal with the patient's mouth, an inlet conduit connected to at least one of the nares portion and the mouth portion to deliver pressurized, breathable gas to the patient, wherein the nares portion and the mouth portion are adapted to connect to each other, and the mouth portion is adapted to selectively function in both a first configuration where at least a portion of the pressurized, breathable gas is delivered to the patient's mouth and in a second configuration where the mouth portion functions as a mouth seal that prevents any of the pressurized, breathable gas from being delivered to the patient's mouth.

Another aspect of the present technology relates to a mask system for delivery of respiratory therapy to a patient, the mask system including a sealing portion including a nares sealing portion and a mouth sealing portion, the nares sealing portion adapted to form a seal with the patient's nares, the nares sealing portion structured to extend or curve outwardly from a supporting wall defining an air path into the nares sealing portion, the mouth sealing portion adapted to form a seal with the patient's mouth, the sealing portion adapted to connect to at least one inlet conduit to receive a supply of pressurized, breathable gas and headgear for retaining the sealing assembly in position on the head of the patient.

Another aspect of the present technology relates to a method of providing a mask system kit for delivering respiratory therapy to a patient, the method including providing a nares portion adapted to form a seal with the patient's nares, providing a mouth portion including a mouth chamber and a mouth sealing portion adapted to form a seal with the patient's mouth, the mouth chamber including an opening adapted to selectively receive pressurized, breathable gas, and providing an inlet conduit connectable to at least one of the nares portion and the mouth chamber to deliver the pressurized, breathable gas, wherein, at the option of the patient, the mask system is adapted to selectively utilize the nares portion and/or the mouth portion in at least first and second modes, the first mode utilizing the nares portion and the mouth portion to provide the respiratory therapy to the patient's nares, wherein the mouth portion is configured to provide the respiratory therapy to the patient's mouth or to seal the mouth portion, and in the second mode utilizing the nares portion to provide the respiratory therapy to the patient's nares and not utilizing the mouth portion as a seal or to deliver respiratory therapy.

Another aspect of the present technology relates to a method of converting a mask system between first and second modes, the mask system for delivery of respiratory therapy to a patient, the method including providing a nares portion adapted to form a seal with the patient's nares, providing a mouth portion including a mouth chamber and a mouth sealing portion adapted to form a seal with the patient's mouth, the mouth chamber including an opening adapted to selectively receive pressurized, breathable gas, assembling the mask system in the first mode utilizing the nares portion and the mouth portion to provide the respiratory therapy to the patient's nares, utilizing the mouth portion to provide the respiratory therapy to the patient's mouth or utilizing the mouth portion as a mouth seal, and converting the mask system in the second mode utilizing the nares portion to provide the respiratory therapy to the patient's nares and not utilizing the mouth portion.

Another aspect of the present technology relates to a mask system for delivery of respiratory therapy to a patient, the mask system including a mouth portion including a mouth chamber and a mouth sealing portion adapted to form a seal with the patient's mouth, the mouth chamber including an opening adapted to selectively receive pressurized, breathable gas, and a nares portion docking station formed on the mouth portion, the nares portion docking station adapted to receive a nares portion, wherein the nares portion is capable of functioning as a nares only device for delivering pressurized gas to the nares of the patient.

Another aspect of the present technology relates to a medical package including a kit for converting a CPAP device comprising a nares only portion to a CPAP device having a nares and a mouth portion, the medical package including a mouth portion including a mouth chamber and a mouth sealing portion adapted to form a seal with the patient's mouth, the mouth chamber including an opening adapted to selectively receive pressurized, breathable gas, a vent plug adapted to plug an aperture in the nares only portion, and headgear adapted to secure at least the mouth portion to a patient's head.

Another aspect of the present technology relates to a system kit adapted to convert a nares only device for delivering respiratory therapy to a patient into a nares and mouth device for delivering respiratory therapy to a patient, the system kit including a mouth portion including a mouth chamber and a mouth sealing portion adapted to form a seal with the patient's mouth, the mouth chamber including an opening adapted to selectively receive pressurized, breathable gas, the mouth portion adapted to function with the nares only device as a nares and mouth device, a plug adapted to connect to either the opening in the mouth chamber or an opening in the nares only device, and headgear adapted to secure at least the mouth portion to the patient's head.

Another aspect of the present technology relates to a mask system for delivery of respiratory therapy to a patient, the mask system including a nares portion adapted to form a seal with the patient's nares, a mouth portion including a mouth chamber and a mouth sealing portion adapted to form a seal with the patient's mouth, and a double elbow, e.g., having one branch connected to the nares portion and another branch connected to the mouth portion to deliver the pressurized breathable gas to the nares portion and the mouth portion.

Another aspect of the present technology relates to a mask system for delivery of respiratory therapy to a patient, the mask system including a nares portion adapted to form a seal with the patient's nares, a mouth portion including a mouth chamber and a mouth sealing portion adapted to form a seal with the patient's mouth, and a covering flap extending from the mouth portion to cover the nares portion and/or the patient's nares in use.

Another aspect of the present technology relates to a mask system for delivery of respiratory therapy to a patient, the mask system including a nares portion including a nares sealing portion adapted to form a seal with the patient's nares, a mouth portion including a mouth sealing portion adapted to form a seal with the patient's mouth, the mouth sealing portion being oriented generally horizontally and the nares sealing portion being oriented generally vertically.

Another aspect of the present technology relates to a mask system for delivery of respiratory therapy to a patient, the mask system including a nares portion including a nares sealing portion and a nares supporting portion, the nares sealing portion adapted to form a seal with the patient's nares, a mouth portion including a mouth sealing portion adapted to form a seal with the patient's mouth, the nares supporting portion being a semi-rigid material and the nares sealing portion being a flexible material.

Another aspect of the present technology relates to a mask system for delivery of respiratory therapy to a patient, the mask system including a nares portion including a nares sealing portion and a nares supporting portion, the nares sealing portion adapted to form a seal with the patient's nares, a mouth portion including a mouth sealing portion adapted to form a seal with the patient's mouth, the mouth portion and/or the nares portion including a magnet to retain the mouth portion and/or the nares portion in position.

Another aspect of the present technology relates to a mask system for delivery of respiratory therapy to a patient, the mask system including a nares portion adapted to form a seal with the patient's nares, a mouth portion adapted to form a seal with the patient's mouth, and a foam portion adapted to clip onto at least one of the nares portion and the mouth portion to form a seal between the mask system and the patient.

Another aspect of the present technology relates to a mask system for delivery of respiratory therapy to a patient, the mask system including a nares portion including a nares sealing portion and a nares supporting portion, the nares sealing portion adapted to form a seal with the patient's nares, a mouth portion including a mouth sealing portion adapted to form a seal with the patient's mouth, and a connecting ring adapted to connect the mouth portion to the nares portion, the connecting ring having a first channel adapted to receive the mouth portion and a second channel adapted to receive the nares portion.

Another aspect of the present technology relates to a mask system for delivery of respiratory therapy to a patient, the mask system including a nares portion including a nares sealing portion and a nares supporting portion, the nares sealing portion adapted to form a seal with the patient's nares, a mouth portion including a mouth sealing portion adapted to form a seal with the patient's mouth, wherein the nares sealing portion has indentations adapted to form an interference fit with the mouth portion.

Another aspect of the present technology relates to a mask system for delivery of respiratory therapy to a patient, the mask system including a nares portion including a nares sealing portion and a nares supporting portion, the nares sealing portion adapted to form a seal with the patient's nares, a mouth portion including a mouth sealing portion adapted to form a seal with the patient's mouth, upper headgear adapted to connect to the nares portion, the upper headgear including a back strap adapted to wrap around a back of the patient's head, and lower headgear adapted to connect to the mouth portion, the lower headgear having a loop adapted to receive the back strap of the upper headgear.

Another aspect of the present technology relates to a mask system for delivery of respiratory therapy to a patient, the mask system including a nares portion including a nares sealing portion adapted to form a seal with the patient's nares, an elbow connected to the nares portion to deliver pressurized gas, the elbow including a lug portion, a mouth portion including a mouth sealing portion adapted to form a seal with the patient's mouth, the mouth portion including an aperture selectively connectable to the lug portion of the elbow to connect the mouth portion to the nares portion.

Another aspect of the present technology relates to a mask system for delivery of respiratory therapy to a patient, the mask system including a nares portion including a nares sealing portion adapted to form a seal with the patient's nares, a mouth portion including a mouth sealing portion adapted to form a seal with the patient's mouth, the mouth sealing portion including a cushion having a pocket or lower stiffness region, shaped and adapted to receive the nares portion.

Another aspect of the present technology relates to a mask system for delivery of respiratory therapy to a patient, the mask system including a nares portion including a nares sealing portion and a nares supporting portion, the nares sealing portion adapted to form a seal with the patient's nares, a mouth portion including a mouth sealing portion adapted to form a seal with the patient's mouth, the mouth portion including a cushion and a cushion fascia portion, the cushion fascia portion adapted to connect to the cushion, the cushion having a connecting portion with an aperture, the aperture adapted to receive a ring to connect the nares portion to the mouth portion.

Another aspect of the present technology relates to a mask system for delivery of respiratory therapy to a patient, the mask system including a mouth portion including a mouth sealing portion adapted to form a seal with the patient's mouth, the mouth sealing portion not comprising a pocket.

Other aspects, features, and advantages of the present technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various examples of this technology. In such drawings:

FIG. 1-2 depicts a front view of a mask system on a model patient's head in a nares and mouth mode according to an embodiment of the present technology;

FIG. 1-3 depicts a front view of a mask system on a model patient's head in a nares and mouth mode according to an embodiment of the present technology;

FIG. 1-4 depicts a front view of a mask system on a model patient's head in a mouth only mode according to an embodiment of the present technology;

FIG. 1-5 depicts a front exploded view of a mask system illustrating how the nares portion may connect to the mouth portion according to an embodiment of the present technology;

FIG. 2 depicts a front view of the mask system of FIGS. 1-1 to 1-5 without the elbow connector according to an embodiment of the present technology;

FIG. 3 depicts a rear view of the mask system of FIGS. 1-1 to 1-5 according to an embodiment of the present technology;

FIG. 4 depicts a rear isometric view of the mask system of FIGS. 1-1 to 1-5 according to an embodiment of the present technology;

FIG. 5-1 depicts a front isometric view of a mask system on a model patient's head according to another embodiment of the present technology;

FIG. 5-2 depicts a front isometric view of the mask system of FIG. 5-1 on a model patient's head in a nares only mode;

FIG. 29-1 depicts a schematic cross-sectional view of a modular mask system on a model patient's head according to an embodiment of the present technology;

FIG. 29-2 depicts a schematic top view of a mouth sealing portion of the mask system of FIG. 29-1 according to an embodiment of the present technology;

FIG. 29-3 depicts a schematic cross-sectional view of a modular mask system on a model patient's head according to an embodiment of the present technology;

FIG. 30-1 depicts a schematic cross-sectional view of a modular mask on a model patient's head according to an embodiment of the present technology;

FIG. 30-2 depicts a schematic cross-sectional view of a modular mask system on a model patient's head according to an embodiment of the present technology;

FIGS. 32(*a*)-(*k*) are schematic views the flow of pressurized gas through the mask system various configurations according to embodiments of the present technology;

FIG. 80 depicts a cross sectional view along lines 80-80 from FIG. 77;

FIG. 81 depicts a cross sectional view along lines 81-81 from FIG. 77;

FIG. 82 depicts a cross sectional view along lines 82-82 from FIG. 77;

FIG. 83 depicts a cross sectional view along lines 83-83 from FIG. 77;

FIG. 86 depicts a rear view of the cushion portion of the mask system of FIG. 68;

FIG. 87 depicts a right side view of the cushion portion of the mask system of FIG. 68;

FIG. 88 depicts a left side view of the cushion portion of the mask system of FIG. 68;

FIGS. 90, 91A, and 91B illustrate a headgear system that is convertible between two point and four point support in accordance with a sample of the current technology;

FIGS. 92A to 92E and 93A to 93I illustrate a mouth cushion according to a variant of the current technology;

FIGS. 94-102 illustrate a cushion-to-fascia connection according to an example of the present technology;

FIG. 103 illustrates a lip seal according to an example of the present technology;

FIG. 117 is a right side view of the mouth cushion of the mask system of FIG. 104;

FIG. 118 is a front view of the mouth cushion of the mask system of FIG. 104;

FIG. 119 is a cross section view of the mouth cushion along the line 119-119 in FIG. 118;

FIG. 120 is a cross section view of the mouth cushion along the line 120-120 in FIG. 118;

FIG. 121 is a cross section view of the mouth cushion along the line 121-121 in FIG. 118;

FIG. 122 is a cross section view of the mouth cushion along the line 122-122 in FIG. 118;

FIG. 123 is a cross section view of the mouth cushion along the line 123-123 in FIG. 118;

FIG. 124 is a cross section view of the mouth cushion along the line 124-124 in FIG. 118;

FIG. 125 is a rear isometric view of the cushion clip of the mask system of FIG. 104;

FIG. 126 is a front isometric view of the cushion clip of FIG. 125;

FIG. 127 is a top view of the cushion clip of FIG. 125;

FIG. 128 is a bottom view of the cushion clip of FIG. 125;

Figure 104:
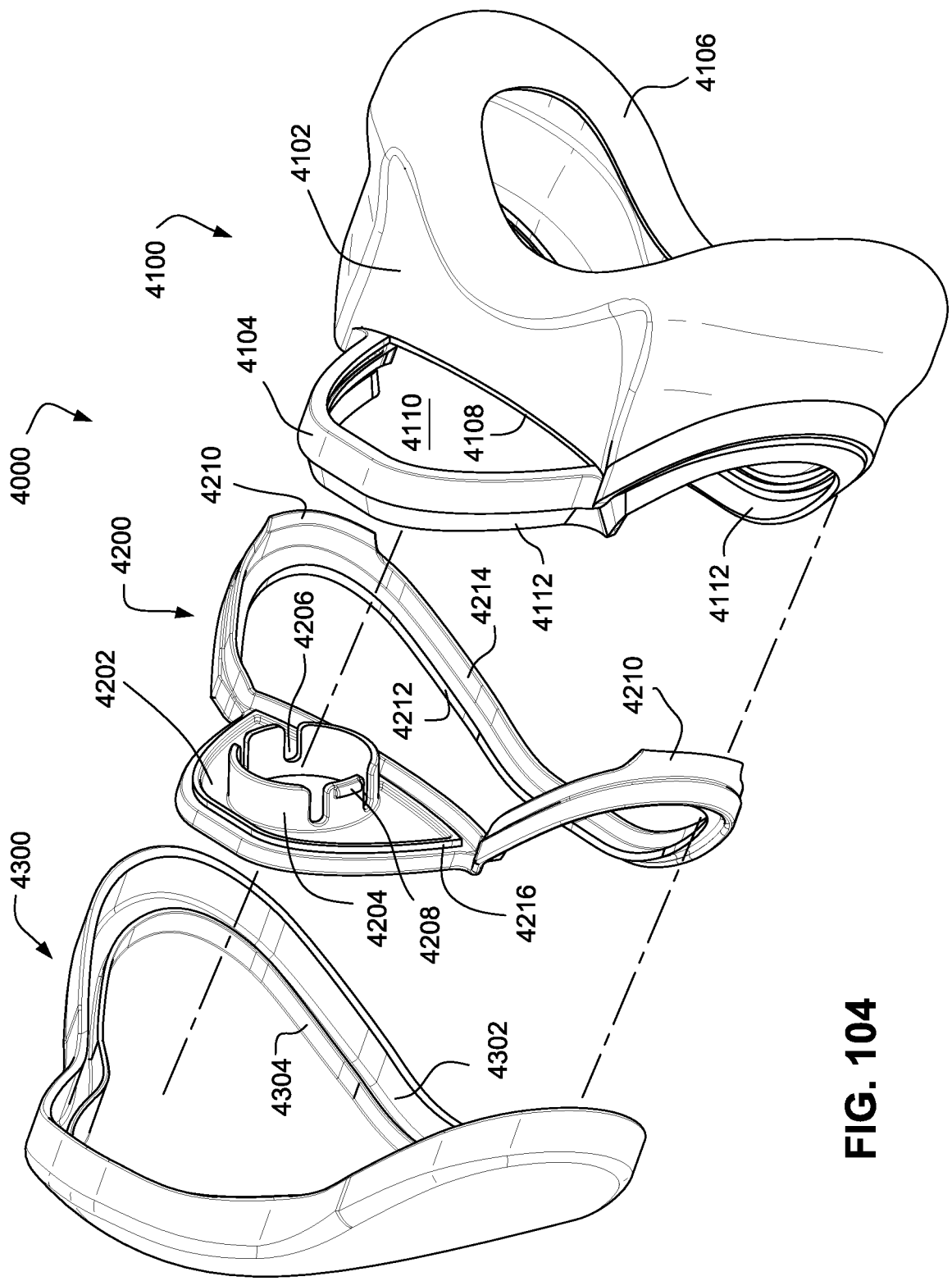
FIG. 104 is an exploded assembly view of a mask system according to an embodiment of the present technology.
Figure 105:
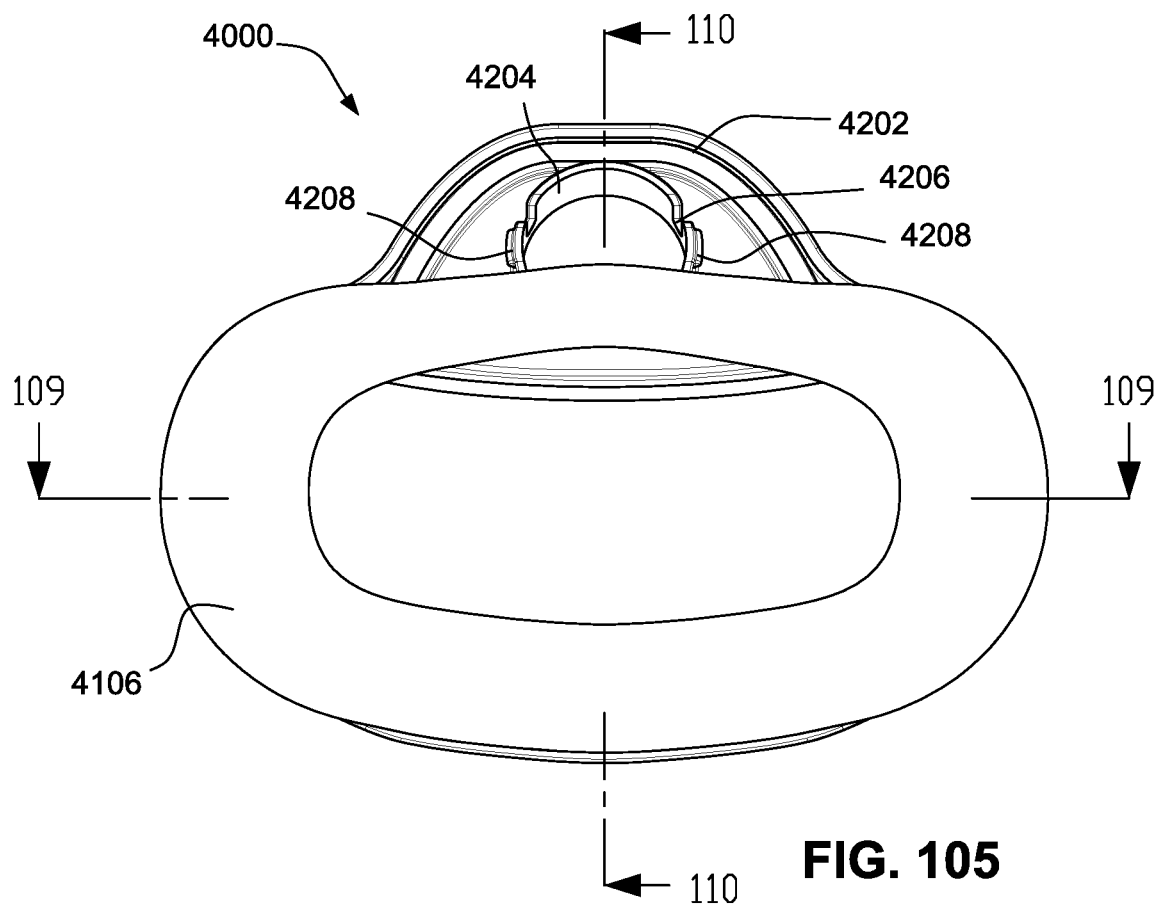
FIG. 105 is a rear view of the mask system of FIG. 104 in the assembled state.
Figure 106:
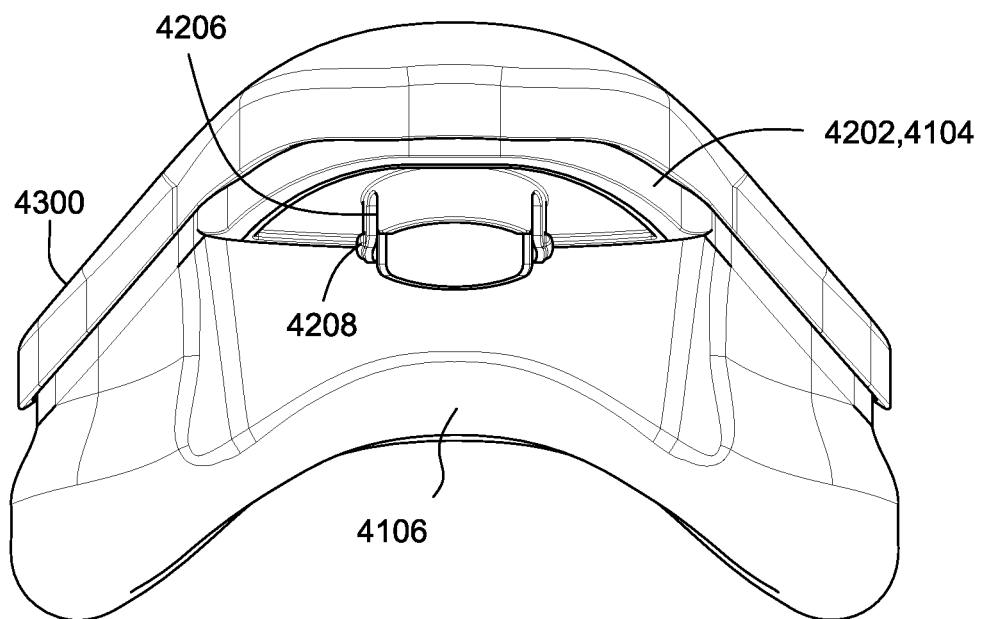
FIG. 106 is a top view of the mask system of FIG. 104 in the assembled state.
Figure 107:
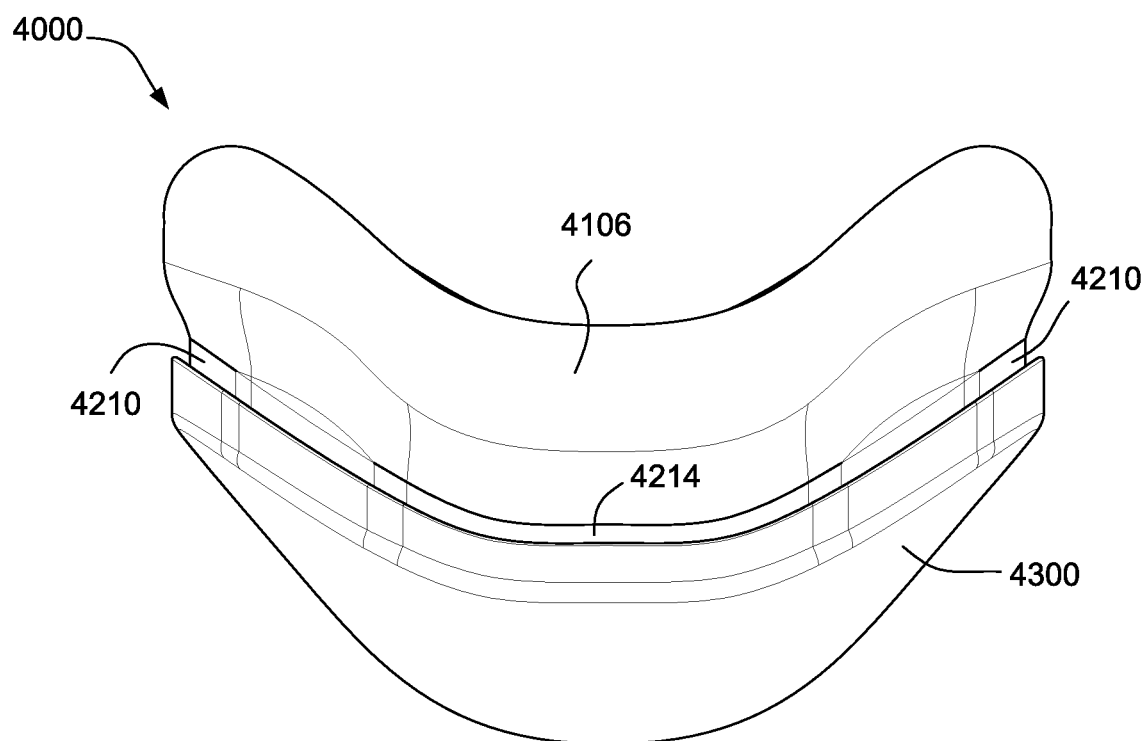
FIG. 107 is a bottom view of the mask system of FIG. 104 in the assembled state.
Figure 108:
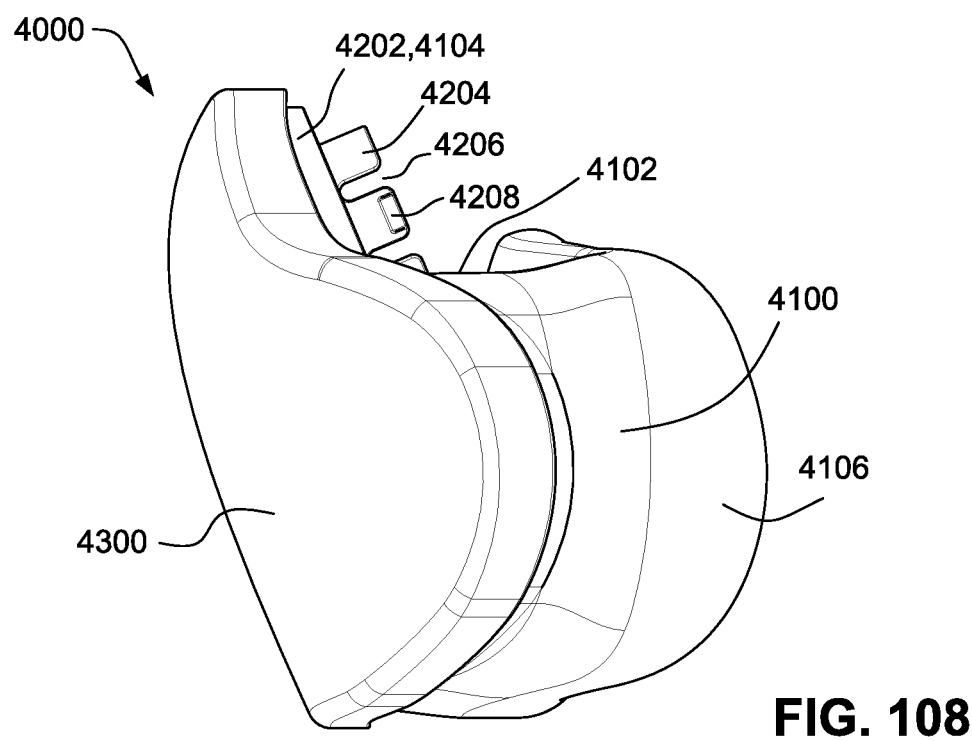
FIG. 108 is a left side view of the mask system of FIG. 104 in the assembled state.
Figure 109:
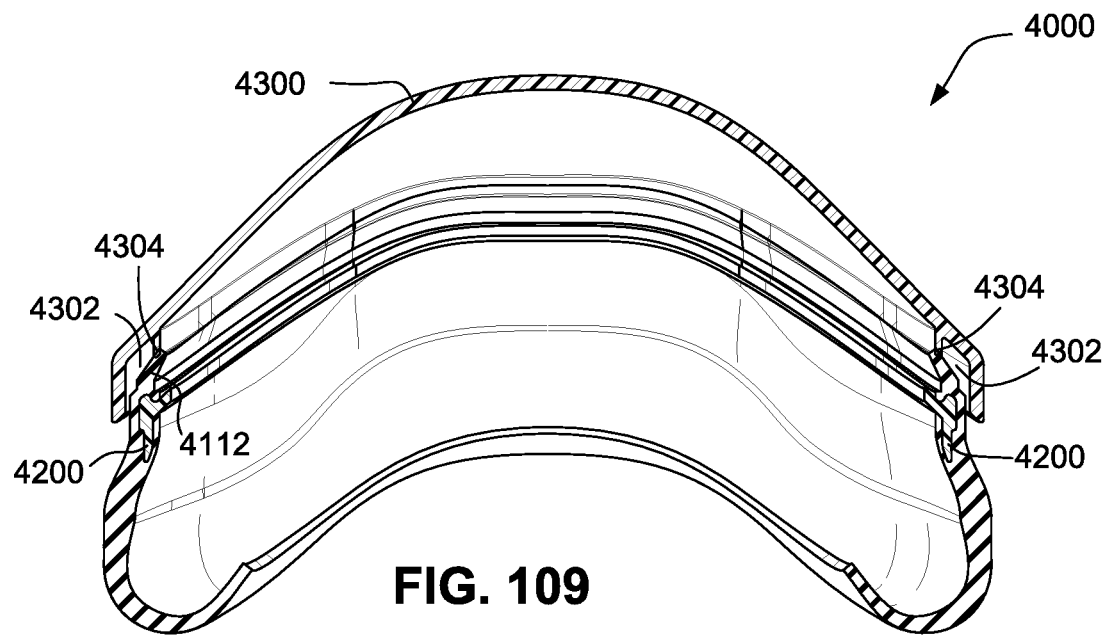
FIG. 109 is a cross section view along the line 109-109 in FIG. 105.
Figure 110:
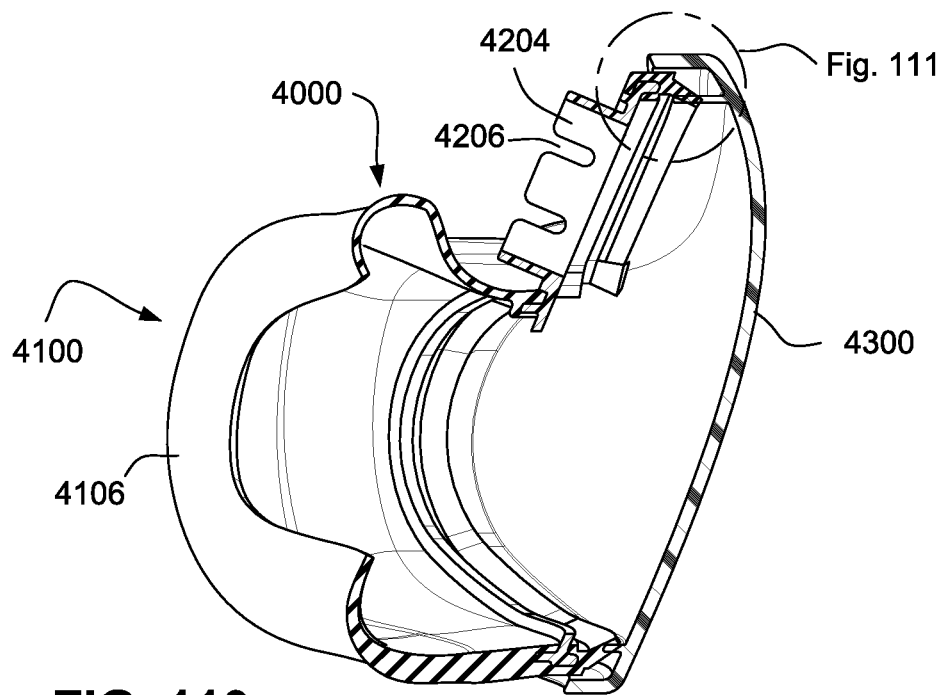
FIG. 110 is a cross section view along the line 110-110 in FIG. 105.
Figure 111:
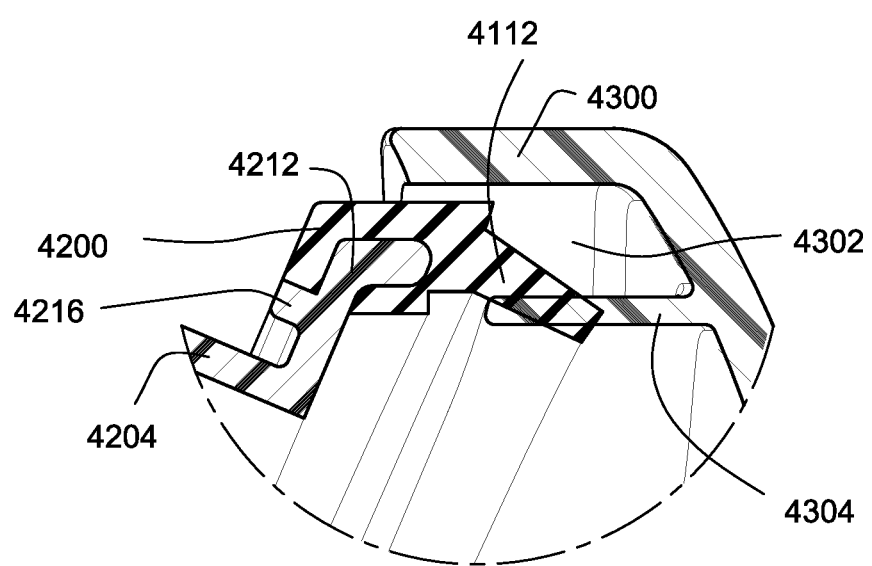
FIG. 111 is a detailed view of a portion of FIG. 110.
Figure 112:
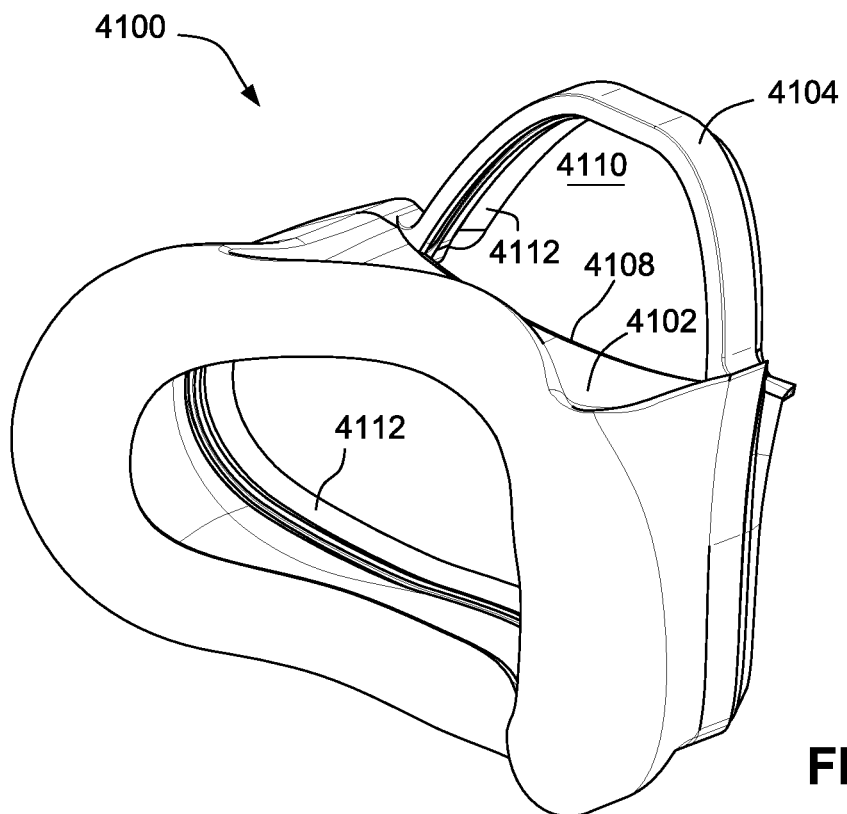
FIG. 112 is a rear isometric view of the mouth cushion of the mask system of FIG. 104.
Figure 113:
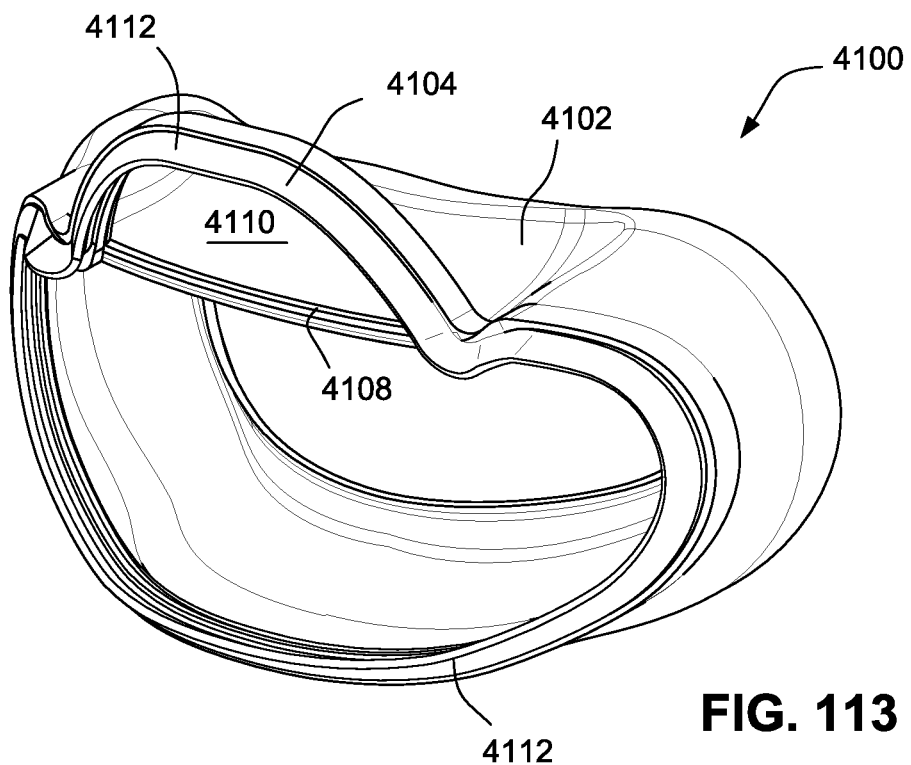
FIG. 113 is a front isometric view of the mouth cushion of the mask system of FIG. 104.
Figure 114:
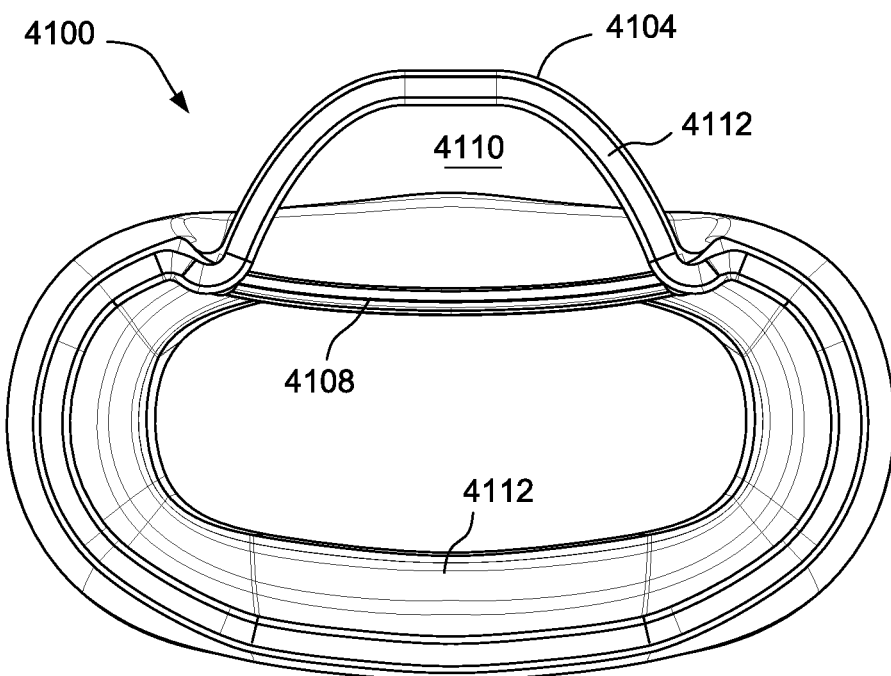
FIG. 114 is front view of the mouth cushion of the mask system of FIG. 104.
Figure 115:
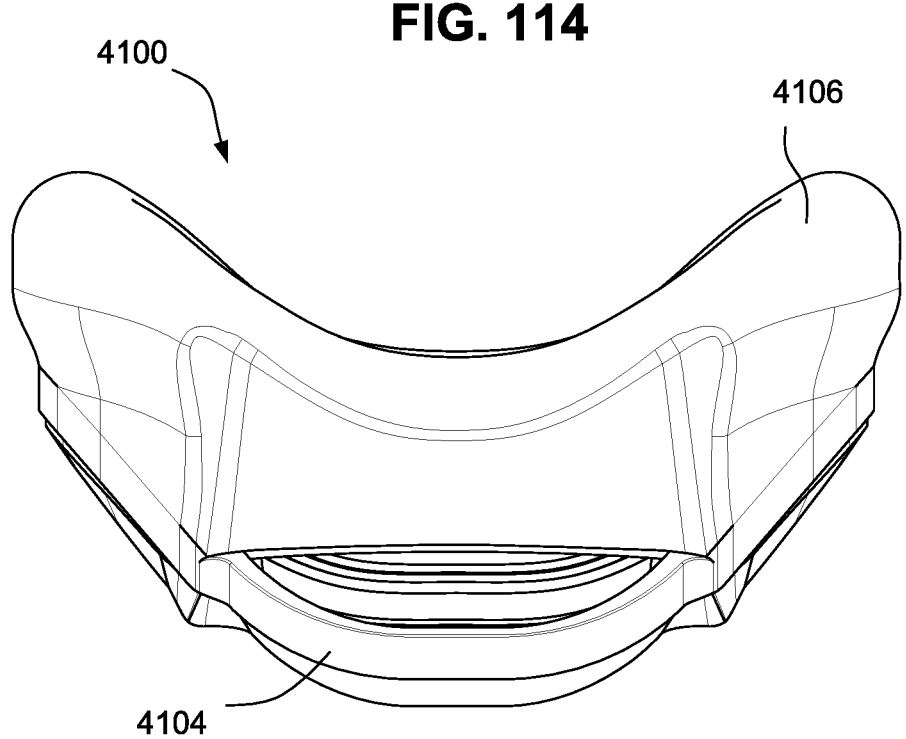
FIG. 115 is a top view of the mouth cushion of the mask system of FIG. 104.
Figure 116:
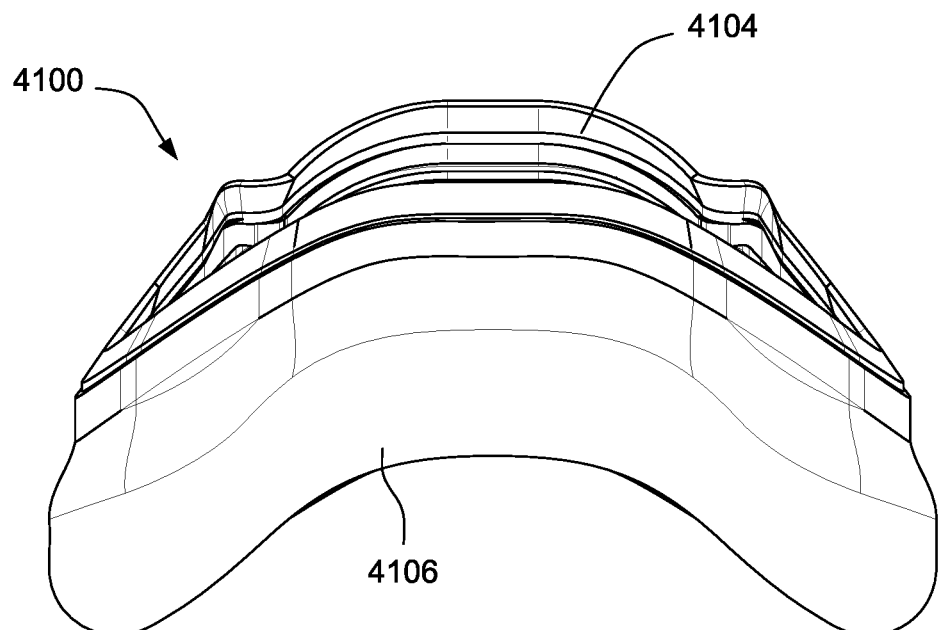
FIG. 116 is a bottom view of the mouth cushion of the mask system of FIG. 104.
Figure 117:
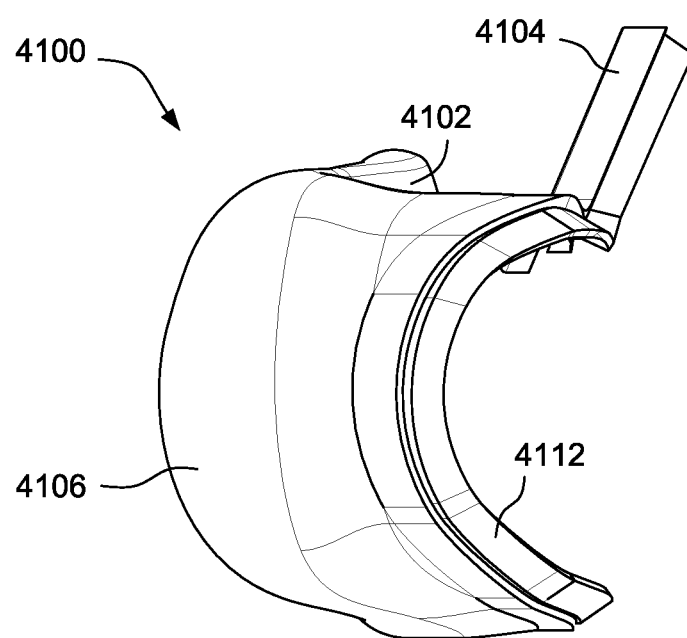
Figure 118:
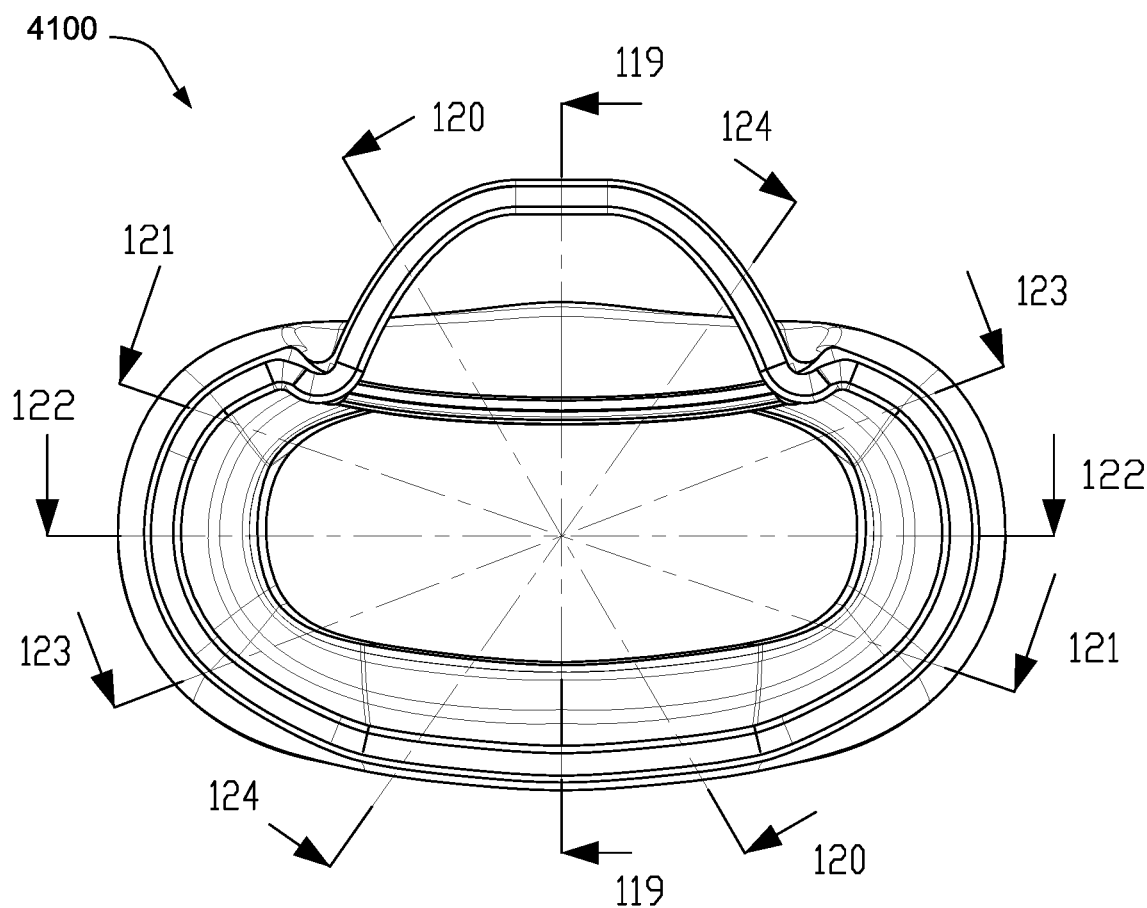
Figure 119:
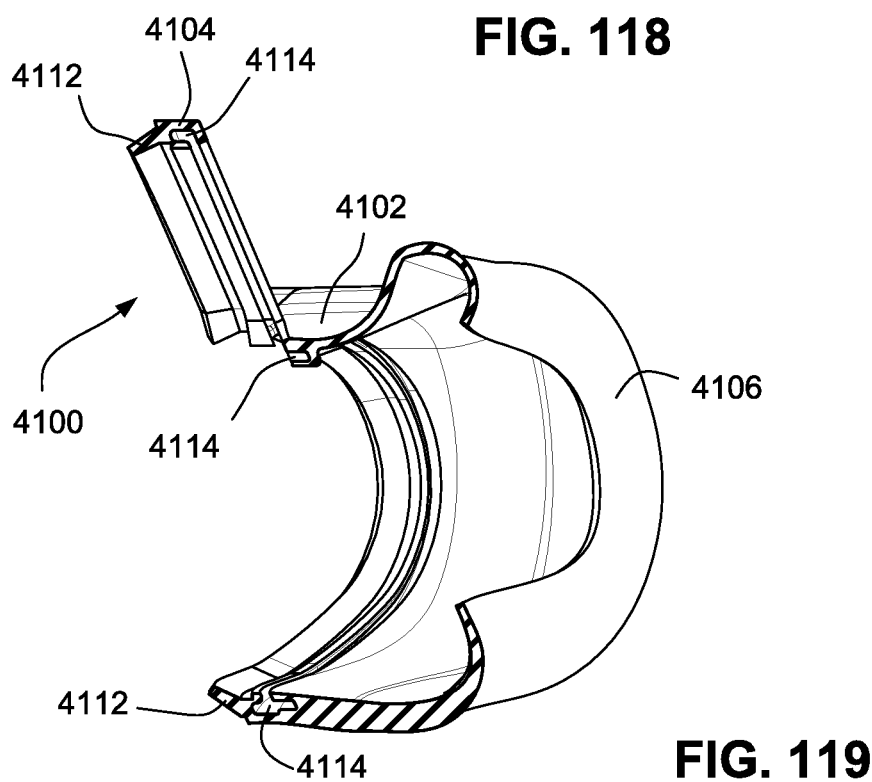
Figure 120:
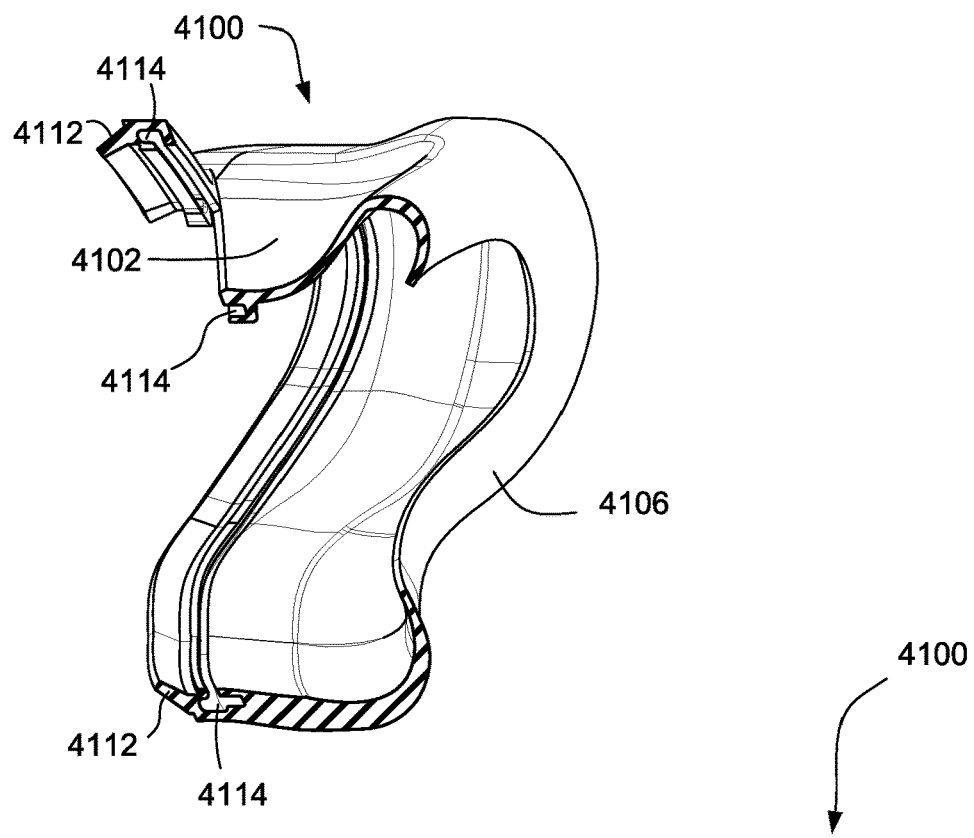
Figure 121:
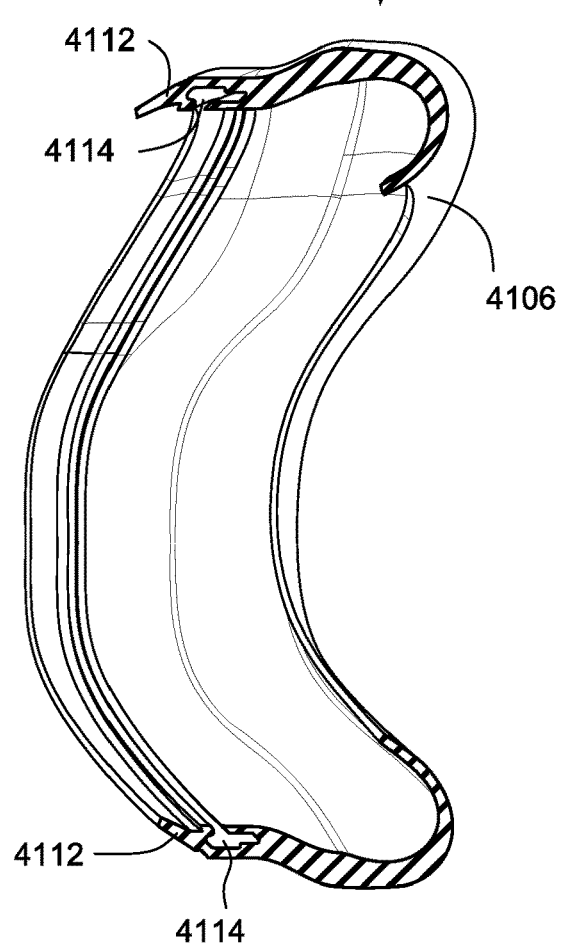
Figure 122:
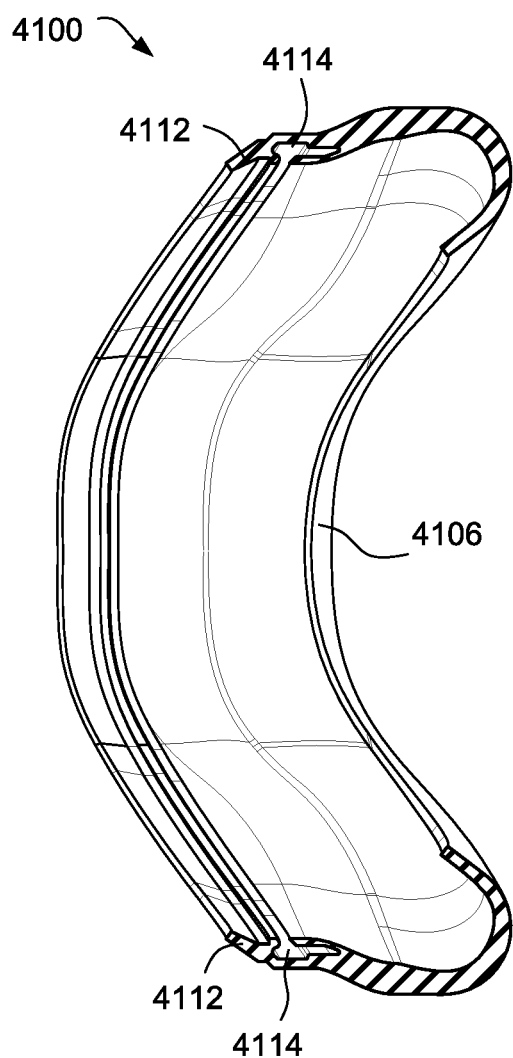
Figure 123:
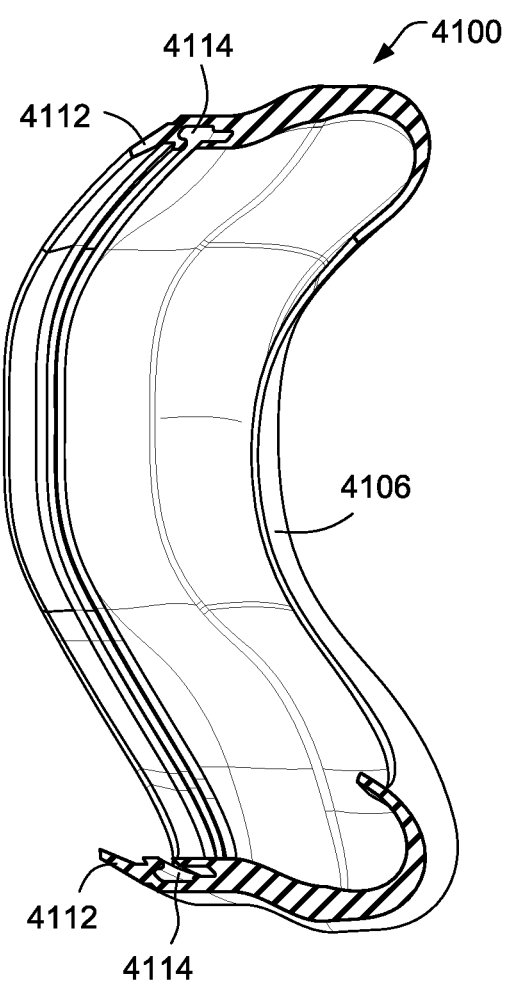
Figure 124:
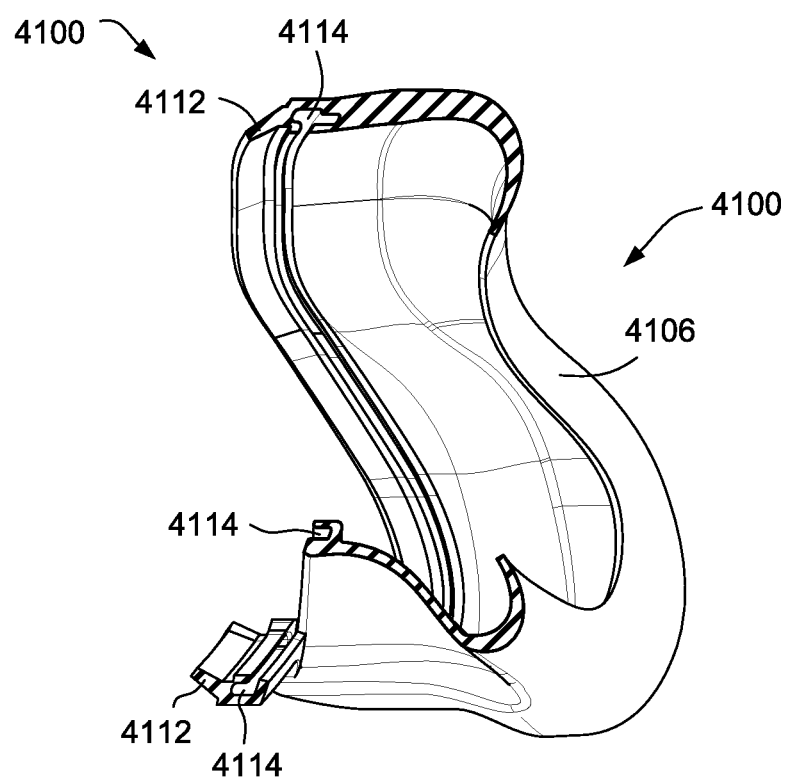
Figure 125:
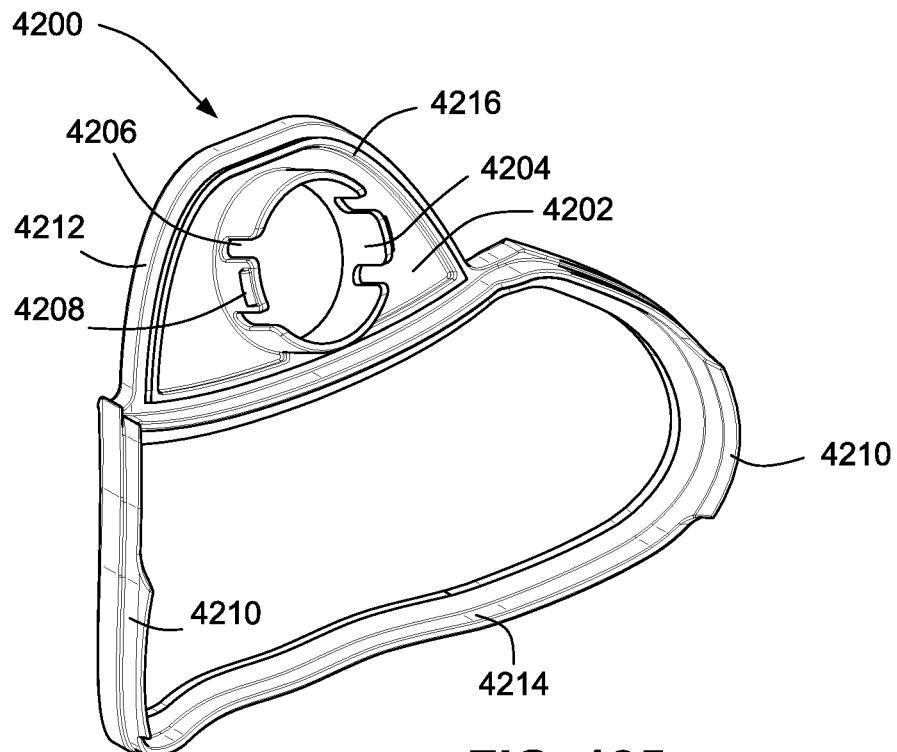
Figure 126:
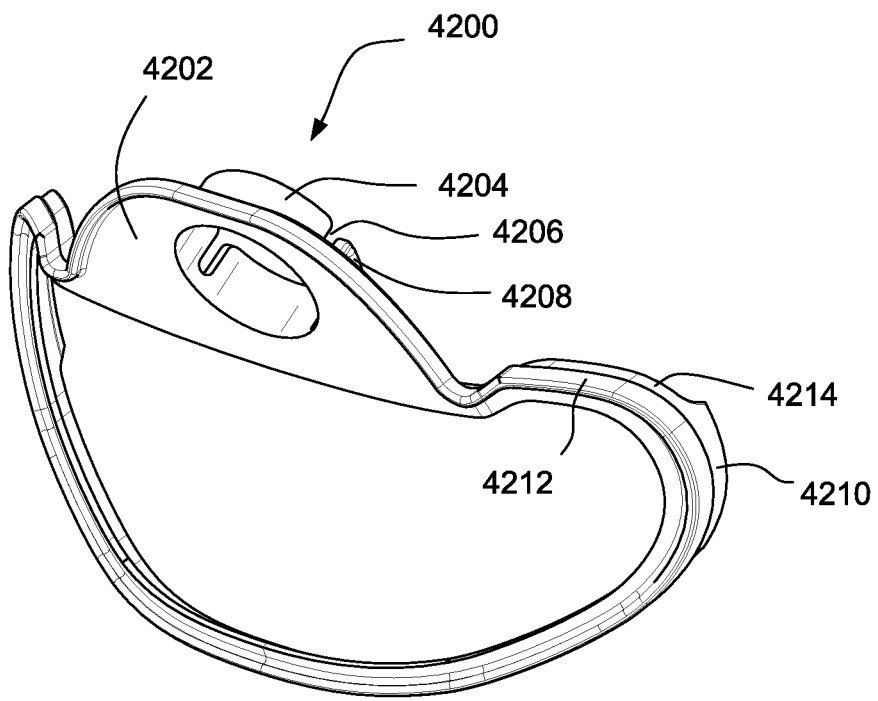
Figure 127:
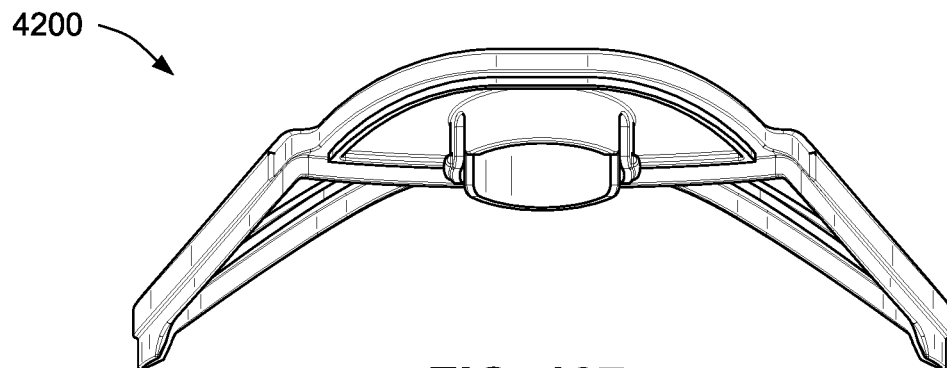
Figure 128:
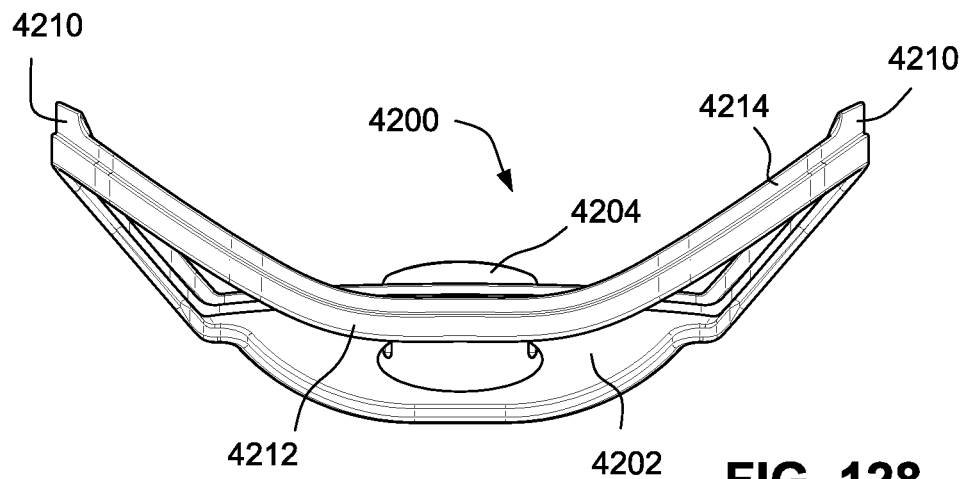
Figure 129:
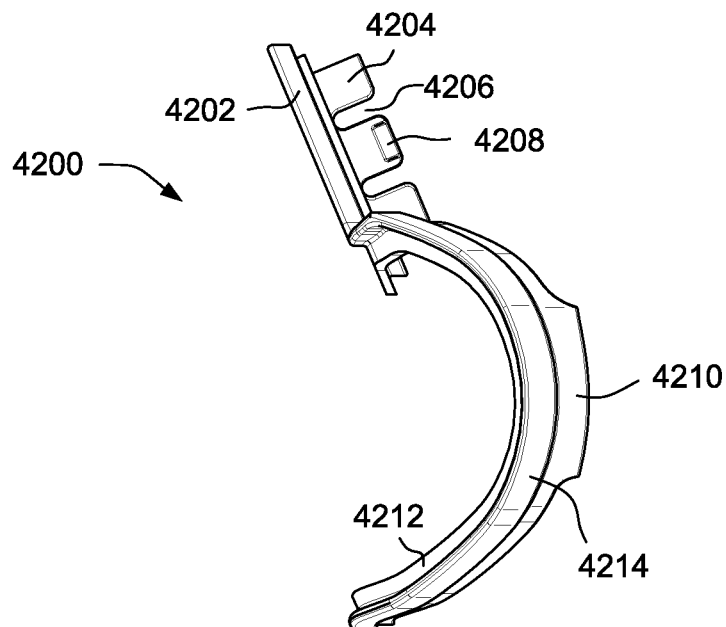
Figure 130:
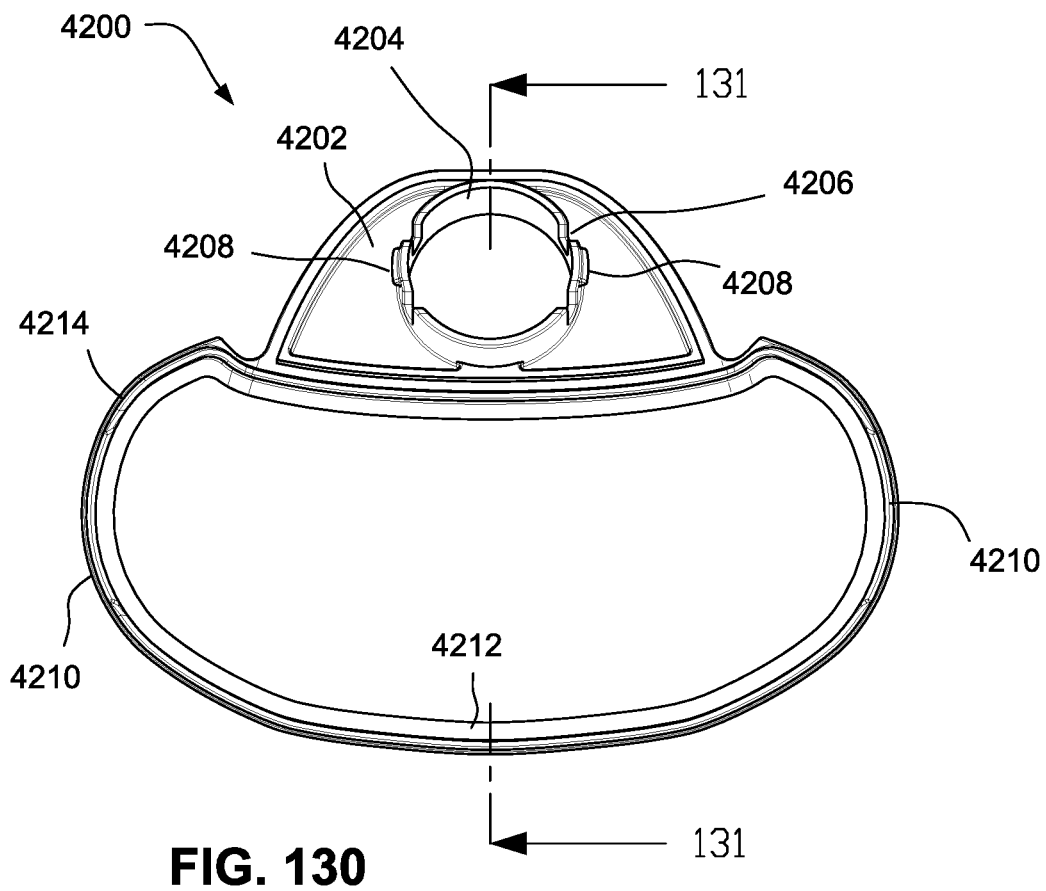
Figure 131:
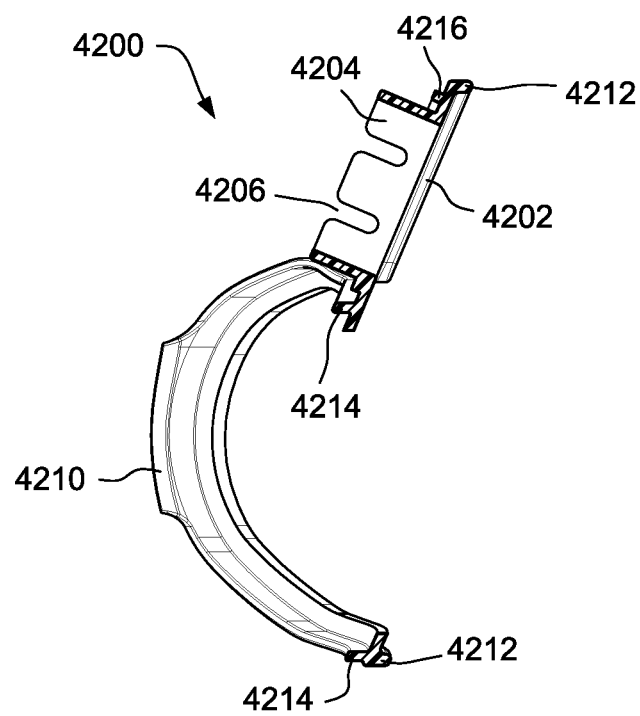
Figure 132:
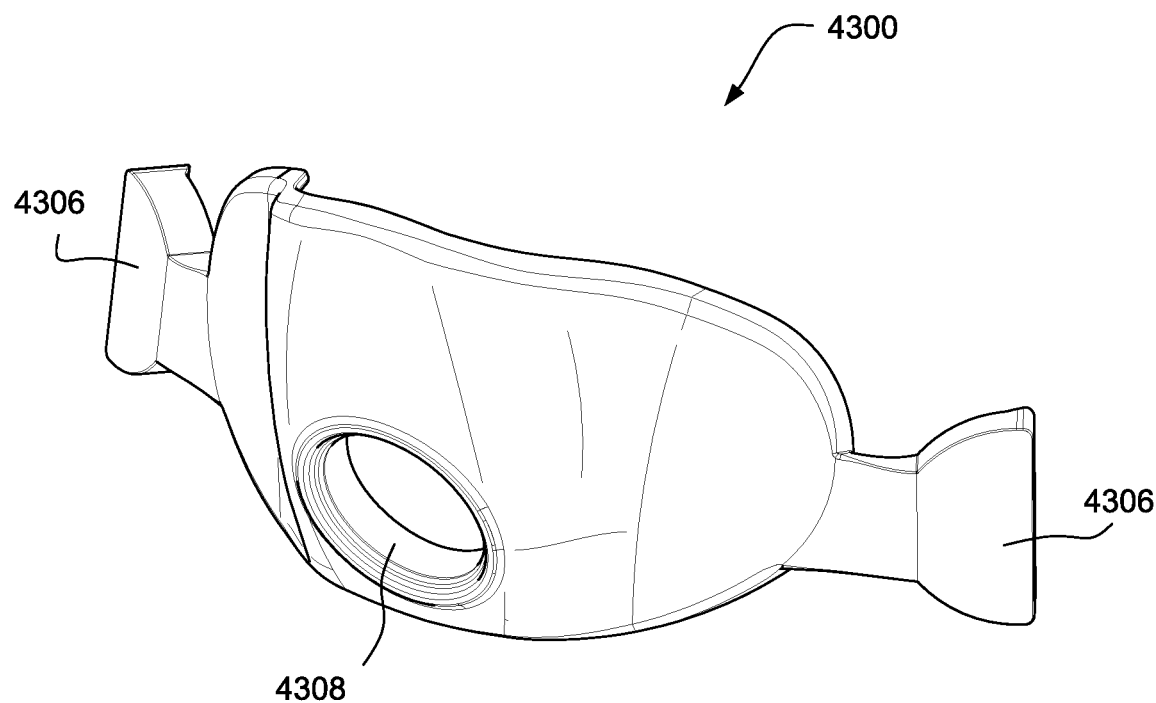
Figure 133:
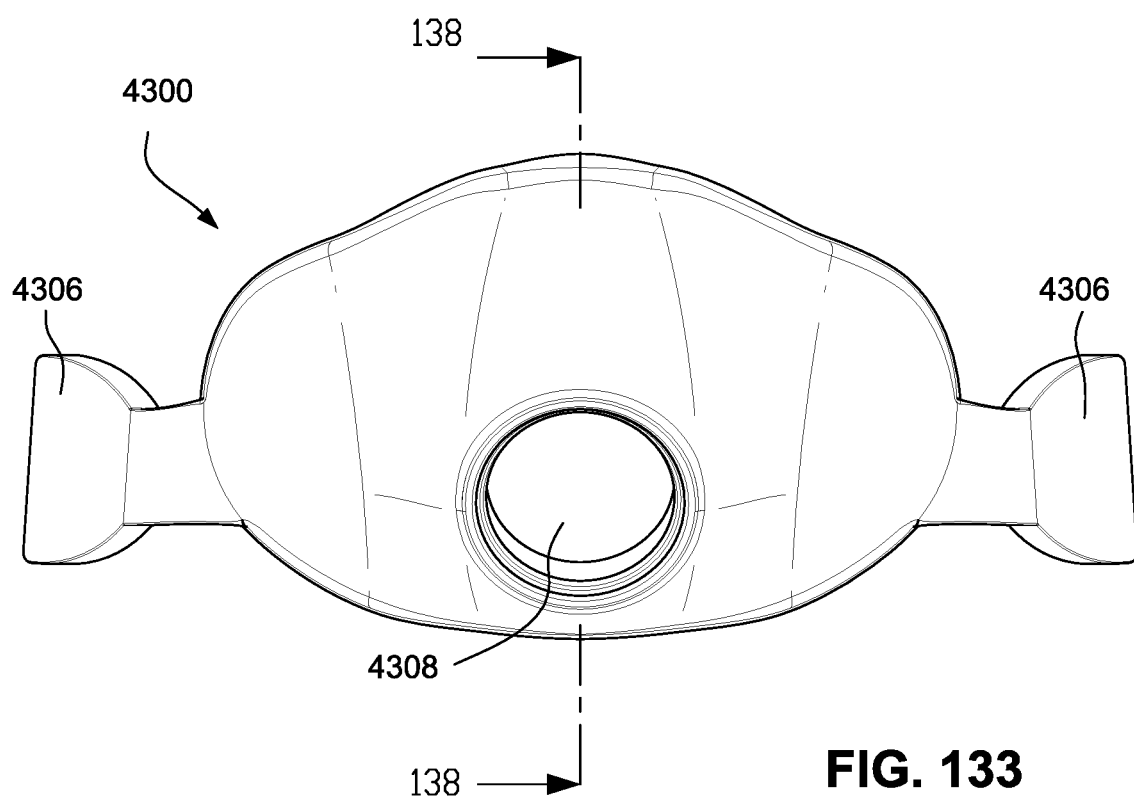
Figure 134:
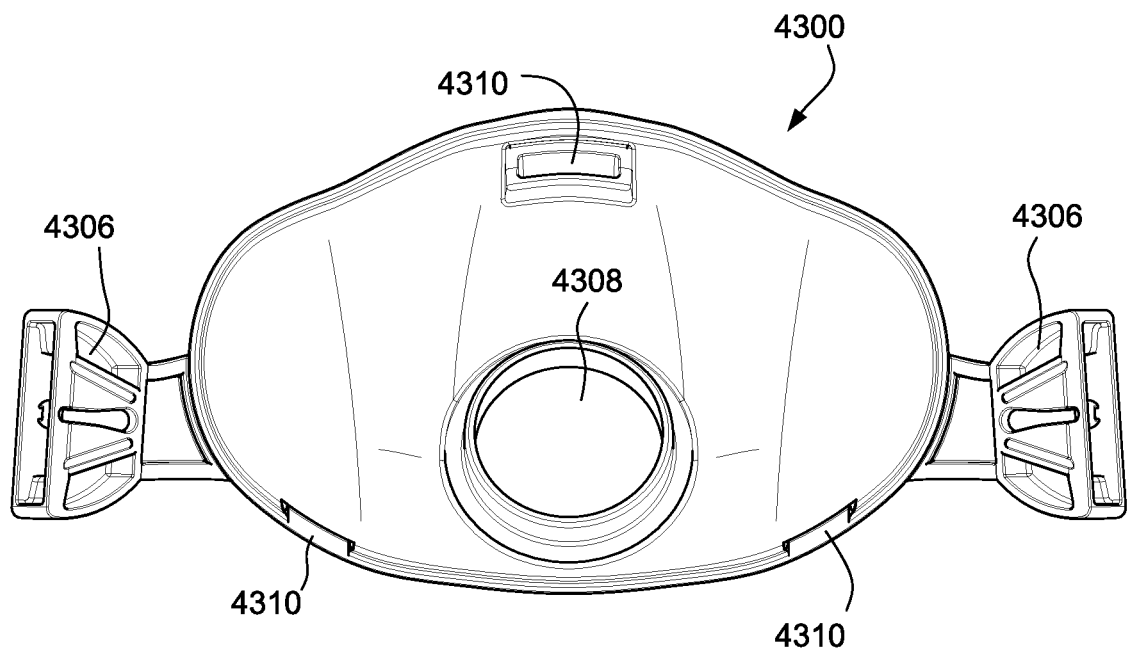
Figure 135:
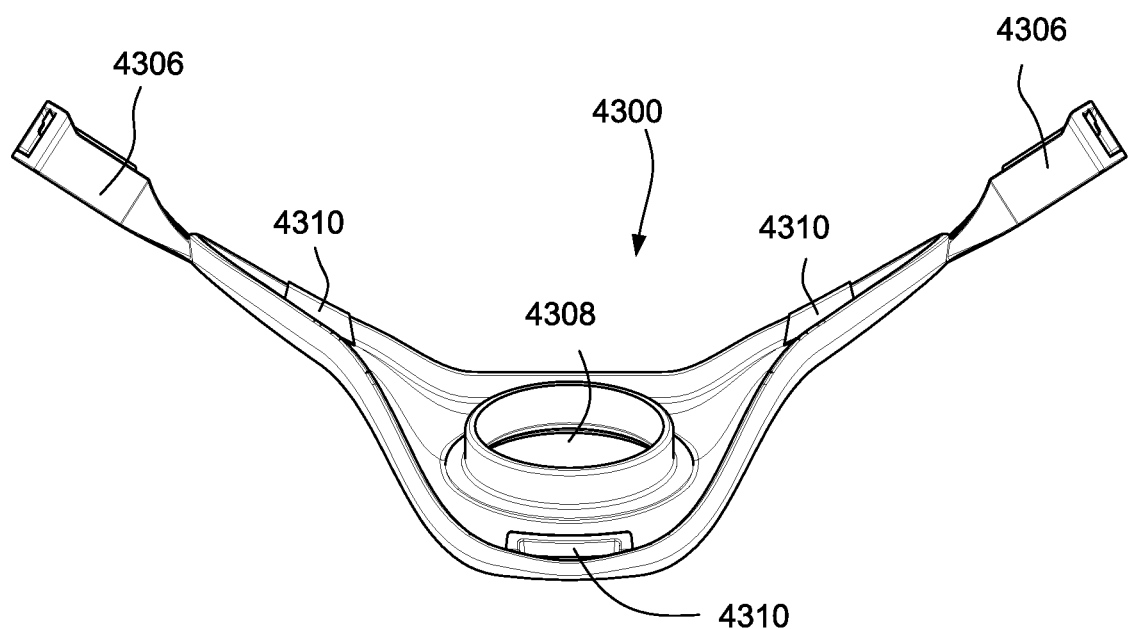
Figure 136:
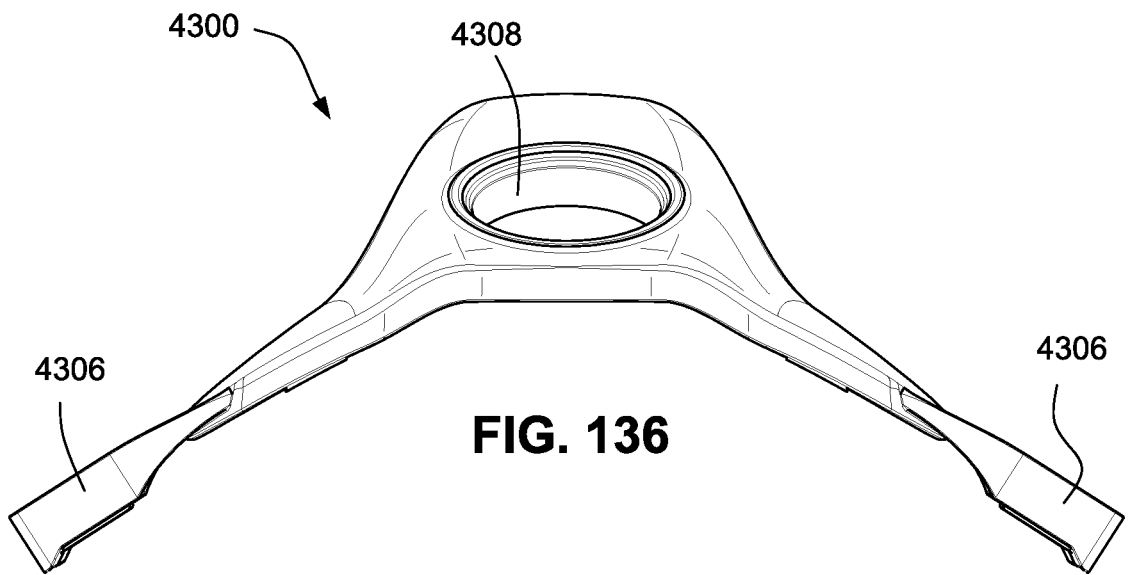
Figure 137:
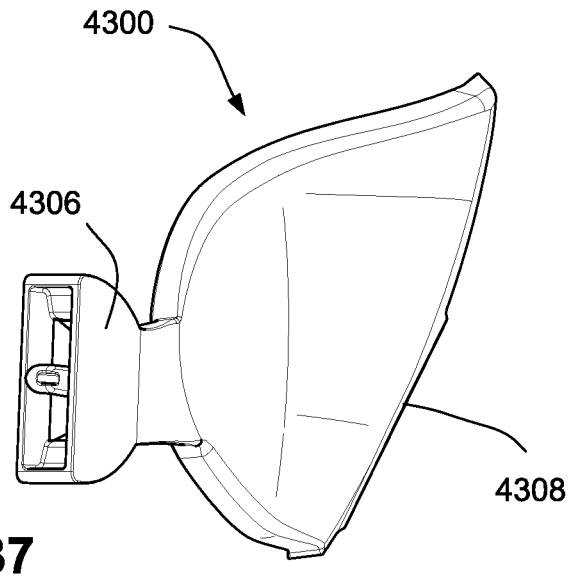
Figure 138:
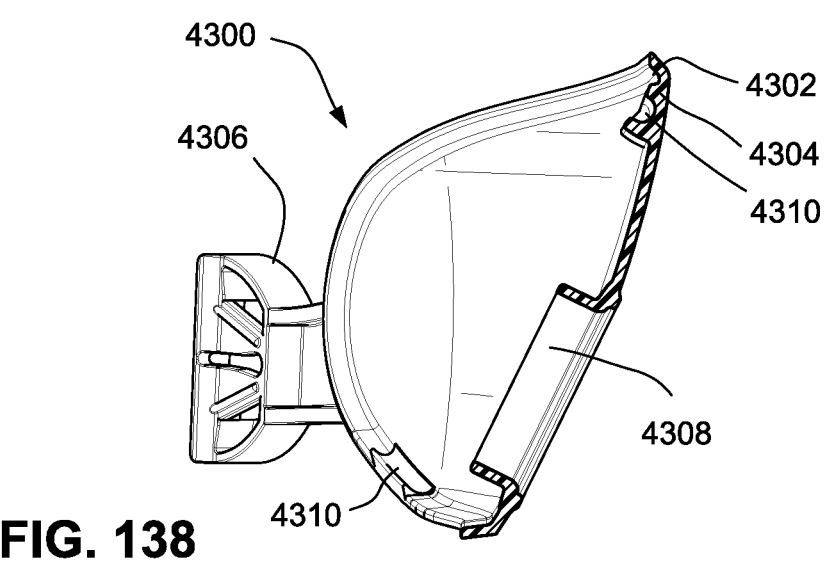
Figure 139:
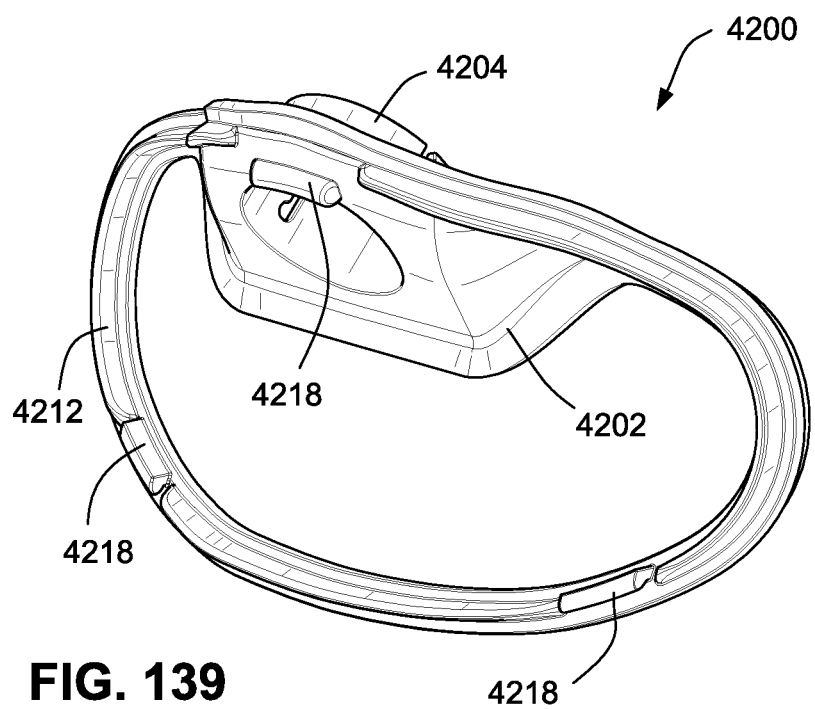
Figure 140:
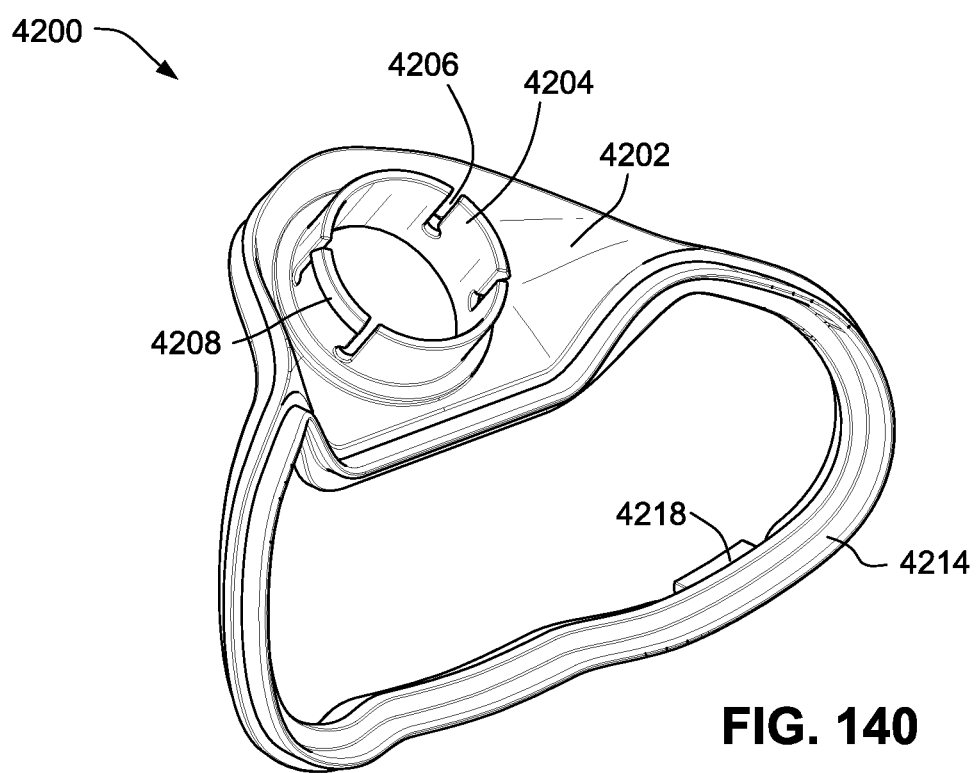
Figure 141:
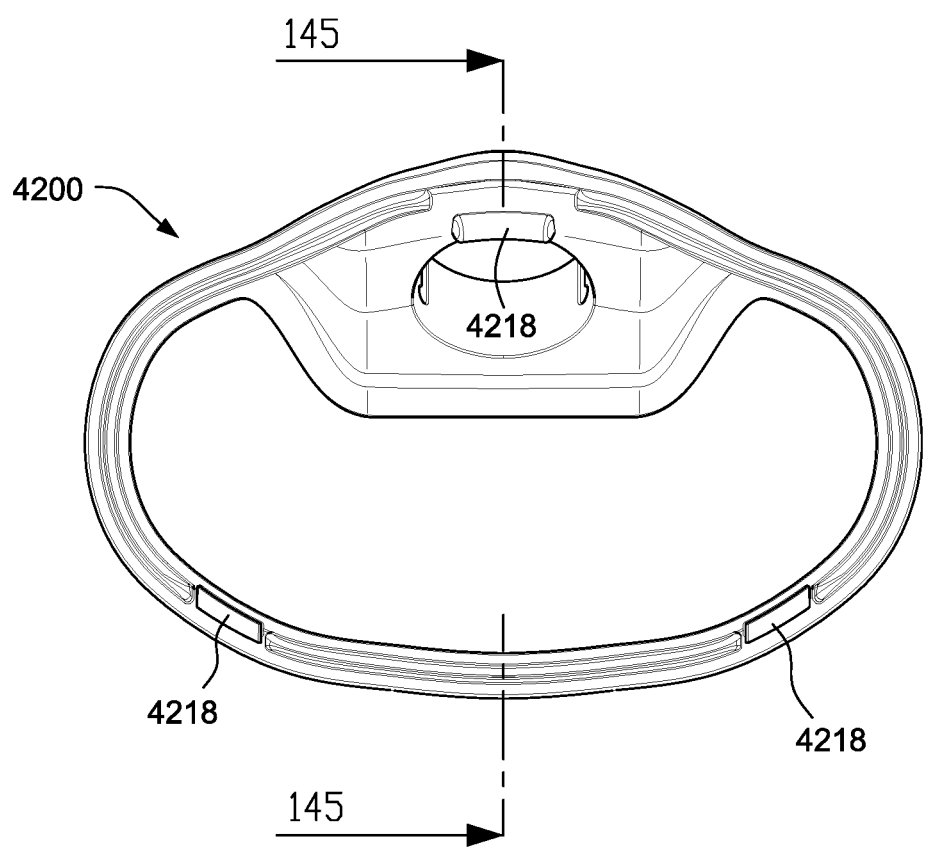
Figure 142:
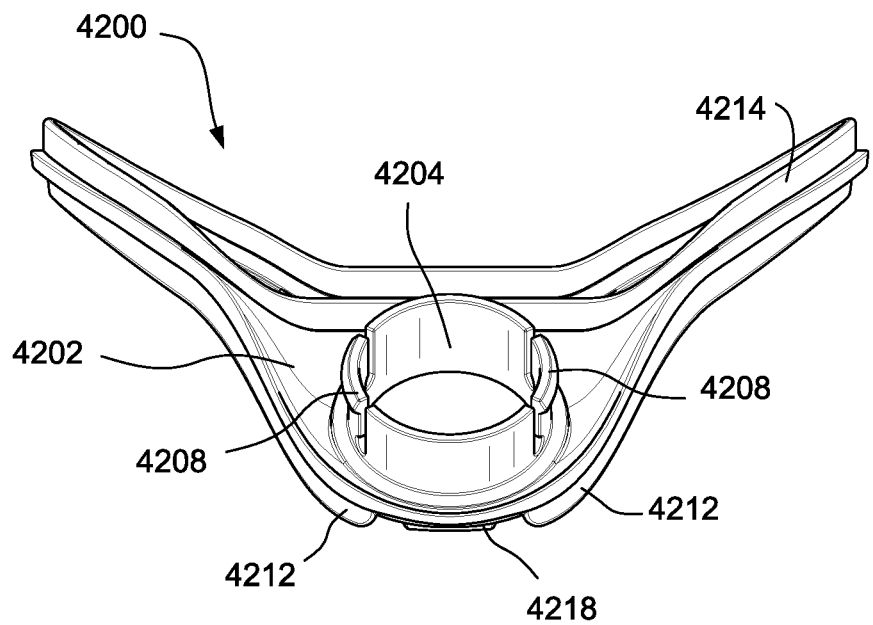
Figure 143:
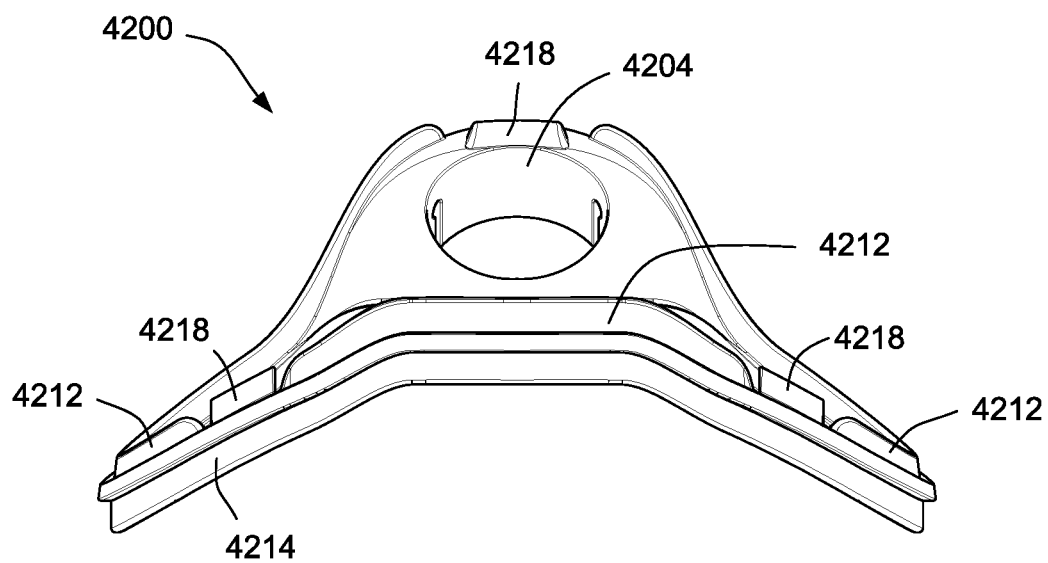
Figure 144:
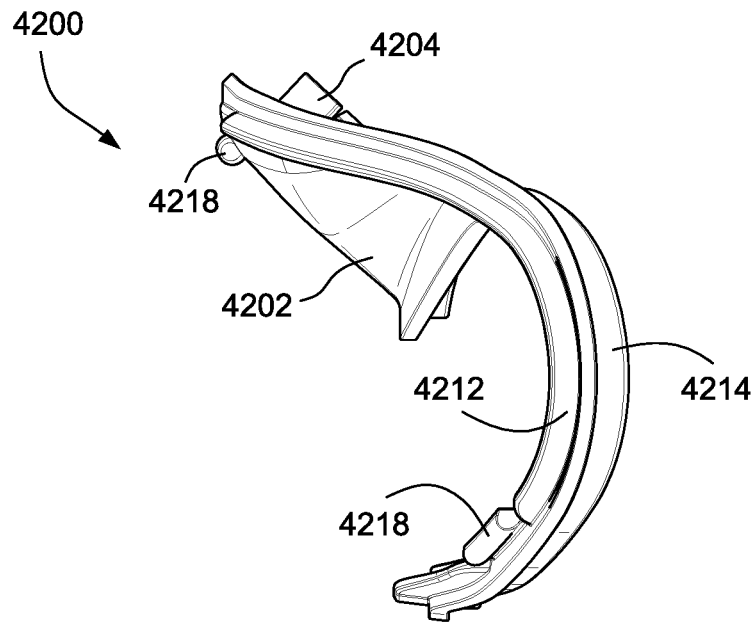

FIG. 129 is a left side view of the cushion clip of FIG. 125;

FIG. 130 is a rear view of the cushion clip of FIG. 125;

FIG. 131 is a cross section view along lines 131-131 in FIG. 130;

FIG. 132 is a front isometric view of a fascia of the mask system of FIG. 104;

FIG. 133 is a front view of the fascia of FIG. 132;

FIG. 134 is a rear view of the fascia of FIG. 132;

FIG. 135 is a top view of the fascia of FIG. 132;

FIG. 136 is a bottom view of the fascia of FIG. 132;

FIG. 137 is a right side view of the fascia of FIG. 132;

FIG. 138 is a cross section view along the line 138-138 in FIG. 133;

FIG. 139 is a front isometric view of a cushion clip according to an embodiment of the present technology;

FIG. 140 is a rear isometric view of the cushion clip of FIG. 139;

FIG. 141 is a front view of the cushion clip of FIG. 139;

FIG. 142 is a top view of the cushion clip of FIG. 139;

FIG. 143 is a bottom view of the cushion clip of FIG. 139;

FIG. 144 is a left side view of the cushion clip of FIG. 139; and

Figure 145:
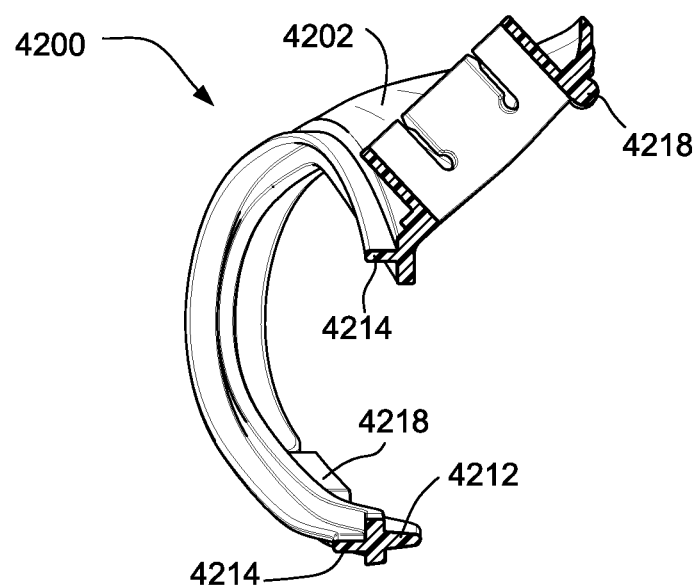

FIG. 145 is a cross section view along lines 145-145 in FIG. 141.

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is acknowledged that the CPAP flow generator systems or blowers described herein may be designed to pump fluids other than air.

1. Mask System

The mask system of the present technology delivers pressurized breathable gas to the patient and includes a nares portion, a mouth portion, a positioning and stabilizing structure, and an air delivery system. A sealing portion may be included with the nares portion and/or the mouth portion to form a seal or substantially seal with the nose and/or mouth of the patient. One or more vents may also be included to vent gas exhaled by the patient on the nares portion and/or the mouth portion. However, the mask may be non-vented and be used in a hospital/ventilation scenario. The mask system my also be provided with an anti-asphyxia valve (AAV).

The sealing portion is arranged to form a seal or substantially seal with the nose and/or mouth of the patient to deliver pressurized gas to the patient. Preferably, the sealing portion has a nares sealing portion and a mouth sealing portion. The nares sealing portion and the mouth sealing portion may be integrally formed, or they may be in the form of separate elements. The nares sealing portion and mouth sealing portion may be connected or otherwise positioned so as to independently or discretely seal with the nose and mouth of the patient, respectively.

A positioning and stabilizing structure may be connected to the sealing portion and is adapted to engage the sealing portion with the patient. The positioning and stabilizing structure may have an upper portion and a lower portion that is constructed and arranged to avoid the patient's eyes and ears in use. The upper and lower portions may be integrated with one another, in separate pieces that do not connect with one another, or in separate pieces that are coupled to one another. The positioning and stabilizing structure may have a rear portion adapted to engage with the back of a patient's head in use. The rear portion may interconnect the upper and lower portions.

The air delivery system may connect the sealing portion to a flow generator. The air delivery system may include an elbow and/or a tube.

The mask system provides patients with options for therapy (nares only, mouth only or nares and mouth therapy) without the system becoming too expensive and also improving intuitive use of the mask system. This allows the patient to use the mask system without too much or any instruction.

The mask system may be a modular mask system having the nares portion and the mouth portion, where the nares portion is adapted to be utilized without the mouth portion to provide respiratory therapy to a patient's nares, or the nares portion may be adapted to be utilized with the mouth portion to provide respiratory therapy to the patient's nares and mouth, or to provide respiratory therapy to the patient's nares and to utilize the mouth portion as a mouth seal.

The mask system may be a modular mask system having the nares portion and the mouth portion, where the mouth portion is adapted to be utilized without the nares portion to provide respiratory therapy to a patient's mouth, or the mouth portion is adapted to be utilized with the nares portion to provide respiratory therapy to the patient's nares and mouth, or to provide respiratory therapy to the patient's mouth and to utilize the nares portion as a nares seal.

The mask system may be an integrated mask system having a nares portion and a mouth portion, where the nares portion and the mouth portion are integrated and formed in a single piece. Pressurized gas may be provided to the nares and mouth portions for delivery to the nose and mouth, or pressurized gas may be delivered only to the nares or mouth portion, with the other portion being blocked off from the pressurized gas.

Figure 1:
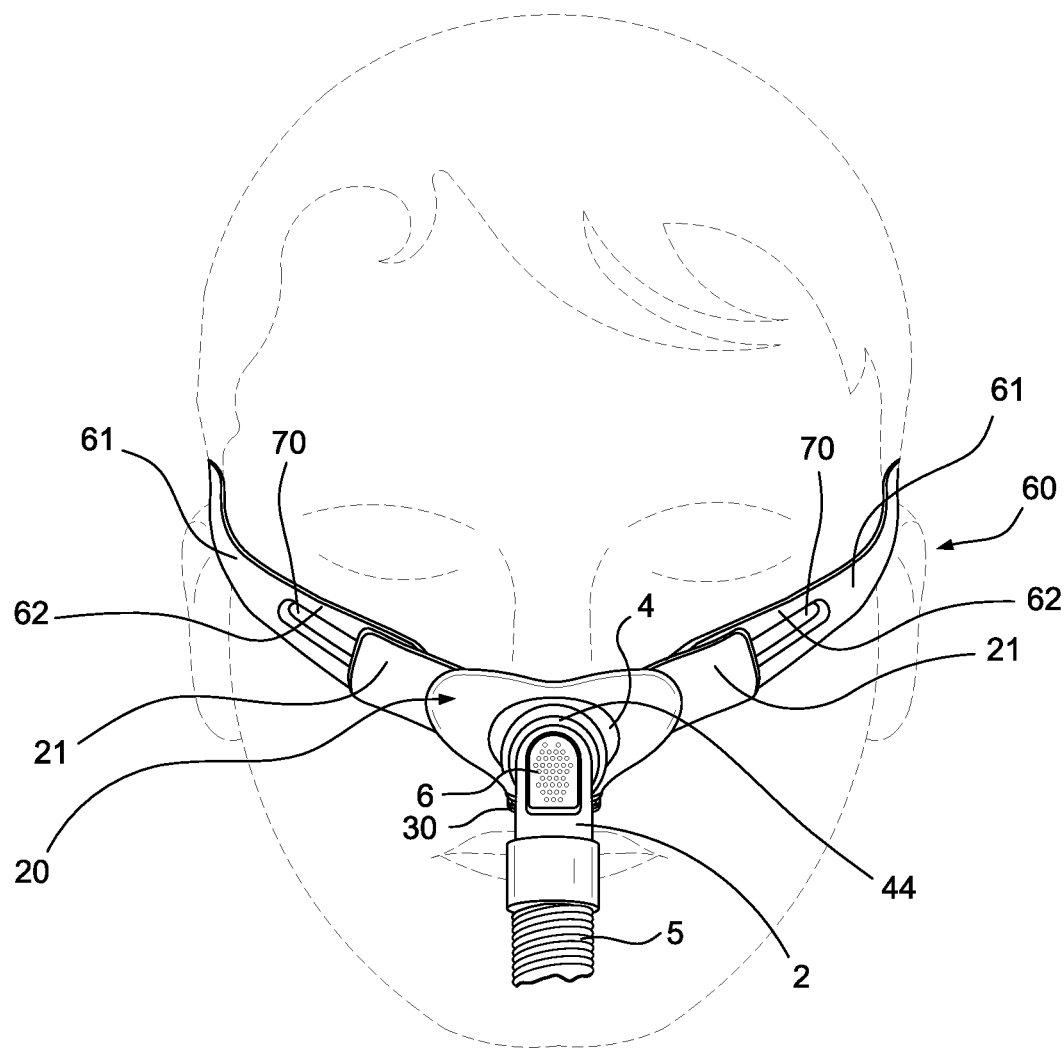
FIG. 1-1 depicts a front view of a mask system in a nares only mode on a model patient's head according to an embodiment of the present technology.
Figures 1, 2:
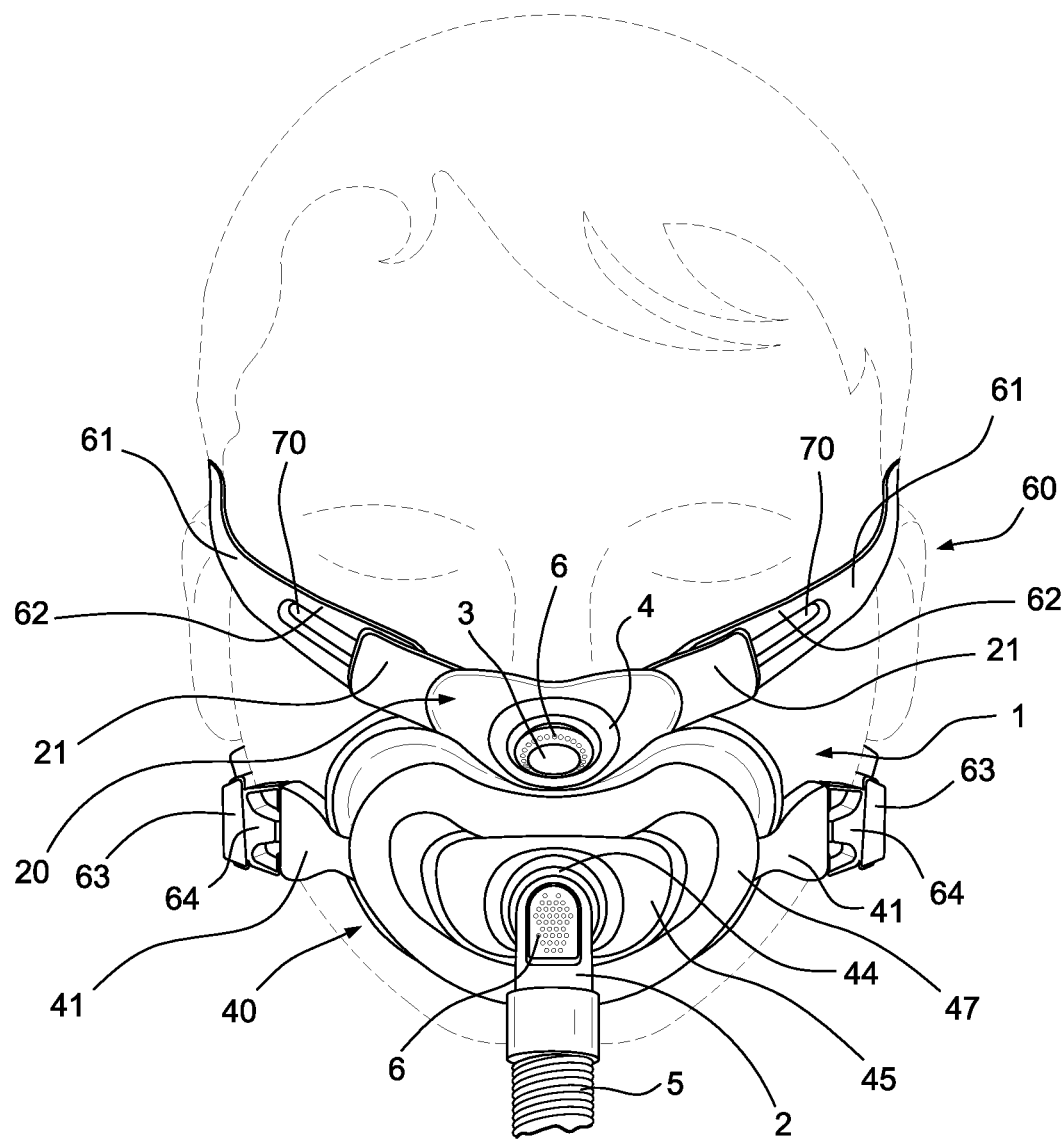
Figures 1, 2, 3:
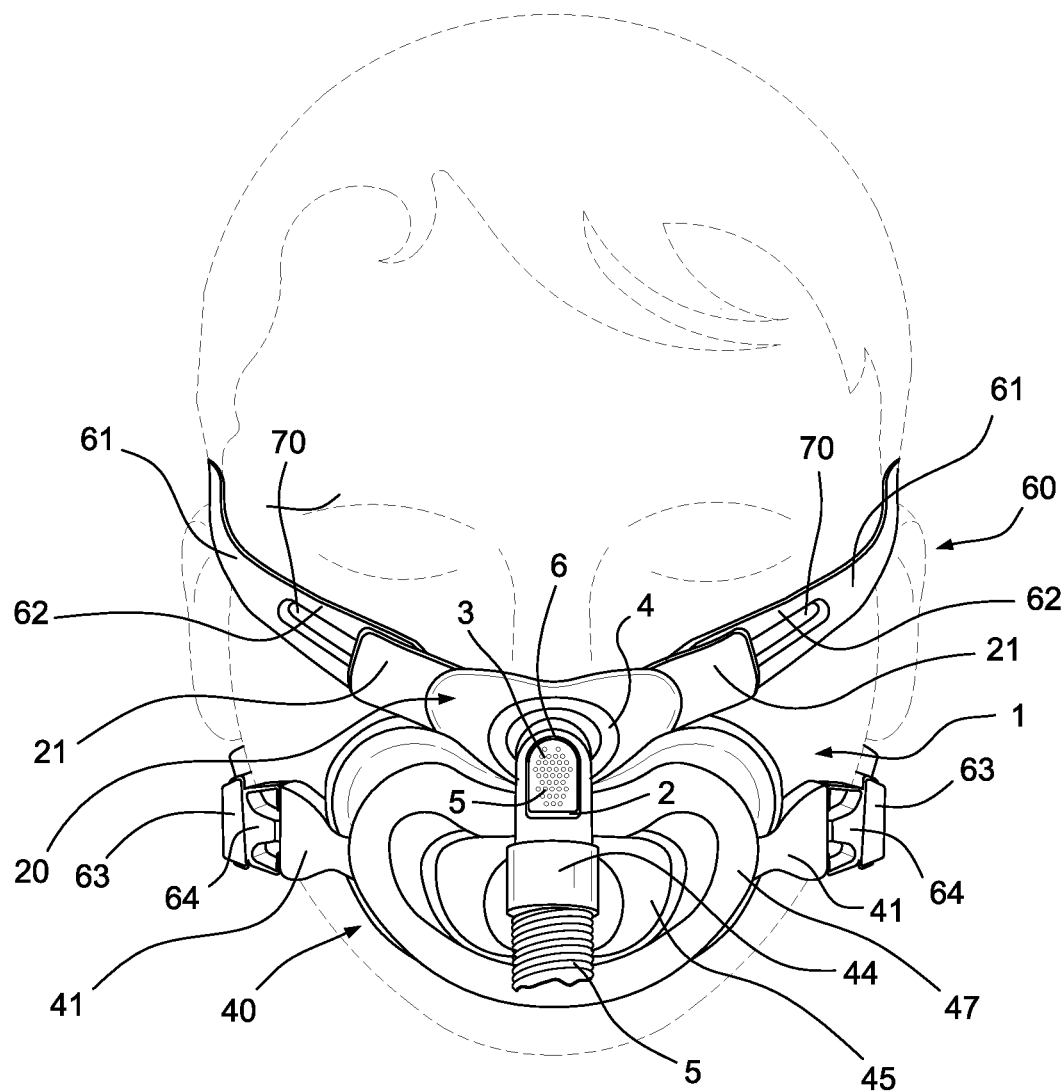
Figures 1, 2, 3, 4:
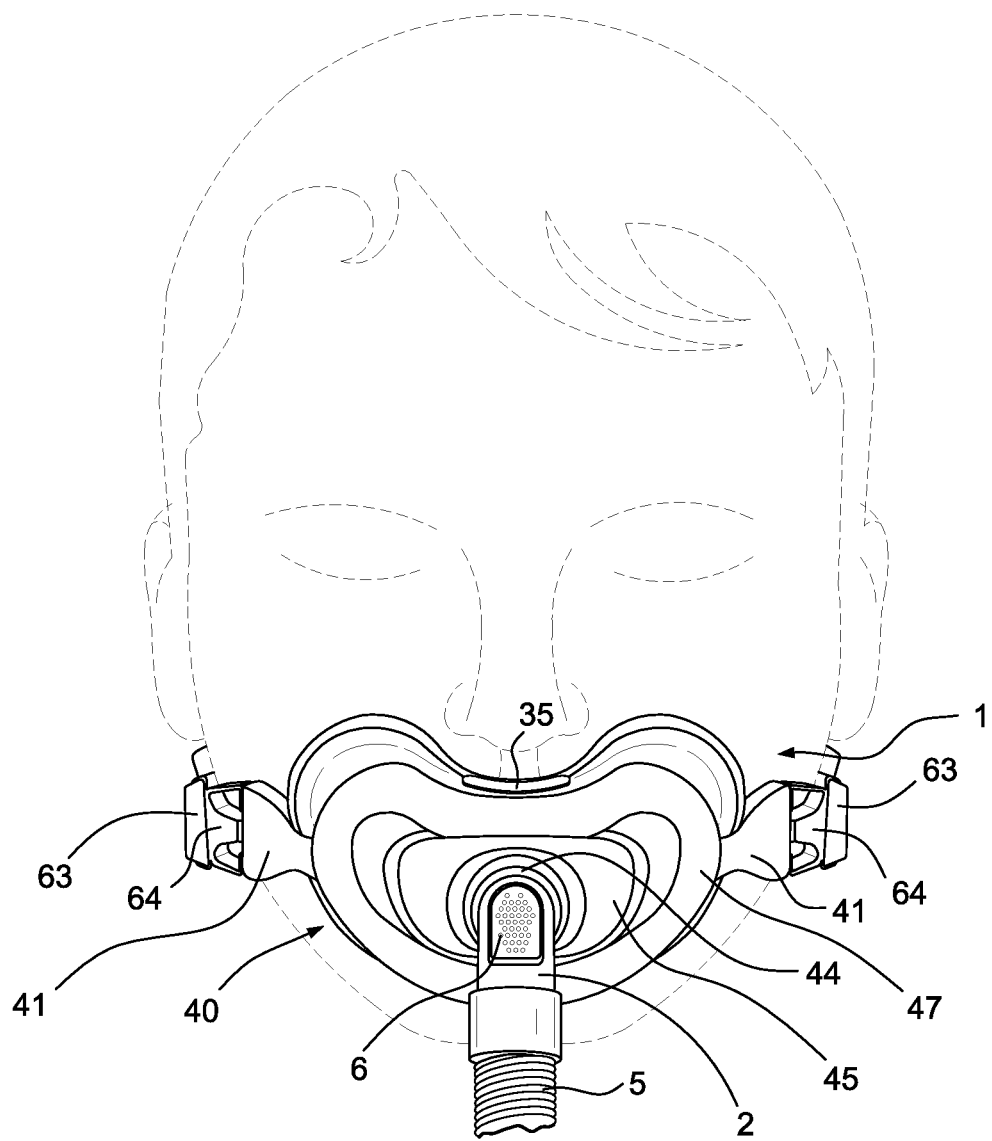

As illustrated in FIGS. 1-1 to 4, for example, a mask system 1 may include a nares portion 20, a mouth portion 40 and positioning and stabilizing structure, which may include headgear 60. An air delivery system may deliver air to the mask system 1, such as through flexible tube 5. The mask system of FIGS. 1-1 to 4 is a modular mask system in which the nares portion 20 and the mouth portion 40 are both adapted to be used without each other (in a nares only mode or in a mouth only mode), or the nares portion 20 and the mouth portion 40 may be utilized together (in a nares and mouth mode). When utilized in the nares and mouth mode, one of the nares portion 20 and the mouth portion 40 may be utilized to deliver pressurized gas, while the other of the nares portion 20 and the mouth portion 40 may be utilized as a nares or mouth seal. In another form, when utilized in the nares and mouth mode, both the nares portion 20 and the mouth portion 40 may be utilized to deliver pressurized gas to the patient's airways. Alternatively, the mask system 1 may be formed as an integrated mask system, where the nares portion 20 and the mouth portion 40 are formed as a single element.

Figures 1, 2, 3, 4, 5:
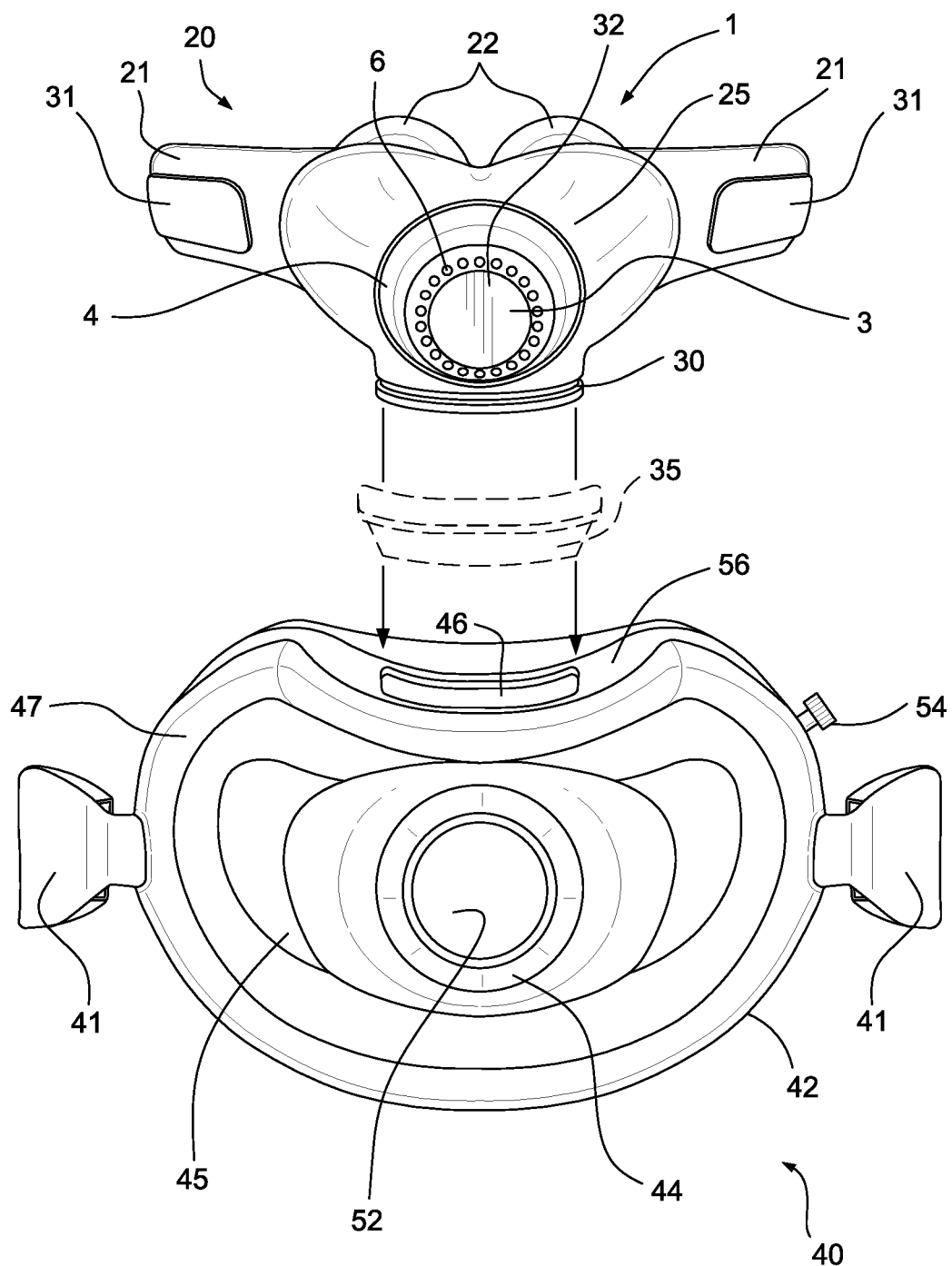
Figure 2:
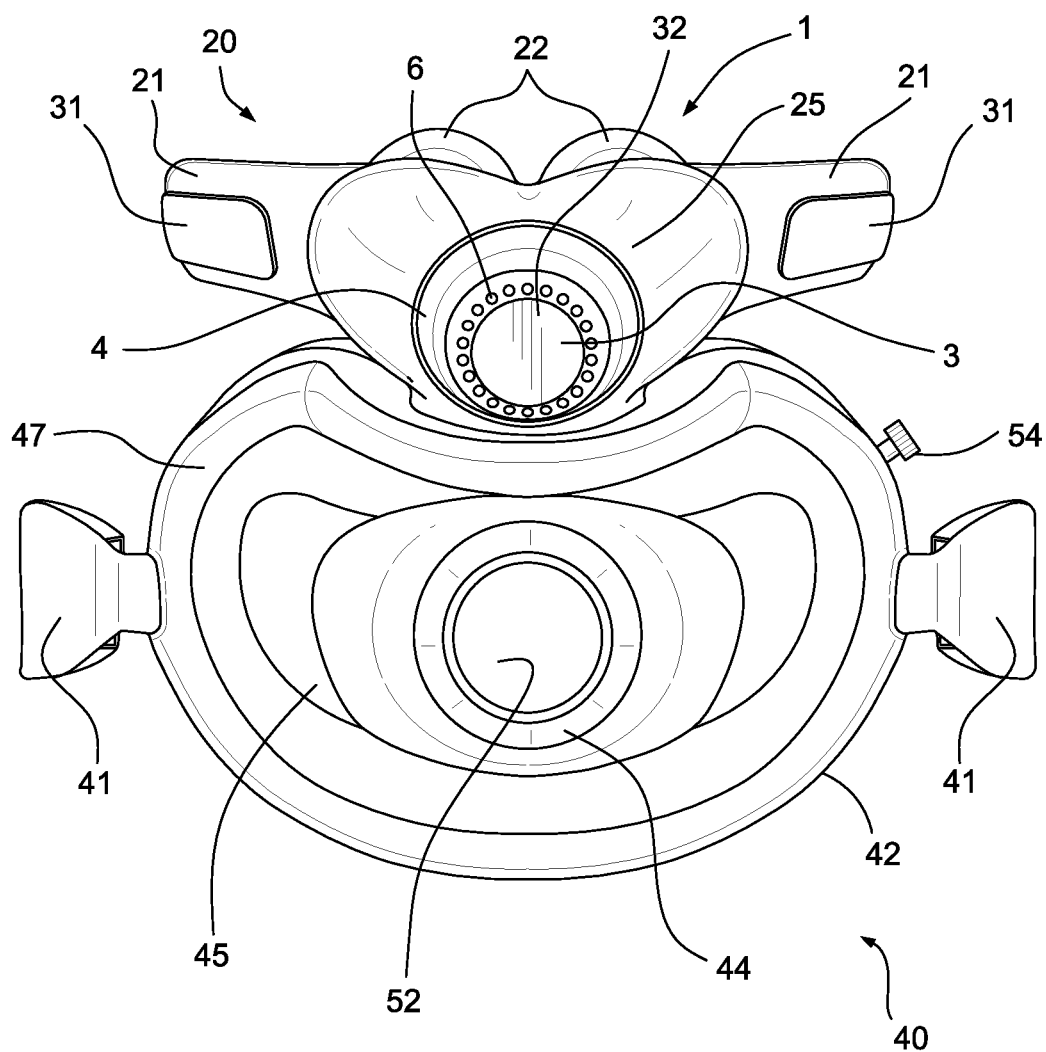
Figure 3:
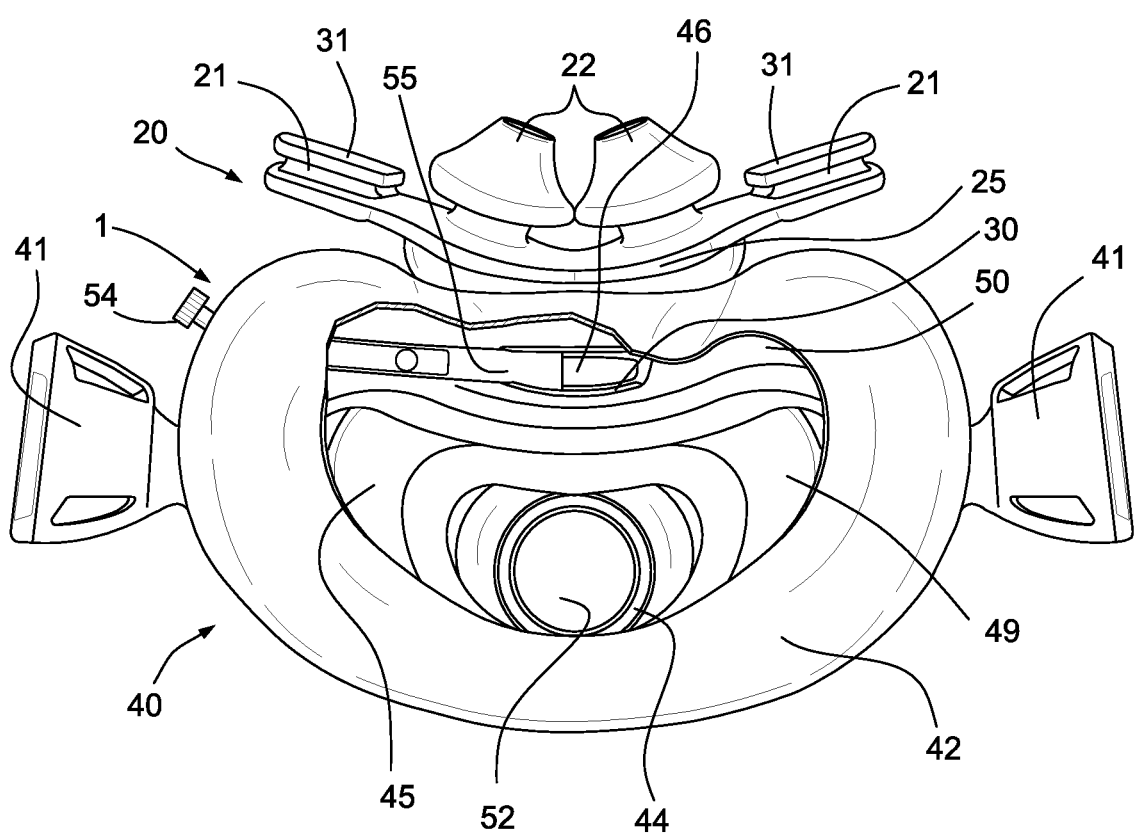
Figure 4:
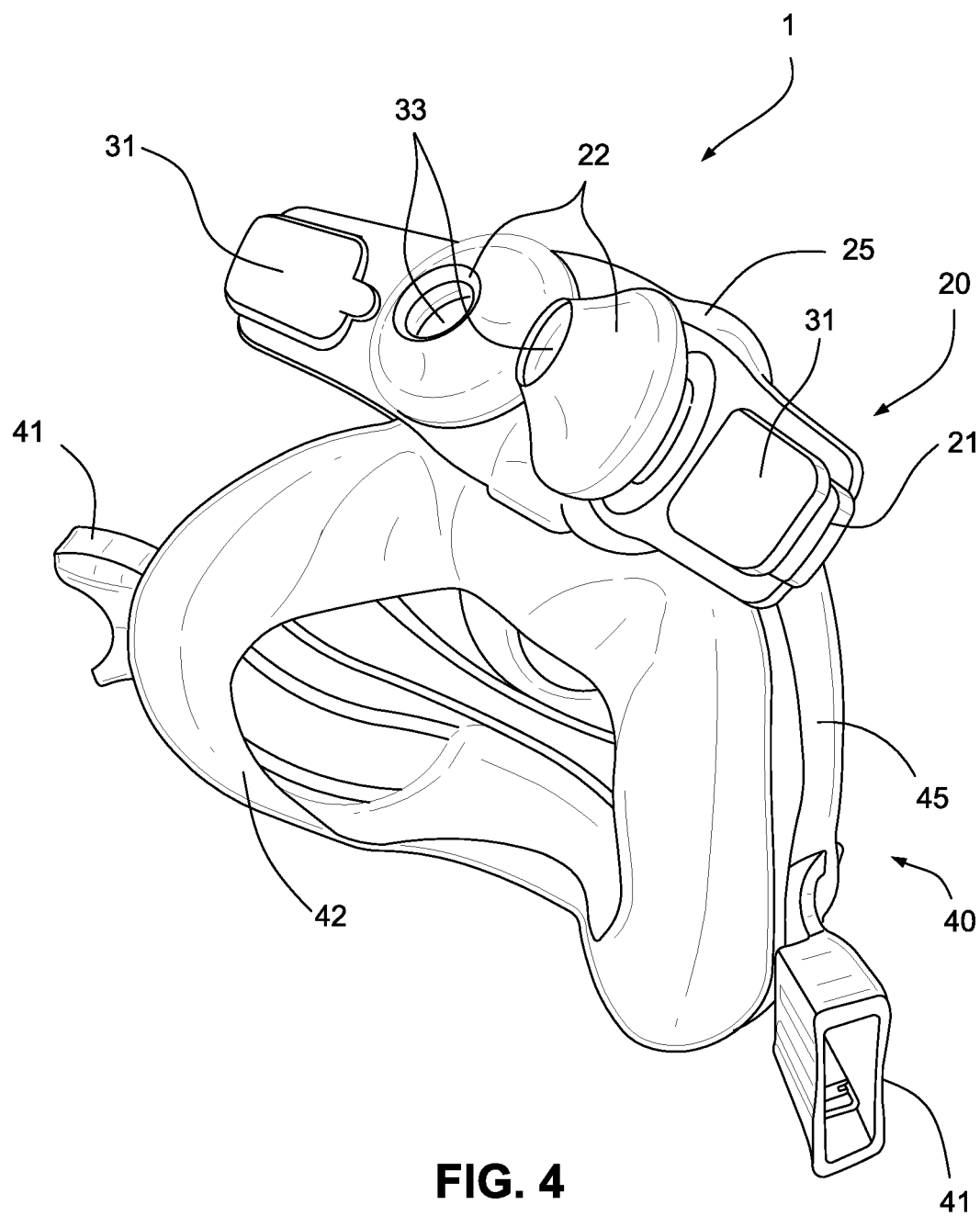
Figures 1, 5:
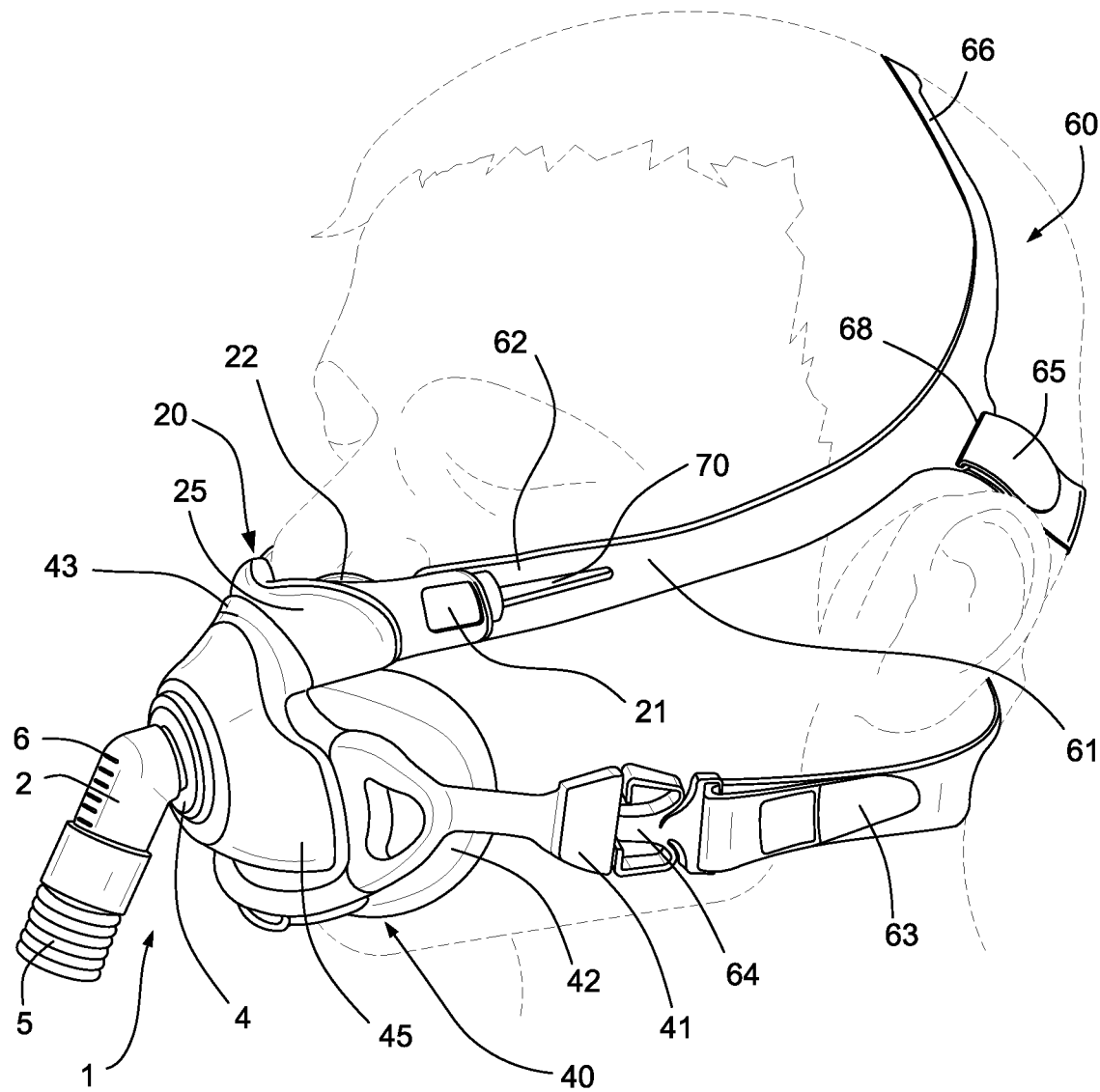
Figures 2, 5:
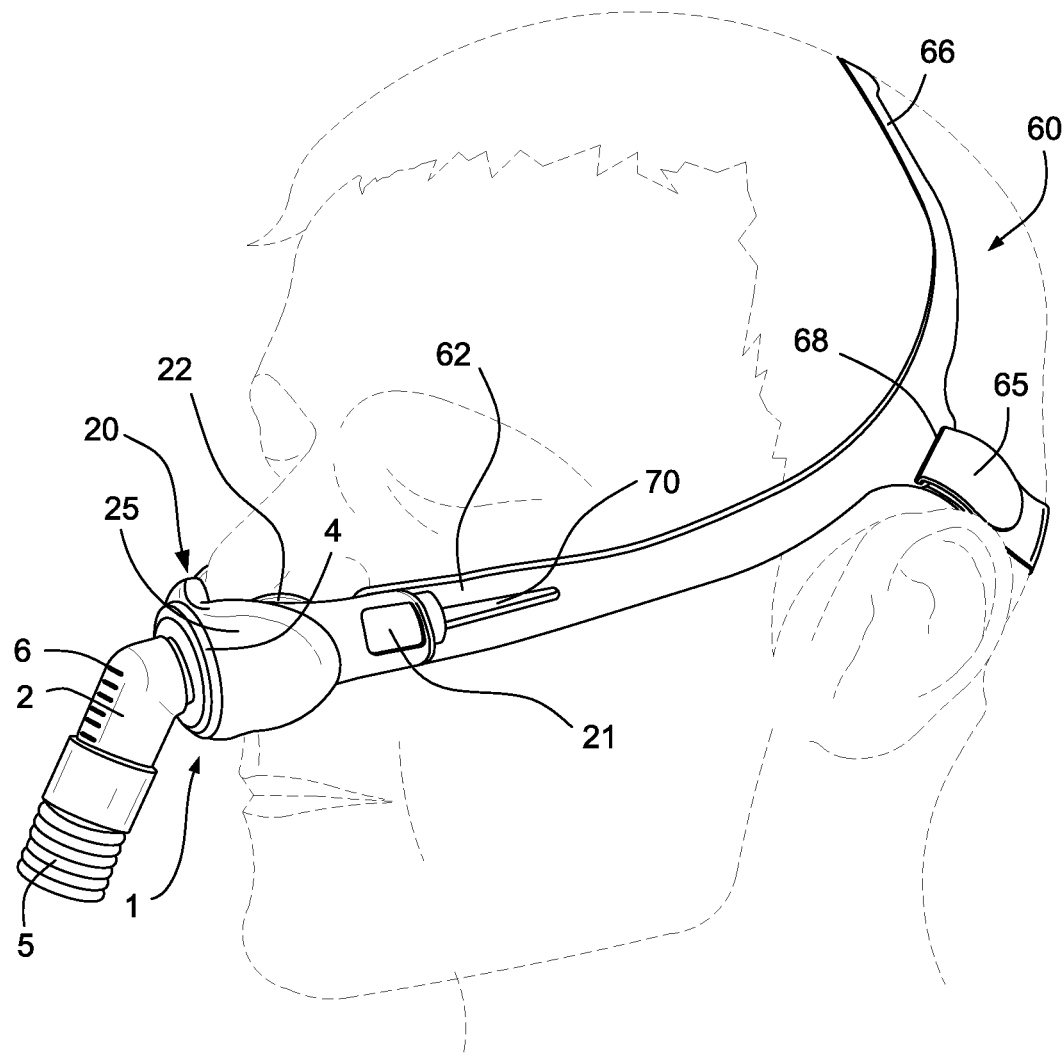
Figure 13:
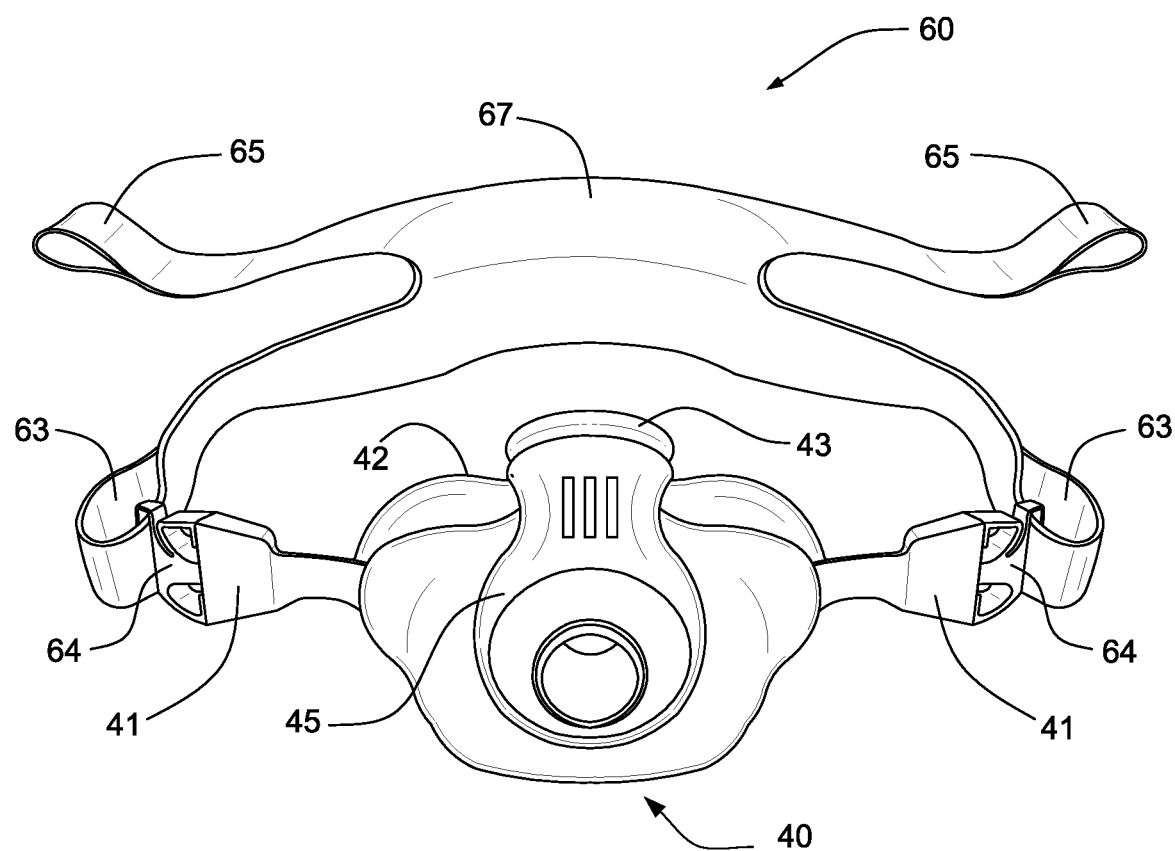
FIG. 13 depicts a front view of a portion of the mask system of FIG. 5-1 without the nares portion and without the elbow connector and including a headgear according to an embodiment of the present technology.

FIGS. 5-1 to 13 illustrate another mask system 1 that may be in the form of a modular mask, where the nares portion 20 and the mouth portion 40 may be adapted to be used without each other, or the nares portion 20 and the mouth portion 40 may be adapted to function together to deliver the breathable, pressurized gas to the patient's nares and mouth. In FIGS. 5-1 and 6 to 13, the flexible tube 5 is connected to the swivel ring 4 via the elbow 2, to direct the pressurized, breathable gas to the chamber of the mouth portion 40 and to the nares portion 20. FIG. 5-1 and FIGS. 6 to 12 illustrate the modular mask system 1 in a nares and mouth mode, where the nares portion 20 and the mouth portion 40 are both utilized. FIG. 5-2 illustrates the mask system 1 in a nares only mode, where the nares portion 20 is used without the mouth portion 40. In the nares only mode, the elbow 2, flexible tube 5 and the swivel ring 4 are connected to an opening in the nares portion 20.

Figure 14:
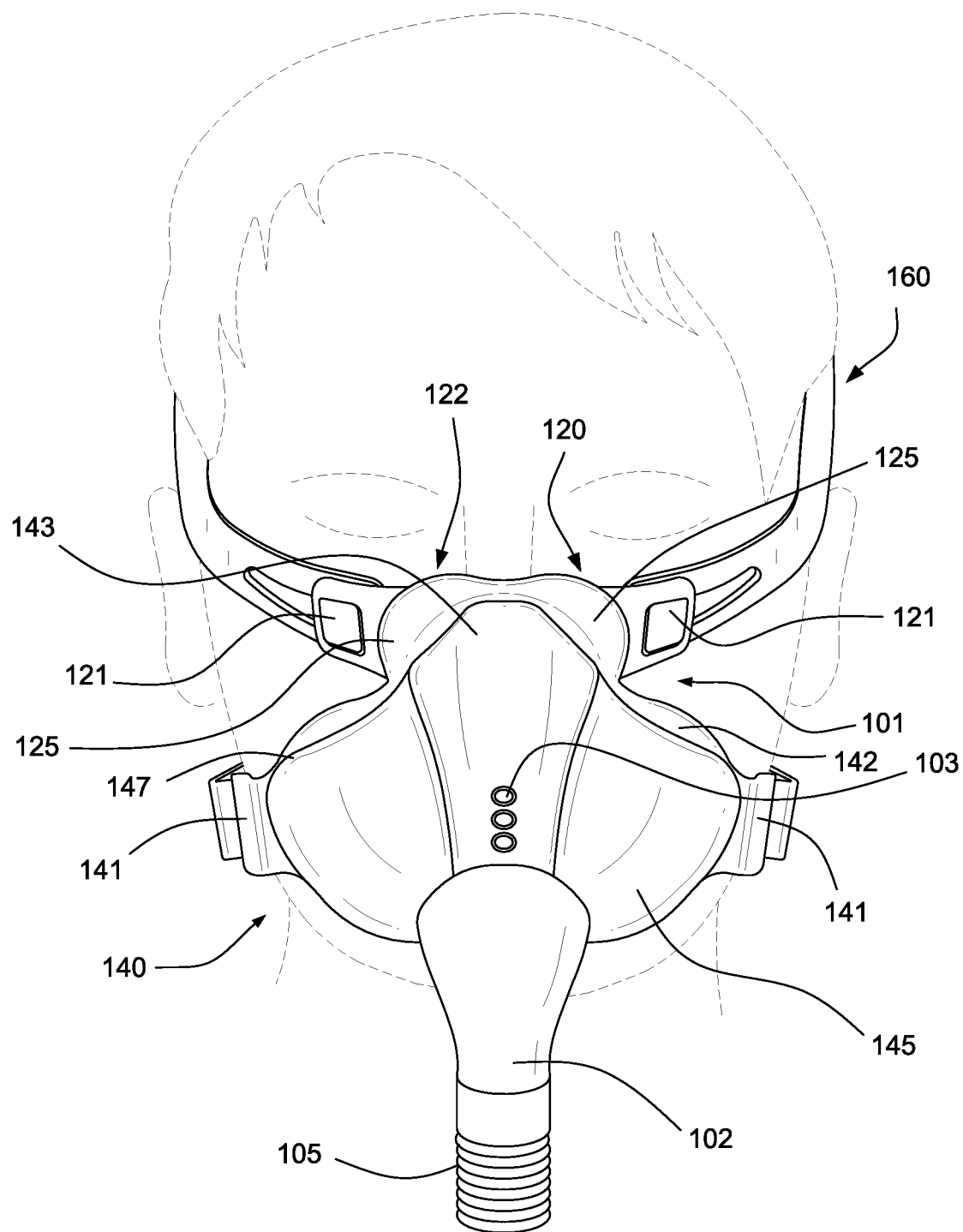
FIG. 14 depicts a front view of a mask system on a model patient's head according to another embodiment of the present technology.
Figure 15:
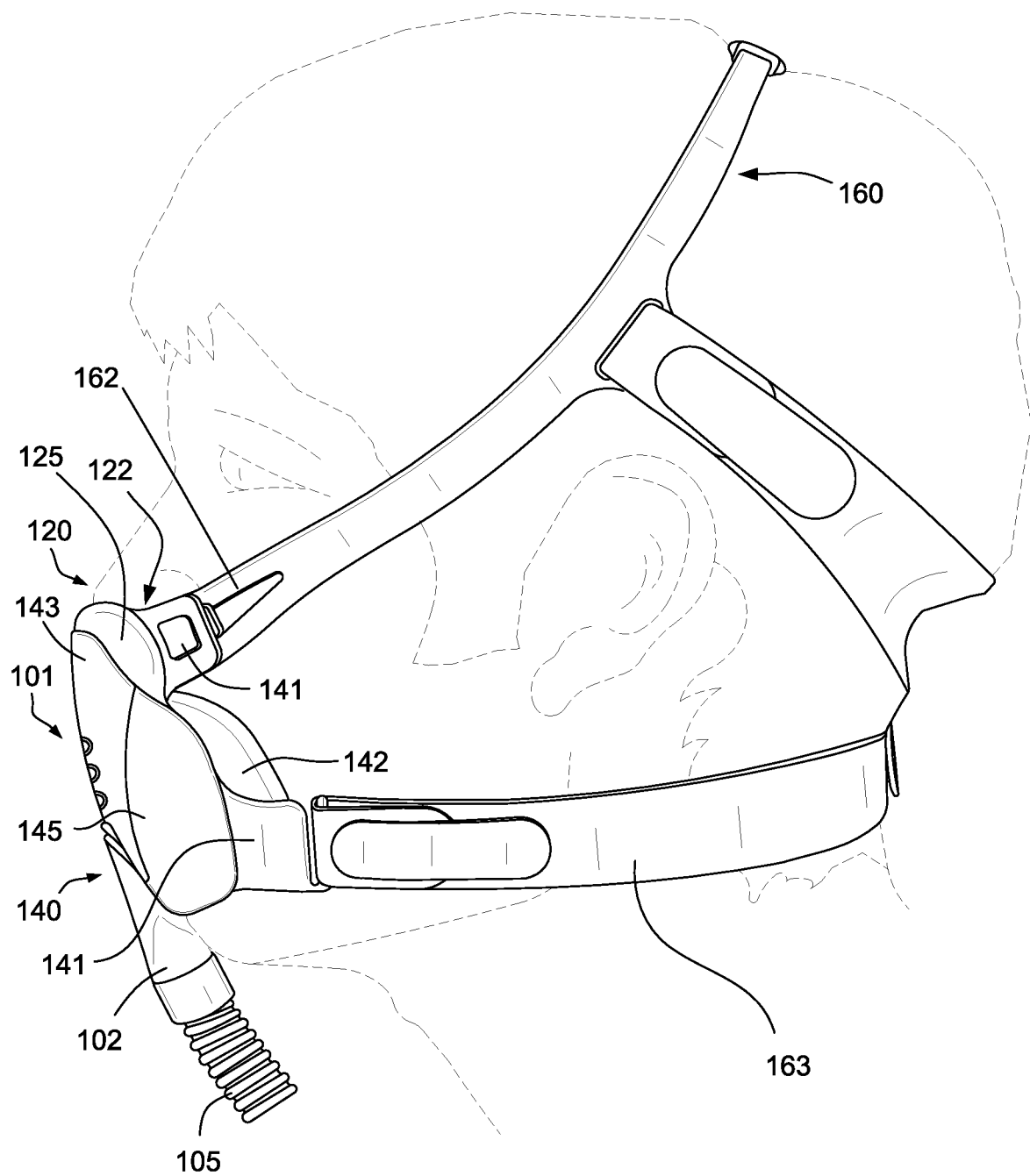
FIG. 15 depicts a side view of the mask system of FIG. 14 on a model patient's head according to an embodiment of the present technology.

FIGS. 14 and 15 illustrate an integrated mask system 101, which includes a nares portion 120, a mouth portion 140, and positioning and stabilizing structure, which may include headgear 160. In the integrated mask system, the nares portion 120 and the mouth portion 140 are not separable, and are typically formed together in a single piece. An air delivery system may deliver air to the mask system 101, such as through and a flexible tube 105 connected to the mouth portion 140 via an elbow 102.

Figure 16:
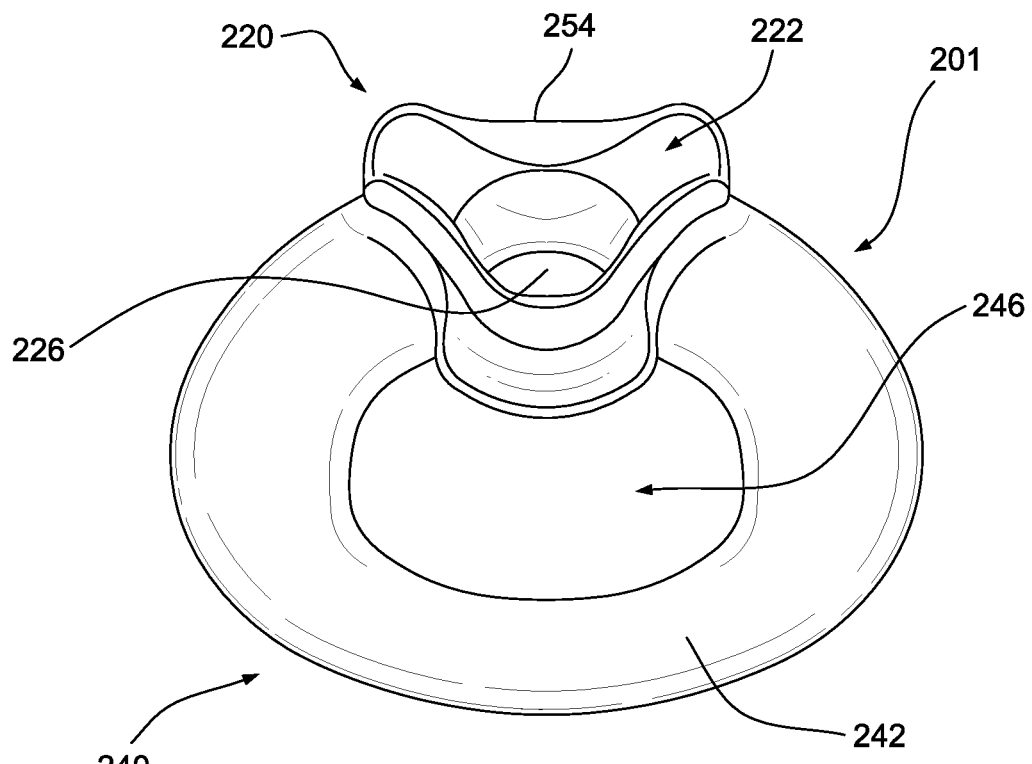
FIG. 16 depicts a rear view of a mask system with a decoupling portion and connecting portion removed according to another embodiment of the present technology.
Figure 17:
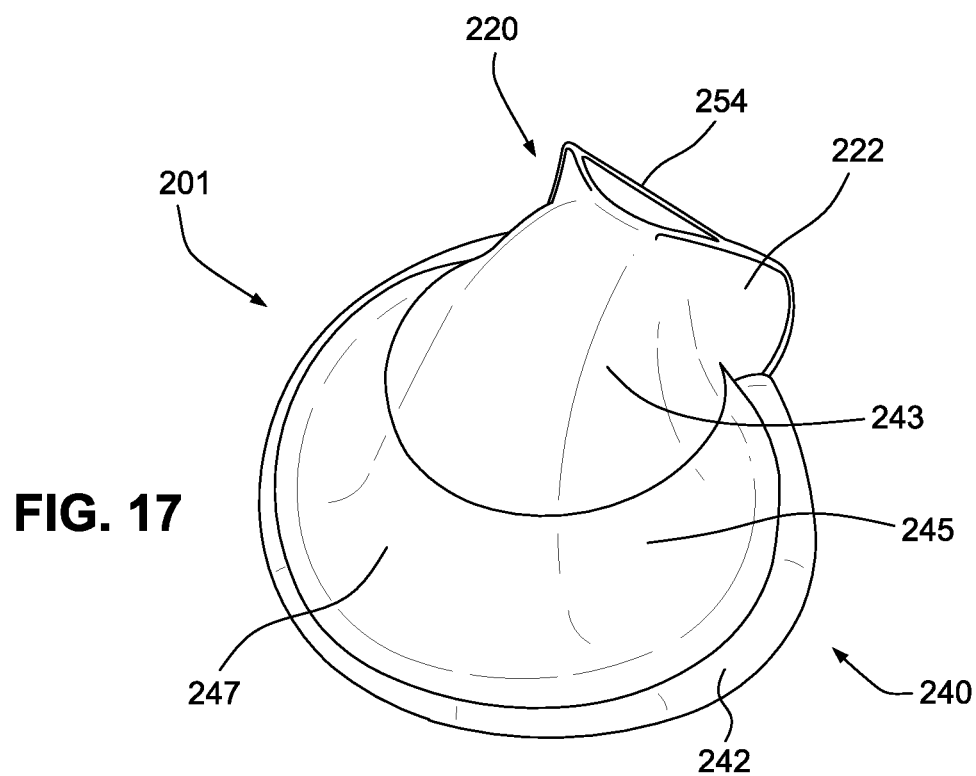
FIG. 17 depicts a front isometric view of the mask system of FIG. 16 according to an embodiment of the present technology.
Figure 18:
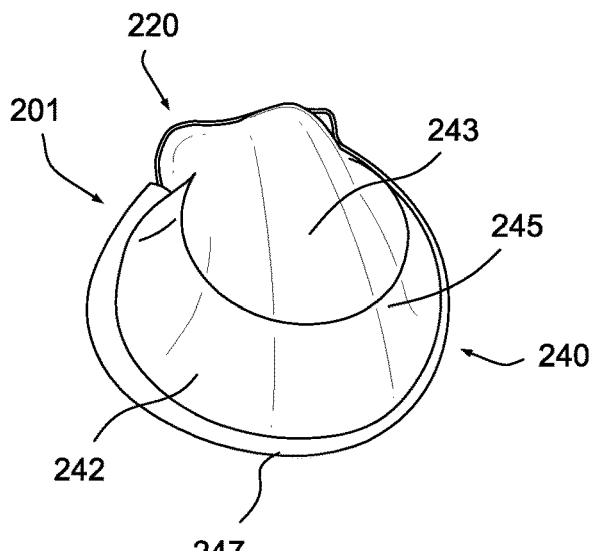
FIG. 18 depicts a front isometric view of the mask system of FIG. 16 according to an embodiment of the present technology.

FIGS. 16-18 illustrate another mask system 201, which may be an integrated mask system, and which includes a nares portion 220 and a mouth portion 240. An air delivery system may deliver air to the mask system 201.

Figure 21:
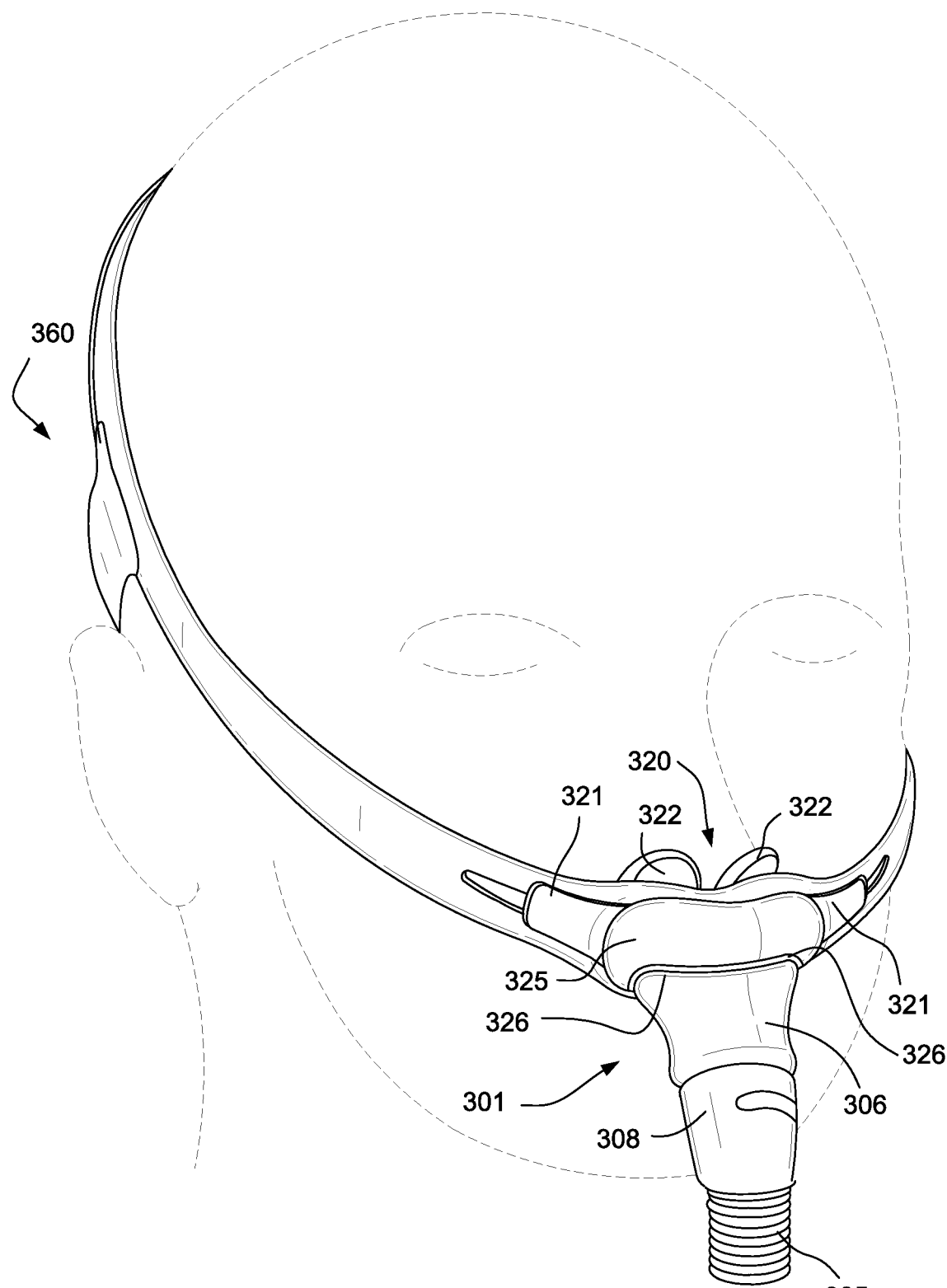
FIG. 21 depicts a front isometric view of a mask system on a model patient's head in a nares only mode according to another embodiment of the present technology.
Figure 22:
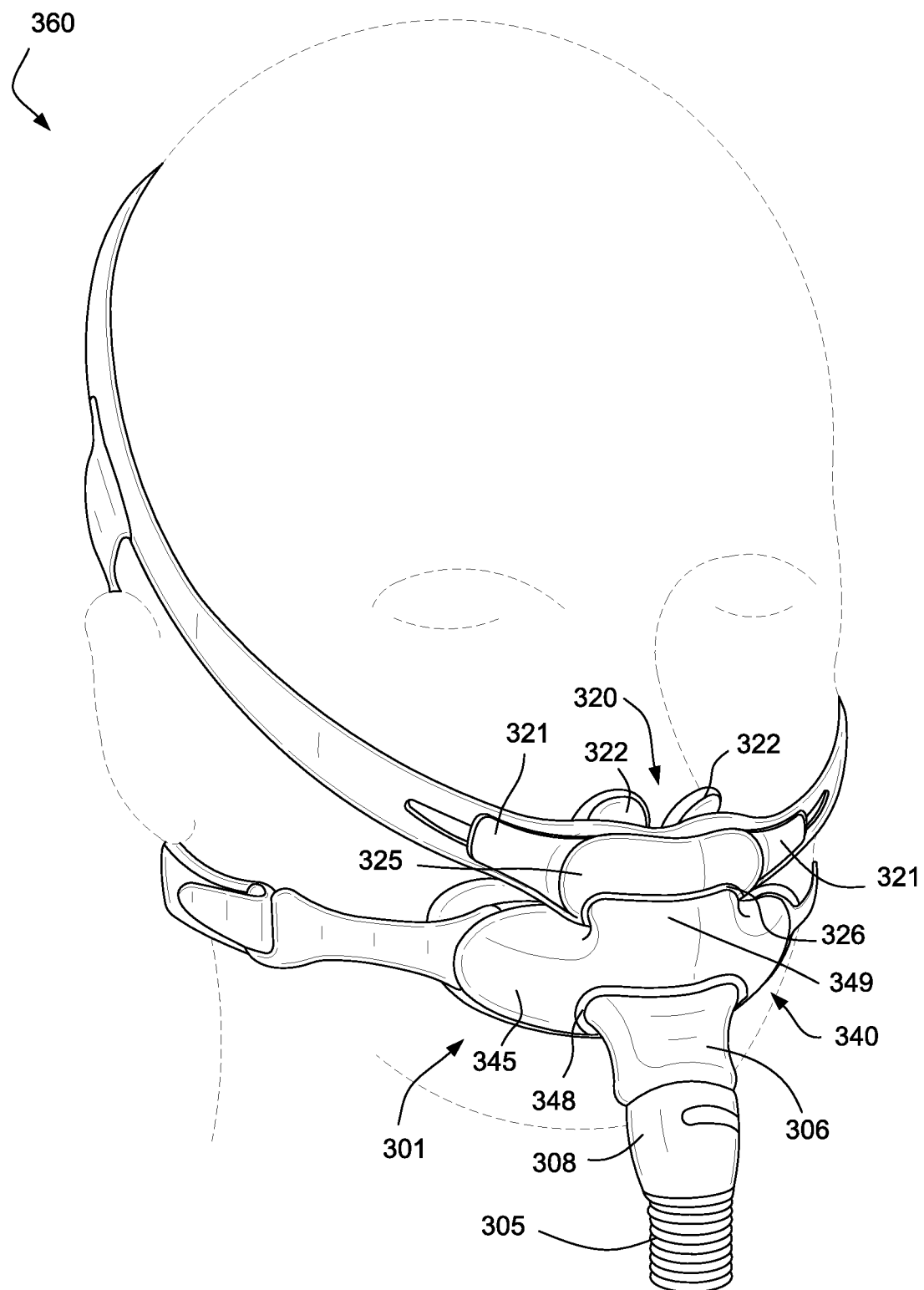
FIG. 22 depicts a front isometric view the mask system of FIG. 21 on a model patient's head in a nares and mouth configuration according to an embodiment of the present technology.

FIGS. 21 and 22 illustrate a modular mask system 301 in accordance with an embodiment of the present technology. The mask system 301 includes a nares portion 320, a mouth portion 340 and headgear 360. An air delivery system may deliver air to the mask system 301, such as through flexible tube 305 connected to the mouth portion 340 or nares portion 320 via connector 306 and optional swivel connector 308. The connector 306 may be in the form of an elbow or other type of connector. The connector 306 may be a flexible portion that is able to absorb external forces that may otherwise dislodge the seal of nares portion 320 and/or mouth portion 340 with the patient, for example as may be caused by tube drag forces. FIG. 21 illustrates the mask system 301 in the nares only mode, and FIG. 22 illustrates the mask system 301 in the nares and mouth mode.

Figure 23:
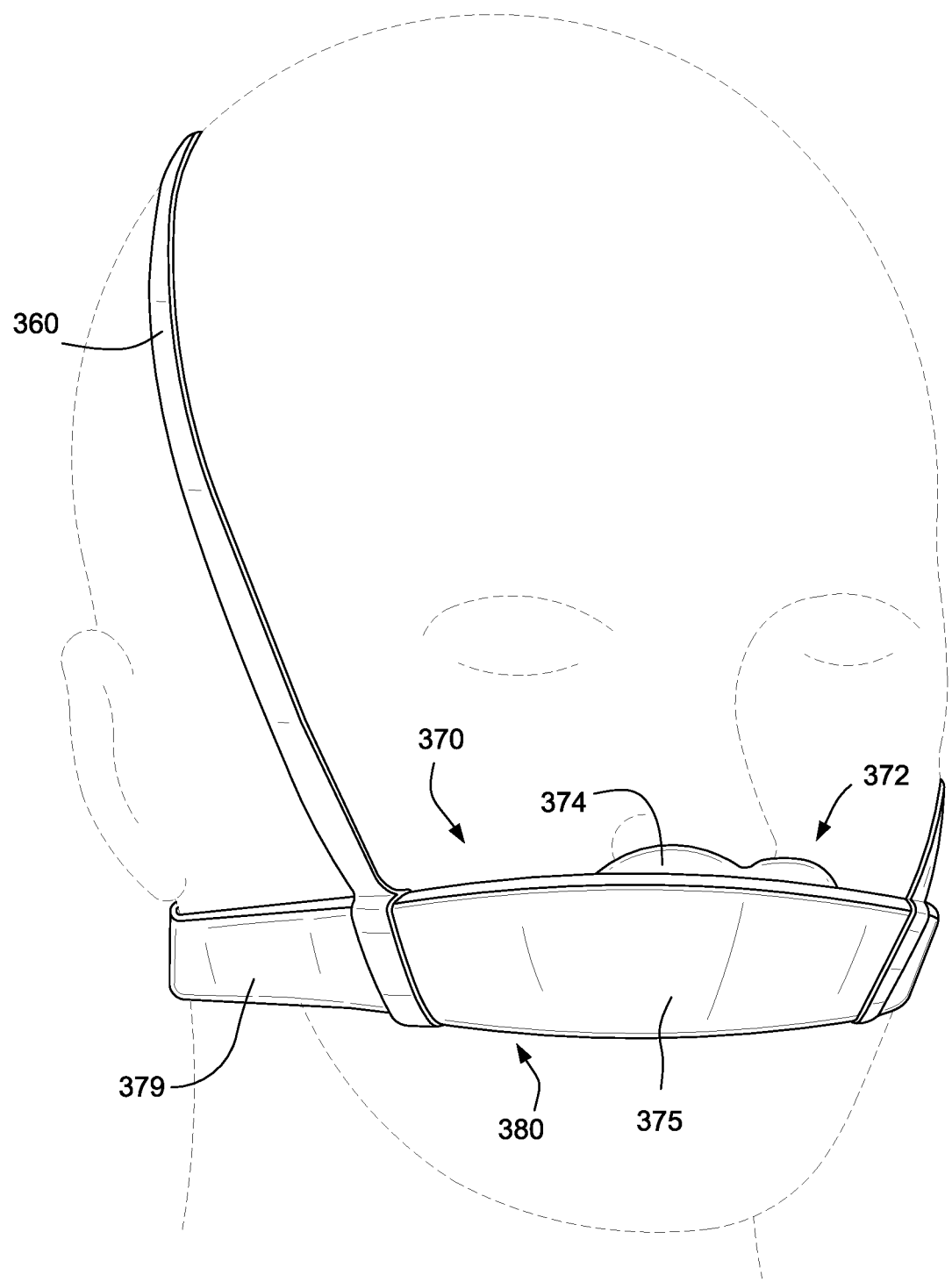
FIG. 23 depicts a front isometric view of a mask system on a model patient's head according to another embodiment of the present technology.

FIG. 23 illustrates a modular mask system 370 in accordance with an embodiment of the present technology. The mask system 370 includes a nares portion 372, a mouth portion 380, and headgear 360. An air delivery system including an air delivery tube or conduit 379 may deliver air to the mask system 370. Further, tube 379 may function as headgear in addition to being an air delivery tube or conduit.

Figure 24:
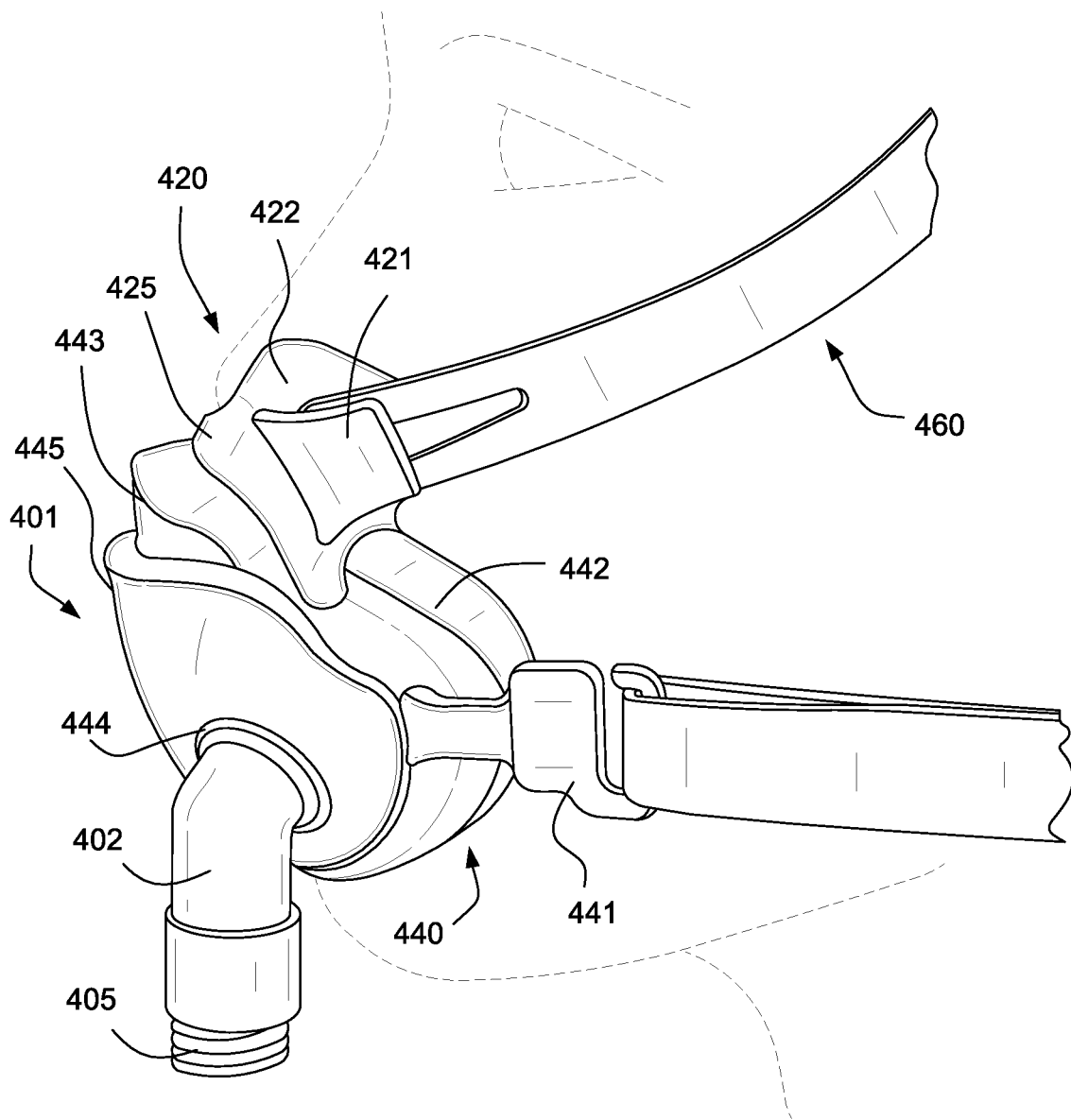
FIG. 24 depicts a side view of a mask system on a model patient's head according to another embodiment of the present technology.

FIG. 24 illustrates a modular mask system 401 in accordance with an embodiment of the present technology. The mask system 401 includes a nares portion 420, a mouth portion 440, and headgear 460. An air delivery system may deliver air to the mask system 401, such as through a flexible tube 405 connected to the mouth portion 440 via connector 402 and optional swivel connector 444.

Figure 25:
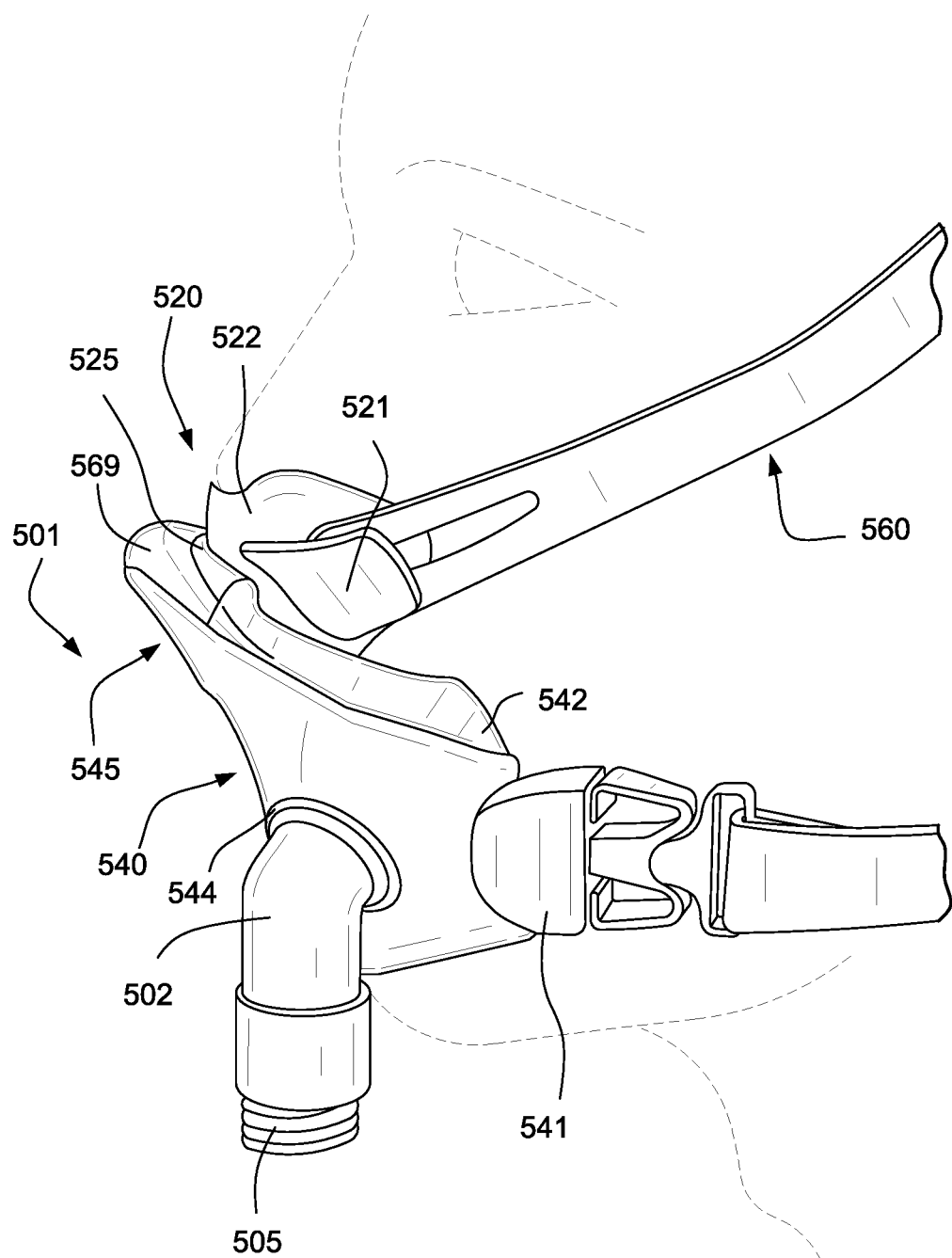
FIG. 25 depicts a side view of a mask system on a model patient's head according to another embodiment of the present technology.

FIG. 25 illustrates an integrated mask system 501 in accordance with an embodiment of the present technology. The mask system 501 includes a nares portion 520, a mouth portion 540, and headgear 560. An air delivery system may deliver air to the mask system 501, such as through a flexible tube 505 connected to the mouth portion 540 via connector 502 and optional swivel connector 544.

Figure 34:
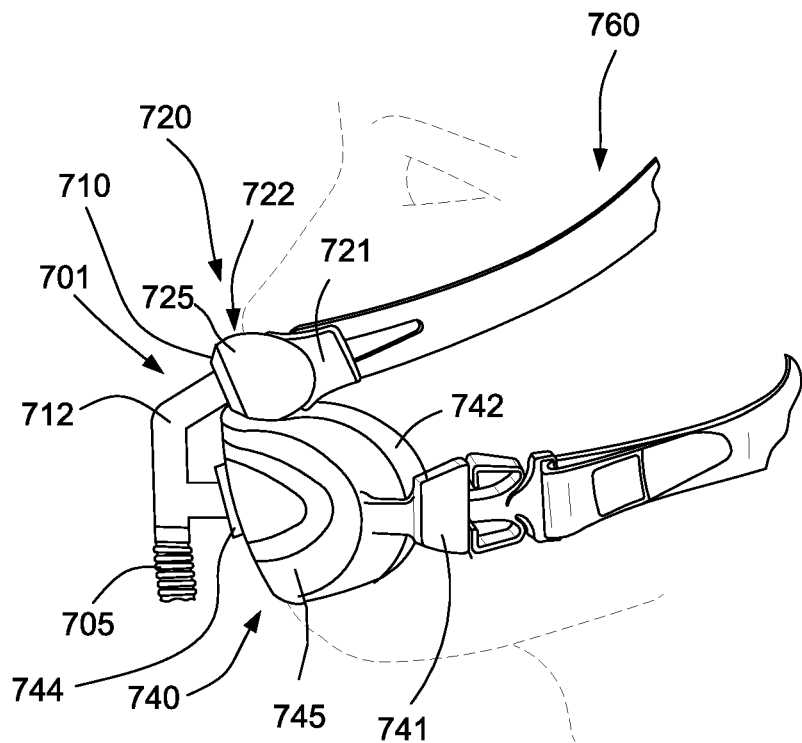
FIG. 34 depicts a schematic view of a modular mask system on a model patient's head according to an embodiment of the present technology.

FIG. 34 illustrates mask system 701 that may be in the form of a modular mask, where the nares portion 720 and the mouth portion 740 may be adapted to be used without each other, or the nares portion 720 and the mouth portion 740 function together to deliver the breathable, pressurized gas to the patient's nares and mouth. FIG. 34 illustrates the mask system 701 utilized in the nares and mouth mode, with the flexible tube 705 connected to the swivel rings 710 and 744 via the double elbow 712, to direct the pressurized, breathable gas to the chamber of the mouth portion 740 and to the nares portion 720.

In a nares only mode, only the nares portion 720 is utilized and the mouth portion 740 is not utilized. In this mode, the double elbow 712 is removed and the mouth portion 740 is removed. The patient utilizes the nares portion 720 only, and connects the tube 705 to the swivel ring or other connector 710. An elbow such as elbow 2 may be utilized to connect the tube 705 to the swivel ring or other connector 710.

In a mouth only mode, only the mouth portion 740 is utilized and the nares portion 720 is not utilized. In this mode, the double elbow 712 is removed and the nares portion 720 is removed. The patient utilizes the mouth portion 740 only, and connects the tube 705 to the swivel ring or other connector 744. An elbow such as elbow 2 may be utilized to connect the tube 705 to the swivel ring or other connector 744.

1.1 Nares Portion

The nares portion is intended to form a seal with the patient's nasal airway in use. The nares portion could be a seal that is disposed on the outside of the patient's nose, for example a cradle type mask or a typical nasal mask. Alternatively, it could be an around the nares type seal like a pillows type mask, or it could be an in the nose type seal like nasal plugs. A nares seal may be an appropriate choice for patient's who have upper airway obstructions. Breathing through the nose may also have other benefits like a natural filtration of the inhaled air.

As illustrated in FIGS. 1-1 to 4, the modular mask system 1 may include a nares portion 20. The nares portion 20 may include nares sealing portion 22, a decoupling portion 25, headgear connectors 21, a swivel ring 4, and a plug 3. The headgear connectors 21 may include headgear tabs 31 adapted to connect to headgear.

The decoupling portion 25 may function to decouple forces applied to the nares portion 20 from the nares sealing portion 22, such as tube drag forces applied at the swivel ring 4 by movement of flexible tube 5. The swivel ring 4 fits into an opening in the decoupling portion 25 on a front of the nares portion 20. The decoupling portion 25 may comprise a thin walled section, for example less than 1 mm to enable flexibility of this portion.

The plug 3 is adapted to fit into the swivel ring. The plug 3 may include a plurality of optional vent holes 6 that allow air exhaled by the patient's nose to be vented out of the nares portion 20. Preferably, vent holes 6 are arranged in a diffuse array to prevent jetting of air from the vent. In some embodiments, the plug 3 may be removed and replaced with a connection to the tube 5.

FIG. 1.1 illustrates the nares portion 20 of mask system 1 utilized in a nares only mode. Nares portion 20 is utilized without mouth portion 40, and the elbow 2 and flexible tube 5 are connected to the swivel ring 4 on the nares portion 20.

The nares portion 20 illustrated in FIGS. 1-1 to 4 may be a modified version of the commercially sold Swift™ FX by ResMed Ltd, (e.g., as described in WO 2009/052560 A1 and WO 2010/139014 A1, both of which are incorporated by reference herein in their entirety), for example, although other nares portions may be utilized. The nares portion 20 may be modified from the commercially sold Swift™ FX by ResMed Ltd. to include a connector 30, as illustrated in FIGS. 1-1, 1-5 and 3, the connector 30 adapted to connect a chamber 49 of the nares portion 20 at an opening 46 in mouth portion 40, so that air is pneumatically allowed to flow between the nares portion 20 and the mouth portion 40. When used in the nares only configuration as illustrated FIG. 1-1, the connector 30 is removed from the opening 46 as shown in the exploded view of FIG. 1-5, and the connector 30 is engaged with plug 35. The plug 35 is shaped so as to fit into either the opening 46 or the connector 30 as needed. The plug 3 is removed from the nares portion 20, and the elbow 2 and flexible tube 5 may be connected via the swivel ring 4 to the nares portion 20 to deliver the pressurized breathable gas to the nares portion 20.

FIGS. 5-1 to 13 illustrate a mask system 1 that includes a nares portion 20. The nares portion 20 may include nares sealing portion 22, a decoupling portion 25, headgear connectors 21, and a swivel ring 4. The headgear connectors 21 may include headgear tabs 31 adapted to connect to headgear 60.

The nares portion 20 illustrated in FIGS. 5 to 13 may be the commercially sold Swift™ FX by ResMed Ltd, for example, although other nares portions may be utilized. Further details of such a nares portion 20 are disclosed in WO 2009/05256 A1, the disclosure of which is incorporated herein by reference in its entirety.

Figure 19:
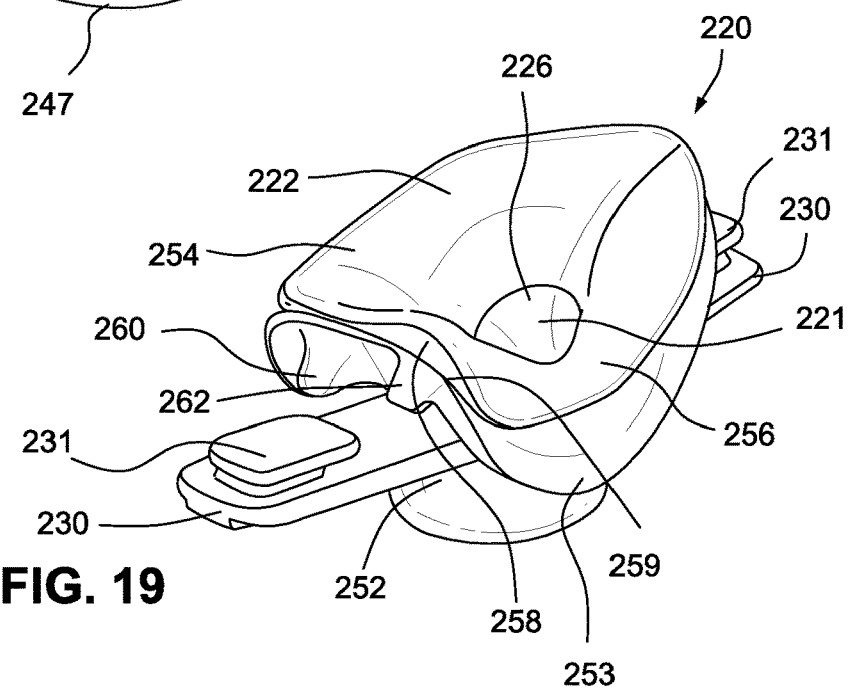
FIG. 19 depicts a rear isometric view of a nares portion that may be used with mask systems according to an embodiment of the present technology.
Figure 20:
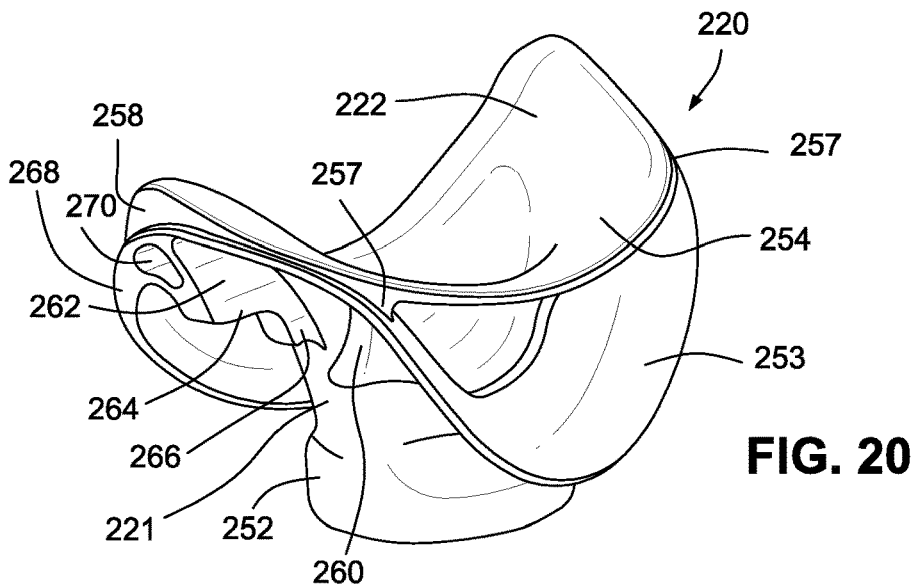
FIG. 20 depicts a front isometric view of the nares portion of FIG. 19 according to an embodiment of the present technology.

FIGS. 19 and 20 illustrate another nares portion 220, which may be utilized with any of the embodiments disclosed herein. The nares portion 220 may include nares sealing portion 222, a support membrane 252, a supporting portion 253, and headgear connectors 230 with headgear tabs 231 for connecting to headgear. The support membrane 252 may be adapted to connect to a swivel ring or other connector for connection to a supply of pressurized, breathable gas. Further details of the nares portion 220 are disclosed in WO 2010/139014 A1, the entire contents of which are incorporated herein by reference.

FIGS. 14 and 15 illustrate an integrated mask system 1, which includes the nares portion 120. The nares portion 120 may include nares sealing portion 122, decoupling portion 125 and headgear connectors 121 adapted to connect to headgear 160. A nares portion such as the commercially sold Swift™ FX nares portion, the modified version of the commercially sold Swift™ FX nares portion, or the nares portion of FIGS. 19 and 20 may be utilized and integrated with the embodiment of FIGS. 14 and 15.

FIGS. 16-18 illustrate a mask system 201 that may include nares portion 220. The nares portion 220 may include nares sealing portion 222 and an orifice 226 for receiving pressurized, breathable gas. The mask system 201 is illustrated with a nares portion 220 such as illustrated in FIGS. 19 and 20, although other nares portions could be utilized, such as the commercially sold Swift™ FX nares portion or the modified version of the commercially sold Swift™ FX nares portion.

FIGS. 21 and 22 illustrate a modular mask system 301, which includes nares portion 320. The nares portion 320 may include nares sealing portion 322, decoupling portion 325 and headgear connectors 321 for connecting to headgear 360. Nares portion 320 may be adapted to connect to connector 306 by including opening 326 adapted to receive connector 306.

FIG. 23 illustrates an integrated mask system that includes a nares portion 372 connected to a mouth portion 380 and headgear 360. The nares portion 372 includes nares sealing portion 374 adapted to form a seal with the patient's nares.

FIG. 24 illustrates an integrated mask system 401 that includes a nares portion 420 connected to a mouth portion 440, and headgear 460. The nares portion 420 includes nares sealing portion 422 adapted to form a seal with the patient's nares, decoupling portion 425, and headgear connectors 421 adapted to connect to headgear 460. The nares portion 420 is illustrated as the membrane type illustrated in FIGS. 19 and 20, although other nares portions could be utilized, such as the commercially sold Swift™ FX nares portion or the modified version of the commercially sold Swift™ FX nares portion.

FIG. 25 illustrates an integrated mask system 501 that includes a nares portion 520 connected to a mouth portion 540, and headgear 560. The nares portion 520 includes nares sealing portion 522 adapted to form a seal with the patient's nares, decoupling portion 525, and headgear connectors 521 adapted to connect to headgear 560. The nares portion 520 is illustrated as the membrane type illustrated in FIGS. 19 and 20, although other nares portions could be utilized, such as the commercially sold Swift™ FX nares portion or the modified version of the commercially sold Swift™ FX nares portion.

FIG. 34 illustrates a modular mask system 701 that includes a nares portion 720 connected to a mouth portion 740, and headgear 760. The nares portion 720 includes nares sealing portion 722 adapted to form a seal with the patient's nares, decoupling portion 725, and headgear connectors 721 adapted to connect to headgear 760. The nares portion 720 may be the commercially sold Swift™ FX nares portion, although other nares portions could be utilized, such as the commercially sold Swift™ FX nares portion or the nares portion illustrated in FIGS. 19 and 20.

Figure 56:
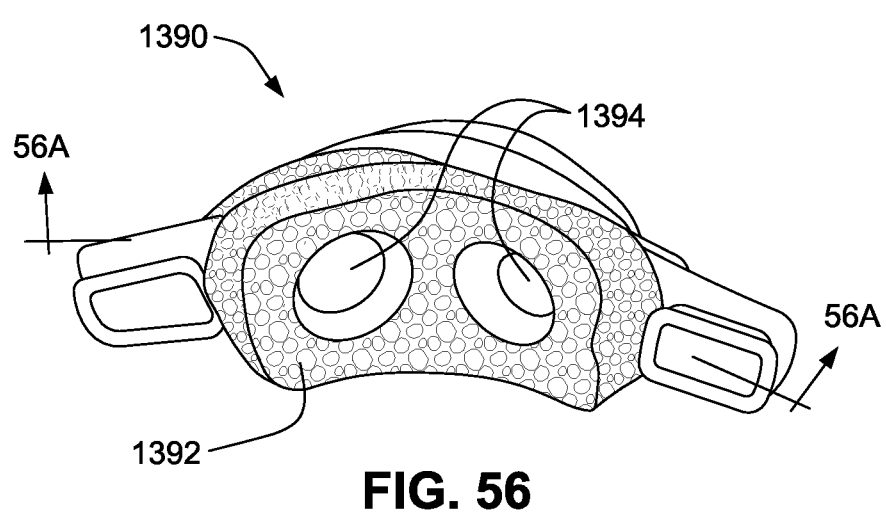
FIG. 56 depicts a rear view of a nasal portion of a mask system according to an embodiment of the present technology.
Figure 56A:
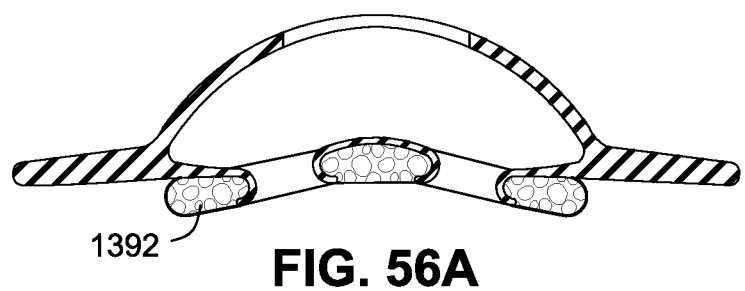
FIG. 56A is a cross-sectional view through line 56A-56A of FIG. 56.

FIGS. 55, 55A, 56, and 56A illustrate nares portions 1380, 1390, each including foam portions 1382, 1392. The foam portions 1382, 1392 have holes 1384, 1394 allowing passage of air to the nares of a patient. As shown FIG. 55A, the foam portion 1382 is compliant and will reveal the nasal prong once compressed. As shown in FIG. 56A, the nasal prong rolls back to hold the foam portion 1392 in place and provide a relatively flat surface to contact with the nose.

1.2 Mouth Portion

The mouth portion may be adapted to surround the patient's mouth and form a seal with the patient's airway at the mouth. The seal of the mouth portion could be a flap type seal like a membrane type seal, or it could be a compression seal utilizing materials such as foam, gel, fabric, etc.

A mouth portion 40 as illustrated in FIGS. 1-2 to 4 may include mouth sealing portion 42, a decoupling portion 45 to decouple forces applied to the mouth portion 40 from the mouth sealing portion 42, lower headgear connectors 41, and a swivel connector 44. The mouth portion 42 forms a chamber 49 into which air may be delivered and directed to the patient's mouth.

A swivel connector 44 may be disposed in a front aperture 52 of the mouth portion 40. The swivel connector 44 may be a swivel ring adapted to connect to a tube connector, such as elbow 2, for connecting to flexible tube 5, which may deliver breathable gas to the mouth portion 40. The swivel connector 44 may be removed from the front aperture of the mouth portion 40. Alternatively, the tube 5 may connect directly to the mouth portion 40.

The mouth portion 40 illustrated in FIGS. 1-1 to 4 is also adapted to connect to the nares portion 20. Specifically, the mouth portion 40, as illustrated in FIGS. 1-4 and 1-5, may include an aperture or opening 46 adapted to receive and seal with the connector 30 of the nares portion 20, to pneumatically connect the nares portion 20 to the chamber 49 of the mouth portion 40. A plug 35 may be included with the mask system 1, the plug 35 being adapted to fit within and plug the connector 30 or the aperture 46. Also, the nares portion 20 may function in a nares mode only without the mouth portion 40.

The mouth portion 40 may function as a docking station, where the mouth portion 40 is adapted to provide docking (the mouth portion is adapted to removably receive the nares portion) with respect to the nares portion 20. As illustrated in FIG. 1-5, the mouth portion may include a nares portion docking station 56 formed on the mouth portion 40, where the nares portion docking station 56 is adapted to receive a nares portion 20. The received nares portion 20 is capable of functioning as a nares only device for delivering pressurized breathable gas to the nares of a patient.

The nares portion docking station 56 may be adapted to receive the nares portion 20 by having a shape selected to mate with a shape of the nares portion. For example, as shown in FIG. 1-5, the nares portion docking station may have a curved upper surface to match a curved lower of the mouth portion 40. The nares portion docking station 56 may be adapted to receive the nares portion 20 by having an opening or aperture, such as aperture 46, adapted to receive a protrusion or connector in the nares portion 20, such as connector 30. Alternative connections of the docking station 56 to the nares portion 20 are possible, such as utilizing undercuts or grooves to hold the nares portion 20 in place. A plug 35 may be provided, the plug 35 adapted to plug either the connector 30 or the opening 46.

When the connector 30 of the nares portion 20 is connected to the aperture 46 of the mouth portion, the plug 35 may be placed in the connector 30 to prevent air from pneumatically flowing between the nares portion 20 and the mouth portion 40. The mouth portion 20 may alternatively be adapted to prevent air from pneumatically flowing between the nares portion 20 and the mouth portion 40, by including a valve 55 as illustrated in FIG. 3, the valve 55 selectively opening and closing the opening 46. The patient can selectively operate the valve 55, such as by turning a knob 54 illustrated in FIGS. 2 and 3.

In some embodiments, such as illustrated in FIG. 1-3, the elbow 2 and flexible tube 5 may not be connected to the swivel connector 44, but may instead be replaced with plug 3, which may or may not include the optional vent holes 6.

FIGS. 5-1 to 13 illustrate a modular mask system 1 which includes a mouth portion 40 that includes an alternative connection to nares portion 20. In particular, in the embodiments of FIGS. 5-1 to 13, a nares portion connector 43 is utilized to connect the mouth portion 40 to the nares portion 20. The nares portion connector 43 is adapted to fit over and seal with the nares portion 20, so that the air from the flexible tube 5 may be delivered into the mouth portion 40, and through nares portion connector 43 to the nares portion. The decoupling portion 45 may decouple forces at swivel ring 4, such as tube drag forces, from both the sealing portion 22 of the nares portion 20 and from the sealing portion 42 of the mouth portion 40.

The sealing portion 42 of the mouth portion 40 may include a bottom portion 79, side portions 81, a top portion 85 and a neck portion 87. The bottom portion 79 may be adapted to form a seal with a patient's lower lip or chin area.

The top portion 85 may be adapted to form a seal with the patient's upper lip area. The side portions may be adapted to form a seal with the patient's face on side areas of the patient's mouth. The side portions 81 extend between the bottom portion 79 and the top portion 85. The neck portion 87 connects the top portion 85 to the nares portion connector 43. The sealing portion 42 transitions from the top portion 85 sweeping into the neck portion 87, with the neck portion 42 being narrower than the top portion 85 to conform to the size and shape of the nares portion connector 43. By having the narrower neck portion 42, the pressure and flow of air into the sealing portion 42 may be improved.

FIGS. 14 and 15 illustrate a mask system 101 that includes the mouth portion 140. The mouth portion 140 may include a structural portion 147, a mouth sealing portion 142, decoupling portion 145, headgear connectors 141 for connecting to headgear, and vent 103, which may include one or more vent holes or slots for venting gas exhaled by the patient. A nares portion connector 143 for connecting to the nares portion 120 may be utilized when the nares portion 120 and the mouth portion 140 are not formed as a unitary element. Flexible tube 105 may be connected to the mouth portion 140 via an elbow 102. Structural portion 147 may be constructed and arranged to stiffen the outer perimeter of the sealing portion to the shape of the sealing portion is maintained and sufficient sealing force is applied to the patient's face.

FIGS. 16 to 18 illustrate a mask system 201 that includes the mouth portion 240. The mouth portion 240 includes a mouth seal portion 242 which may be in the form of a cushion for sealing with the mouth of the patient, a frame 247, a mouth orifice 246 for receiving the pressurized, breathable air, a decoupling portion 245, and a nares connecting portion 243 for connecting with the nares portion. FIG. 16 is illustrated with the frame 247, the decoupling portion 245 and the connecting portion 243 removed. Although not illustrated, the mouth portion may include connection to a flexible tube for delivery of the pressurized, breathable gas, such as the swivel connector, elbow and flexible tube illustrated in other embodiments.

FIGS. 21 and 22 illustrate a modular mask system 301 that includes a mouth portion 340. The mouth portion 340 includes decoupling portion 345, opening 348 and connector 349. The connector 306 is adapted to connect to either opening 326 in the nares portion 320 as illustrated in FIG. 21 or to opening 348 in the mouth portion 340 as illustrated in FIG. 22. The connector 349 of the mouth portion is adapted to connect to opening 326 in nares portion 320, when the mask 301 is utilized in a nares and mouth mode. A plug may be provided to plug the connector 349 when the mask 301 is utilized in a mouth only mode.

The mask system 375 illustrated in FIG. 23 may include a mouth portion 380. The mouth portion 380 may include a mouth sealing portion 375, and may be adapted to connect to headgear 360, and to connect to nares portion 372. The mask system may include air delivery conduit or tube 379 which may be integrated into the headgear. The air delivery tube 379 thus eliminates the need for an elbow connected to the mouth portion 380, providing a "ducted" air delivery and giving the mask system 375 a more streamlined look.

The mask system 401 illustrated in FIG. 24 includes a mouth portion 440. The mouth portion 440 includes a mouth sealing portion 442, headgear connectors 441 for connecting to headgear 460 and a decoupling portion 445. The swivel connector 444 may connect the mouth portion 440 to elbow 402 and flexible hose 405, which delivers pressurized, breathable gas to the mask system 401.

The mask system 501 illustrated in FIG. 25 includes a mouth portion 540. The mouth portion 540 includes a mouth sealing portion 542, headgear connectors 541 for connecting to headgear 560, swivel connector 544 and foam patient contacting portion 569. The foam may be placed around a perimeter of the mouth sealing portion 542, but optionally could be placed only at selected portions, e.g., just at a top lip portion for comfort. Silicone or another sealing means could be placed in the areas around the perimeter of the mouth sealing portion 542 not containing the foam. The mouth portion may 540 also include an optional decoupling portion 545. The swivel connector 544 may connect to elbow 502 and flexible hose 505, which delivers pressurized, breathable gas to the mask system 501. The foam patient contacting portion 569 may contact with and form a seal with the upper lip area of the patient, and thus form part of the mouth seal.

The mask system 701 illustrated in FIG. 34 includes a mouth portion 740. The mouth portion 740 may include a mouth sealing portion 742, a decoupling portion 745 and headgear connectors 741 for connecting to headgear 760. A swivel ring or other connector 744 may also be used to connect to flexible hose 705 via double elbow 712.

1.3 Sealing Portions

The sealing portion may consist of at least two portions: a nares sealing portion and a mouth sealing portion. By providing at least a nares sealing portion and a mouth sealing portion, the patient may receive pressurized breathable gas selectively through their nose and/or mouth.

The nares sealing portion may function independently of the mouth sealing portion. Therefore, in some embodiments, the patient may remove the mouth sealing portion by removing the mouth portion and use only the nares portion with the nares sealing portion if desired. The mouth sealing portion may function independently of the nares sealing portion. Thus, in some embodiments, the patient may remove the nares portion and the nares sealing portion and use only the mouth portion and the mouth sealing portion.

The nares sealing portion and the mouth sealing portion may both need to form a seal with the upper lip of the patient. However, due to the limited amount of surface area in which to position the nares sealing portion and the mouth sealing portion in the upper lip region, the various embodiments utilize structural elements to accomplish sealing of both the nares sealing portion and the mouth sealing portion in the upper lip region of the patient.

The mouth sealing portion may fit a wide range of the population. The mouth sealing portion may have a single size that fits most people. However, the mouth sealing portion may be provided in various sizes to accommodate a wide range of the population. The mouth seal may be lengthwise adjustable to accommodate the varying anthropometric range of the population.

The nares sealing portion may fit a wide range of the population. Preferably, the nares sealing portion may be provided in one or two sizes to accommodate a wide range of the population.

1.3.1 Nares Sealing Portion

The nares sealing portion is adapted to provide a comfortable and effective seal with the nares of a patient.

The nares sealing portion may be in the form of pillows, prongs, a membrane seal such as a nasal cradle, and/or a nasal chamber.

The nares sealing portion may be the pillows seal such as disclosed in PCT Application No. WO 2009/052560 A1, which is incorporated herein by reference in its entirety.

Preferably the nares sealing portion may be flexible and compliant so as to conform to the shape of the patient's nose and/or nares in use.

Preferably the nares sealing portion may be constructed from a polymer such as silicone, thermoplastic elastomer, thermoplastic urethane. Alternatively the nares seal portion may be constructed of foam, gel, fabric or other compliant material. Alternatively, the nares sealing portion may be constructed of a combination of materials such as a foam and fabric lamination, fabric and polymer combination or any other combination of the afore mentioned materials.

As illustrated in FIGS. 1-1 to 4, embodiments of the present technology may include a nares sealing portion 22 in the form of a pillows or prongs type nares seal. The nares sealing portion 22 may alternatively be a membrane type nares seal or a nasal chamber. Nares sealing portion 22 is adapted to form a seal with the nares of a patient in use. Nares sealing portion 22 may be positioned to sit underneath the patient's nose, and be shaped to form an effective seal.

As illustrated in FIGS. 19 and 20, a nares portion 220 may include nares sealing portion 222, a support membrane 252, a supporting portion 253, and headgear connectors 230 with headgear tabs 231 for connecting to headgear. All of the embodiments disclosed herein may use a nares sealing portion in the form of the nares sealing portion 222 when utilized with a membrane type nares portion.

The nares sealing portion 222 may include a nose tip engagement portion 254, an upper lip engagement portion 256, and thickened corner regions 258. The supporting portion 253 may include rear thickened portions 262 and front thickened portions 260. A higher stiffness material in portions of the supporting portion 253 may be used instead of or in addition to the thickened portions 260 and 262 to provide additional support in these areas. The front thickened portions 260 are positioned adjacent to an area of the sealing portion that contacts with sides of the patient's nose in use, and transfer headgear load into a pinch force on the sides of a patient's nose to provide an effective seal. The front thickened portion 260 may have a thickness that increases from a top to a bottom. The rear thickened portions 262 may include a lower portion 266 having a first thickness and an upper portion 264 having a second thickness greater than the first thickness.

The nose tip engagement portion 254 is formed as a hanging, flexible membrane. The sides of the sealing portion 222 are connected to or bonded to the supporting portion 253, while there is a front gap between a central portion of the sealing portion 222 and the supporting portion 253 between front anchor points 257. By utilizing this hanging, flexible membrane, the nose tip engagement portion 254 provides a flexible surface that remains in tensile contact with the nose during patient interface movement, and better accommodates varying nose geometries. The nose tip engagement portion 254 engages with and seals with the patient's nose, and stretches towards the supporting portion 253. The sides of the sealing portion 222 engage with and seal with the sides of the patient's nose.

The sealing portion 222 includes an upper lip engagement portion 256 that engages with a patient's upper lip in use. The upper lip engagement portion 256 is formed as a hanging, flexible membrane, with a rear gap between the upper lip engagement portion 256 of the sealing portion 222 and the supporting portion 253. The rear gap is positioned between rear anchor points 259 that anchor the sealing portion 222 to the supporting portion 253. The flexible, hanging membrane provides a flexible surface that remains in tensile contact with the upper lip of the patient during patient interface movement, and can stretch to accommodate varying facial geometries by allowing movement of the upper lip engagement portion 256.

The rear thickened portions 262 may have a curved portion 268. The rear thickened portions 262 may include a cored out portion 270 to reduce a bulk of the silicone and to reduce a curing time. The rear thickened portions 262 are positioned directly below the thickened corner regions 258 of the sealing portion 222, as may be seen in FIG. 20. When utilized with headgear connectors such as illustrated in FIGS. 24 and 25, the rear thickened portions 262 transfer a load from the headgear connectors to the thickened corner regions 258 and to the lower corners of the patient's nose to aid in providing an effective seal, and when the headgear is tensioned, the transfer of load to the lower corners of the patient's nose is increased. The bending force from the headgear connectors is transferred in use by the rear thickened portions 262 to the thickened corner regions 258 of the sealing portion 222 to apply a sealing force as an anchor force to regions of the patient's nose adjacent the nasal labial creases.

The nares sealing portion 222 is structured to extend or curve outwardly from a supporting wall 221 formed in aperture 226 which defines an air path through the nares portion 220.

Further details of the nares sealing portion 222 are disclosed in WO 2010/139014 A1, which is incorporated herein by reference in its entirety.

All of the embodiments disclosed herein may use a nares sealing portion in the form of a pillows or prongs type nares seal, a membrane type nares seal such as illustrated in FIGS. 19 and 20, or a nasal chamber.

Figure 35:
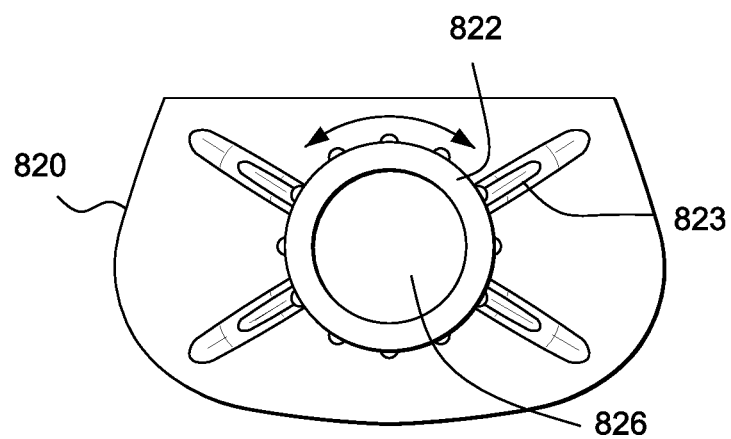
FIG. 35 depicts a front view of a nares sealing portion according to an embodiment of the present technology.
Figure 36:
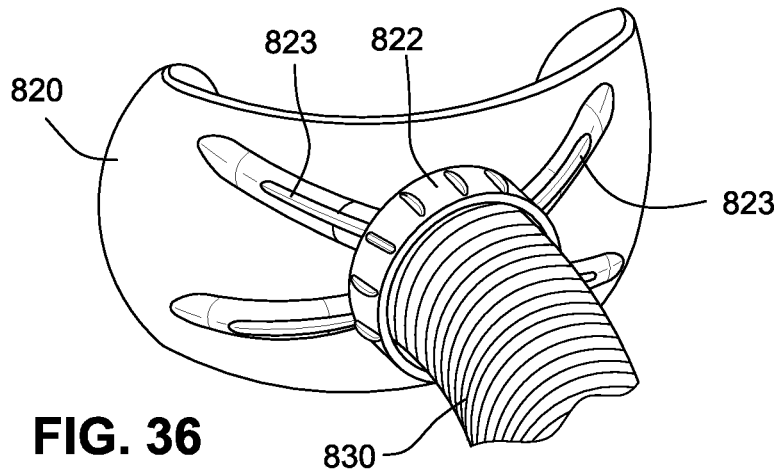
FIG. 36 depicts a front perspective view of the nares sealing portion of FIG. 35 according to an embodiment of the present technology.

FIGS. 35 and 36 illustrate a nares sealing portion 820 that may be utilized to form a seal with a patient's nares to deliver pressurized, breathable gas to the patient's nares via opening 826 and inlet tube 830 in a mask system. The nares sealing portion 820 may be a membrane type nares seal, such as the sealing portion 222 illustrated in FIGS. 19 and 20.

A dial 822 and rigid elements 823 are disposed on a bottom surface of the nares sealing portion 820. There may be four such rigid elements 823, although any number could be used. The rigid elements 823 may be disposed to extend radially from the dial 822, and the dial 822 may be disposed around the opening 826. Turning the dial 822 rotates a beveled gear, causing the rigid elements 823 to move upwards or downwards, in turn causing the sides of the nares sealing portion 820 to move upwards or downwards, increasing or decreasing a pinching force on the sides of the patient's nares in use.

1.3.2 Mouth Sealing Portion

The mouth sealing portion may be adapted to seal with the mouth of a patient. Preferably, the mouth sealing portion may be flexible and compliant so as to conform to the shape of the patient's nose and/or nares in use. The mouth sealing portion may include a membrane that can stretch over the upper lip and chin regions of the patient, i.e. be more flexible than the side regions of the membrane that interface with the cheeks of the patient. The cheeks or side of the mouth region are less sensitive to pressure from the force of the mask so more force can be applied in the cheeks or side region thereby anchoring the mouth portion over the mouth of the patient. Further, the flexibility of the upper lip and chin regions means that the mouth sealing portion is able to flex from a generally planar position to fit flat/pancake faces, and can also fit pointy/angular faces by flexing into a concave position.

Preferably the mouth sealing portion may be constructed from a polymer such as silicone, thermoplastic elastomer, or thermoplastic urethane. Alternatively the mouth seal portion may be constructed of a foam, gel, fabric or other compliant material. Alternatively, the mouth seal portion may be constructed of a combination of materials such as a foam and fabric lamination, fabric and polymer combination or any other combination of the afore mentioned materials.

As illustrated in FIGS. 1-1 to 4, embodiments of the present technology may include a mouth sealing portion 42. Mouth sealing portion 42 is adapted to form a seal with the mouth of a patient in use. Mouth sealing portion 42 may be positioned to sit around the patient's mouth, and be shaped to form an effective seal. The mouth sealing portion 42 may be in the form of a cushion, which forms a rear opening 50 for insertion of the patient's mouth. The cushion may be a soft silicone cushion, which contacts with the patient's mouth area and forms a seal. All of the embodiments disclosed herein may include a mouth sealing portion as described above.

Figure 26:
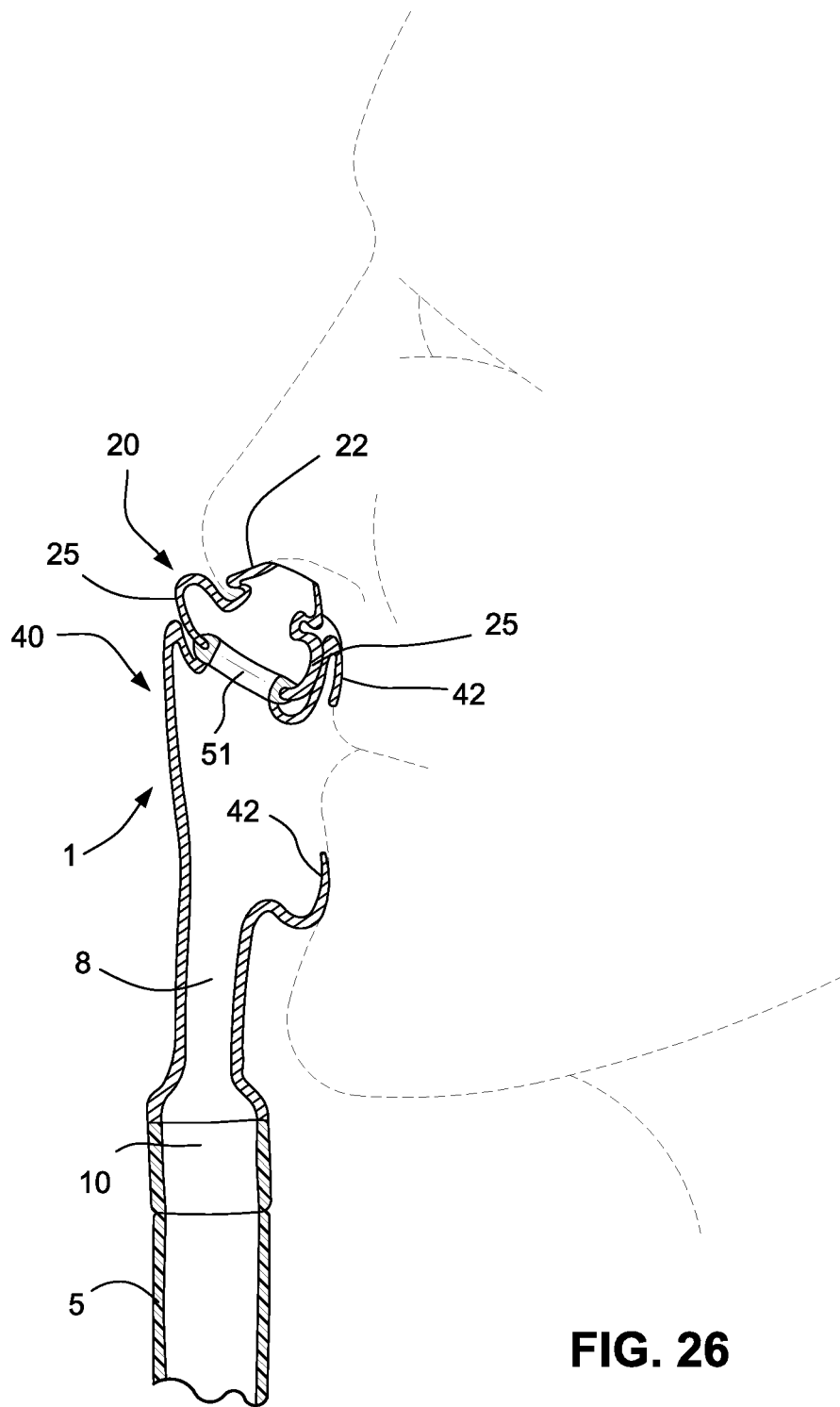
FIG. 26 depicts a schematic cross-sectional view of a modular mask system on a model patient's head according to an embodiment of the present technology.

As illustrated in the schematic cross-sectional view of FIG. 26, the mouth sealing portion 42 may seal with the patient around the patient's mouth, in the areas of the patient's upper lip and an area between the patient's lower lip and the patient's chin. As further illustrated in FIG. 26, the mouth sealing portion 42 may be disposed between the decoupling portion 25 and the patient's upper lip.

Most preferably, the mouth sealing portion may be constructed of a flap seal, such as the one disclosed in U.S. Pat. No. 7,658,189, which is incorporated herein by reference in its entirety. The mouth sealing portion may be constructed of a dual wall seal or a single wall seal.

1.3.3 Decoupling

There may be a decoupling or force absorbing element positioned as part of the nares portion or the mouth portion. A decoupling element may be positioned between a first portion of the nares portion and a second portion of the nares portion, and/or between a first portion of the mouth portion and a second portion of the mouth portion, to prevent movement or forces acting on a the nares or mouth portions from disrupting the seal of the respective sealing portions.

In an embodiment, the decoupling element may be a spring. In another embodiment, the decoupling element may be a gusset or flexible chamber.

As illustrated in FIGS. 1-4, a decoupling portion 25 may be disposed between the nares seal portion 22 and the swivel ring 4. The decoupling portion 25 may be a thin, flexible region of elastic material adapted to absorb force and/or movement by flexing and/or altering its shape. For example, the decoupling portion 25 decouples forces or movement acting on the swivel ring 4 from being transferred to the nares sealing portion 22.

Mouth sealing portion 40 may also include a decoupling portion 45 that may be disposed between the frame 47 and swivel connector 44. The decoupling portion 45 may be a thin, flexible region adapted to absorb force and/or movement by flexing and/or altering its shape. For example, the decoupling portion 45 decouples forces or movement acting on the flexible tube 5, swivel connector 44, and/or the elbow 2 from being transferred to the mouth sealing portion 42, such as tube drag forces, providing a more effective seal with the patient. All of the embodiments disclosed herein may include one or more decoupling portions as described that may be part of the nares portion and/or the mouth portion.

Figure 46:
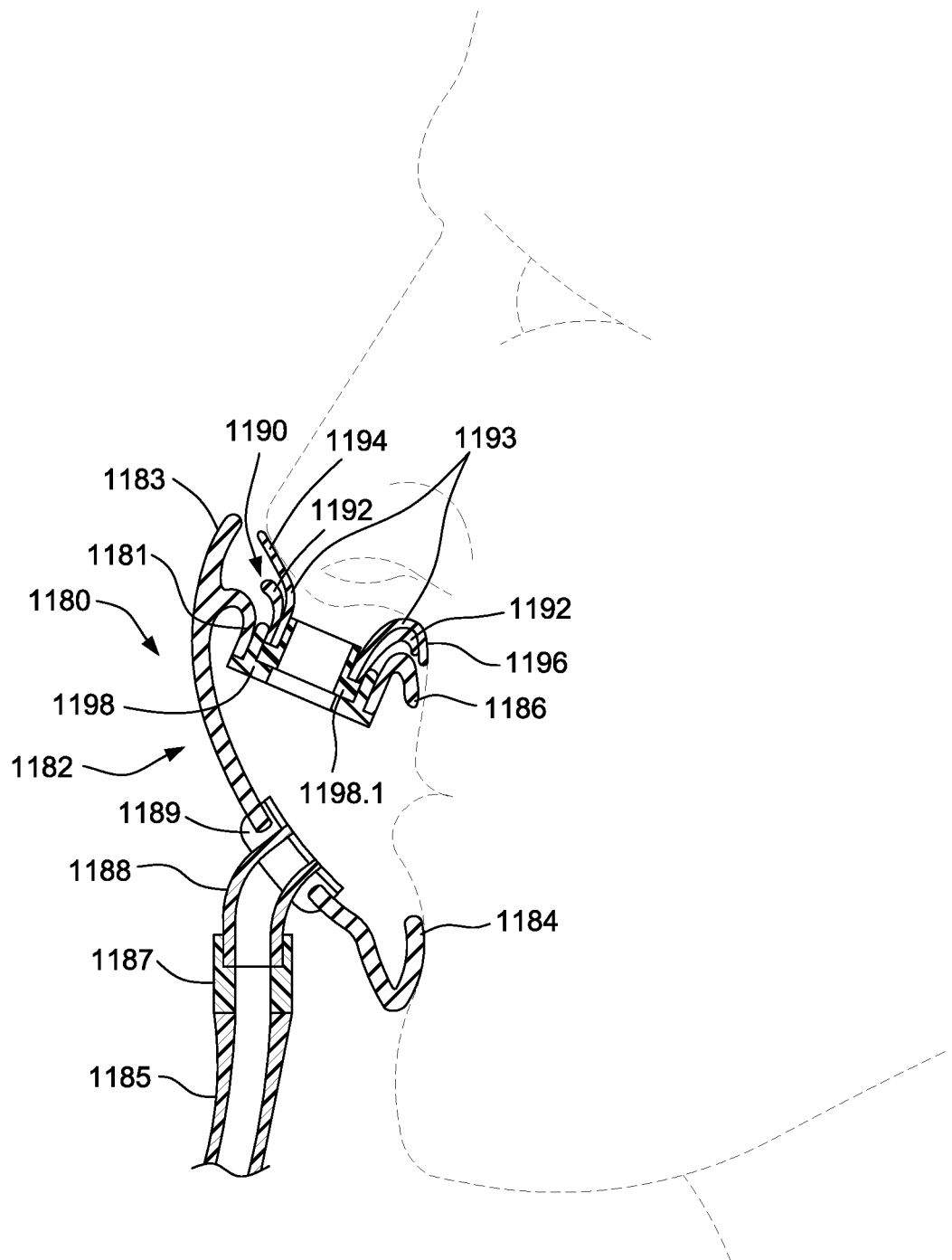
FIG. 46 depicts a schematic cross-sectional view of a modular mask system on a model patient's head according to an embodiment of the present technology.

In the mask system 1180 of FIG. 46, the nares portion 1190 is decoupled from movement in the mouth portion 1182 by decoupling portion 1181. The decoupling portion 1181 allows the nares portion 1190 to remain in sealing engagement with the patient's nares if the air hose 1185 and/or mouth portion 1182 move. The nares portion 1190 may rotate relative to the mouth portion 1182. The covering flap 1183 will move with the air hose 1185 and/or mouth portion 1182.

1.3.4 Relationship between Nares and Mouth Sealing Portions

The sealing portion may be constructed in one piece, with the one piece including the nares sealing portion and the mouth sealing portion.

The sealing portion may be constructed in more than one piece and then may be joined together to operate as a nose and mouth mask. For example, the nares sealing portion may be constructed in a first piece and the mouth sealing portion may be constructed in a second piece, and the first and second pieces may then be joined together.

In a further preferred embodiment, the sealing portions may be constructed in more than one piece, where each piece can be used independently of the other pieces or joined to the other pieces, each arrangement still providing treatment to the patient. For example, the nares portion including the nares sealing portion may be separate from the mouth portion including the mouth sealing portion, and the nares portion including the nares sealing portion can be used without the mouth portion including the mouth sealing portion attached yet still be able to deliver treatment to the patient's nares.

1.3.5 Connection of Nares and Mouth Portions to Headgear

The headgear 60 can connect to each of the nares portion 20 and the mouth portion 40. This is unlike many prior art arrangements where the headgear connects to the mouth portion only and the mouth portion is structured and arranged to adapt the nares portion into sealing engagement with the patient's nose.

As illustrated in FIGS. 1-1 to 13, the nares portion 20 may include headgear connectors 21. The headgear connectors 21 may include headgear tabs 31 that may interface or connect with apertures 62 which may be in the form of a slot or loop on the headgear strap 61.

The mouth portion 40 may include a lower headgear connector 41 for receiving a locking device 64 from lower headgear strap 63.

Alternative connecting devices are possible for the nares portion 20 and the mouth portion 40. For example, hook and loop type connections, push fit connections, interference fits, ball and socket joints, etc. may be used.

1.4 Positioning and Stabilizing Structure

The positioning and stabilizing structure in the form of headgear 60 may be adapted to maintain the mask system in sealing engagement with the nares and mouth of a patient. The headgear 60 may include straps adapted to secure the position of the headgear 60 on the head of the patient. The straps may include a side strap headgear strap 61, a lower headgear strap 63, a rear headgear portion 65 and a crown headgear portion 66. The straps may also direct a tension force on the mask adapted to seal the mask with the face of the patient.

1.4.1 Headgear Side Portion

FIGS. 1-1 to 1-3 and 5-1 to 7 show a headgear 60 in use. Side headgear straps 61 may be adapted to be positioned over the cheeks, underneath the eyes and above the ears of the patient. Side headgear straps 61 may be connected to the headgear connectors 21 of the nares portion 20.

Side headgear straps 61 may include side headgear connectors 62 for connection with the headgear connectors 21 of the nares portion 20. Side headgear connectors 62 may be in the form of a loop for capturing on the headgear tabs 31 on the nares portion 20. Any connection method may be possible, for example hook and loop connection, clips, push fit tabs. Alternatively, side headgear straps 61 may be integrally formed with nares portion 20.

Side headgear straps 61 may preferably be constructed of a flexible material that may be lengthwise stretchable. Side strap 61 may be constructed of a fabric, foam, foam and fabric composition, silicone, nylon, elastic, or any other flexible material.

Side headgear straps 61 may provide an upwards vector to the mask system 1 to assist in maintaining the mask system 1 in the desired position. The upwards vector may be angled upwards with respect to a vector applied by the lower headgear strap 63.

1.4.2 Headgear Crown Portion

Headgear 60 may further include a crown strap portion or top strap 66 that may be adapted to be positioned in use over the top or crown of the patient's head. Crown strap portion 66 may provide an upwards vector to the mask system to assist in maintaining the mask system in the desired position.

Crown strap portion 66 may be continuous with or otherwise connected to side headgear strap 61. Crown strap portion 66 and/or side headgear strap 61 may further include strap loop 68. Strap loop 68 may be structured to receive a rear portion 65.

Crown strap portion 66 may further include adjustment mechanism (such as a buckle). The adjustment mechanism may be that described in WO 2009/052560 A1, which is incorporated herein by reference in its entirety.

Crown strap portion 66 may preferably be constructed of a flexible material that may be lengthwise stretchable. Crown strap portion 66 may be constructed of a fabric, foam, foam and fabric composition, silicone, nylon, elastic, or any other flexible material.

1.4.3 Headgear Lower Portion

Headgear 60 may further include lower headgear strap 63, which may connect to the mouth portion 40 of the mask system 1. Lower headgear strap 63 may direct a tension force on the mouth portion 40 to provide a vector force normal to the patient's face and hence sealing of the mouth portion 40 on the patient's face.

Lower headgear strap 63 may be a strap that is directed substantially under the ears of the patient.

Lower headgear strap 63 may connect or be otherwise formed with headgear rear portion 65.

1.4.4 Headgear Rear Portion

Headgear 60 may further include a rear portion or strap 65. Rear portion 65 may be continuous with or otherwise attached to side headgear strap 61 or crown strap portion 66. Rear portion 65 may be threaded through strap loop 68, and positioned above the ears of the patient. Rear portion 65 may travel down the sides of the patient's head in use and capture the occiput to anchor the headgear 60 in position. Rear portion 65 may further attach to a lower headgear strap 63 at connecting region 67.

Rear portion 65 may provide a downwards and rearwards (i.e. away from the patient's face) vector to balance the upwards vector of the crown strap portion 66, and assist in pulling the mask system 1 into sealing engagement with the patient's face.

Figure 7:
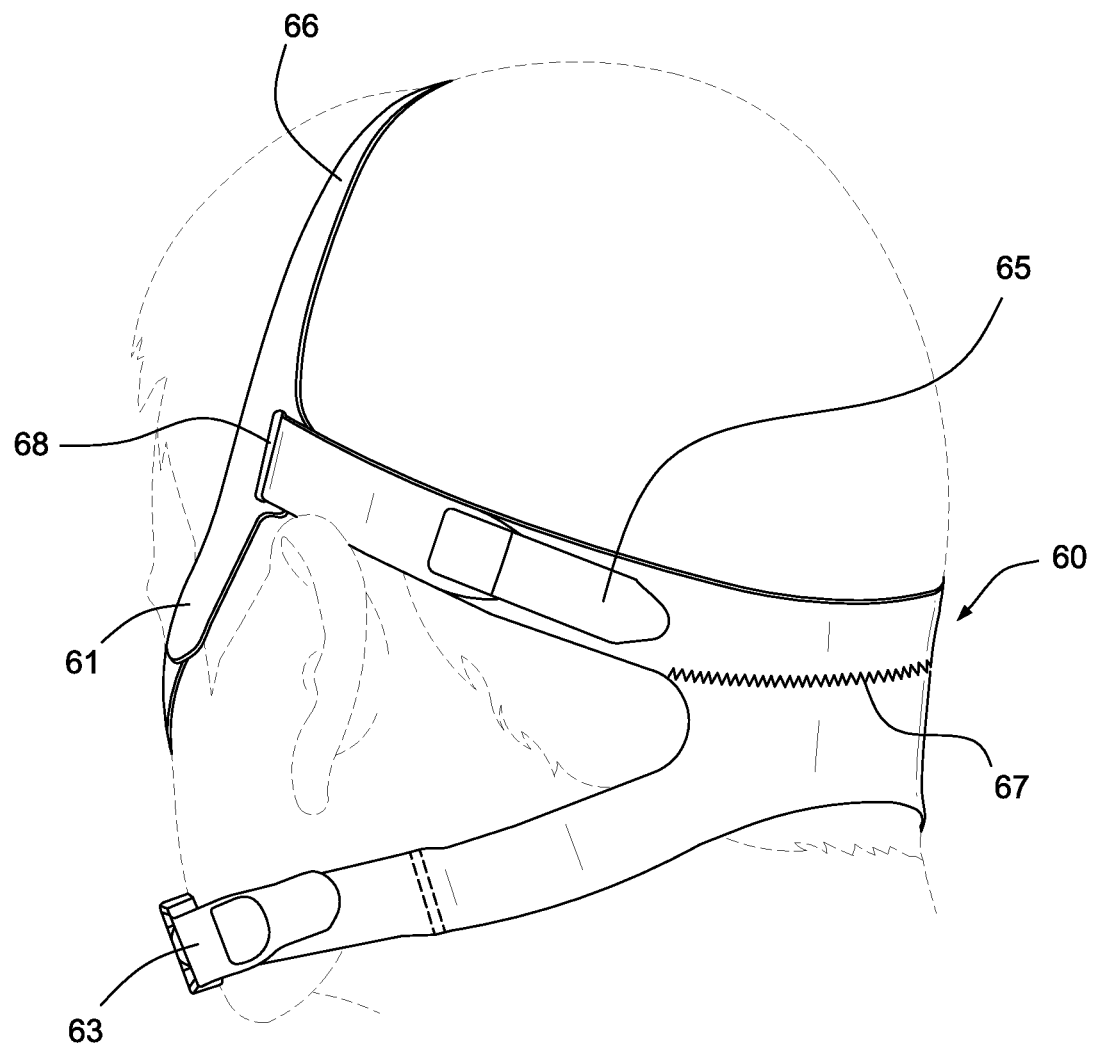
FIG. 7 depicts a rear isometric view of a headgear utilized with the mask system of FIG. 5-1 according to an embodiment of the present technology.
Figure 8:
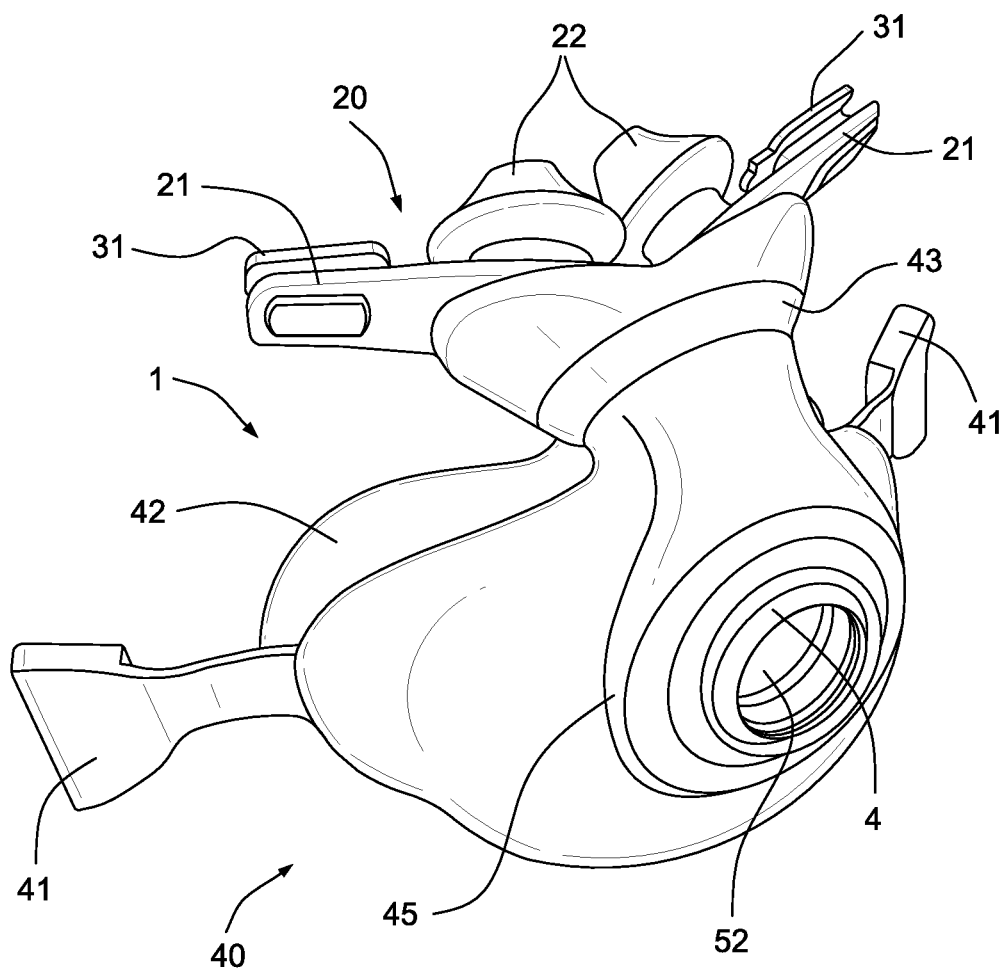
FIG. 8 depicts a front isometric view of the mask system of FIG. 5-1 without the elbow connector according to an embodiment of the present technology.
Figure 9:
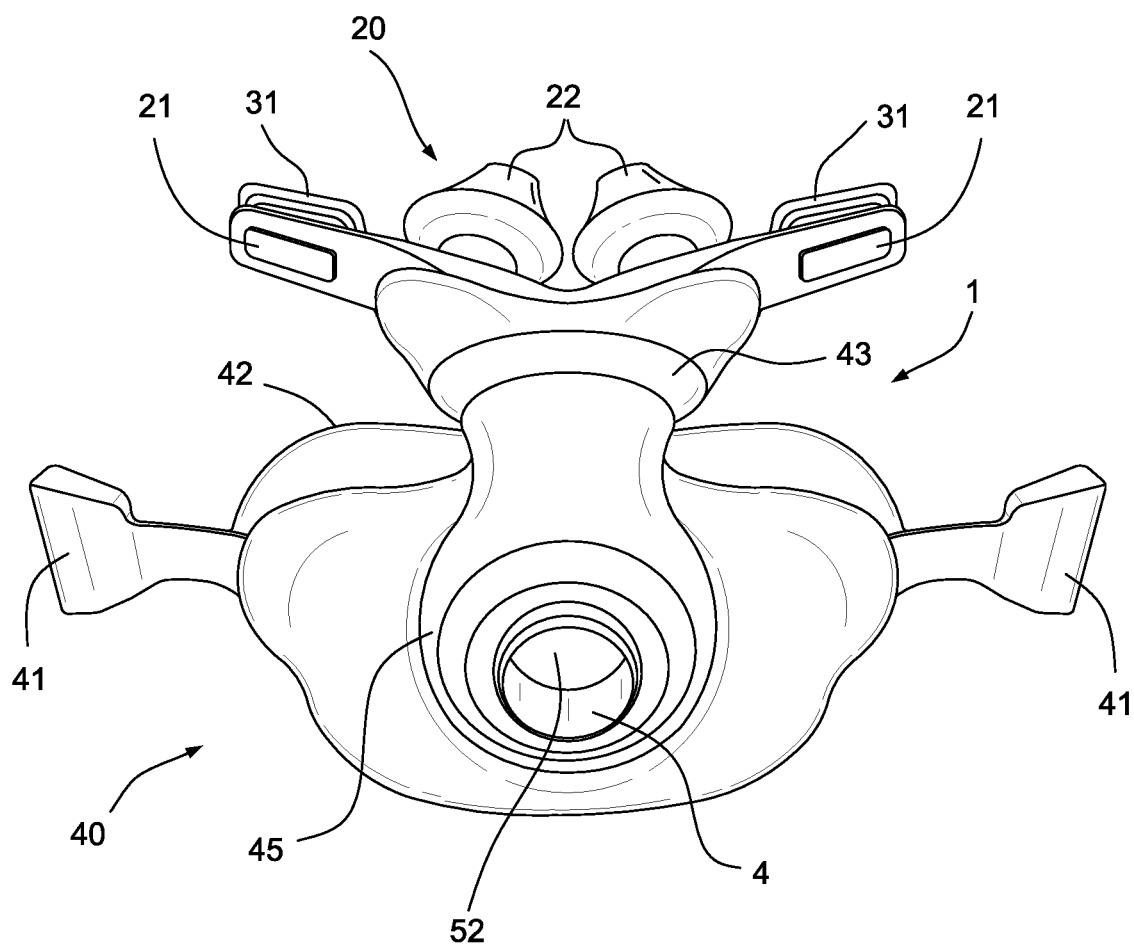
FIG. 9 depicts a front view of the mask system of FIG. 5-1 without the elbow connector according to an embodiment of the present technology.
Figure 10:
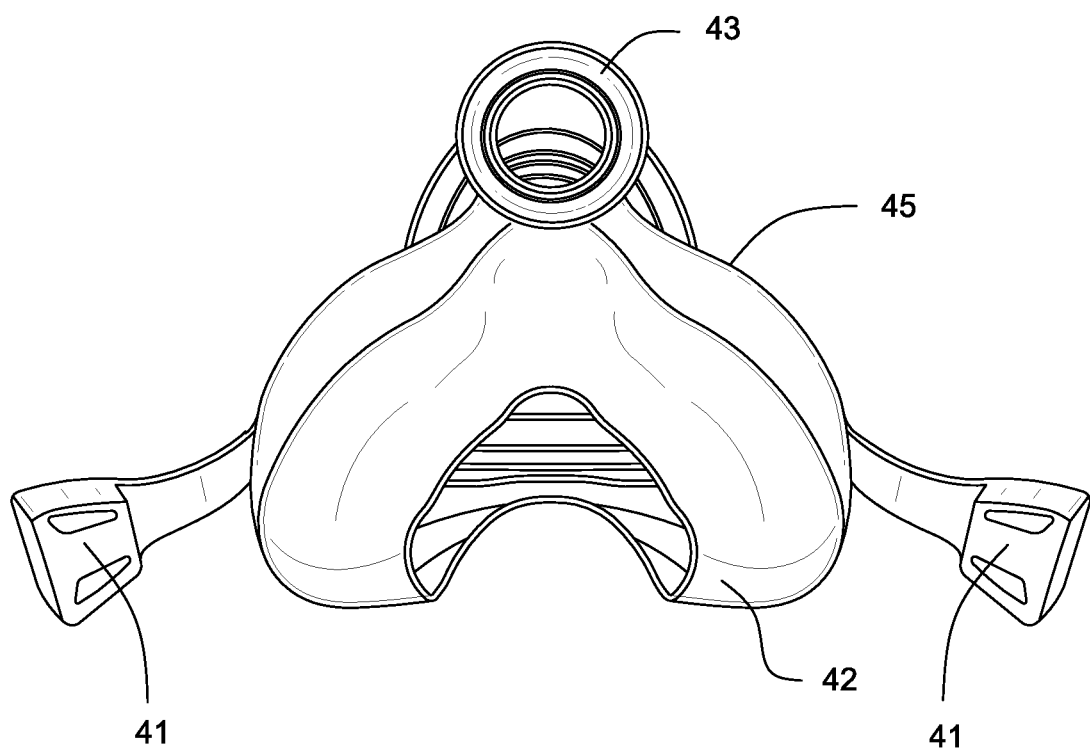
FIG. 10 depicts a top view of the mask system of FIG. 5-1 without the nares portion according to an embodiment of the present technology.
Figure 11:
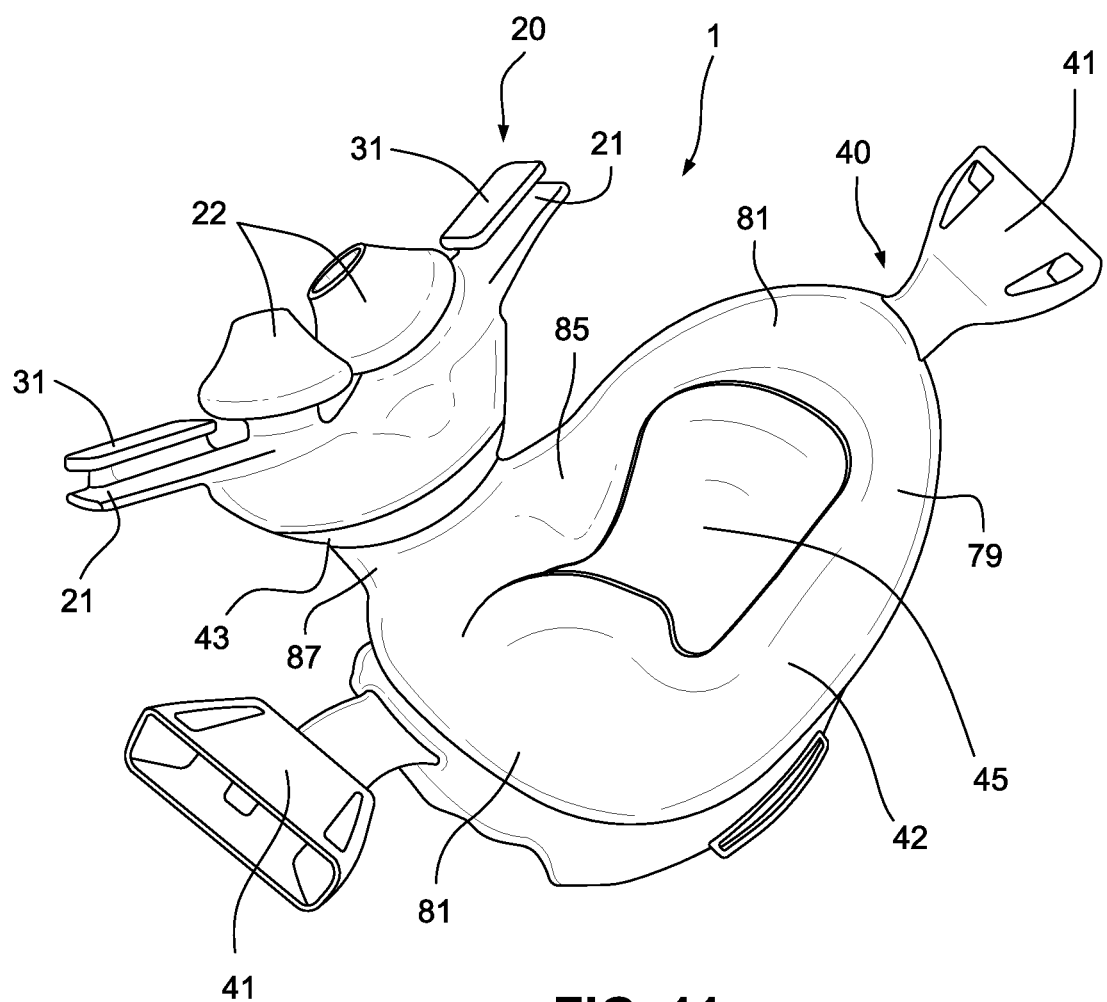
FIG. 11 depicts a rear isometric view of the mask system of FIG. 5-1 according to an embodiment of the present technology.
Figure 12:
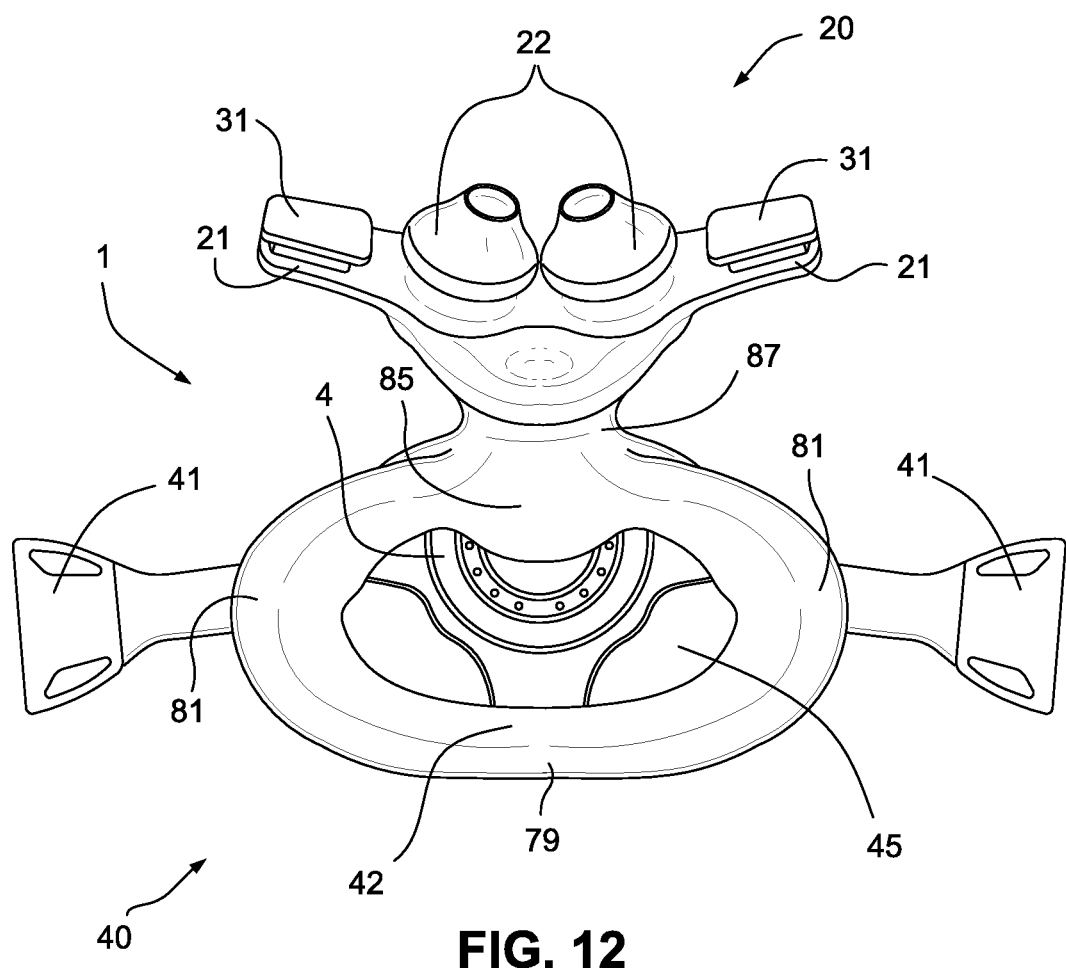
FIG. 12 depicts a rear view of the mask system of FIG. 5-1 according to an embodiment of the present technology.

Rear portion 65 may be secured in position under the patient's occiput by attachment to a lower strap 63 (see FIG. 7). Attachment may be at connection region 67. Connection region 67 may comprise a stitched join, hook and loop join or any other join. Connection region 67 may also be a permanent join such that rear portion 65 and lower strap 63 are formed in one piece.

Rear portion 65 may preferably be constructed of a flexible material that may be lengthwise stretchable. Rear portion 65 may be constructed of a fabric, foam, foam and fabric composition, silicone, nylon, elastic, or any other flexible material.

1.4.5 Headgear Options

Figure 33:
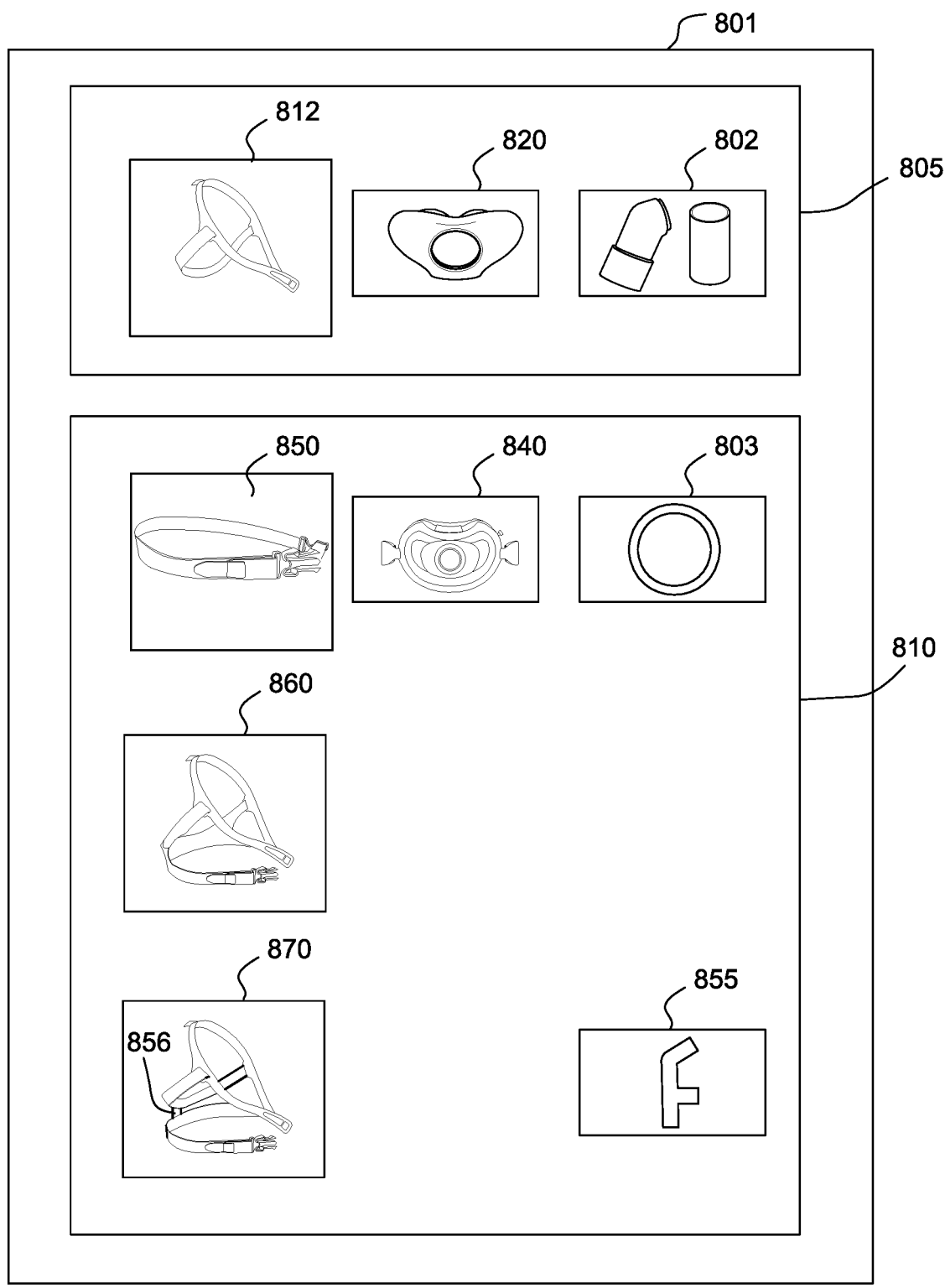
FIG. 33 depicts a schematic view of a nares and mouth kit according to embodiments of the present technology.

The various mask system and kit embodiments may include various headgear options such as illustrated in FIG. 33. For example, when utilized in a nares only mode, nares portion headgear 812 adapted to secure the nares portion to the patient's head may be utilized. When utilized in a mouth only mode, mouth portion headgear 850 adapted to secure the mouth portion to the patient's head may be utilized.

The nares portion headgear 812 utilizes headgear vectors that are angled upwards to align the nares sealing force with the patient's nares. The mouth portion headgear 850 utilizes headgear vectors that are generally oriented in the horizontal plane to align the mouth sealing force with the patient's mouth. The headgear vectors are angled relative to one another in the examples shown in FIG. 33 and FIGS. 37-38. However, in the examples of FIGS. 40-41, the headgear vectors are generally parallel to one another due to the nature of the cushion and the sealing forces involved.

When utilized in a nares and mouth mode, nares portion headgear 812 and mouth portion headgear 850 may be utilized together to secure the nares portion and the mouth portion to the patient's head. Alternatively, nares and mouth portion headgear 860 may be utilized, which includes a connection region in the back portion, such as connection region 67 illustrated in FIG. 7. The nares and mouth portion headgear 860 creates headgear vectors that go back and up along the patient's head to secure the nares portion 820 to the patient's nares, and that go back along the patient's head to secure the mouth portion 840 to the patient's head.

Also, connected nares and mouth portion headgear 870 may be utilized, which includes a connector 856 for connecting the nares only headgear and the mouth only headgear at a back portion. The connector 856 may be a Velcro connector, a hook or loop material connector, or the like. Any of the above described headgear options may be utilized with the various embodiments.

Other alternatives for allowing selective attachment and detachment are possible, see, e.g., FIG. 66 described below, which includes a back loop 1622 through which the back strap 1699 extends.

Figure 90:
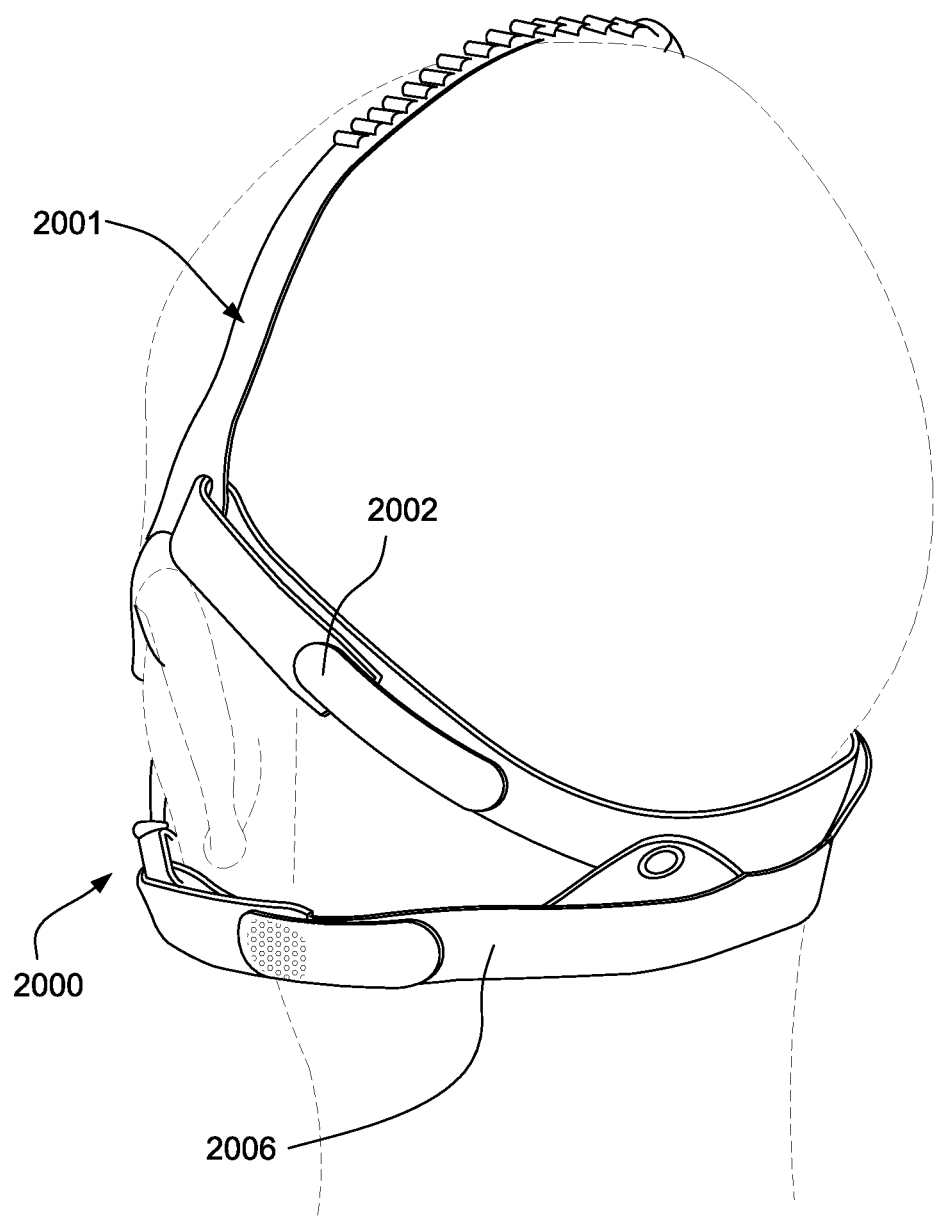
Figure 92D:
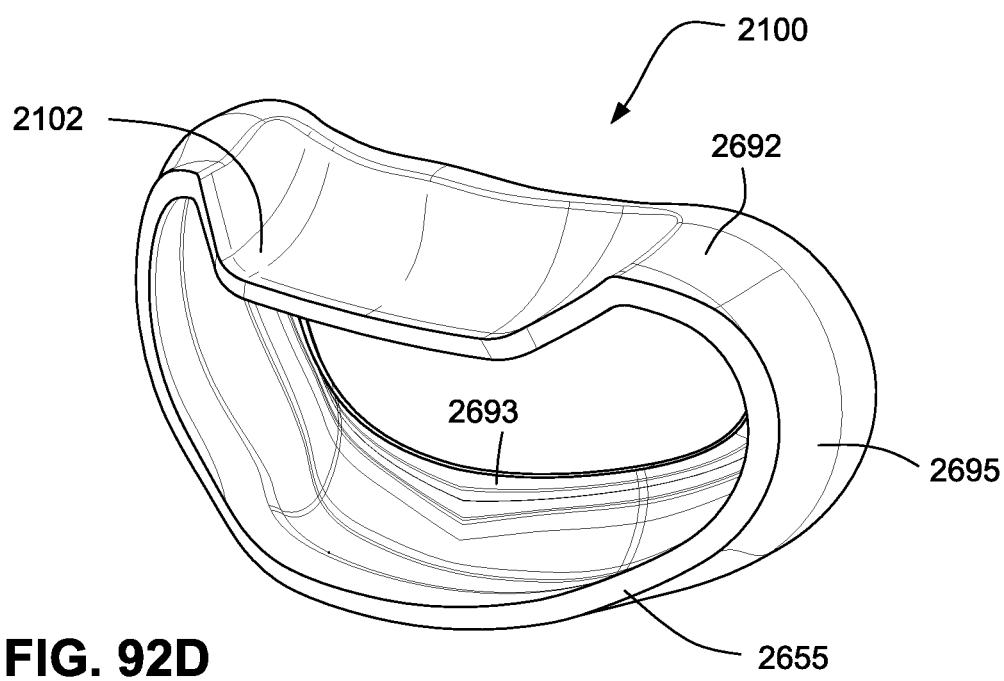
Figure 92E:
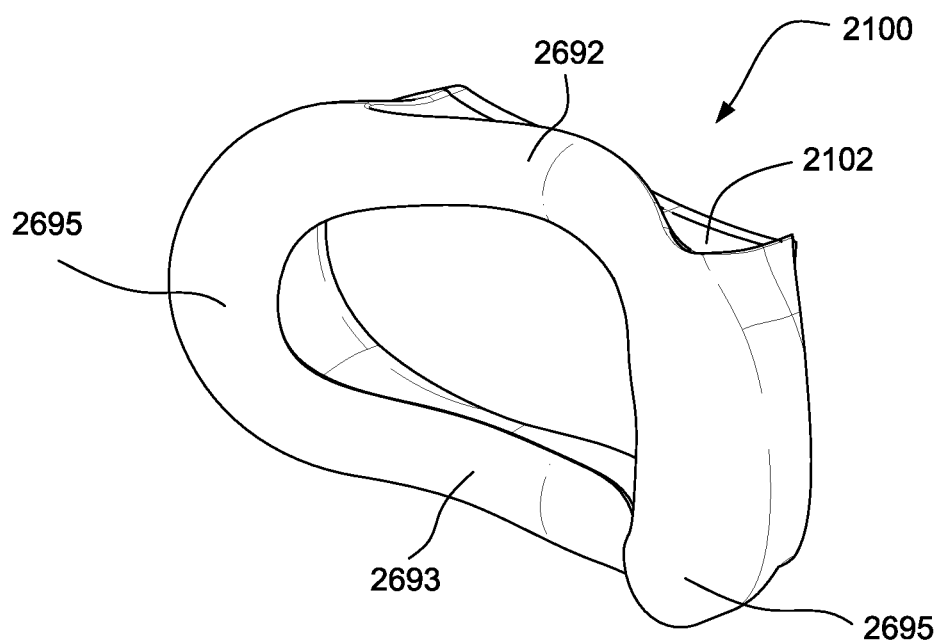

Another variant is shown in FIGS. 90 and 91 which show another option for converting from a two point headgear to a four point headgear. The headgear 2000 includes the two point headgear 2001 as shown in FIG. 33 and FIG. 66, including a pair of front straps to support the mask. In addition, the rear of the headgear 2000 includes the first rear strap 2002 connected to the pair of front straps and a second rear strap 2006 that may be connected to the first rear strap, e.g., by a press stud arrangement or snaps. In particular, the first rear strap 2002 may have a male part 2002.1, and the second rear strap 2006 may have a complementary/female part 2006.2, to allow selected attachment and detachment.

1.5 Vent

Embodiments of the present technology may utilize one or more vents in the mask system to vent gas exhaled by the patient. The vent or vents may be disposed to vent exhaled gas from the nares portion 20, from the mouth portion 40 or from the nares portion 20 and the mouth portion 40.

For example, a plug 3 is included on nares portion 20 and may include a vent 6 to vent exhaled gas from the patient's nares. Another vent 6 may optionally be included on the elbow 2 connected to the mouth portion 40, to vent exhaled gas from the patient's mouth. Either of the vents 6 may be excluded, particularly if one of the nares portion 20 or the mouth portion 40 is to be used as a sealed portion, e.g., a portion not delivering breathable gas to the patient.

Figure 6:
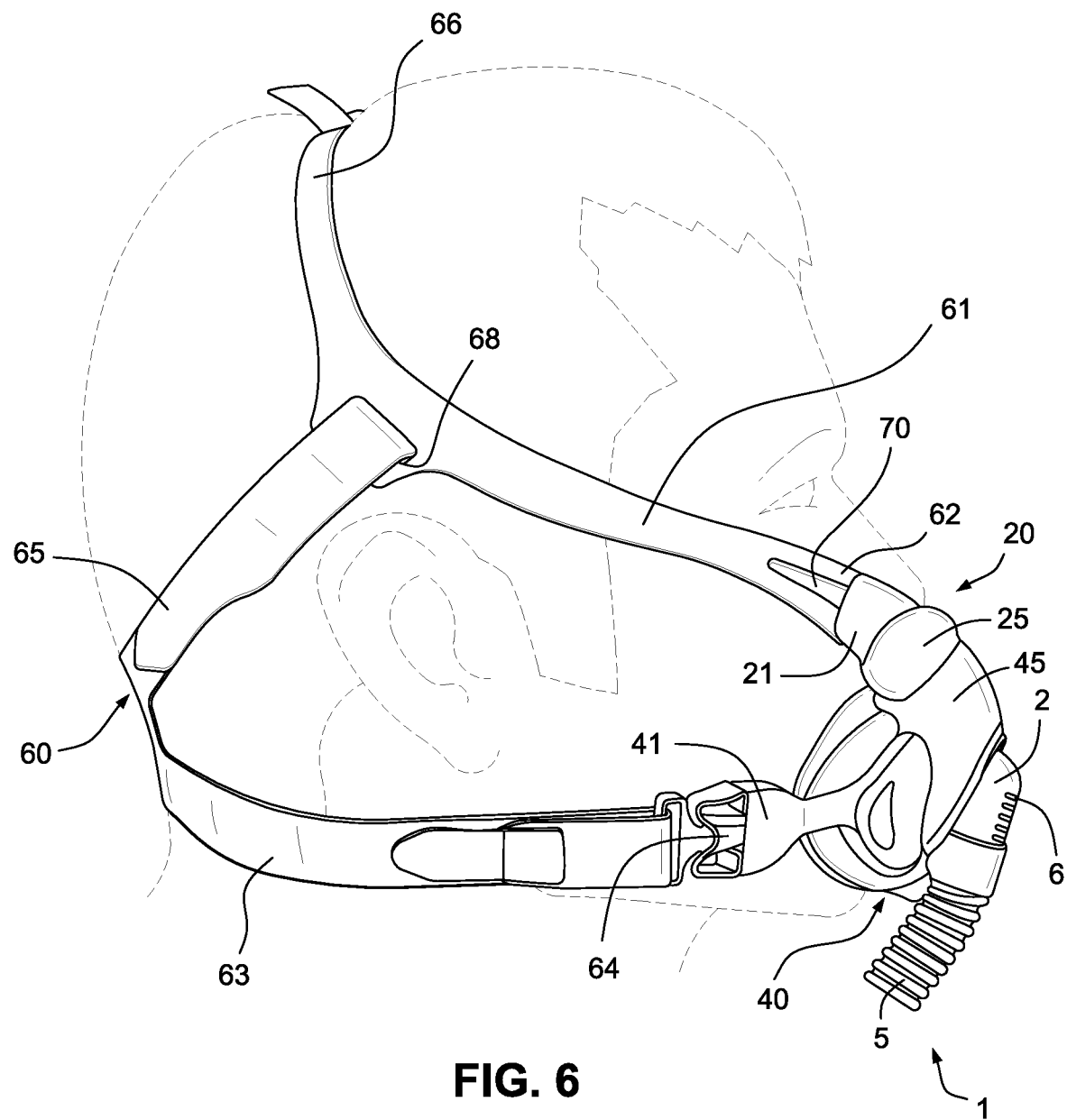
FIG. 6 depicts a side view of the mask system of FIG. 5 in use according to an embodiment of the present technology.

The vents 6 may be in the form of a series or array of individual vent holes. Alternatively, the vent 6 may be in the form of one or a series of slots, such as illustrated in FIGS. 5 and 6, or another aperture or apertures.

1.6 Air Delivery System

Air delivery in the form of pressurized, breathable gas is delivered to the mask system 1 through the flexible tube 5. The flexible tube 5 is coupled to a blower/humidifier or other air delivery device, which is adapted to deliver the pressurized, breathable gas to the patient to provide therapy.

1.7 Modular Mask System

The mask system embodiments disclosed herein may be modular mask systems, including a nares portion, a mouth portion and headgear. The modular mask systems may be adapted to allow a patient to selectively utilize the nares portion and/or the mouth portion in a first mode and in a second mode. In the first mode, the patient may utilize both the nares portion and the mouth portion. In the second mode, the patient may utilize only the nares portion without utilizing the mouth portion.

Some of the embodiments may also allow the modular mask system to be utilized in a third mode, where the mouth portion is utilized, and the nares portion is not utilized. In embodiments that provide the third mode, the mouth portion is utilized to provide air to the patient's mouth, while the nares portion is not utilized and not worn by the user. In addition, in some embodiments, the nares portion and the mouth portion may be adapted to allow air to freely flow between the chambers of the nares portion and the mouth portion, such as an opening and/or a connector between the chambers. Some embodiments may include a plug or a selectively operated valve that may be used to plug the opening or connector to prevent air from flowing between the nares portion and the mouth portion. The plug may also be used to plug the opening or connector when the nares portion or the mouth portions are used alone. All of the modular mask systems may alternatively be formed as integrated mask systems, where the nares portions are not separable and individually useable from the mouth portions.

FIGS. 32(a) to 32(k) are schematic illustrations of a nares portion 20 and a mouth portion 40 utilized with the various modes. In the first mode, the patient may utilize both the nares portion and the mouth portion, as illustrated in FIGS. 32(e), 32(f), 32(g), 32(h) and 32(k), by utilizing the nares portion 20 to deliver air to the patient's nares while utilizing the mouth portion 40 to deliver air to the patient's mouth. In FIG. 32(e), the nares portion 20 and the mouth portion 40 do not include a connection between the chambers of the nares portion and the mouth portion, and the pressurized air is applied separately to both the nares portion 20, which delivers the air to the patient's nares, and to the mouth portion 40, which delivers the air to the patient's mouth. In FIG. 32(f), there is a connection between the chambers of the nares portion 20 and the mouth portion 40. The pressurized air is applied to the chamber of the mouth portion 40, and flows through the mouth portion 40 to the patient's mouth, and flows from the mouth portion 40 through the connection to the nares portion 20 and to the patient's nares.

In FIG. 32(g), there is a connection between the chambers of the nares portion 20 and the mouth portion 40. The pressurized air is applied to the chamber of the nares portion 20, and flows through the nares portion 20 to the patient's nares, and flows from the nares portion 20 through the connection to the mouth portion 40 and to the patient's mouth. In FIG. 32(h), there is a connection between the chambers of the nares portion 20 and the mouth portion 40. The pressurized air is applied to the chamber of the nares portion 20 and to the chamber of the mouth portion 40, and may flow through the connection between the nares portion 20 and the mouth portion 40. In FIG. 32(k), there is a connection between the chambers of the nares portion 20 and the mouth portion 40, but the connection is blocked by a plug, a valve or the like. The pressurized air is applied to the chamber of the nares portion 20 and to the chamber of the mouth portion 40, and flows through the nares portion 20 to the patient's nares and through the mouth portion 40 to the patient's mouth.

In the first mode, the patient may also utilize both the nares portion 20 and the mouth portion 40, as illustrated in FIGS. 32(c) and 32(i) by utilizing the nares portion 20 as a nares seal while utilizing the mouth portion 40 to deliver air to the patient's mouth. In FIG. 32(c), there is no connection between the nares portion 20 and the mouth portion 40, and the pressurized air is delivered through the mouth portion 40 to the patient's mouth, while the nares portion is utilized as a nares seal. In FIG. 32(i), there is a connection between the nares portion 20 and the mouth portion 40, but the connection is blocked by a plug, a valve or the like. The pressurized air is delivered through the mouth portion 40 to the patient's mouth, and the nares portion 20 is utilized as a nares seal.

In the first mode, the patient may utilize both the nares portion 20 and the mouth portion 40, as illustrated in FIGS. 32(d) and 32(j), by utilizing the nares portion 20 to deliver air to the patient's nares while utilizing the mouth portion 40 as a mouth seal. In FIG. 32(d), there is no connection between the nares portion 20 and the mouth portion 40, and the pressurized air is delivered through the nares portion 20 to the patient's mouth, while the mouth portion 40 is utilized as a mouth seal.

In the second mode, as illustrated in FIG. 32(a), the nares portion 20 is used alone to deliver air to the patient's nares, while the mouth portion is not used and is not worn by the patient. In embodiments that utilize a connection allowing air to flow between the nares portion and the mouth portion, when the nares portion 20 is utilized alone, a plug, a valve or the like may be utilized to plug the opening.

In the third mode, as illustrated in FIG. 32(b), the mouth portion 40 is used alone to deliver air to the patient's mouth, while the nares portion 20 is not used and is not worn by the patient. In embodiments that utilize a connection allowing air to flow between the nares portion 20 and the mouth portion 40, when the mouth portion 40 is utilized alone, a plug, a valve or the like may be utilized to plug the opening.

The embodiment of FIGS. 1-1 to 4 is a modular mask system 1, where the nares portion 20 may be used by a patient in a nares only mode without the mouth portion 40, the mouth portion 40 may be utilized by a patient in a mouth only mode without the nares portion 20, and the nares portion 20 may be utilized with the mouth portion 40 in a nares and mouth mode. FIGS. 1-2 and FIGS. 2 to 4 illustrate the mask system 1 in a nares and mouth mode where the nares portion 20 is utilized with the mouth portion 40. When utilized in the nares and mouth mode, the mask system 1 may utilize the nares portion 20 to deliver air to the nares of a patient and the mouth portion 40 to deliver air to the mouth of the patient, the mask system 1 may utilize the nares portion 20 to deliver air to the nares of a patient and the mouth portion 40 may be utilized as a mouth seal that does not deliver air to the mouth of the patient, or the mask system 1 may utilize the mouth portion 40 to deliver air to the mouth of the patient and the nares portion 20 may be utilized as a nares seal that does not deliver air to the nares of the patient.

Both the nares portion 20 and the mouth portion 40 are adapted to connect to a source of the pressurized, breathable gas. In particular, in the embodiments of FIGS. 1-2 to 4, both the nares portion 20 and the mouth portion 40 are adapted to connect to a source of the pressurized, breathable gas, such as flexible tube 5 via elbow 2, although only one of the portions may be connected. The flexible tube 5 may be connected to either or both of the nares portion 20 and the mouth portion 40. A connection to both the nares portion 20 and the mouth portion 40 may be made by utilizing a connector such as double elbow 712 illustrated in FIG. 34, for example.

In the embodiments of FIGS. 1-2 and FIGS. 2 to 4, the nares portion 20 and mouth portion 40 are internally connected allowing air to flow therebetween, such as by utilizing the connector 30 in the nares portion connected to the opening 46 in the mouth portion 40, although other connections could be used. If it is desired to prevent the air flowing between the nares portion 20 and the mouth portion 40, the connection may be block by using the plug 35 or the valve 55 activated by the knob 54.

The mask system 1 may be utilized where the pressurized, breathable gas is received by the patient's nares and mouth by connecting the elbow 2 and flexible tube 5 to either of the swivel connector 4 of the nares portion 20 or the swivel connector 44 of the mouth portion 40, and the breathable gas can flow through the connector 30 and opening 46. The mask system 1 can also function as a mouth seal or nares seal, where the connector 30 and/or opening 46 would be blocked, by utilizing plug 35, or by activating the valve with the knob 54, and connecting only one of the nares portion 20 or the mouth portion 40 to the elbow 2 and flexible tube 5. For example, if the elbow 2 and flexible tube 5 are connected to the nares portion 20, and the connector 30 and/or opening 46 are blocked by utilizing plug 35 or by activating the valve 55 with the knob 54, then the pressurized air is delivered to the nares portion 20 and the mouth portion 40 acts as a mouth seal that does not deliver the pressurized air to the patient's mouth. Alternatively, if the elbow 2 and flexible tube 5 are connected to the mouth portion 40, and the connector 30 and/or opening 46 are blocked by utilizing plug 35 or by activating the valve 55 with the knob 54, then the pressurized air is delivered to the mouth portion 40 and the nares portion 20 acts as a nares seal that does not deliver the pressurized air to the patient's nares.

The mask system 1 is also adapted to function in a nares only mode utilizing the nares portion 20 without the mouth portion 40, as illustrated in FIG. 1-1. In this mode, the mouth portion 40 and headgear 63 are not utilized, the plug 3 is removed from the nares portion 20, and the elbow 2 and the flexible tube 5 are connected to the nares portion 20 to deliver the pressurized, breathable gas to the patient's nares. The connector 30 is plugged with plug 35.

The mask system 1 is also adapted to function in a mouth only mode utilizing the mouth portion 40 without the nares portion 20, as illustrated in FIG. 1-4. In this mode, the nares portion 20 along with the headgear 61 are not utilized, and the elbow 2 and the flexible tube 5 are connected via the swivel connector 44 to the mouth portion 40 to deliver the pressurized, breathable gas to the patient's mouth. The opening 46 on the mouth portion is plugged with the plug 35.

FIGS. 5-1 to 13 illustrate another embodiment of a mask system 1 that may be a modular mask system. FIGS. 5-1 and 6-13 illustrate the modular mask system 1 in a nares and mouth mode. The flexible tube 5 is connected via the swivel ring 4 to the elbow 2, to direct the pressurized, breathable gas to the chamber of the mouth portion 40 and to the nares portion 20 via the nares portion connector 43.

The decoupling portion 45 is connected between the swivel ring 4 and both the nares portion 20 and the mouth portion 40. In addition, the nares portion 20 also may include the decoupling portion 25, such that the nares portion benefits from two decoupling portions to decouple forces or movements applied to the flexible tube 5, the elbow 2, and/or the swivel ring 4 from being transferred to the sealing portion 22 of the nares portion 20.

In the embodiments of FIGS. 5-1 to 13, the nares sealing portion 22 may be in the form of nasal pillows such as illustrated in FIGS. 8, 9, 11 and 12, or may be in the form of prongs, a membrane seal such as a nasal cradle, and/or a nasal chamber. For example, the nares portion of FIGS. 5-13 may be in the form of the nares portion 220 illustrated in FIGS. 19 and 20. The supporting portion 252 may or may not be included. When utilizing the nares portion 220, the sealing portion 222 sealing with the patient's nares is structured to extend or curve outwardly from a supporting wall 221 defining an air path through the sealing portion 222, and forms a seal with the nose tip, upper lip and nares of the patient.

As illustrated in FIG. 5-2, the mask system may be utilized in a nares only mode. In this mode, the mask system is utilized with the nares portion 20, and the mouth portion 40 is not utilized by the patient. To convert the mask system from the nares and mouth mode to the nares only mode, the swivel ring 4, the elbow 2 and the flexible tube 5 are removed from mouth portion 40, the mouth portion 40 is removed from connection with the nares portion 20 by disconnecting the nares portion connector 43 from the nares portion 20, and the swivel ring 4, the elbow 2 and the flexible tube 5 are connected to the nares portion. While the headgear 60 illustrated is shown with a connection region 67, the connection region 67 may be omitted to facilitate usage of the mask system 1 in the nares only configuration without the lower headgear strap 63.

FIGS. 21 and 22 illustrate a mask system 301 in accordance with an embodiment of the present technology. The mask system 301 is adapted to be utilized in a nares only mode, in a mouth only mode, or in a nares and mouth mode. The mask system 301 includes a nares portion 320, a mouth portion 340 and headgear 360, connector 306, optional swivel connector 308 and flexible tube 305. The connector 306 may be in the form of an elbow or other type of connector.

The nares portion 320 includes nares sealing portion 322, headgear connectors 321 for connecting to headgear 360, decoupling portion 325 and opening 326. The nares sealing portion 322 may be in the form of pillows, prongs, a nasal chamber, or a membrane seal, and may be in the form of nares sealing portion 222 illustrated in FIGS. 19 and 20. The mouth portion 340 includes decoupling portion 345, opening 348 and connector 349. The connector 306 is adapted to connect to either opening 326 in the nares portion 320 or opening 348 in the mouth portion 340.

As illustrated in FIG. 21, the mask system 301 is adapted to be used by a patient in a nares only mode without the mouth portion 340. Connector 306 is connected to the opening 326 in the nares portion 320. The optional swivel connector 308 may be utilized between the connector 306 and the flexible tube 305, which delivers the pressurized, breathable gas to the nares portion 320.

As illustrated in FIG. 22, the nares only configuration of FIG. 21 may be converted into a nares and mouth configuration by removing the connector 306 from opening 326 in the nares portion 326, connecting connector 349 of the mouth portion to opening 326, and connecting connector 306 to opening 348 in the mouth portion 340. In the nares and mouth configuration, the nares portion may receive the pressurized, breathable gas through the connector 349 and the opening 326. Alternatively, the nares portion 320 may be used as a nares seal by placing a plug in the connector 349, so that the pressurized, breathable air is not delivered to the nares portion 320.

The mouth portion 340 may also be utilized without the nares portion 320 in a mouth only configuration. In the mouth only configuration, the nares portion 320 is not utilized, and a plug is placed in connector 349 to provide a seal.

FIG. 24 illustrates a modular mask system 401 in accordance with an embodiment of the present technology. The mask system 401 includes a nares portion 420, a mouth portion 440, and headgear 460.

The nares portion 420 includes a nares sealing portion 422 for forming a seal with the patient's nares, and headgear connectors 421 adapted to connect to headgear 460. The nares portion 420 is illustrated with a nares sealing portion 422 such as the type illustrated in FIGS. 19 and 20, although other nares sealing portions could be utilized, such as pillows, prongs, a nasal chamber, etc. An optional decoupling portion 425 may be included for decoupling any forces applied to the nares portion 420. The headgear 460 may be the same as the headgear 60 illustrated in FIGS. 1-1 to 4.

The mouth portion 440 includes a mouth sealing portion 442, headgear connectors 441 for connecting to headgear 460, and swivel connector 444. The mouth portion may also include an optional decoupling portion 445. The swivel connector 444 may connect to elbow 402 and flexible hose 405, which delivers pressurized, breathable gas to the mask system 401. The mask system 401 could alternatively be formed as a modular mask system, where the mouth portion 440 is separable from the nares portion 420 and both portions are individually useable, and the flexible tube 405 is connectable via the swivel connector 444 or the like to the nares portion 420. A flexible portion 443 may be disposed between the decoupling portion 425 and the decoupling portion 445. The flexible portion 443 may be a gusset or collapsible portion between the mouth portion 440 and the nares portion 420, which allows the nares portion 420 to adopt the nasolabial angle (the angle between the septum of the nose and the top lip of the patient).

FIG. 25 illustrates a modular mask system 501 in accordance with an embodiment of the present technology. The mask system 501 includes a nares portion 520, a mouth portion 540, and headgear 560.

The nares portion 520 includes nares sealing portion 522 adapted to form a seal with the nares of the patient, and headgear connectors 521 for connecting to headgear 560. The nares portion 520 is illustrated with a nares sealing portion 522 such as the type illustrated in FIGS. 19 and 20, although other nares sealing portions could be utilized, such as pillows, prongs, a nasal chamber, etc. An optional decoupling portion 525 may be included for decoupling any forces applied to the nares portion 520. The headgear 560 may be the same as the headgear 60 illustrated in FIGS. 1-1 to 4.

The mouth portion 540 includes a mouth sealing portion 542, headgear connectors 541 for connecting to headgear 560, swivel connector 544 and foam sealing or patient contacting portion 569. The foam patient contacting portion 569 may be a wedge utilized as at least a part of a portion of the mouth seal. The mouth portion may 540 also include an optional decoupling portion 545. The swivel connector 544 may connect to elbow 502 and flexible hose 505, which delivers pressurized, breathable gas to the mask system 501. The mask system 501 could alternatively be formed as an integrated mask system, where the mouth portion 540 is separable from the nares portion 520 and both portions are individually useable, and the flexible tube 505 is connectable via the swivel connector 544 or the like to the nares portion 420.

FIG. 34 illustrates another modular mask system 701. The mask system 701 includes a nares portion 720, a mouth portion 740, and headgear 760. In this embodiment, the nares portion 720 is in a modular connection with the mouth portion 740, so that the nares portion 720 may be utilized without the mouth portion 740 in a first nares only mode, the mouth portion 740 may be utilized without the nares portion in a second mouth only mode, or the nares portion 720 may be utilized with the mouth portion 740 in a third nares and mouth mode.

The nares portion 720 may include a sealing portion 722 adapted to form a seal with the patient's nares, an optional decoupling portion 725, and headgear connectors 721 for connecting to headgear 760. A swivel ring or other connector 710 may also be utilized. The sealing portion 722 may be in the form of pillows, prongs, a nasal chamber or a nares sealing portion, such as the membrane type illustrated in FIGS. 19 and 20.

The mouth portion 740 may include a mouth sealing portion 742, a decoupling portion 745 and headgear connectors 741 for connecting to headgear 760. A swivel ring or other connector 744 may also be used.

In a mouth and nares mode such as illustrated in FIG. 34, the nares portion 720 and the mouth portion 740 are both utilized and connected to flexible tube 705 through double elbow 712. Double elbow 712 includes two elbow joints so that it may connect to both the nares portion 720 and the mouth portion 740 to deliver the pressurized, breathable air to the patient's nares and mouth. The nares portion 720 and the mouth portion 740 may or may not be connected pneumatically.

In a nares only mode, only the nares portion 720 is utilized and the mouth portion 740 is not utilized. In this mode, the double elbow 712 is removed and the mouth portion 740 is removed. The patient utilizes the nares portion 720 only, and connects the tube 705 to the swivel ring or other connector 710. An elbow such as elbow 2 may be utilized to connect the tube 705 to the swivel ring or other connector 710.

In a mouth only mode, only the mouth portion 740 is utilized and the nares portion 720 is not utilized. In this mode, the double elbow 712 is removed and the nares portion 720 is removed. The patient utilizes the mouth portion 740 only, and connects the tube 705 to the swivel ring or other connector 744. An elbow such as elbow 2 may be utilized to connect the tube 705 to the swivel ring or other connector 744.

FIG. 26 illustrates a schematic cross-section view of a mask system 1 utilized in a nares and mouth mode. In this embodiment, the mouth portion 40 may include a sealing ring 51 adapted to connect and seal the mouth portion 40 to the nares portion 20. Alternatively, the sealing ring 51 may be formed as part of the nares portion 20 and connect and seal with the mouth portion 40. Further, other types of connectors could be utilized or the nares portion 20 and the mouth portion 40 could be formed as a unitary element so that a sealing ring or other type of connector would not be needed.

In FIG. 26, the flexible tube 5 is connected to the mouth portion 40 via a gusset 8 and an optional inline AAV (anti-asphyxia valve) adaptor 10, and does not utilize the elbow 2 and swivel connector 4. This embodiment presents a very streamlined appearance by moving the flexible tube 5 away from the front of the patient's face.

Figures 1, 29:
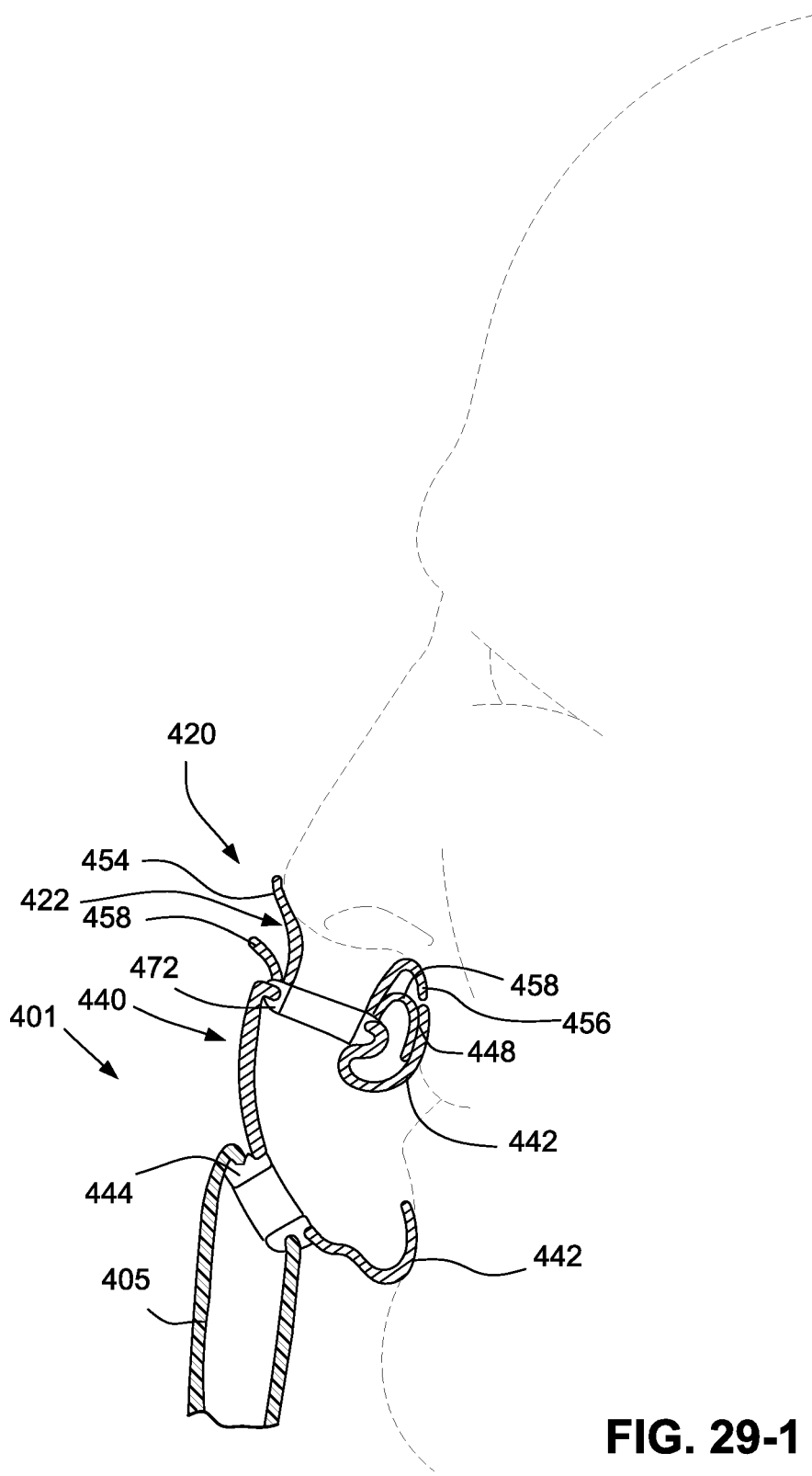
Figures 2, 29:
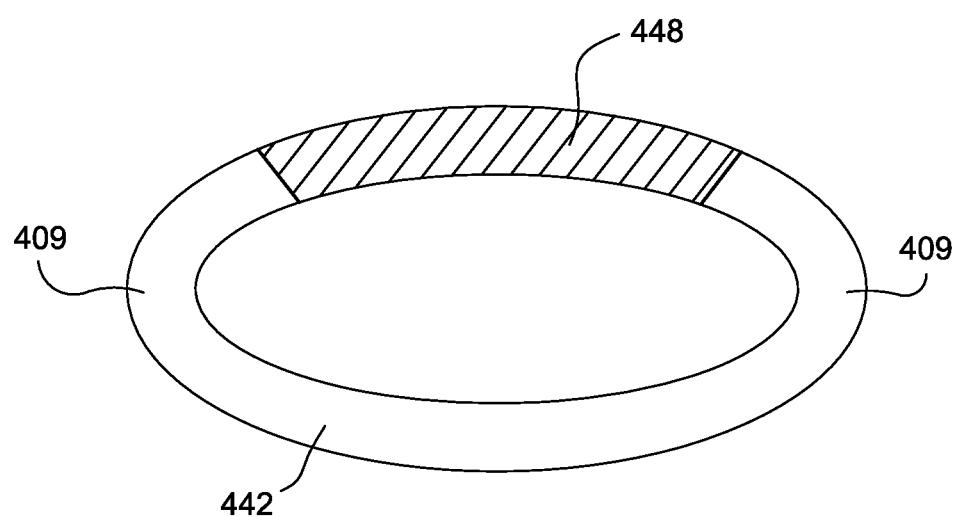
Figures 3, 29:
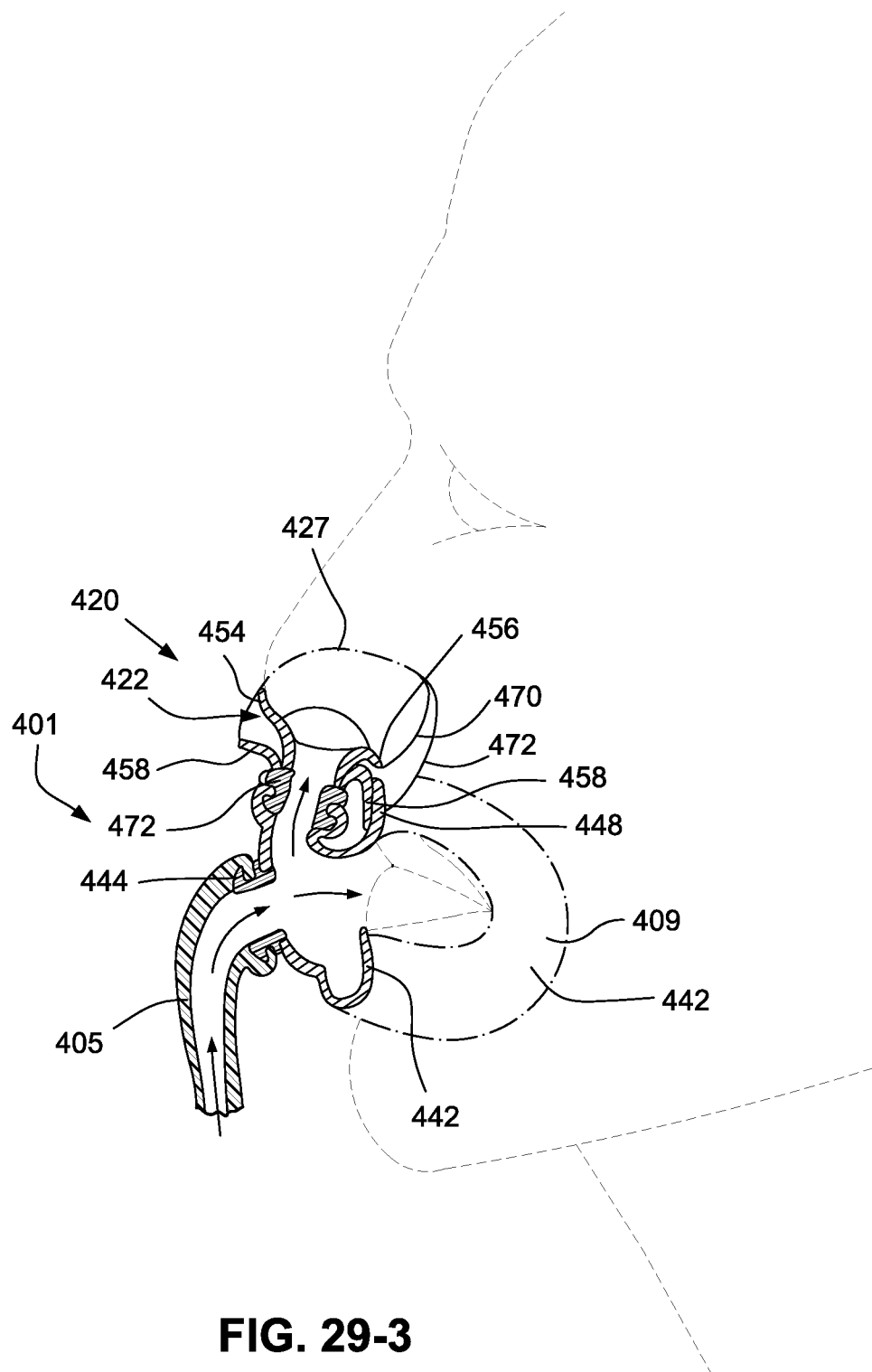

FIG. 29-1 illustrates a schematic cross-section view of a mask system 401 utilized in a nares and mouth mode. The nares portion 420 may include a supporting portion 458 and a sealing portion 422. The sealing portion 422 includes a nose tip engagement portion 454 that engages and seals with the patient's nose tip, an upper lip engagement portion 456 that engages and seals with the patient's upper lip area, and a sealing ring 472 that engages and seals with the mouth portion 440. The sealing ring 472 may optionally be part of the mouth portion 440, instead of being part of the nares portion 420.

Mouth portion 440 may include swivel ring 444, which connects to flexible tube 405. The flexible tube 405 may connect directly to the swivel ring 444, or may be connected through an elbow, such as elbow 402. The mouth sealing portion 442 forms a seal around the patient's mouth, and includes an upper lip engagement portion 448 that forms a seal with the patient's upper lip area.

There is a limited amount of room on the patient's upper lip for the upper lip engagement portion 456 of the nares portion 420 and for the upper lip engagement portion 448 of the mouth portion. Accordingly, the upper lip engagement portion 448 may be disposed between the support portion 458 of the nares portion 420 and the patient's upper lip. FIG. 29-2 illustrates the mouth sealing portion 442, with the upper lip engagement portion 448. The upper lip engagement portion 448 may be an ultra thin flat membrane having a thickness of about 0.1 to 0.3 mm, preferably about 0.2 mm, as compared to the rest of the mouth sealing portion 442, which may have a thickness of about 0.3 to 2 mm, preferably about 0.5 mm. However, portions of the mouth sealing portion 442 could include thickened portions 409 around the sides of the mouth region corresponding to a cheek area of a patient for added support. These thickened regions 409 could have a thickness of about 1.5 mm, for example.

FIG. 29-3 is a schematic cross-sectional view that illustrates further details of the mask system 401. In particular, FIG. 29-3 illustrates how the mouth sealing portion 442 extends around the mouth of the patient and how the nares flare engagement portion 427 engages with the flares of the patient's nares. Additionally, the back edge of the nasal sealing area 470 is illustrated along with an edge 472 of the nares sealing portion 422.

Figures 1, 30:
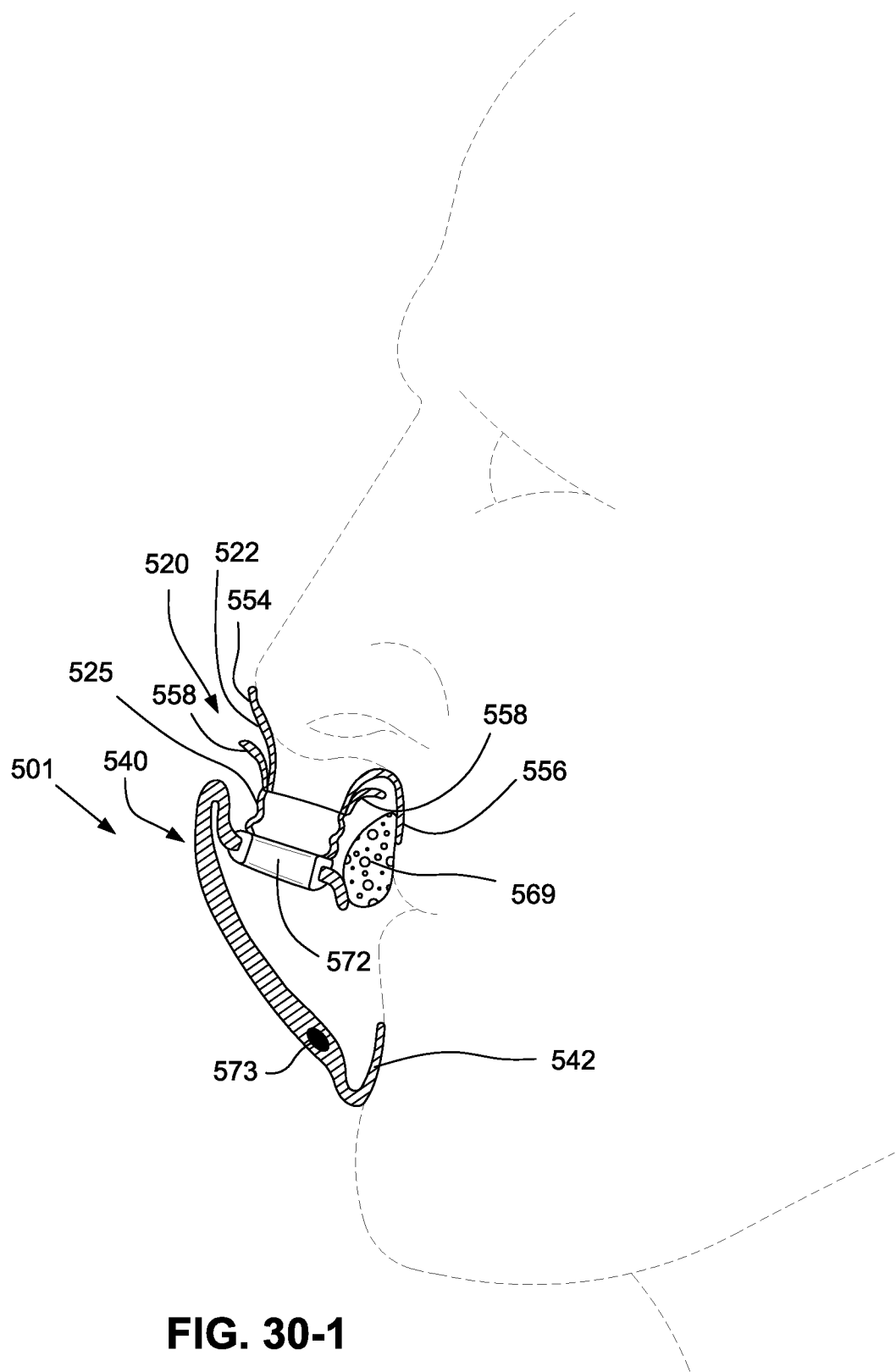
Figures 2, 30:
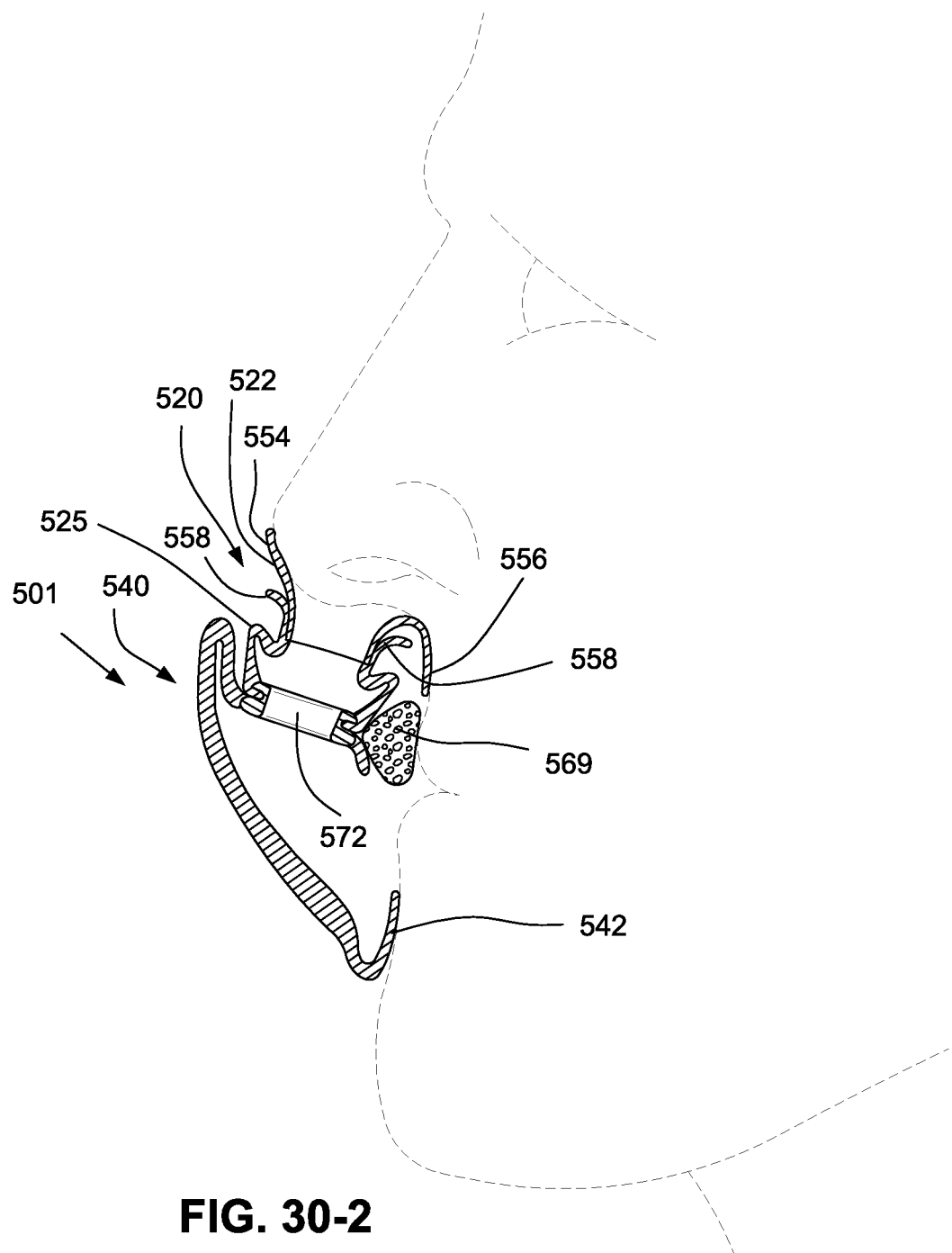

FIG. 30-1 illustrates a schematic cross-sectional view of a mask system 501 utilized in a nares and mouth mode. The nares portion 520 may include a supporting portion 558, a sealing portion 522 and an optional decoupling portion 525. The sealing portion 522 includes a nose tip engagement portion 554 that engages and seals with the patient's nose tip, and an upper lip engagement portion 556 that engages and seals with the patient's upper lip area. A sealing ring 572 that engages and seals with the mouth portion 540 may be attached to the decoupling portion. The sealing ring 572 may optionally be part of the mouth portion 540 instead of being part of the nares portion 520.

The mouth portion 540 may include an optional cushion rigidizer 573 to increase the rigidity of the sealing portion 522. The cushion rigidizer 573 may be made from a polymer such as polycarbonate, nylon, polypropylene, high density foam, a fabric having low stretch properties like a 3D weave, or a higher shore hardness silicone or gel, e.g. 70 Shore A. There is a limited amount of room on the patient's upper lip for the upper lip engagement portion 556 of the nares portion and for an upper lip engagement portion of the mouth portion. Accordingly, the foam patient contacting 569 may be disposed in a gap between the cushion on the mouth portion 540 and the upper lip engagement portion 556. The foam patient contacting 569 may contact with and form a seal with the upper lip area of the patient, and thus form part of the mouth seal.

FIG. 30-2 illustrates a schematic cross-sectional view of the mask system 501 utilized in the second nares and mouth mode. The sealing ring 572 is formed as part of the mouth portion 540 and is adapted to engage and seal with the decoupling portion 525 of the nares portion 520. There is a limited amount of room on the patient's upper lip for the upper lip engagement portion 556 of the nares portion and for an upper lip engagement portion of the mouth portion. In this embodiment, the foam patient contacting portion 569 is disposed against the decupling portion 525 and the cushion on the mouth portion 540, and contacts with and forms a seal with the upper lip area of the patient. The foam patient contacting portion 569 may form part of the mouth seal. The cushion rigidizer 573 of FIG. 30-1 may also be used in the embodiment of FIG. 30-2 and in any of the other embodiments disclosed herein.

Figure 42:
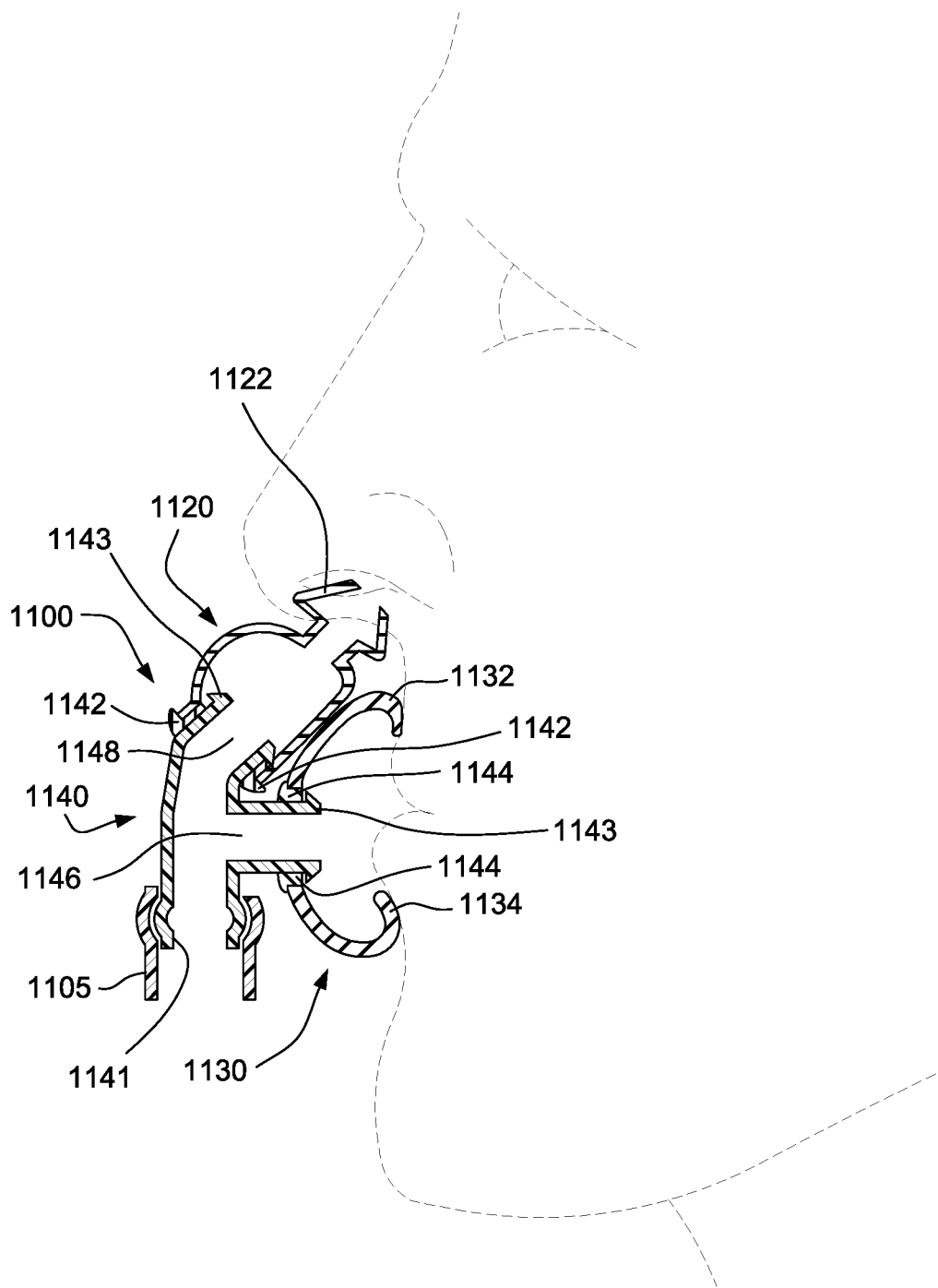
FIG. 42 depicts a schematic cross-sectional view of a modular mask system on a model patient's head according to an embodiment of the present technology.

FIG. 42 illustrates a schematic cross-section view of a mask system 1100 utilized in a nares and mouth mode. The mask system 1100 may be a variation of the mask system 701 illustrated in FIG. 34. The mask system 1100 includes a nares portion 1120, a mouth portion 1130, and a double elbow 1140. A lower end 1141 of the double elbow 1140 is adapted to connect to swivel 1105, which may be connected to a flexible tube to deliver air to the mask system 1100. Lower end 1141 may connect to swivel 1105 with a ball and socket arrangement (as shown) adapted to provide a greater degree of movement of the swivel and therefore the air delivery tube. Alternatively, lower end 1141 may connect to swivel 1105 in any arrangement for example an interference fit, over mold, etc.

A first air passage or branch 1146 of the double elbow 1140 is adapted to communicate with an aperture in mouth portion 1130, and a second air passage or branch 1148 of the double elbow 1140 is adapted to communicate with an aperture in nares portion 1120. A first elbow ring 1142 and a second elbow ring 1144 are used to connect the double elbow 1140 to the nares portion 1120 and the mouth portion 1130, respectively, although other types of connectors may be utilized. The double elbow may include barbed end portions 1143 on the ends of the first branch 1146 and the second branch 1148 to engage with the mouth portion 1130 and the nares portion 1120.

The mouth portion 1130 includes a lower lip engagement portion 1134 adapted to form a seal below the patient's lower lip, and an upper lip engagement portion 1132 adapted to form a seal just above the patient's upper lip. The nares portion 1120 includes nozzles 1122 adapted to locate the nares portion 1120 proximal to the patient's nares and ensure the foam portion 1154 is located in a position to sealingly engage the patient's nares, although pillows, a nasal chamber, a nasal cradle (nares seal) or a membrane seal could also be used to form a seal with the patient's nares.

The mouth portion 1130 may be a single wall or fabric/foam composition mouth portion with a relatively low Shore hardness. The nares portion 1120 may have a hardness of e.g., 40 Shore A.

Figure 43:
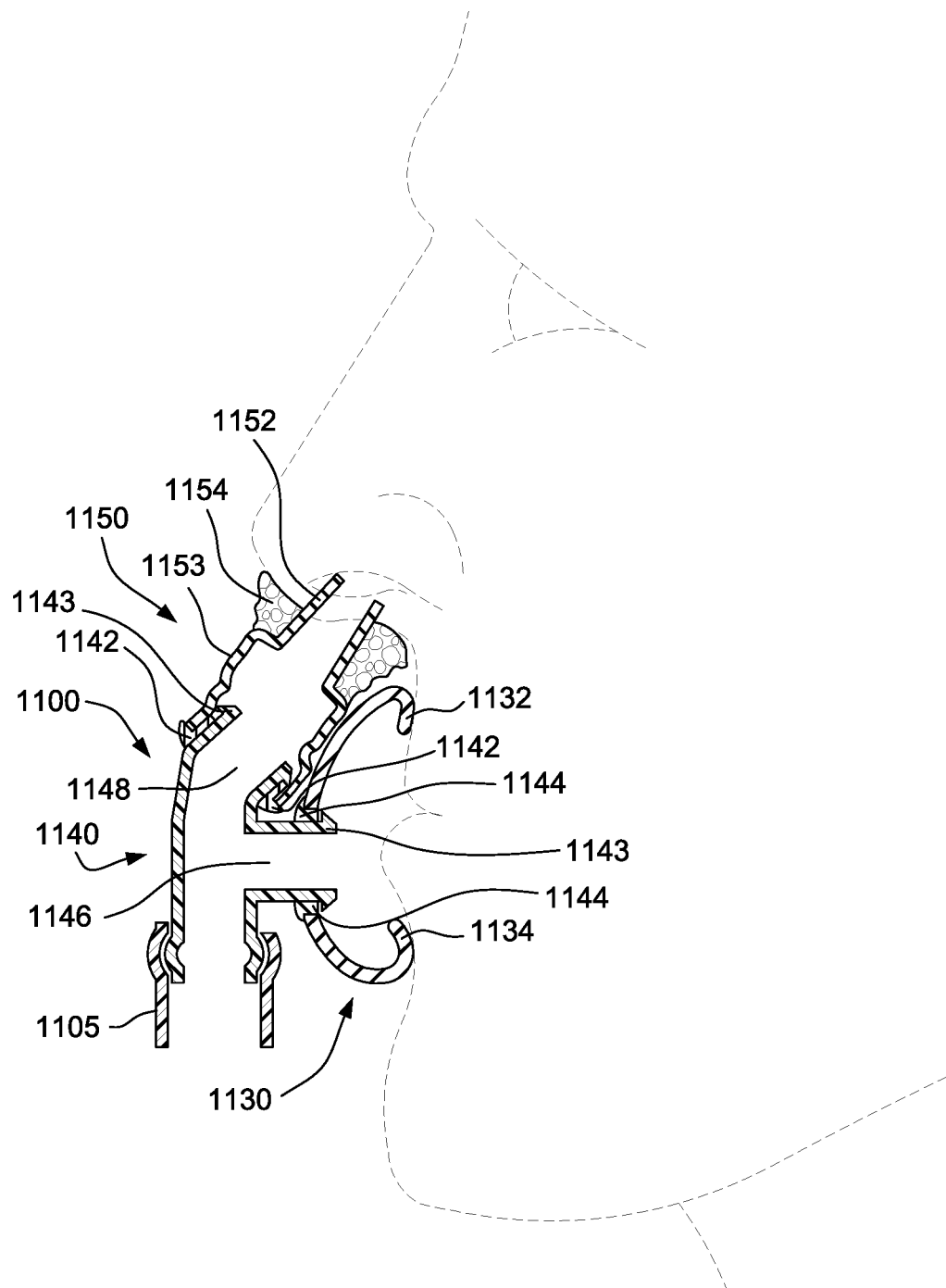
FIG. 43 depicts a schematic cross-sectional view of a modular mask system on a model patient's head according to an embodiment of the present technology.

FIG. 43 illustrates a schematic cross-section view of the mask system 1100 utilized in a nares and mouth mode, and is the same as the mask system 1100 of FIG. 42 with a different nares portion 1150. Nares portion 1150 includes a supporting portion 1153 that supports nozzles 1152, and foam portion 1154. The nozzles 1152 and foam portion 1154 together form a sealing portion adapted to form a seal with the patient's nares. The nozzles 1152 may have an air passage that gradually decreases in size as the air approaches the patient's nares. The supporting portion 1153 may have a hardness of e.g., 40 Shore A. The nozzles 1152 aid in supporting the foam portion 1154 in position proximate to the patient's nares. The foam portion 1154 enables a larger fit range as the foam is able to conform to various nares sizes due to the compressibility of the foam. The foam portion 1154 also provides comfort to the patient.

Figure 44A:
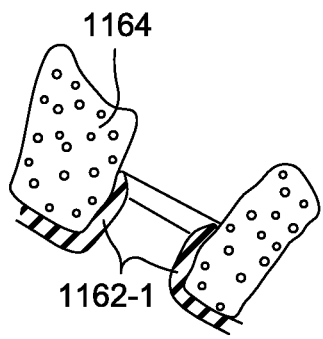
FIG. 44A is a cross-sectional view of a nares portion according to an embodiment of the present technology.
Figure 44B:
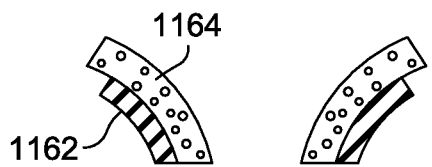
FIG. 44B is a cross-sectional view of a nares portion according to an embodiment of the present technology.
Figure 44:
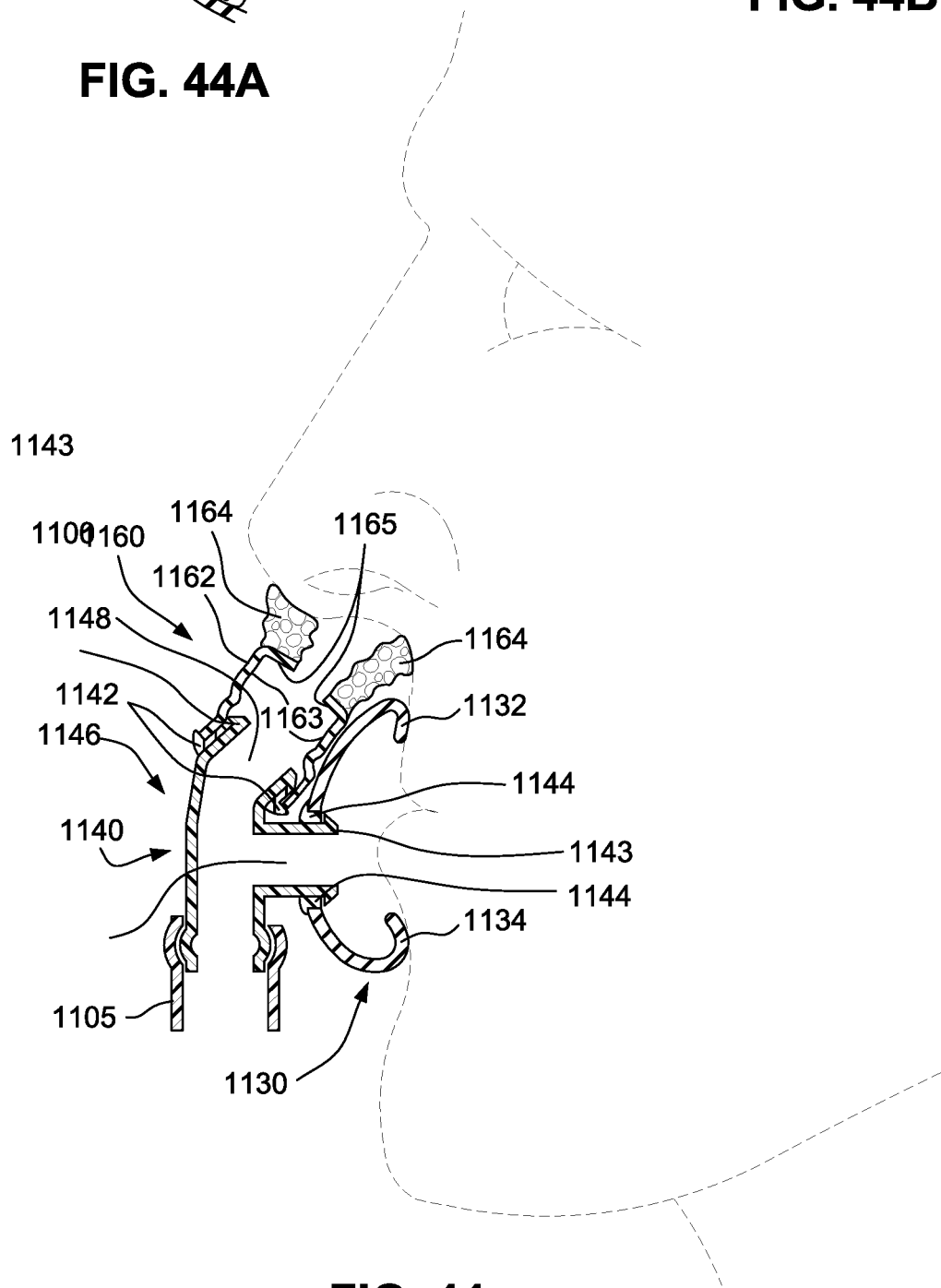
FIG. 44 depicts a schematic cross-sectional view of a modular mask system on a model patient's head according to an embodiment of the present technology.

FIG. 44 illustrates a schematic cross-section view of the mask system 1100 utilized in a nares and mouth mode, with a nares portion 1160. Nares portion 1160 includes a supporting portion 1162 and a sealing portion 1164. The supporting portion 1162 may be constructed of silicone and acts as an intermediate or connecting portion between the double elbow 1140 and the sealing portion 1164.

The supporting portion 1162 positions the sealing portion 1164 underneath the nares of the user and maintains the sealing portion 1164 in this position. The supporting portion 1162 may include substantially parallel side portions and end portions 1165 formed substantially perpendicular to the side portions. The end portions 1165 provide an interface surface for the sealing portions 1164. The sealing portion 1164 may be constructed of foam, gel or other conformable material. Preferably the sealing portion 1164 is more flexible than the supporting portion 1162 so as to aid in the comfort of the seal and the fit range. The sealing portion 1164 may be foam with an aperture, the foam forming a seal with the patient's nose tip, upper lip and nares. In an example, as shown in FIG. 44A, the supporting portion may include support walls 1162-1 (e.g., constructed of silicone or a material with higher stiffness than the foam sealing portion) to prevent the foam from compressing and occluding the nares. In another example, as shown in FIG. 44B, the foam sealing portion 1164 may have a trumpet shape (e.g., flare outwards) with a silicone support wall underneath to ensure structural stability of the foam and also ensure sealing engagement with the patient.

Figure 45:
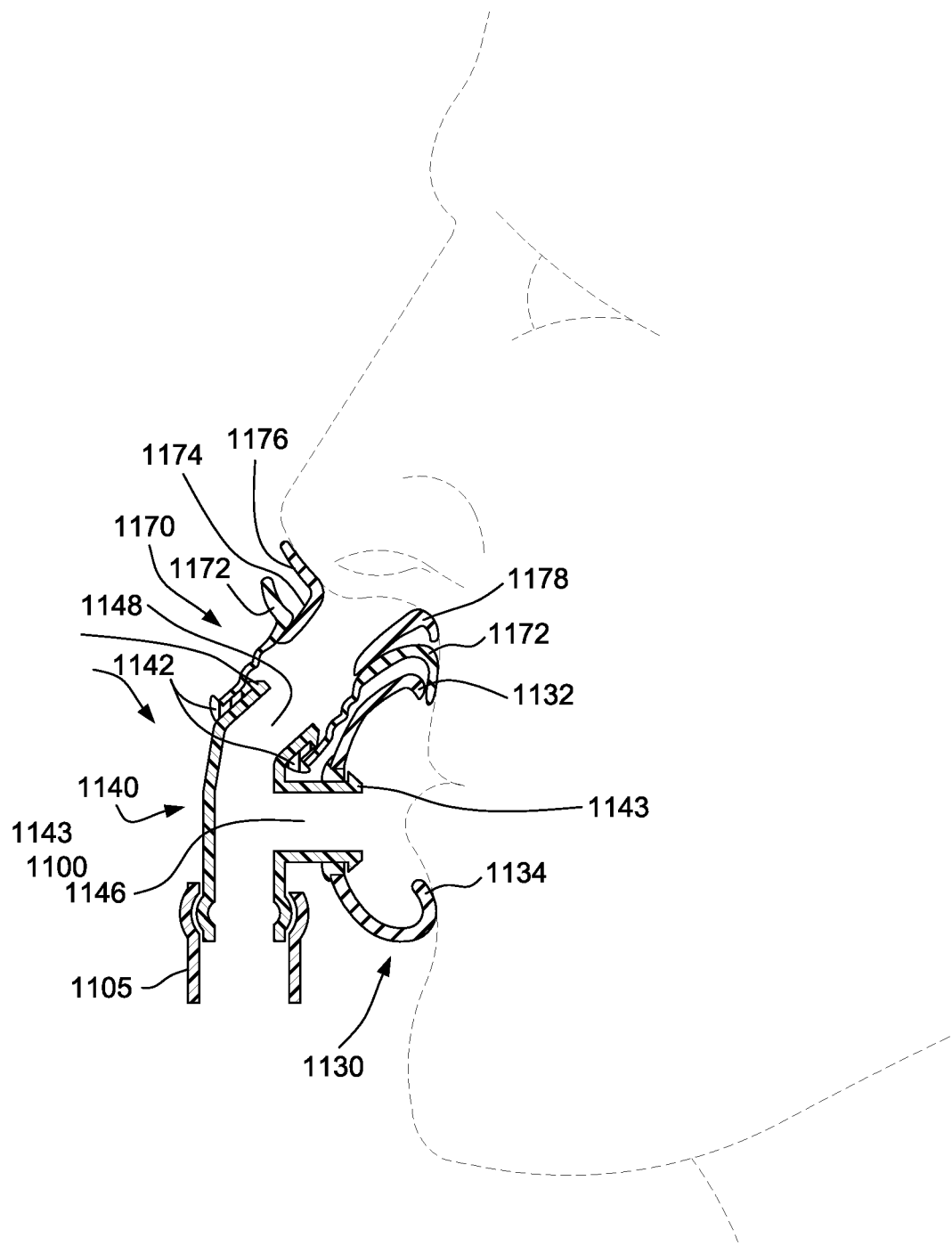
FIG. 45 depicts a schematic cross-sectional view of a modular mask system on a model patient's head according to an embodiment of the present technology.

FIG. 45 illustrates a schematic cross-section view of the mask system 1100 utilized in a nares and mouth mode, with a nares portion 1170. The nares portion 1170 includes a supporting portion 1172 and a sealing portion 1174. The sealing portion 1174 includes a nose tip engagement portion 1176 and an upper lip engagement portion 1178. The supporting portion 1172 may form a seal just above the patient's upper lip, and may be positioned between the patient's upper lip and the upper lip engagement portion 1132 of the mouth portion 1130.

The supporting portion 1172 may have a higher Shore hardness than the sealing portion 1174. For example, the supporting portion may have a Shore A hardness of, e.g., 20-80, preferably 30-60, or about 40 while the sealing portion 1174 has a Shore A hardness of about 5-40 or about 20. The hardness of the sealing portion is generally lower than the supporting portion.

FIG. 46 illustrates a schematic cross-section view of a mask system 1180 utilized in a nares and mouth mode, with mouth portion 1182 and a nares portion 1190. The nares portion 1190 may be removable from the mask system 1180 and replaceable with a plug, so that the mask system 1180 may be used in a mouth only mode.

The mouth portion 1182 includes an aperture for connection of an air supply to deliver air to the mask system 1180. Elbow 1188 connects to the aperture via sealing ring 1189. A swivel 1187 may be connected between the elbow 1188 and the air hose 1185. A swivel cuff (not shown) may be connected between the swivel 1187 and air hose 1185.

The mouth portion 1182 includes a lower lip engagement portion 1184 adapted to form a seal below the patient's lower lip, an upper lip engagement portion 1186 adapted to form a seal just above the patient's upper lip, and a vanity flap to cover nares and/or nose tip—primarily to cover nose tip—or covering flap 1183 adapted to cover the patient's nares and the nares portion 1190, making the mask system 1180 more visually appealing. The covering flap 1183 extends upward a sufficient height to cover the patient's nares and the nares portion 1190.

The nares portion 1190 may include supporting portion 1192 and sealing portion 1193. The sealing portion includes nose tip engagement portion 1194 and upper lip engagement portion 1196. The nares portion 1190 may be connected to an upper aperture in the mouth portion 1182 via a mouth clip 1198 and a nares clip 1198.1, into which the nares portion 1190 may be placed. When the nares portion 1190 is not to be used with the mask system 1180, the nares portion 1190 is removed from the mouth clip 1198, and a plug may be put in the mouth clip 1198 or in the aperture to provide a seal. The mouth clip 1198 may be silicone or another material, e.g., nylon, polypropylene, etc.

Figure 47:
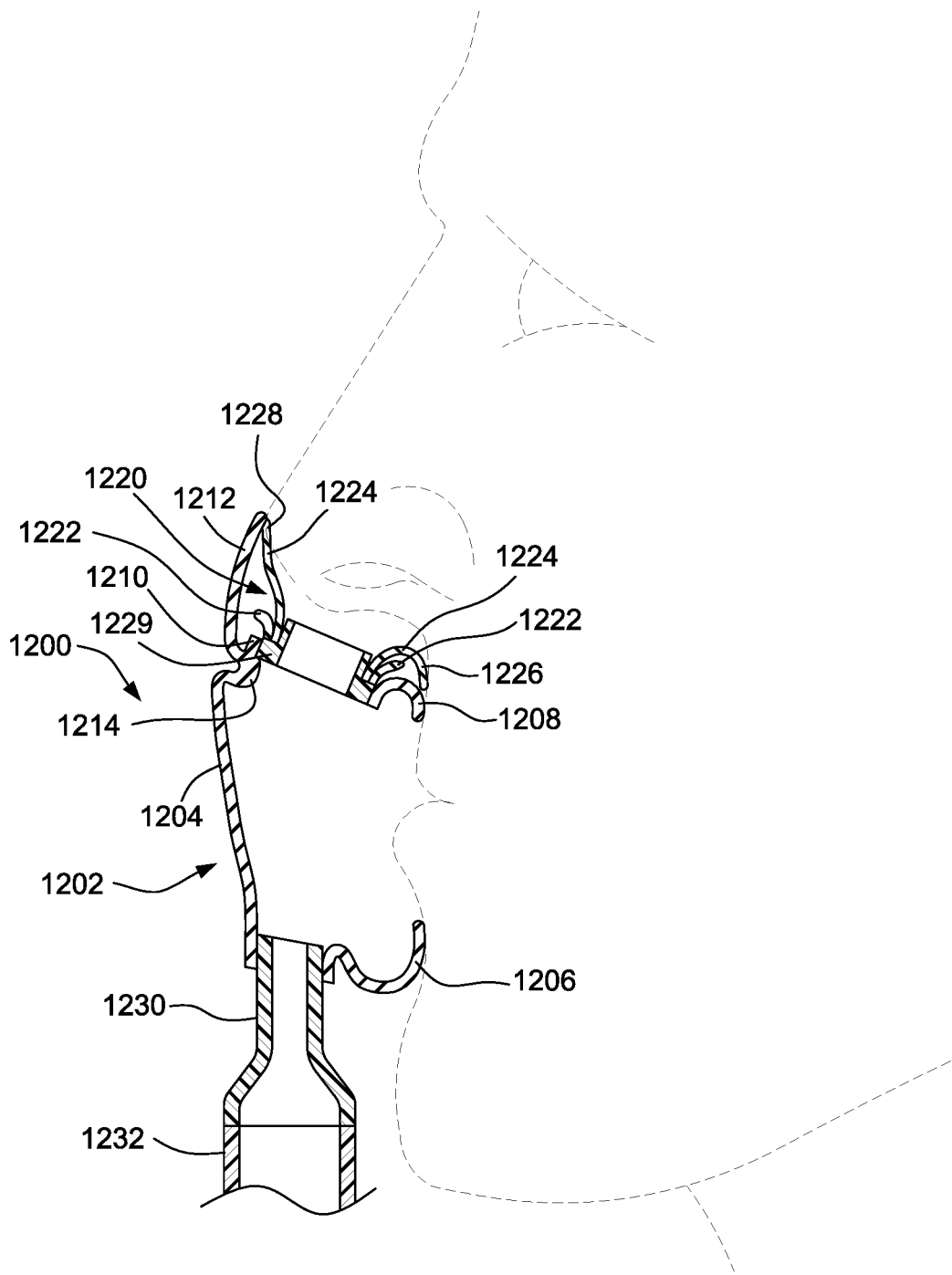
FIG. 47 depicts a schematic cross-sectional view of a modular mask system on a model patient's head according to an embodiment of the present technology.

FIG. 47 illustrates a schematic cross-section view of the mask system 1200 utilized in a nares and mouth mode, with mouth portion 1202 and a nares portion 1220. The nares portion 1220 may be removable from the mask system 1200 and replaceable with a plug, so that the mask system 1200 may be used in a mouth only mode and the nares portion may be used in a nares only mode.

The mouth portion 1202 includes a front portion 1204 or fascia, a lower lip engagement portion 1206, an upper lip engagement portion 1208, a nares portion tab 1210, vanity flap or covering flap 1212, and a decoupling portion 1214. The front portion or fascia 1204 may be a large clear window allowing visibility of the patient's mouth region. The nares portion tab 1210 may be adapted to receive and sealingly engage with the nares portion 1220.

The nares portion 1220 includes an attachment ring 1229 adapted to sealingly engage with the mouth portion 1202, a supporting portion 1222, and a sealing portion 1224. The attachment ring 1229 may be co-molded, welded, permanently snapped or removably attached with the rest of the nares portion 1220. The sealing portion 1224 includes a nose tip engagement portion 1228 adapted to form a seal with the patient's nose tip, and an upper lip engagement portion 1226 adapted to form a seal just above the patient's upper lip.

The covering flap 1212 is located in close proximity with the nose tip engagement portion 1228 of the nares portion 1220. Thus, if the covering flap 1212 moves, the nose tip engagement portion 1228 may also move. Accordingly, the decoupling portion 1214 is included on the mouth portion 1202 at a position below the covering flap 1212. The decoupling portion 1214 serves to decouple forces applied to the mouth portion 1202 (such as could be created by forces applied by movement of the air hose 1232) from being transmitted to the nares portion 1220.

The mouth portion 1202 includes a lower aperture adapted to receive elbow 1230, e.g., gusset elbow, which is connected to air delivery tube 1232. The gusset elbow 1230 may include an anti-asphyxia valve and/or one or more vent holes for venting exhaled gases. The tube may connect to the nose cushion or pillows when in the nose-only mode.

Figure 48:
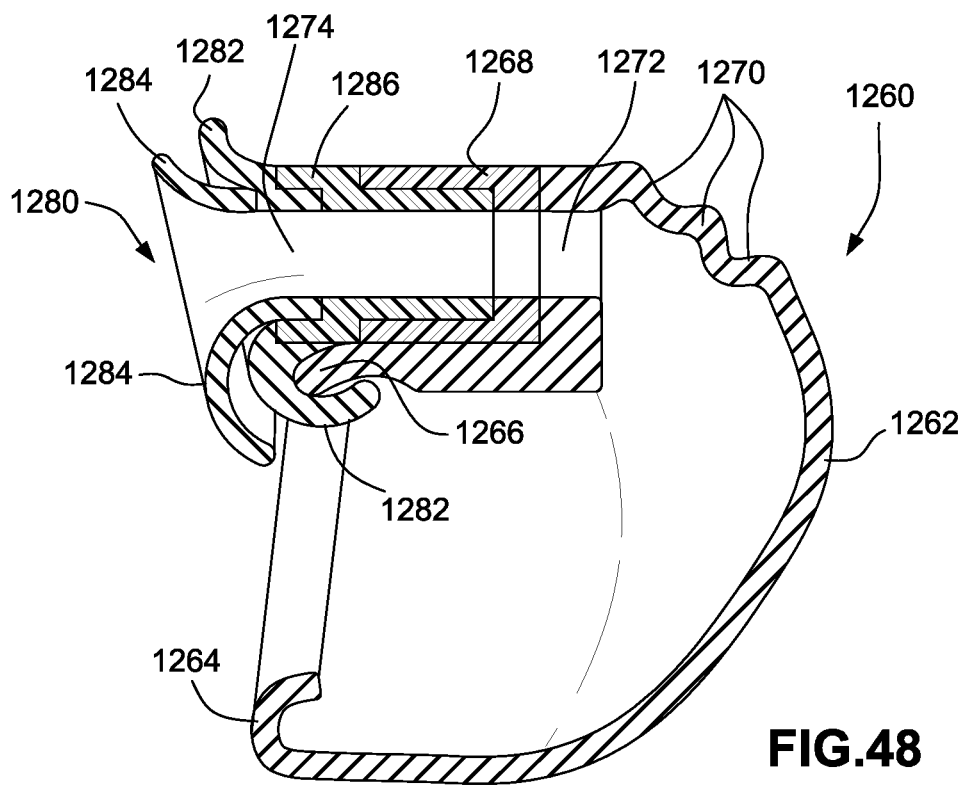
FIG. 48 depicts a schematic partial cross-sectional view of a modular mask system according to an embodiment of the present technology.
Figure 49:
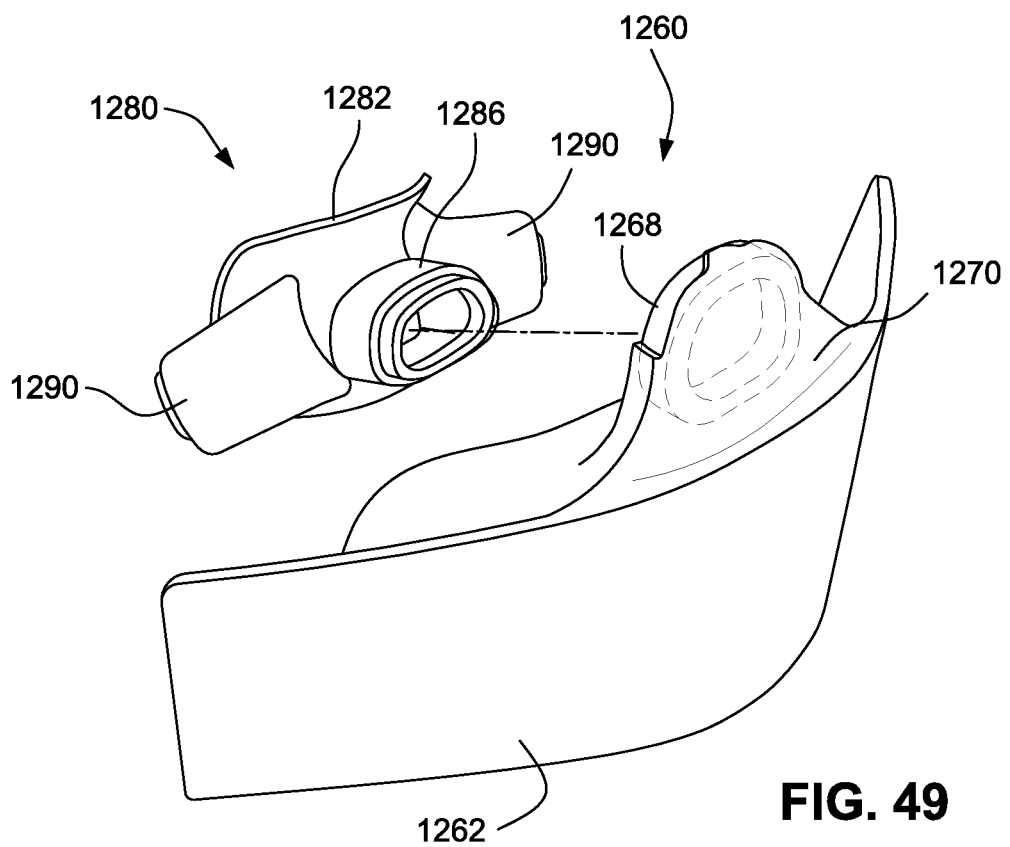
FIG. 49 is an exploded view of a modular mask system on a model patient's head according to an embodiment of the present technology.

FIGS. 48 and 49 illustrate a modular mask system 1260, which includes a mouth portion 1262 and a nares portion 1280. The mask system 1260 is adapted to be used in a mouth only mode, a nares only mode or a mouth and nares mode.

The mouth portion 1262 includes a lower lip engagement portion 1264, an upper lip engagement portion 1266 adapted to push nasal seal into engagement with the face, a decoupling (concertina) portion 1270 and aperture 1272. An aperture (not shown) on the front or bottom of the mouth portion may be provided to connect a supply of air, such as air hose connected by an elbow or the like. The flexible portion 1270 could be air actuated or could be a thinner wall section, e.g., less stiff, and forms a decoupling portion that decouples forces applied to the mouth portion 1262 from being applied to the nares portion 1280. When used in a mouth only mode, the aperture 1272 may be plugged to provide an airtight seal.

The nares portion 1280 includes a supporting portion 1282, a sealing portion 1284 and headgear connectors 1290. The sealing portion 1284 is adapted to seal with the patient's upper lip and nose tip. When used in a nares only mode, the aperture 1274 can be connected to a source of air or plugged if air is alternatively supplied. When used in a nares and mouth mode, a nares clip 1286 may be connected, preferably permanently connected or otherwise form into the supporting portion 1282, and a mouth clip 1268 may be connected, preferably permanently connected or otherwise form into the cushion of the mouth portion 1262. The nares clip 1286 and the mouth clip 1268 are adapted to sealingly connect, such as through notches or the like formed in the clips, so that the mouth portion 1262 may be connected to the nares portion 1280 in a nares and mouth mode.

Figure 54:
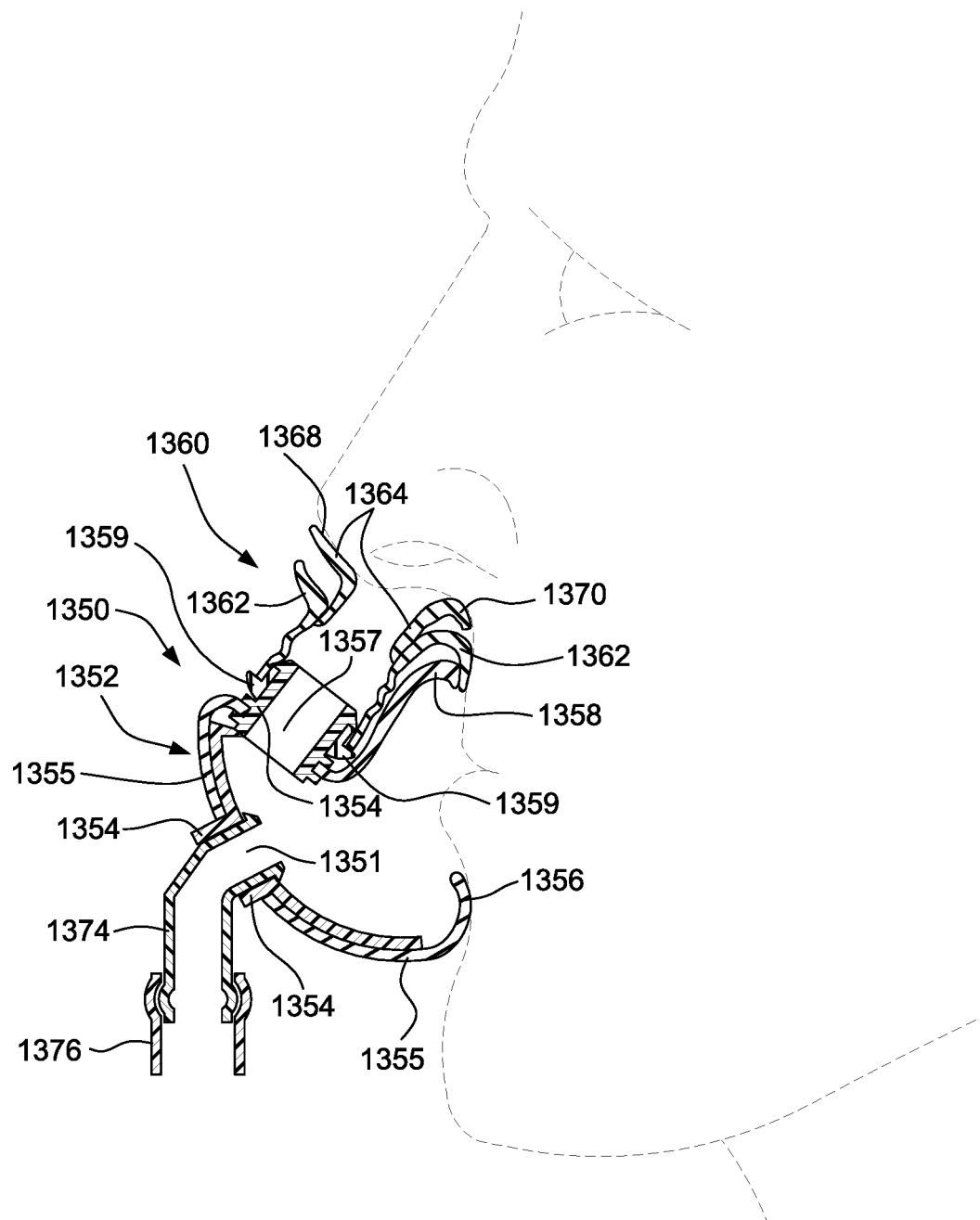
FIG. 54 depicts a schematic cross-sectional view of a modular mask system on a model patient's head according to an embodiment of the present technology.
Figure 55:
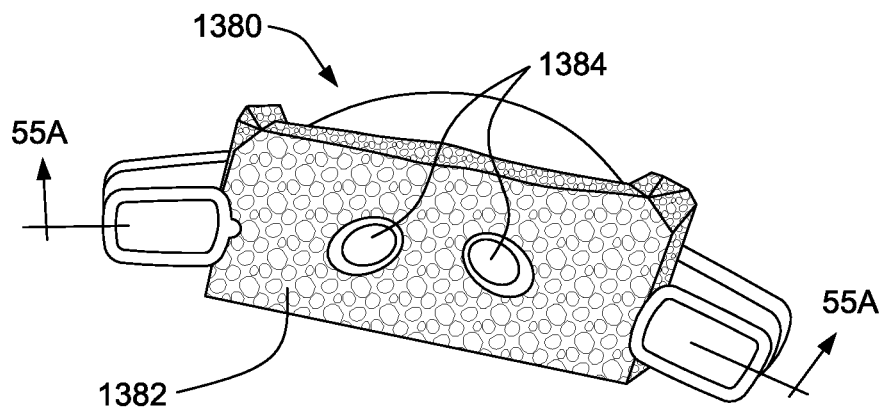
FIG. 55 depicts a rear view of a nasal portion of a mask system according to an embodiment of the present technology.
Figure 55A:
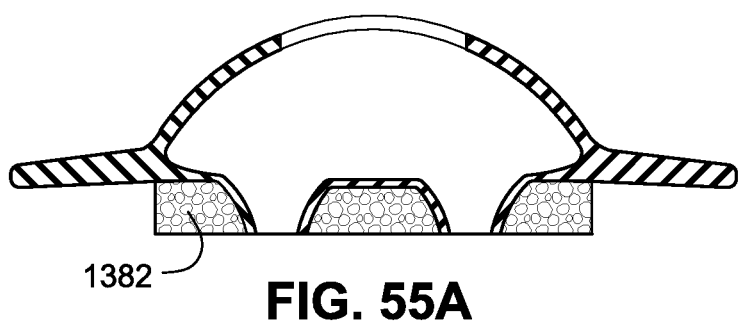
FIG. 55A is a cross-sectional view through line 55A-55A of FIG. 55.

FIG. 54 illustrates a cross section view of modular mask system 1350, which includes a mouth portion 1352 and a nares portion 1360. The nares portion 1360 may be removable from the mask system 1350 and replaceable with a plug, so that the mask system 1350 may be used in a mouth only mode, or the nares portion 1360 may be used in a nares only mode.

The mouth portion includes a frame 1354 and a mouth seal 1355. A first aperture 1351 is positioned in the frame 1354 that is adapted to receive elbow 1374 for delivery via swivel 1376 from an air hose. A second aperture 1357 is formed in the frame 1354 that may be plugged when the mask system is to be used in a mouth only mode, and connected to the nares portion 1360 when the mask system 1350 is used in a nares and mouth mode.

The frame 1354 may be a rigid material, e.g., polycarbonate or a semi-rigid material. The mouth seal 1355 may be a flexible material, e.g., silicone. The mouth seal 1355 includes a lower lip engagement portion 1356 adapted to form a seal below a patient's lower lip, and an upper lip engagement portion 1358 adapted to form a seal just above the patient's upper lip (when used in a mouth only mode).

The nares portion 1360 includes supporting portion 1362 and sealing portion 1364. The sealing portion 1364 includes nose tip engagement portion 1368 adapted to form a seal with the patient's nose tip, and upper lip engagement portion 1370 adapted to form a seal just above the patient's upper lip. The supporting portion 1362 may also form a seal just above the patient's upper lip. A ring 1359 may be used to connect the nares portion 1360 to the mouth portion 1352.

Figure 60:
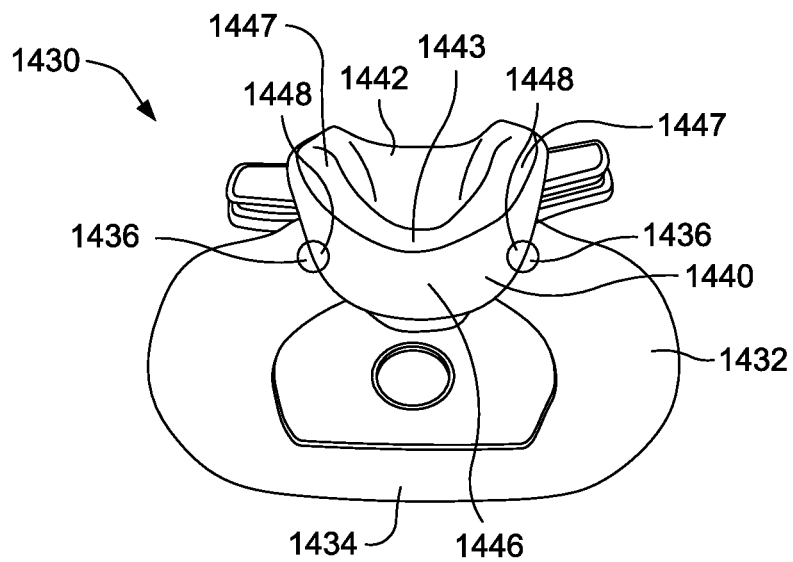
FIG. 60 depicts a rear view of a modular mask system according to an embodiment of the present technology.

FIG. 60 illustrates a modular mask system 1430 that includes a mouth portion 1432 and a nares portion 1440. The mouth portion 1432 includes a cushion portion 1434 adapted to form a seal around the patient's mouth.

The nares portion 1440 includes a supporting portion 1446 and a sealing portion 1442. The sealing portion is adapted to form a seal with the patient's nares, and includes corners of the nose regions 1447 and upper lip engagement portion 1443.

Magnets 1436, 1448 may be placed on the mouth portion 1432 and the nares portion 1440 to ensure that the nares portion 1440 is oriented correctly relative to the mouth portion 1432. Either of the pairs of magnets 1436, 1448 could be replaced by a metal portion. The magnets 1448 in the nares portion 1440 may be placed in the corners of the nose regions 1447 to ensure sufficient tension of the nares seal over the patient's top lip and corners of the nose.

Figure 61:
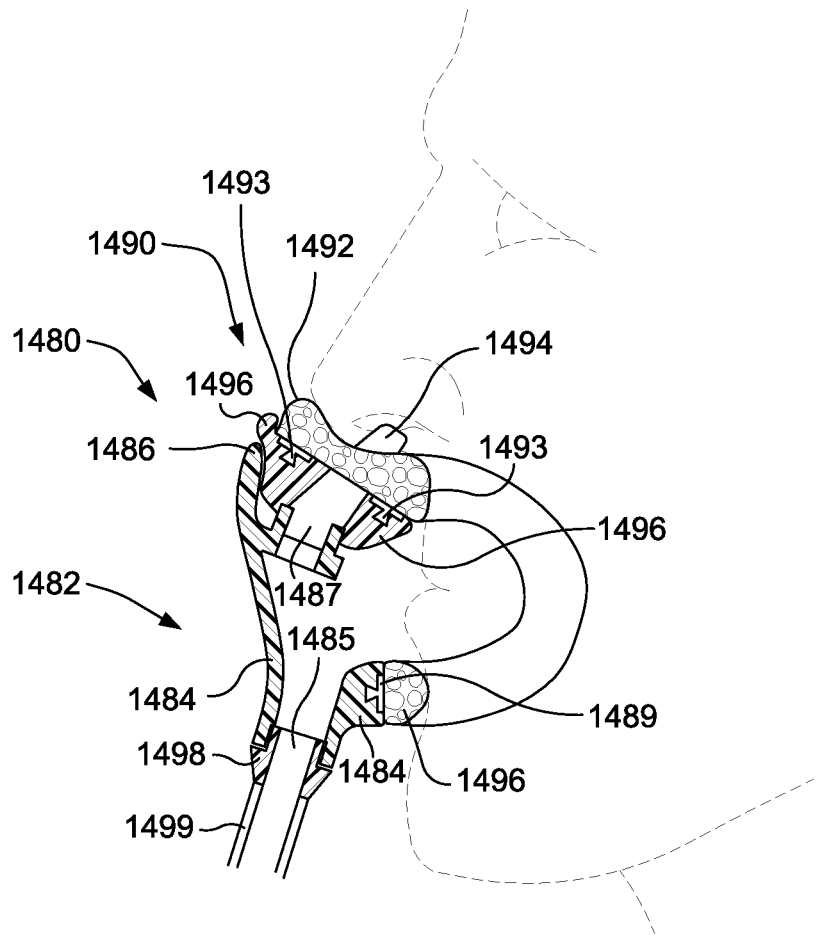
FIG. 61 depicts a schematic cross-sectional view of a modular mask system on a model patient's head according to an embodiment of the present technology.

FIG. 61 illustrates a cross section view of modular mask system 1480, which includes a mouth portion 1482 and a nares portion 1490. The nares portion 1490 may be removable from the mask system 1480 and replaceable with a plug, so that the mask system 1480 may be used in a mouth only mode, or the nares portion 1490 may be used in a nares only mode. Alternatively, the system may be used in nares and mouth mode. In an example, separate foam components may be provided for mouth and nose seal portions so that the mask system may be used in mouth only or nares only modes.

The mouth portion 1482 includes a frame 1484 and a vanity flap or covering flap 1486, a lower aperture 1485 for connection of swivel or cuff 1498 and air hose 1499, and an upper aperture 1487 for connection of nares portion 1490. The frame 1484 may be a rigid material, e.g., polycarbonate, or a semi-rigid material, e.g., semi-rigid nylon. A foam portion 1492 may have a clip 1493 for attaching to the frame 1484.

The nares portion 1490 may include a flexible portion 1496, a foam portion 1492 connectable to the flexible portion 1496 with one or more clips 1493 and a nozzle portion 1494. The covering portion 1486 of the mouth portion 1482 may support the nares portion 1490. Alternatively, a permanent connection may be used, e.g., foam portion directly onto flexible portion.

Figure 62:
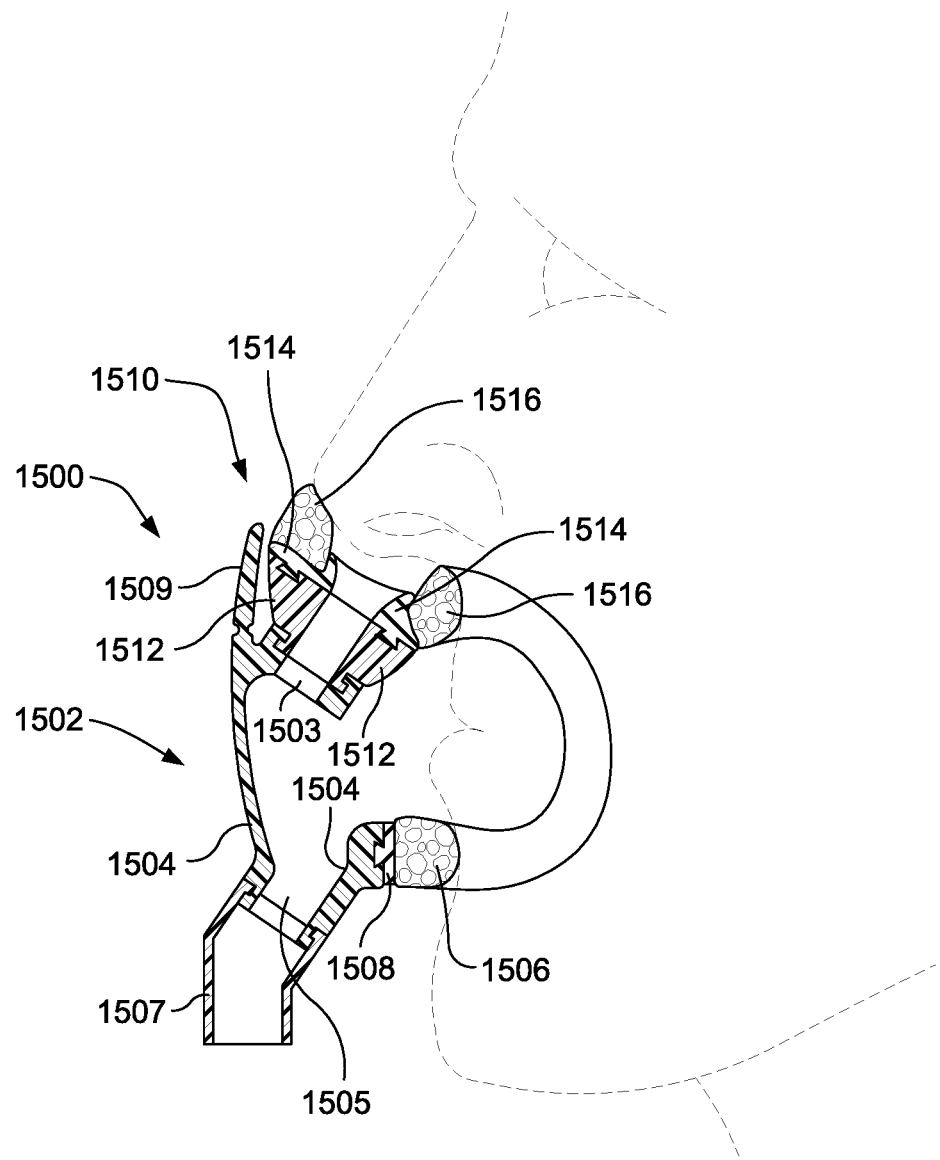
FIG. 62 depicts a schematic cross-sectional view of a modular mask system on a model patient's head according to an embodiment of the present technology.
Figure 63:
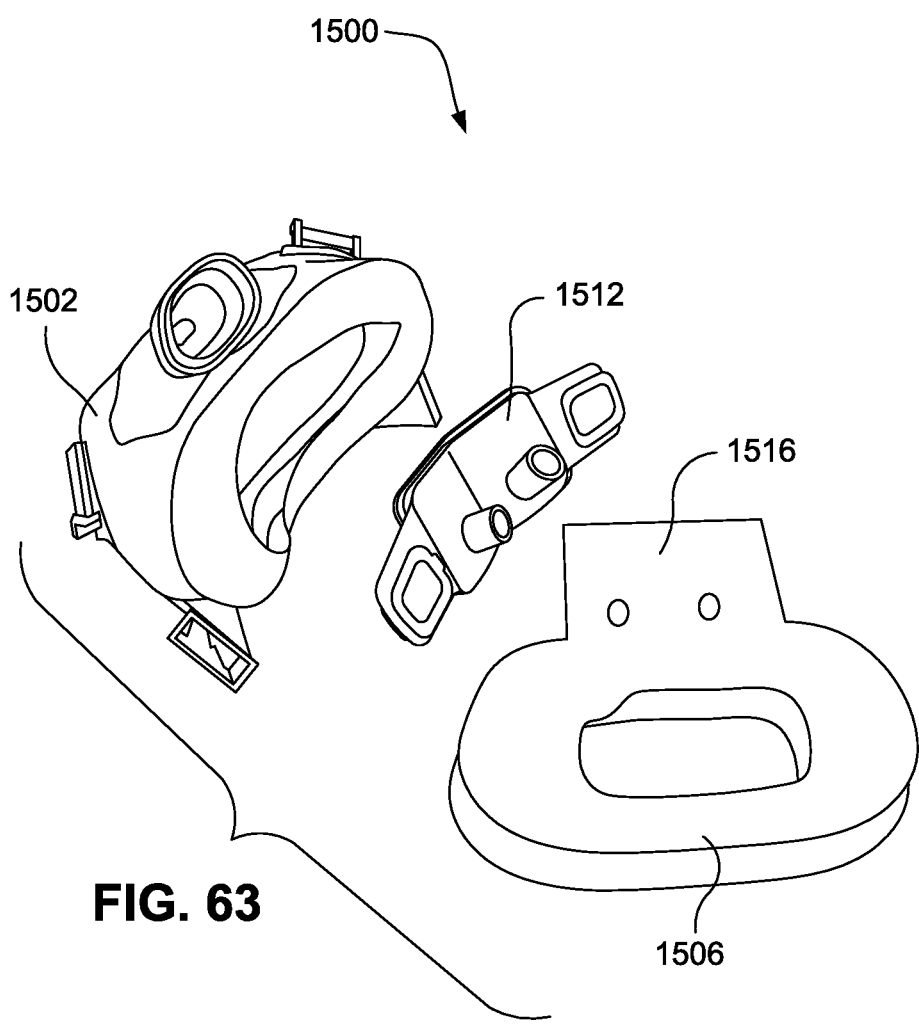
FIG. 63 depicts an exploded view of a modular mask system according to an embodiment of the present technology.

FIGS. 61, 62 and 63 illustrate a modular mask system 1500, which includes a mouth portion 1502 and a nares portion 1510. The nares portion 1510 may be removable from the mask system 1500 and replaceable with a plug, so that the mask system 1500 may be used in a mouth only mode, or the nares portion 1510 may be used in a nares only mode.

The mouth portion 1502 includes a frame 1504 and a vanity flap or covering flap 1509, a lower aperture 1505 for connection of elbow 1507, and an upper aperture 1503 for connection of nares portion 1510. The frame 1504 may be a rigid material, e.g., polycarbonate, semi-rigid or flexible, e.g., nylon, silicone. A foam portion 1506 may have a clip 1508 for attaching to the frame 1504.

The nares portion 1510 may include a flexible portion 1512, e.g., silicone, and a foam portion 1516 connectable to the flexible portion 1512 with one or more clips 1514. The covering portion 1509 of the mouth portion 1502 may be spaced from the nares portion 1510. The clips 1508, 1514 may have a surface facing the foam portion that is angled to bias or promote the foam to apply force in certain directions, e.g., toward the patient's lip.

Figure 64:
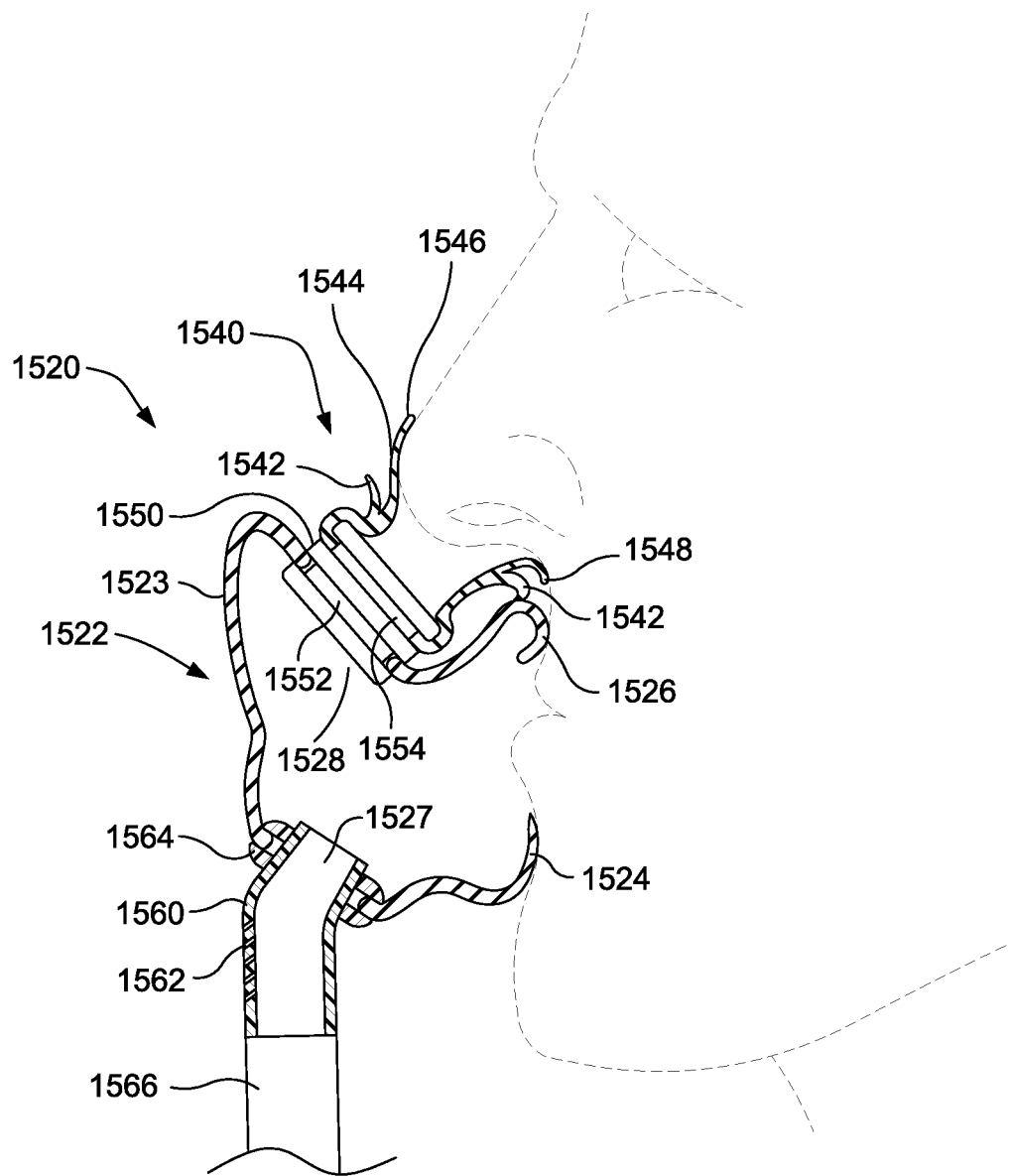
FIG. 64 depicts a schematic cross-sectional view of a modular mask system on a model patient's head according to an embodiment of the present technology.

FIG. 64 illustrates a modular mask system 1520, which includes a mouth portion 1522 and a nares portion 1540. The nares portion 1540 may be removable from the mask system 1520 and replaceable with a plug, so that the mask system 1520 may be used in a mouth only mode, or the nares portion 1540 may be used in a nares only mode. Alternatively, the system may be used in a mouth and nose mode.

The mouth portion 1522 includes a frame 1523, a lower aperture 1527 for connection of elbow 1560 (which may include vent holes 1562) and air hose 1566, and an upper aperture 1528 for connection of nares portion 1540. The frame 1523 may be a rigid material, e.g., polycarbonate, or a more flexible material, e.g., silicone. A lower lip engagement portion 1524 is adapted to form a seal with the patient's lower lip, and an upper lip engagement portion 1526 is adapted to form a seal with the patient's upper lip.

The nares portion 1540 includes a supporting portion 1542 and a sealing portion 1544. The sealing portion 1544 includes an upper lip engagement portion 1548 adapted to seal just above the patient's upper lip and a nose tip engagement portion 1546 adapted to form a seal with the patient's nose tip or region proximate to the nose tip. In the upper lip region, the supporting portion 1542 may be in contact with the upper lip engagement portion 1526 of the mouth portion 1522. When used in a nares only mode, the aperture 1528 can be connected to a source of air or plugged if air is alternatively supplied.

When used in a nares and mouth mode, a connecting ring 1550 may be utilized. The connecting ring 1550 has a first channel 1552 and a second channel 1554. The first channel 1552 is adapted to receive the mouth portion 1522 and the second channel 1554 is adapted to receive the nares portion 1540.

Figure 65:
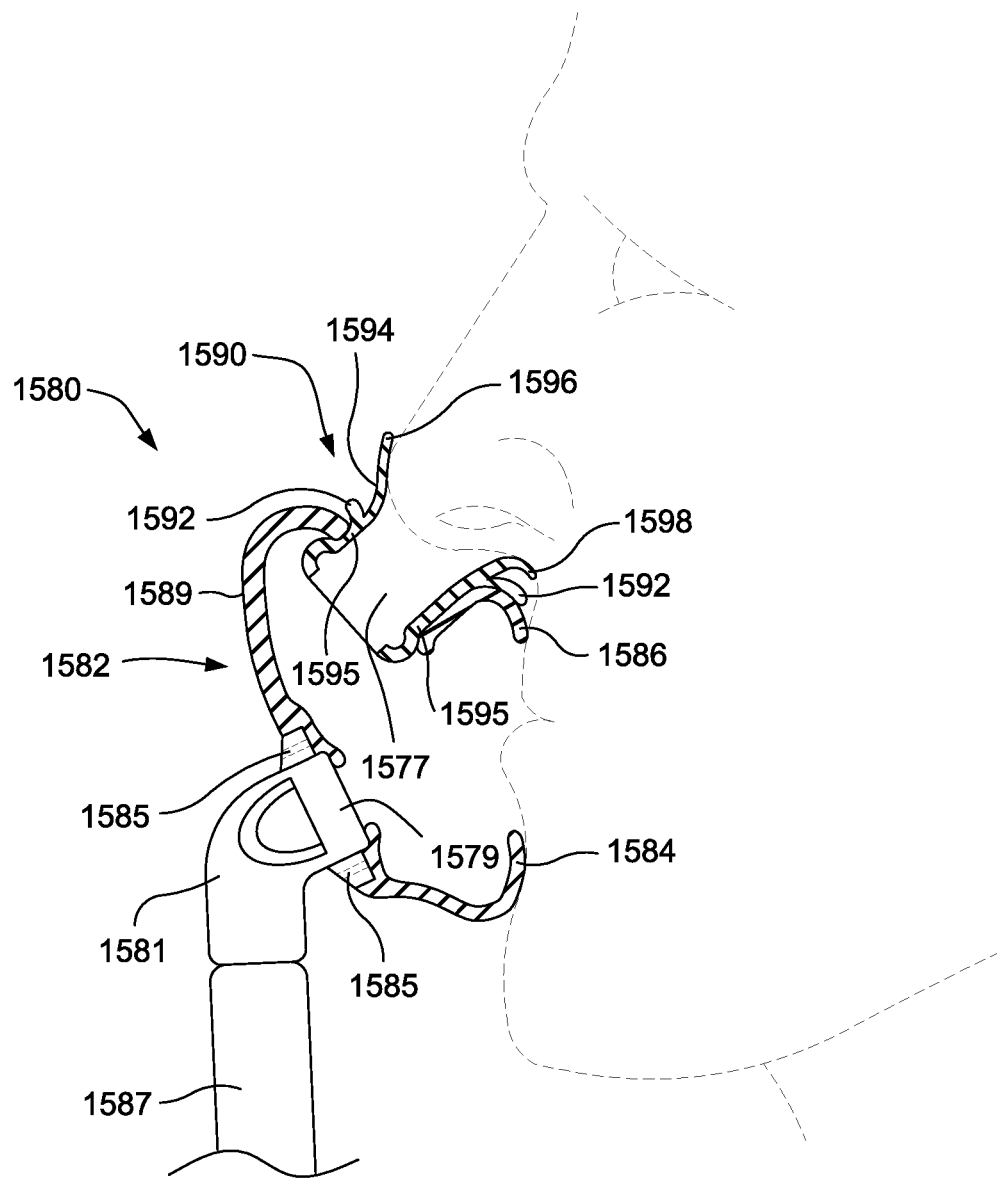
FIG. 65 depicts a schematic cross-sectional view of a modular mask system on a model patient's head according to an embodiment of the present technology.

FIG. 65 illustrates a modular mask system 1580, which includes a mouth portion 1582 and a nares portion 1590 that provide a soft to soft connection of nose and mouth parts. The nares portion 1590 may be removable from the mask system 1580 and replaceable with a plug, so that the mask system 1580 may be used in a mouth only mode, or the nares portion 1590 may be used in a nares only mode.

The mouth portion 1582 includes a frame 1589, a lower aperture 1579 for connection of elbow 1581, an air hose 1587, and an upper aperture 1577 for connection of nares portion 1590. In an example, the elbow may include buttons adapted to permit quick release of the elbow. Vent holes 1585 may be formed in the elbow 1581, e.g., via a vented ring that interconnects the elbow and frame, or alternatively may be formed in the mouth portion 1582. A lower lip engagement portion 1584 is adapted to form a seal with the patient's lower lip, and an upper lip engagement portion 1586 is adapted to form a seal with the patient's upper lip.

The nares portion 1590 includes a supporting portion 1592 and a sealing portion 1594. The sealing portion 1594 includes an upper lip engagement portion 1598 adapted to form a seal with the patient's upper lip and a nose tip engagement portion 1596 adapted to form a seal with the patient's nose tip.

The nares portion 1590 may have indentations 1595 adapted to form an interference fit with the mouth portion 1582. The nares portion 1590 may be resilient and be squeezed inward to accept the mouth portion in the indentations and then snap back into its original shape. The "trumpet" shape on the mouth portion provides a lead-in to guide the nares portion into position. Also, a thin silicone wall may be provided to seal around the nares portion.

Figure 66:
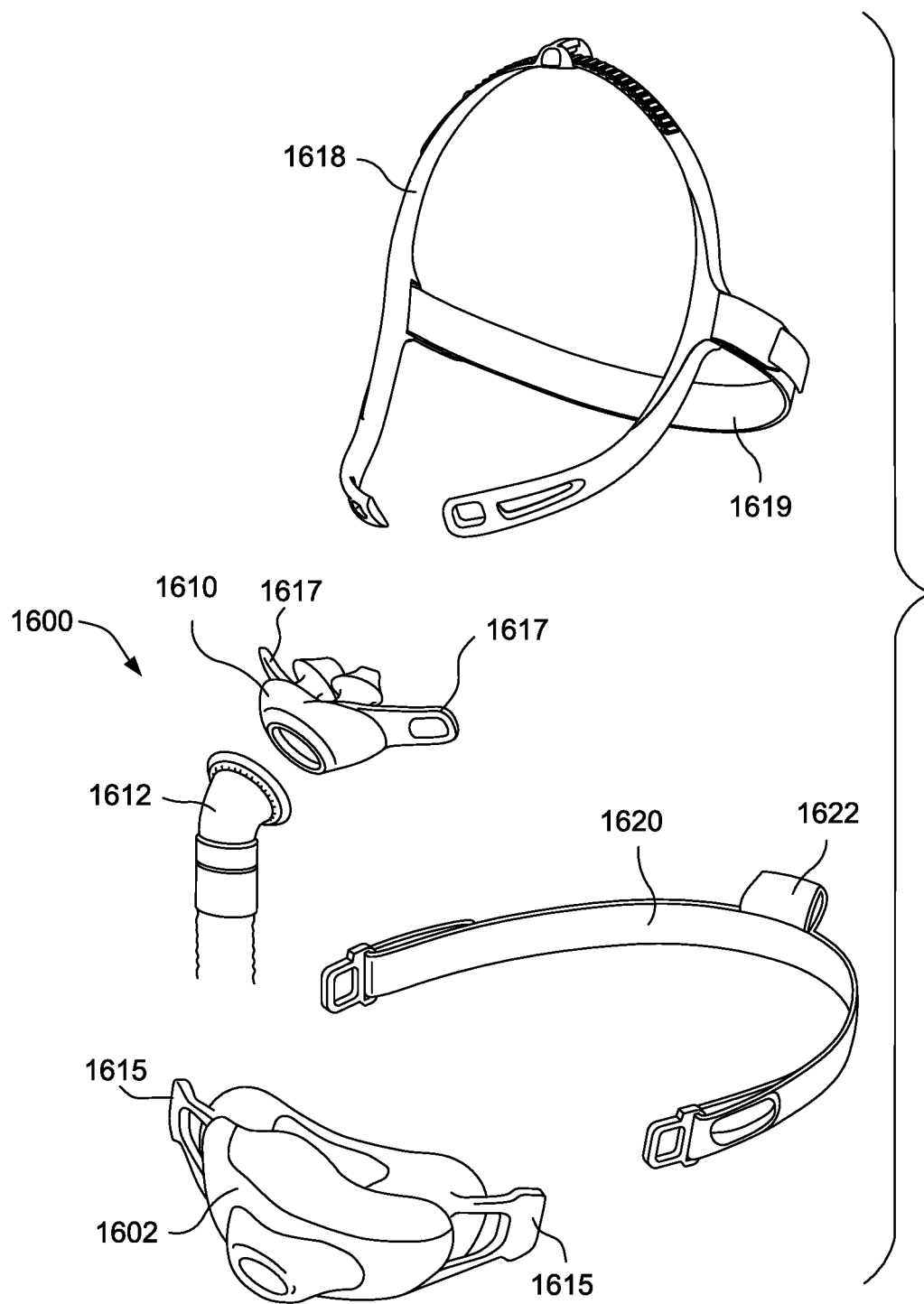
FIG. 66 depicts an exploded view of a modular mask system according to an embodiment of the present technology.

FIG. 66 illustrates a modular mask system 1600 including a mouth portion 1602, a nares portion 1610, elbow and swivel 1612, upper headgear 1618 having a back strap 1619, and lower headgear 1620 having back loop 1622.

The upper headgear 1618 is adapted to connect to nares portion 1610 via connectors 1617, and the lower headgear 1620 is adapted to connect to mouth portion 1602 via connectors 1615. The back strap 1619 of upper headgear 1618 may be inserted through back loop 1622 of lower headgear 1620. Alternatively, another strap could be connected from back strap 1619 to back loop 1622.

Figure 67:
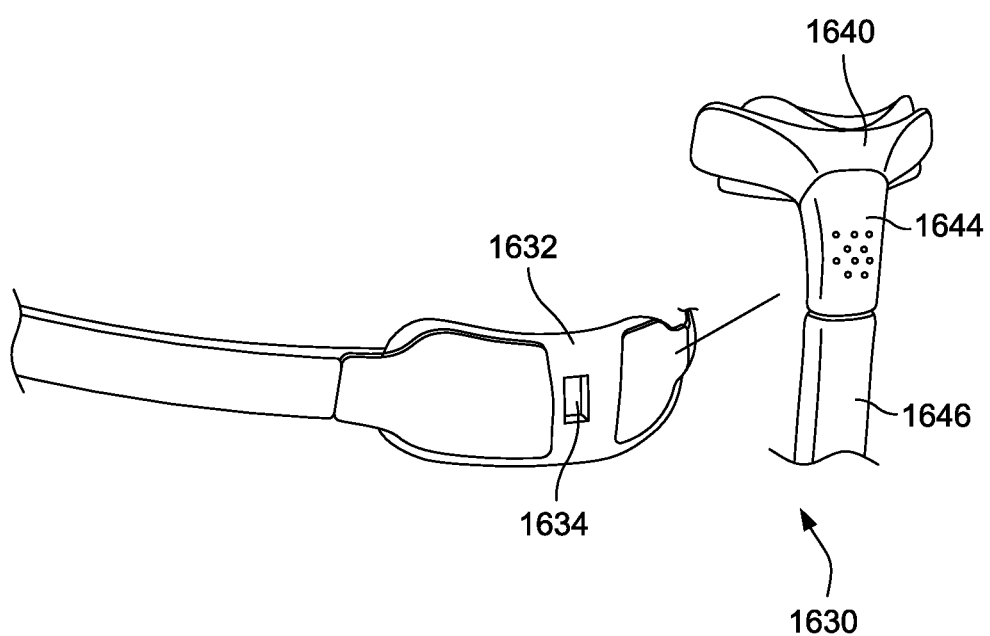
FIG. 67 depicts an exploded view of a modular mask system according to an embodiment of the present technology.
Figure 68:
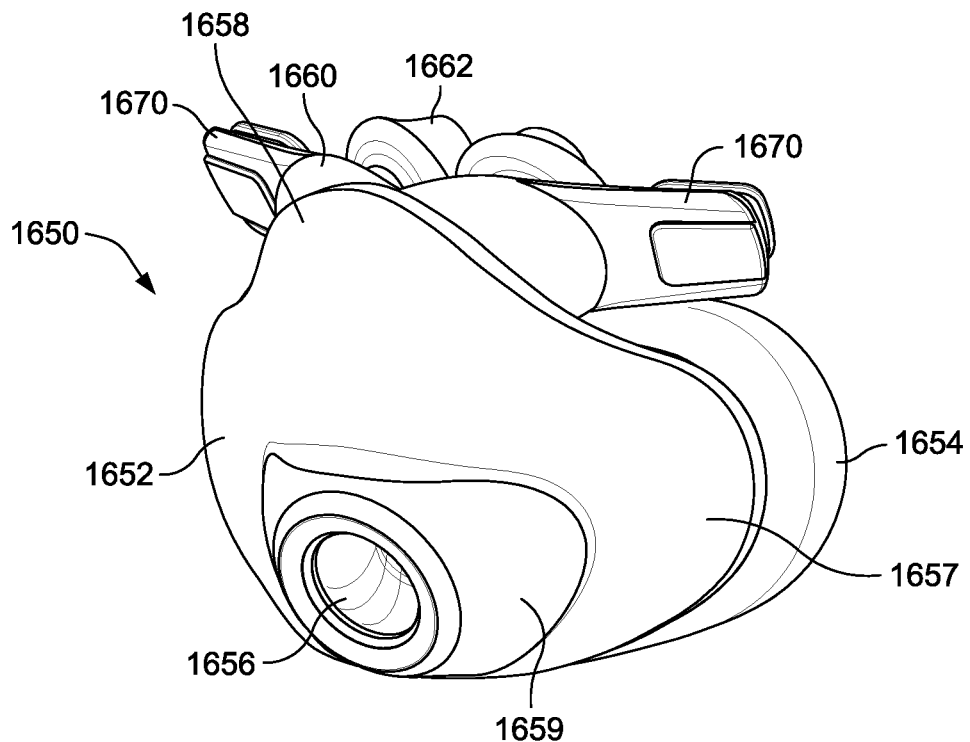
FIG. 68 depicts a perspective view of a modular mask system according to an embodiment of the present technology.
Figure 69:
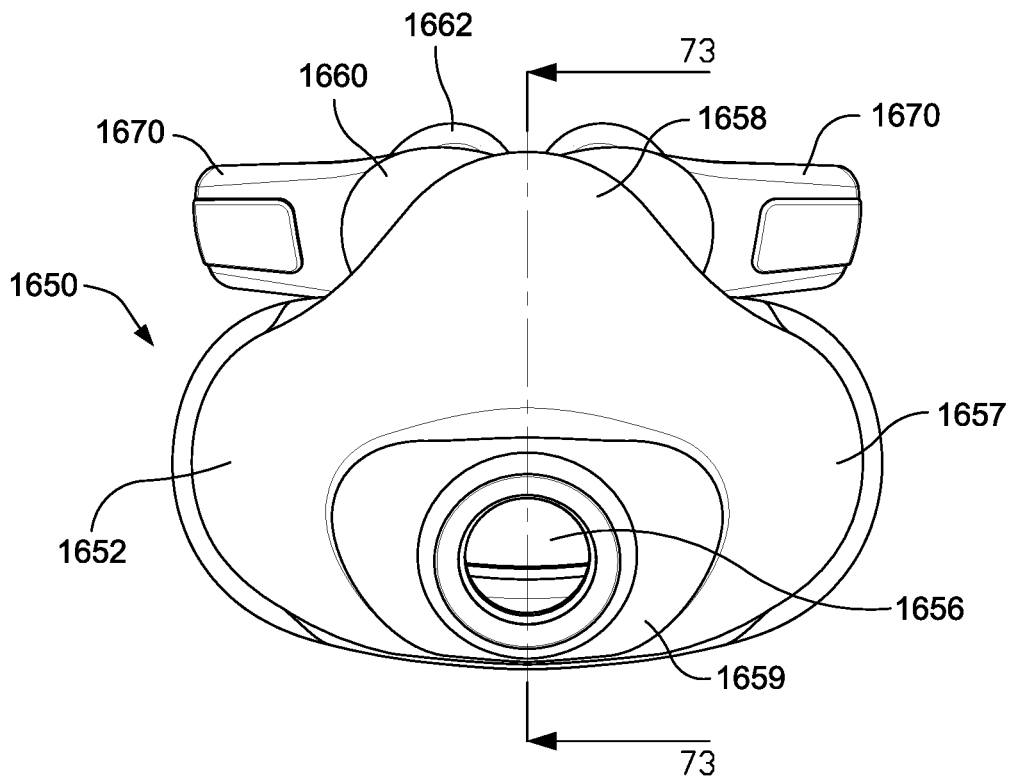
FIG. 69 depicts a front view of the modular mask system of FIG. 68.
Figure 70:
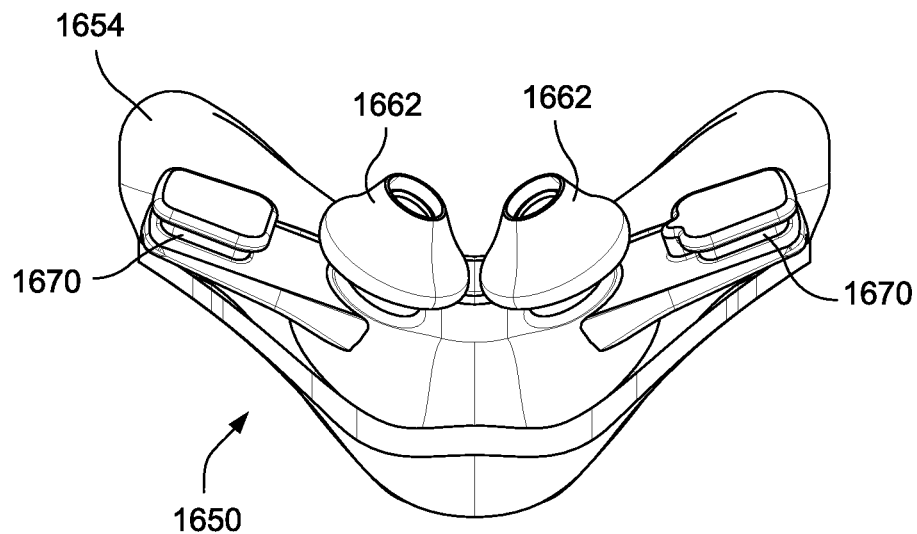
FIG. 70 depicts a top view of the modular mask system of FIG. 68.
Figure 71:
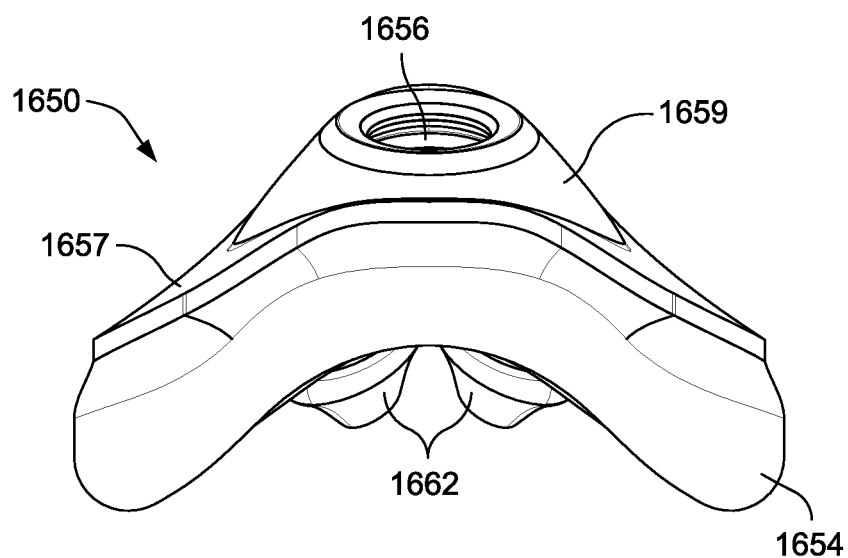
FIG. 71 depicts a bottom view of the modular mask system of FIG. 68.
Figure 72:
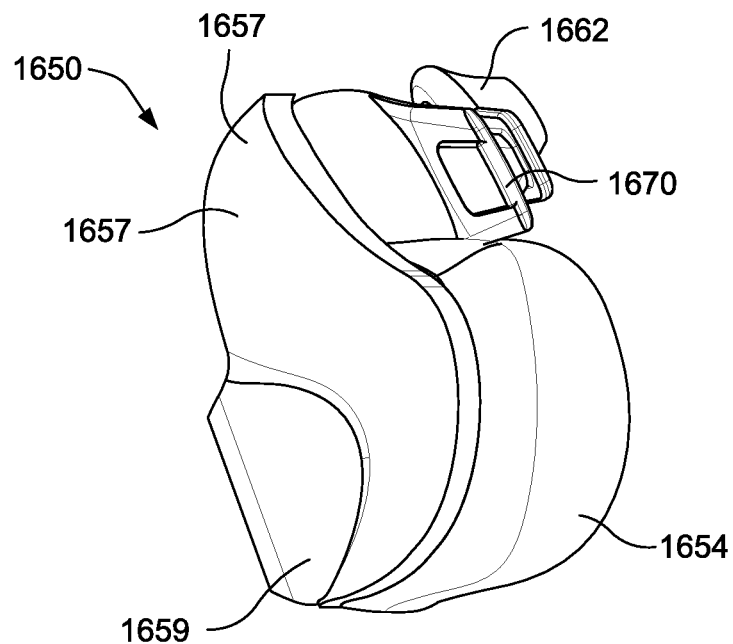
FIG. 72 depicts a side view of the modular mask system of FIG. 68.
Figure 73:
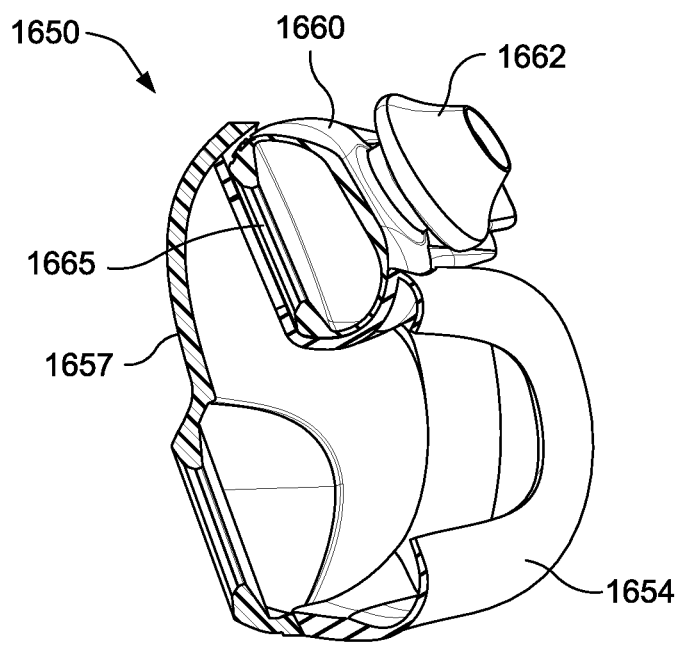
FIG. 73 depicts a cross sectional view along lines 73-73 from FIG. 69.

FIG. 67 illustrates a modular mask system 1630 including a mouth portion 1632, a nares portion 1640, an elbow 1644 and an air hose 1646. The mouth portion 1632 may have an aperture 1634 adapted to receive a lug provided on the back of elbow 1644. In this way, the nares portion 1644 can operate independently of the mouth portion 1632, or can be connected to the mouth portion 1632. In this example, the mouth portion may be connected to the nares portion without disconnecting the elbow.

Example Cushion 1

Figure 74:
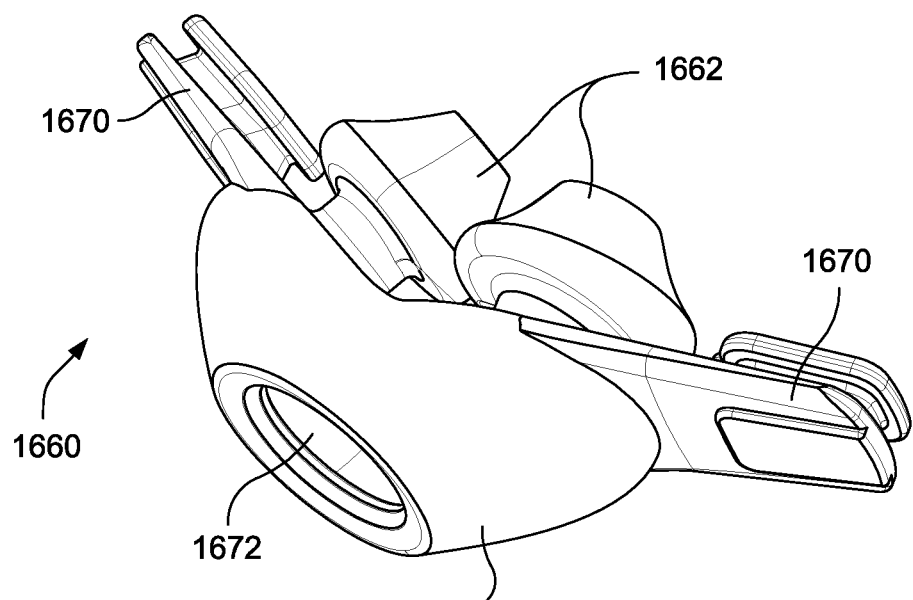
FIG. 74 depicts a perspective view of a nares portion of the mask system of FIG. 68.
Figure 75:
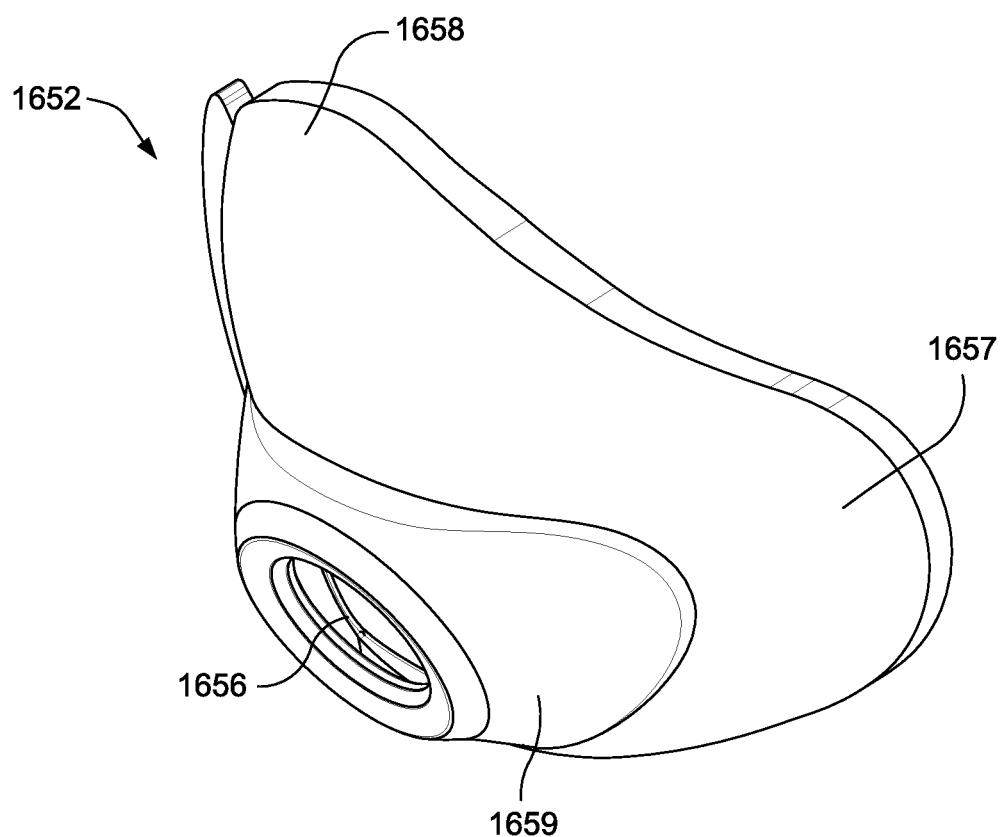
FIG. 75 depicts a perspective view of a mouth portion of the mask system of FIG. 68.

FIGS. 68-73 illustrate mask system 1650, having a mouth portion 1652 and a nares portion 1660. FIG. 74 illustrates the nares portion 1660 and FIG. 75 illustrates the mouth portion, fascia or support structure 1652. FIGS. 76 through 89 illustrate the cushion 1654 of the mouth portion 1652.

The mouth portion 1652 is removably detachable from the nares portion 1660, although both portions may be co-molded. Sealing ring 1665 (FIG. 73) may be used to connect the mouth portion 1652 to the nares portion 1660. An aperture 1656 is adapted to connect to a supply of air to deliver air to the mask system 1650. The mouth portion includes cushion fascia portion 1657 (which may be transparent or semi-opaque), decoupling portion 1659, which may be a thinned portion compared to the remainder of the front of the mouth portion, to decouple forces applied by movement of the elbow/air hose connected to aperture 1656 from the rest of the mask system 1650.

Vanity flap or covering flap 1658 covers/supports the patient's nares region. Preferably, vanity flap covers all or portion of the nares seal portion 1660. Such an arrangement may be less visually obtrusive to the patient and may aid in stabilizing the nares seal portion 1660.

Cushion 1654 connects to the cushion fascia portion 1657 and is adapted to form a seal around a mouth of a patient. The connection of the cushion 1654 to the cushion fascia portion 1658 may be by an interference fit e.g. tongue and groove.

Lower headgear connectors (not shown) may be placed on the front of the mouth portion 1652 in a manner such as illustrated in FIG. 24. The cushion 1654 and the cushion fascia portion 1657 may both have a hardness of 40 Shore A, or similar. Alternatively, the cushion fascia portion 1657 may have a relatively higher hardness compared to cushion 1654. Cushion fascia portion 1657 may be constructed of a semi-rigid polymer such as nylon, polycarbonate, polypropylene. Cushion fascia portion 1657 may have a hardness of 40-80 Shore A. Cushion 1654 may be constructed of a conformable material for example silicone, foam, gel, TPE. Cushion 1654 may be constructed of a material having a hardness of 5-40 Shore A, for example 5-25 Shore A.

Cushion 1654 may be constructed of a combination of materials, for example a first portion proximate the cushion fascia portion having a first hardness and a second portion proximate a patient contacting portion having a second hardness. Preferably the first hardness is greater than the second hardness, to provide structural support to the patient contacting portion. For example, the first portion may have a hardness of 25-60 Shore A, 35-50 Shore A. The second portion may have a hardness of 5-25 Shore A, 5-15 Shore A. The first portion may be thicker than the second portion, for example the first portion may be 1-3 mm, 1-2 mm, and the second portion may be 0.1-2 mm, 0.1-1 mm or about 0.8 mm. The combination of a thin wall section and soft material at the second portion may permit the cushion to be more compliant and flexible, thereby shaping to the patient's face. The thicker first portion provides structure to provide stabilization. Together, they allow a single wall cushion that substantially emulates a dual wall cushion.

Preferably, cushion 1654 may be flexible and/or may have a lower hardness (e.g. 5-15 Shore A) in the chin region 1693 so that when the cushion is placed on the user's face, the cushion stretches over the patient's chin. The stretching of the cushion in the chin region 1693 may cause the cushion to be in tension over the patient's chin, which may form a robust seal with the patient's chin as well as ensuring that the cushion may fit a wider range of chin geometries.

The cushion 1654 includes a cushion fascia connecting portion 1655 (FIG. 76) adapted to connect to the cushion fascia 1657, a ring connecting portion 1680, and a pocket 1684. In an alternative, the cushion fascia and cushion may be formed in one piece. The ring connecting portion 1680 includes an aperture 1682 adapted to receive connecting ring (to connect the mouth portion 1652 to the nares portion 1660). In an alternative, the ring connecting portion and connecting ring may be formed in one piece. In a further alternative, the cushion may be formed with a first connecting ring and the nares portion may be formed with a second connecting ring, first connecting ring being received by the second connecting ring (or vice versa).

The pocket 1684 is adapted and shaped to receive the gusset 1671 (FIG. 74) of the nares portion 1660, or other portion of nares portion 1660 for example the headgear connector portion of nares portion 1660. A different shaped pocket may be used if a different nares portion is used. The pocket 1684 is sunken in the cushion 1654 so as not to disturb the seal of the cushion 1654 when the nares portion 1660 is in the pocket 1684. That is, pocket 1684 may be disposed or offset under or below the uppermost surface of the mouth cushion 1654.

Pocket 1684 may also be a sunken portion, groove, trench, hollow, pouch, alcove, indentation, dip, pit, valley or sinkage—i.e. a region of the cushion that is adapted to receive a nares portion, the region having an alternate or abstract geometry when compared to the rest of the mouth cushion. The pocket may not be a hole, cut out or aperture. Preferably the pocket is air tight. Preferably the pocket is formed by a soft, conformable material such as the mouth cushion, rather than the frame. Such an arrangement is preferable as a conformable pocket may permit adjustment of the position of the nares portion, thereby fitting more patients. Preferably, the pocket permits movement of the nares portion in the superior-inferior direction, to accommodate varying patient nose heights. Preferably the pocket may increase in stiffness when air pressure is applied in the mouth cushion for example. Preferably the pocket may stabilize the nare portion in position in the medial-lateral direction. This may be achieved by the shape of the pocket, adapted to match the shape of the nares portion. such an arrangement may ensure that the nares portion maintains sealing engagement with the patient's nares in use when tube drag or other forces are applied to the side of the mask.

The nasal seal portion may reside or rest in the pocket. The patient contacting portion of the nasal seal portion may be positioned outside, above or higher than the pocket. Such an arrangement may ensure that the patient can see the nasal seal portion contacting their nose to ensure alignment and seal.

In one form the nasal seal portion may not be in air flow communication with the mouth portion via the pocket.

The pocket may have a lower stiffness than surrounding portions of the mouth cushion. The pocket may have a comparably thinner wall section than other regions of the mouth cushion. The pocket may be formed from a different material to the rest of the mouth cushion.

Preferably the pocket is continuous with or formed in one piece with the top lip contacting region of the mouth cushion and is thus in sealing engagement with the patient's top lip.

The mouth cushion may comprise a top lip region adapted to interface with the patient's top lip. The mouth cushion may further comprise a cheek region adapted to interface with the patient's cheek and/or side of mouth. The mouth cushion defines a wall, the wall located between a patient contacting portion of the mouth cushion and a frame contacting portion of the mouth cushion. The wall may comprise different portions, for example a top lip wall portion, a chin wall portion and two cheek wall portions, each corresponding to the respective top lip, chin and cheek regions of the patient's face. In one form, the cheek wall portion may be comparably stiffer than the top lip wall portion. In another form, the chin wall portion may be comparably stiffer than the top lip wall portion. Preferably the top lip portion may be less stiff than the cheek wall portions. In such an arrangement the cheek contacting portion may act in compression on the patient's cheeks, such that the top lip and chin regions may be in tension.

Figure 78:
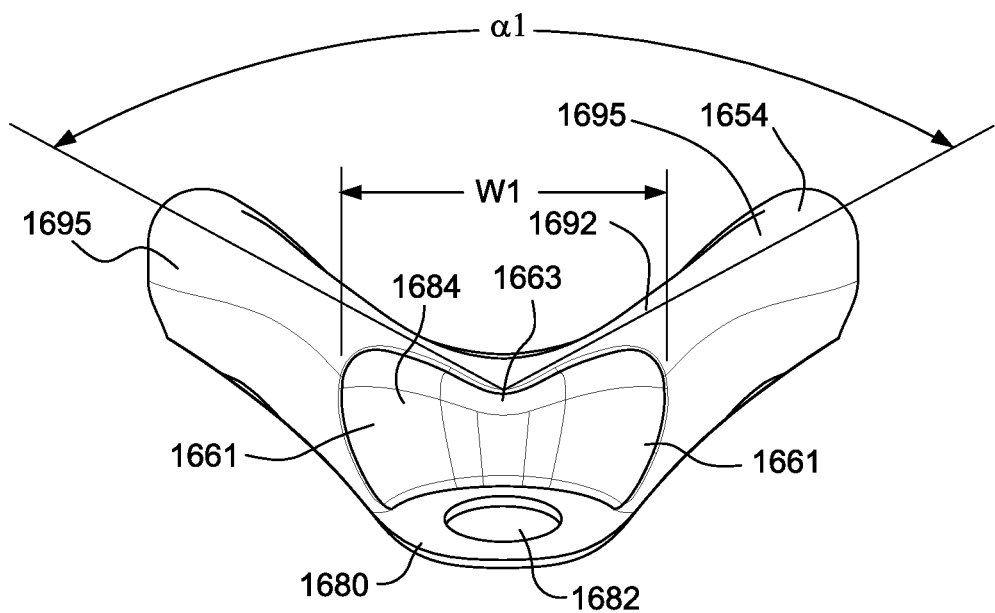
FIG. 78 depicts a top view of the cushion portion of the mask system of FIG. 68.

Pocket 1684 in the present example may comprise a curved groove having lobes or regions 1661 as shown on FIG. 78. Lobes 1661 may be shaped to correspond to gusset 1671 as shown on FIG. 74. The lobes may be separated by a ridge or indentation 1663 adapted to indicate the alignment or positioning of the nasal portion 1660.

Pocket 1684 may have a maximum width w1 of approximately 30-60 mm. Preferably, pocket 1684 may have a maximum width w1 of approximately 35-45 mm. Preferably, pocket 1684 may have a maximum width w1 of approximately 40-45 mm.

Figure 85:
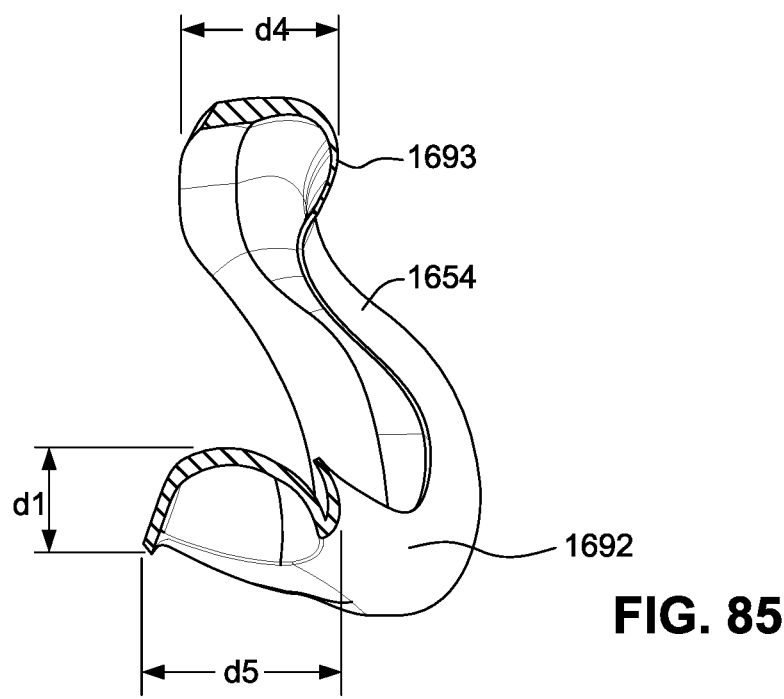
FIG. 85 depicts a cross sectional view along lines 85-85 from FIG. 77.
Figure 89:
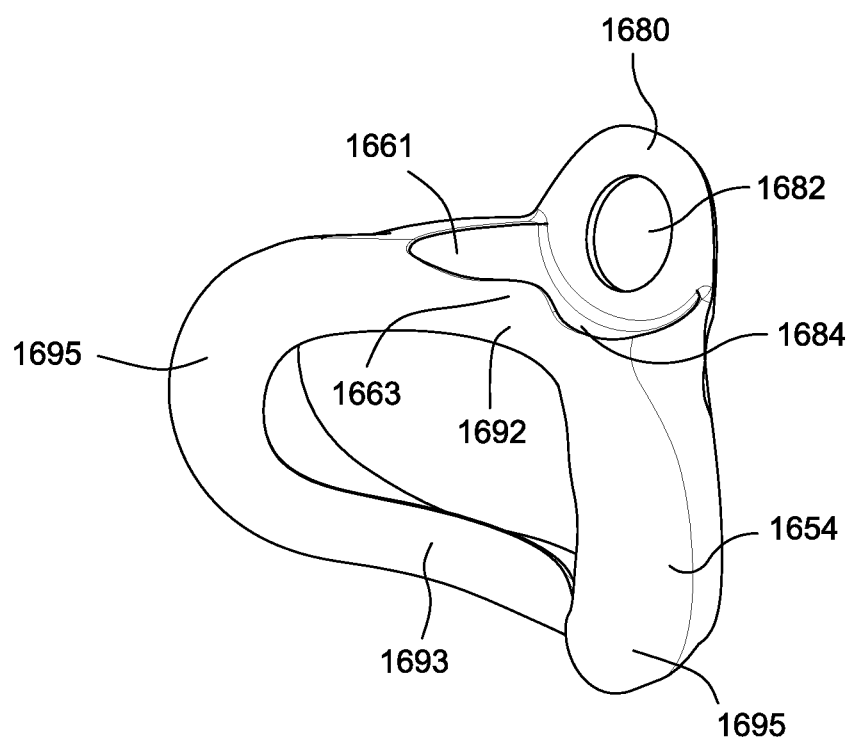
FIG. 89 depicts a perspective view of the cushion portion of the mask system of FIG. 68.

Pocket 1684 may have a length d5, as shown on FIG. 85, of about 15-40 mm. Preferably, pocket 1684 may have a length d5 of about 20-30 mm. This length may be the approximate length from the fascia contacting side of the pocket to the outer most edge of lobe 1661.

Lobes 1661 of pocket 1684 may be offset or angled with respect of one another to position the nasal seal to be positioned at the angular region of the maxilla (patient's top lip). Lobes 1661 of pocket 1684 may be angled with respect of one another by angle $\alpha 1$ of approximately 90-180°. Lobes 1661 of pocket 1684 may be angled with respect of one another by angle $\alpha 1$ of approximately 90-150°. Lobes 1661 of pocket 1684 may be angled with respect of one another by angle $\alpha 1$ of approximately 90-180°. Lobes 1661 of pocket 1684 may be angled with respect of one another by angle $\alpha 1$ of approximately 90-150°.

The chin or lower seal region 1693 of mouth cushion 1654 may be rounded or curved to conform to a patient's chin. Radius of curvature r1 may preferably be 20-50 mm. Radius of curvature r1 may preferably be 30-40 mm. Radius of curvature r1 may preferably be 35-45 mm.

The nares portion may be secured to the cushion 1654 by connection to the connecting ring. The cushion may also have a thickened portion 1686 (FIGS. 80 and 81) to support connection to cushion fascia portion 1657. Also, the thickened portion 1686 supports the sealing portion in position and prevents collapse of the sealing portion, particularly if the sealing portion is constructed of a low hardness, low thickness material, i.e., it will lack structural rigidity.

The nares portion 1660 includes a sealing portion 1662 adapted to form a seal with the nares of the patient, and headgear connectors 1670 for connecting to headgear. The sealing portion 1662 may be in the form of nozzles, although other sealing portions may be used, such as pillows, prongs, etc. Exemplary sealing portions are disclosed in WO 2009/052560 A1, which is incorporated herein by reference in its entirety.

Figure 79:
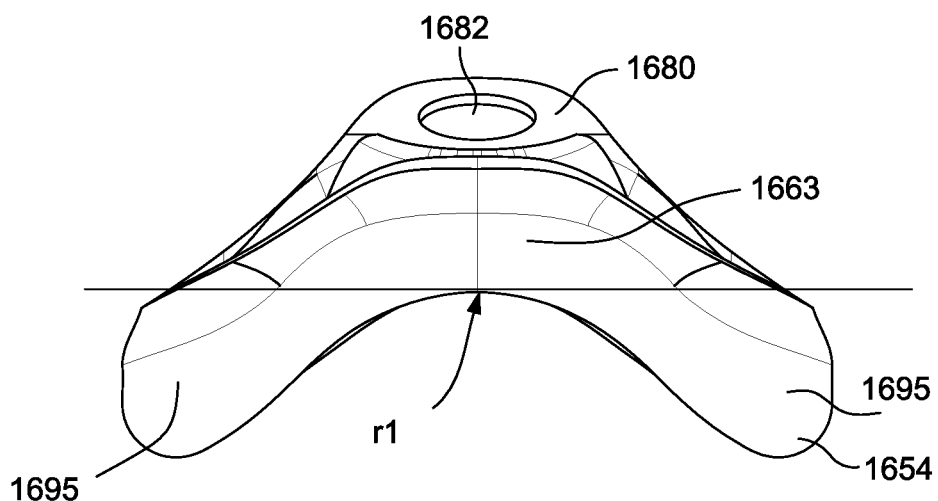
FIG. 79 depicts a bottom view of the cushion portion of the mask system of FIG. 68.
Figure 84:
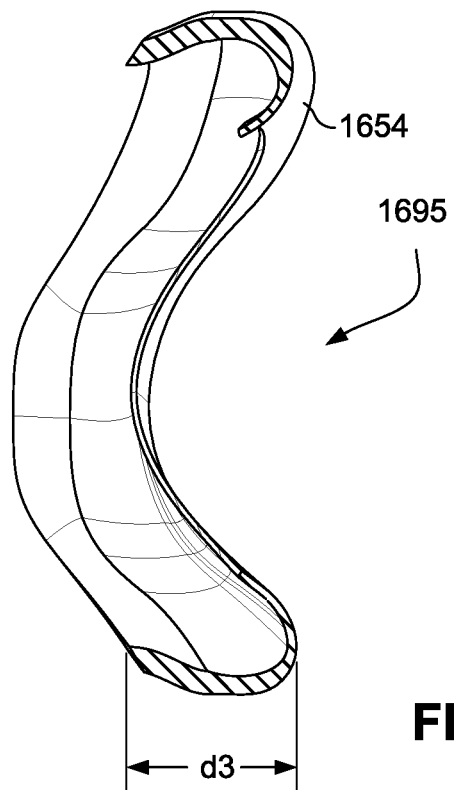
FIG. 84 depicts a cross sectional view along lines 84-84 from FIG. 77.

The cross sections illustrated in FIGS. 82-84 are shaped to accommodate flat faces and more pointy faces of patients due to the question mark like shape of the cross section. FIG. 83 shows the cross section at the horizontal plane that may be positioned generally on the cheeks or the lateral extents of the patient's mouth. In this region, the cross section of the cushion shows that the membrane is comparably longer than at the bony upper or lower jaw regions (shown in FIGS. 82 and 84). This may be to reduce the force of the cushion on the patient's cheeks compared to the bony upper or lower jaw regions, as the longer membrane may absorb more force than the shorter membrane. This may be because the patient's cheeks are more sensitive than the bony regions of the face. The shape of the cushion is shaped to match a shape of a face, as illustrated in FIG. 79, e.g., a C-shape. As illustrated, the sealing membrane includes a varying thickness along its length, e.g., from thick to thin. This varying thickness may be so that a patient contacting portion is supported and positioned by the thicker region, and the patient contacting region may be comfortable and conformable due to the thinner region. The patient contacting portion may be approximately 0.2-2 mm. Preferably, patient contacting portion may be approximately 0.8-1.2 mm. Thicker region 1686 may be approximately 0.5-4 mm. Preferably thicker region 1686 may be approximately 2-3 mm.

In a further example, the load imparted by the cushion on the user's face at the top lip region 1692 may be greater than the load imparted by the cushion on the user's face at the chin region 1693. This may be achieved by having a comparably greater thickness at the top lip region 1692 compared to the thickness at the chin region 1693. Such an arrangement may assist in anchoring the cushion on the patient's face, while ensuring that the force on the lower jaw is low. High forces on the lower jaw may force the upper airway to collapse and thereby exacerbate obstructive sleep apnea, so it is desirable to have a lower force on the patient's lower jaw and hence chin region 1693.

The pocket 1684 is structured to accommodate the nares portion, and air inside the nares portion ensures a seal across the top lip. The nesting nares portion and cushion make the mask less obtrusive. Pocket 1684 may have a depth d1 of approximately 5-30 mm. Preferably, pocket 1684 may have a depth d1 of approximately 5-20 mm. Preferably, pocket 1684 may have a depth d1 of approximately 5-10 mm. The depth of pocket d1 can be seen in FIGS. 80-81.

As best shown on FIG. 80, pocket 1684 may be adjacent or connect to a flap seal portion at the top lip region 1692. A ridge or apex 1694 may be formed between the pocket 1684 and the top lip region 1692. Ridge 1694 may act to divide the pocket from the top lip region, and may also provide a hinge or spring point for the top lip region.

As best shown at FIGS. 80 to 81, pocket 1684 may be generally curved or rounded in a cup like shape as indicated at c1.

At chin region 1693, as best shown on FIG. 80, the cushion may have a depth d2 i.e. the distance from the sealing region or patient contacting portion of the chin region to the connecting region 1655, of approximately 0.5-3 mm. Depth d2 may be approximately 1-2 mm, Preferably depth d2 may be approximately 1.5-2 mm. This depth may be desired so as to ensure different shaped chins may be accommodated by the mouth cushion 1654. Chin lip region 1693 as shown in FIG. 85 demonstrates depth d4. Depth d4 may be substantially similar to depth d1.

Cushion 1654 may have a cheek region 1695, and at the cheek region 1695 the cushion may have a depth d2, shown on FIGS. 82, 83 and 84. Depth d2 may be larger than d1, d4. Such an arrangement may be preferable so that cushion 1654 may flex and deform at the cheeks to a greater extent than at the top lip, so as to anchor the cushion on the top lip and permit variations in the facial geometry of patients. For example, some patients may have relatively flat faces while others may have relatively pointy faces, so the cushion should be able to conform to each of these facial profiles. For example, depth d2 may be approximately 10-50 mm. Preferably, depth d2 may be approximately 20-35 mm. Preferably, depth d2 may be approximately 20-30 mm.

The curvature of the top lip region 1692 of the cushion ensures tension across the patient's top lip and therefore seal. The spring shape cross-section at the top lip lowers force displacement at the patient's top lip (sensitive region).

FIG. 86 shows the mouth cushion 1654 as viewed from the patient contacting side. The top lip region 1692 has a height d6, which may be less than height d7 of chin region 1693. This may be because typically a person's face has a smaller distance between the top lip and bottom of the nose when compared to the distance between bottom lip and the tip of the chin. For example, height d6 may be 5-15 mm. Preferably, height d6 may be approximately 8-10 mm. Height d7 may be approximately 10-25 mm. Preferably, height d7 may be approximately 12-16 mm.

Example Cushion 2

FIGS. 92A-E and 93A-I illustrate a variant of a mouth cushion 2100 which is similar to that shown in FIGS. 76-89, and share common features such as a pocket adapted to receive a nasal seal portion and a single side wall 2104 that is thicker at its base where it connects to the fascia and thinner at its distal end where it seals with the patient. The side wall has a sickle or question mark type shape.

Mouth cushion 2100 may have a top lip region 2692, chin region 2693 and cheek regions 2695. Mouth cushion may further include connecting region 2655 for interfacing the mouth cushion with a clip, frame or other portion of the mask assembly.

The top lip region 2692 and chin region 2693 of the seal portion are formed generally flat such that the seal is stretched (by tension) on the patient's face to enhance the seal. This is beneficial since the headgear, even if tightened, would not be able to significantly change the sealing forces in this area.

Figure 76:
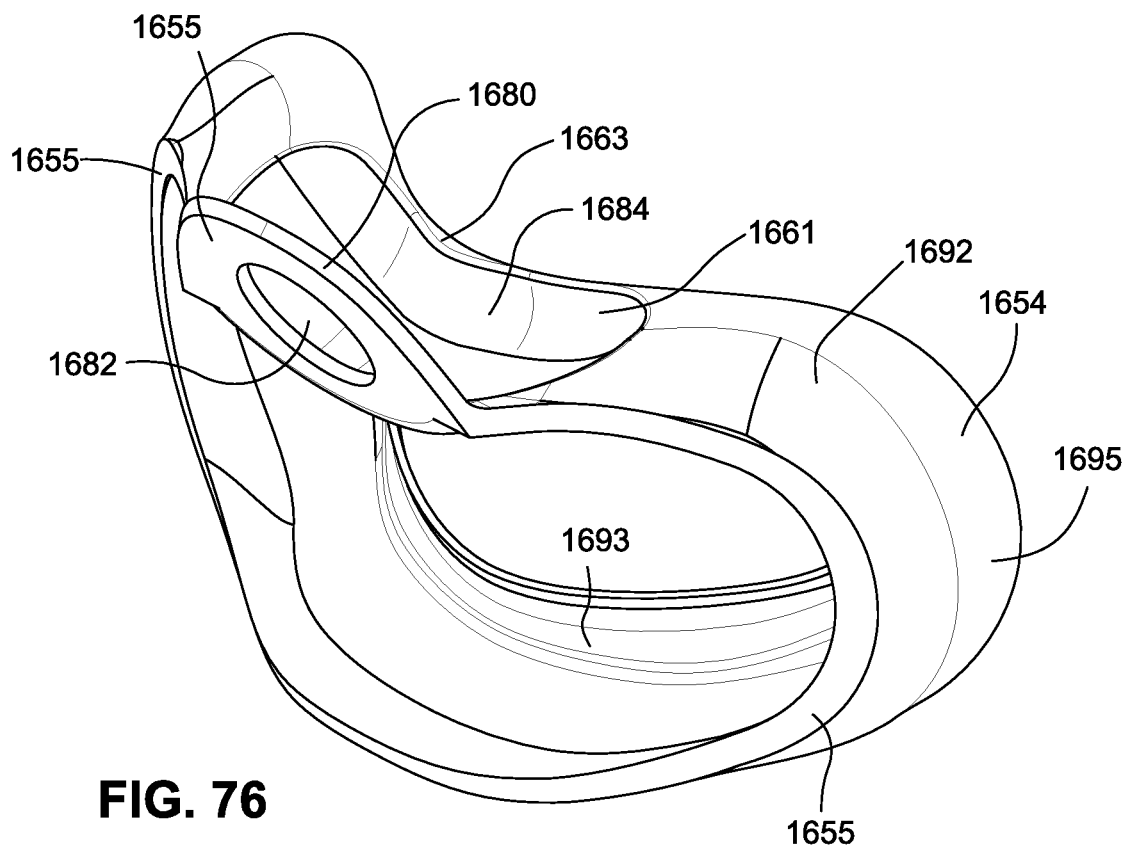
FIG. 76 depicts a perspective view of the cushion portion of the mask system of FIG. 68.
Figure 77:
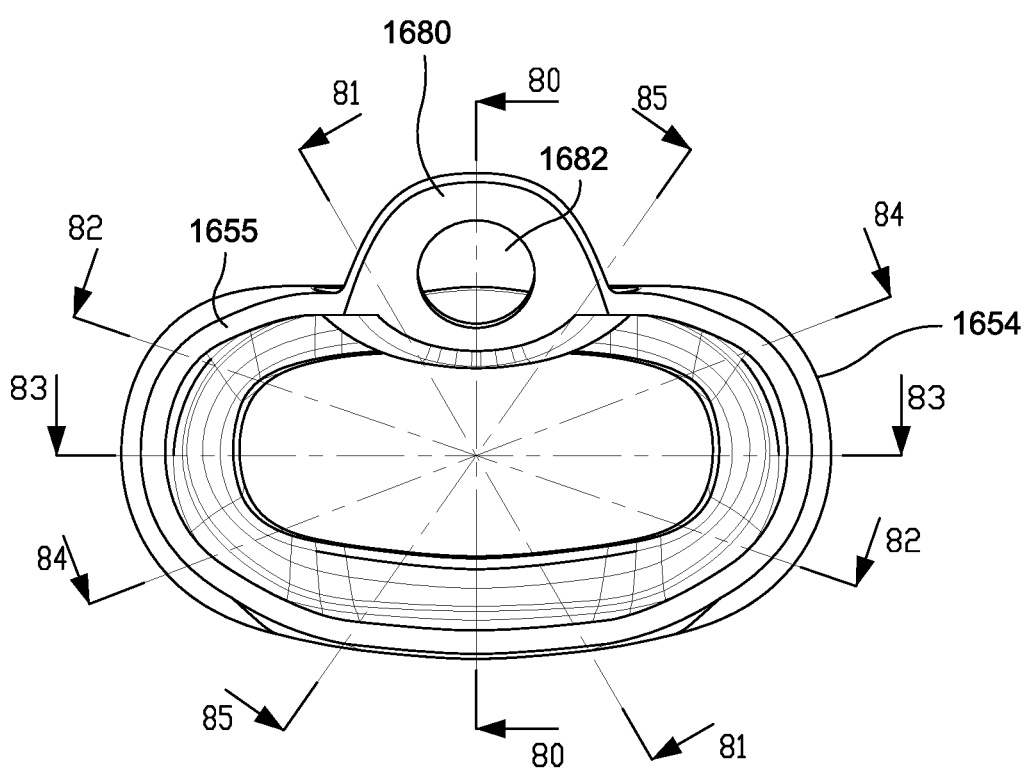
FIG. 77 depicts a front view of the cushion portion of the mask system of FIG. 68.

The pocket 2102 is thinner compared to the pocket 1684 in FIG. 76. This allows the nasal seal to more directly add some component of sealing force—i.e. as the nasal seal is pressurized the nasal seal may become stiffer and thereby impart force on the top lip seal portion. The reduction in thickness may also reduce weight and/or material.

In addition, cushion 2100 does not have a ring connecting portion 1680 as in FIGS. 86-89 (for example). Thus, air flow to the nasal seal portion is not transmitted through the mouth cushion. Instead, a clip may be provided that is adapted to receive both the mouth cushion and the nasal cushion, and may provide the pathway to transmit air to the nasal cushion.

Pocket 2102 may not be a cup like shape, rather it may have an open back and curve upwards (see c2 shown on FIGS. 93D and 93E) to ridge 2694 to then adjoin top lip portion 2692.

Figure 93A:
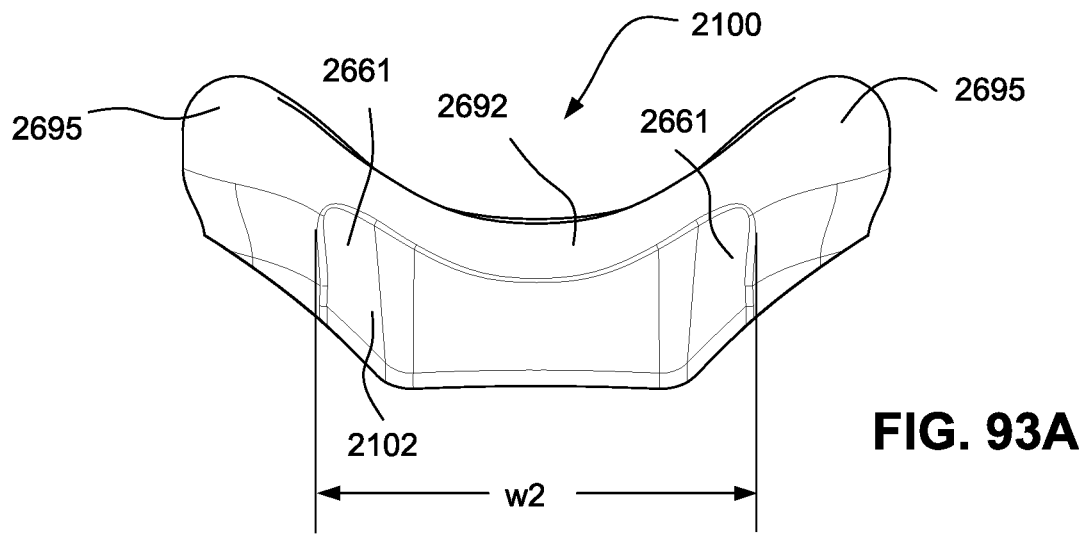
Figure 93B:
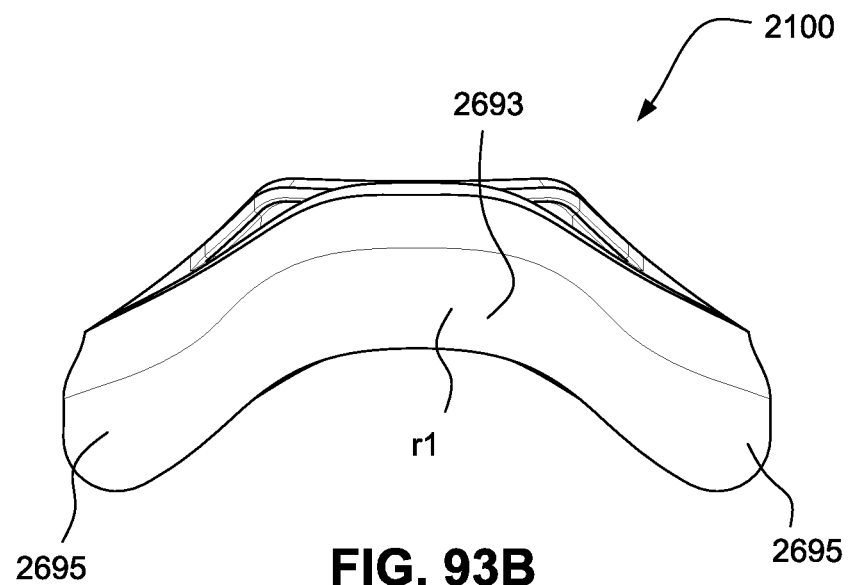
Figure 93C:
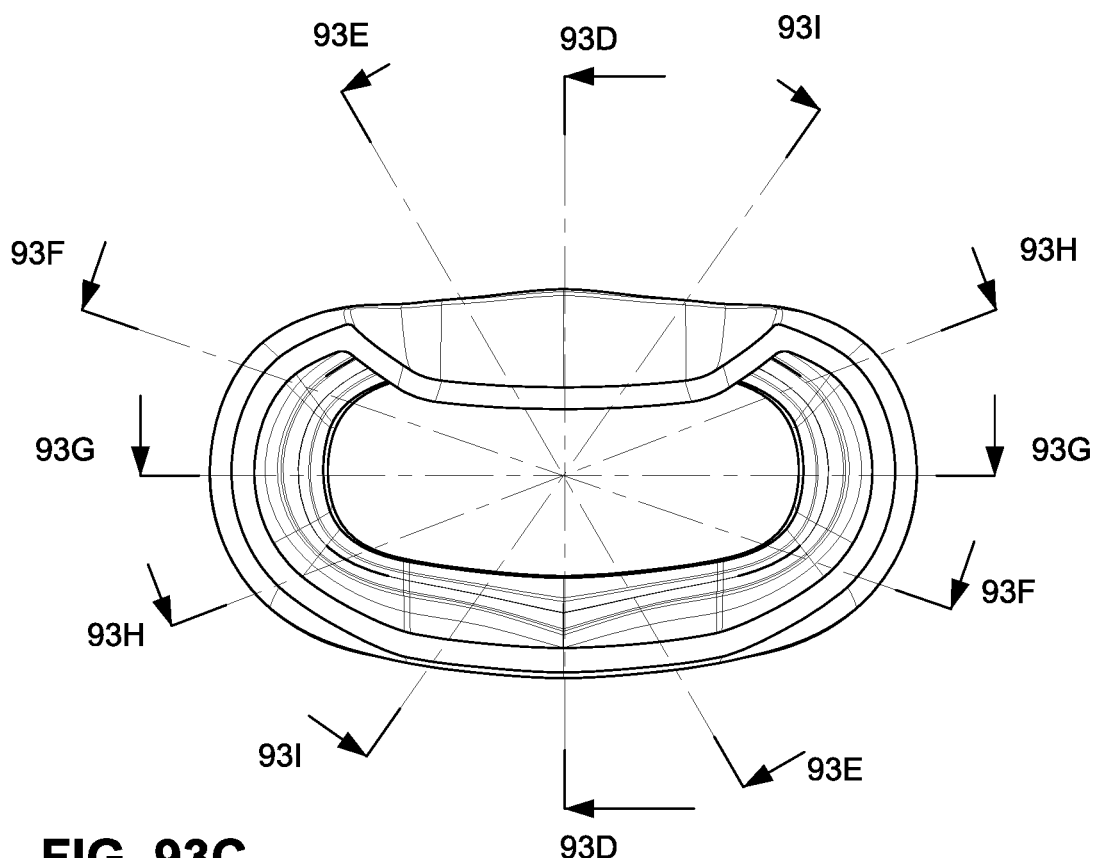
Figure 93D:
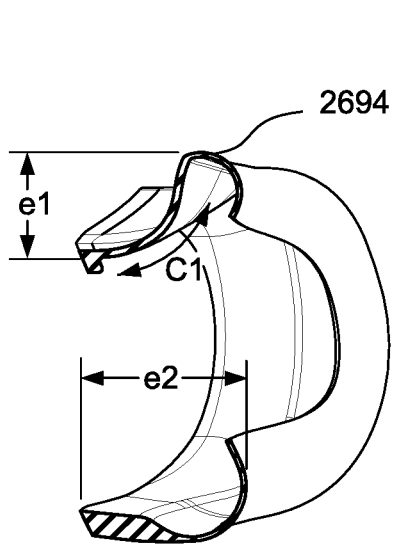
Figure 93E:
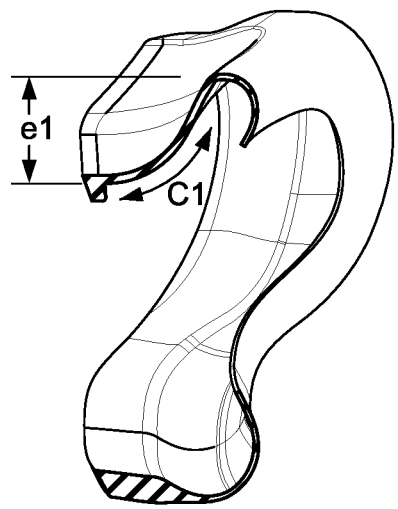
Figure 93F:
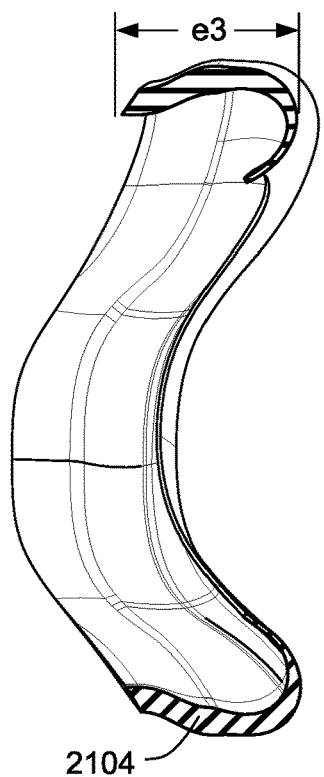
Figure 93G:
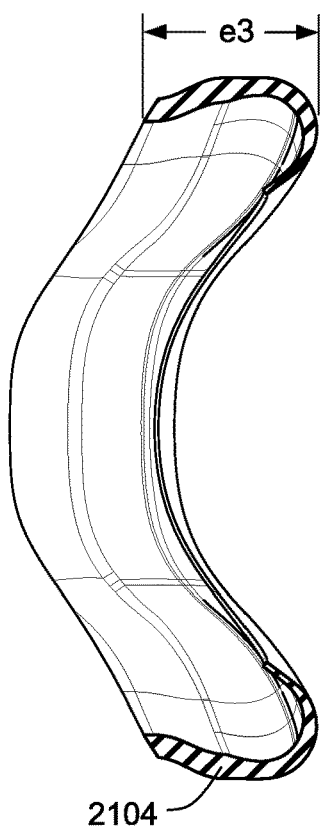
Figure 93H:
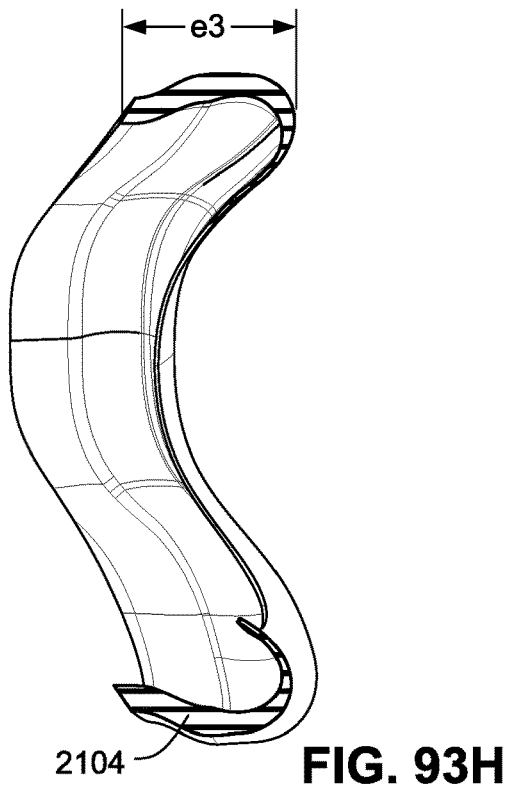
Figure 93I:
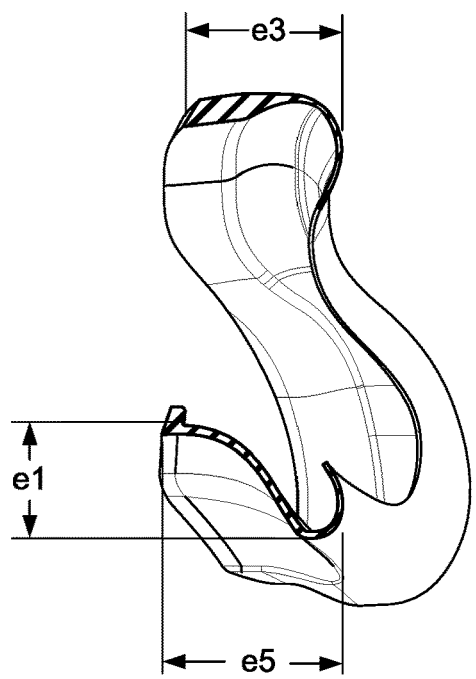

Pocket 2102 may have a similar depth to pocket 1684, as indicated at depth e1 on FIGS. 93D and 93E. Depth e3 may also be similar to depth d3, depth e4 may be similar to depth e4 and length e5 may be similar to length e5.

Depth e2 as indicated on FIG. 93D shows the distance from the edge or connecting region to the patient contacting portion. Depth e2 may be about 10-30 mm, preferably 15-25 mm. Radius of curvature r2 may be larger than the radius of curvature r1 from Example 1. Such a depth and radius of curvature r2 may be to ensure that the depth at the chin region 2693 is similar to that at cheek region 2695. This may flatten out the cushion in the chin region, so that when the patient positions their chin against chin region 2693, the membrane stretches over their chin. This may ensure a more stable seal and a larger fit range.

Width w2 as shown on FIG. 93A may be larger than width w1. This may be to accommodate a longer nasal seal portion or to move the same nasal seal portion from Example 1 further down into mouth seal portion 2100 (i.e. position the nasal seal further from the top surface or deeper in the mouth cushion 2100). Width w2 may be about 50-70 mm. Preferably, width w2 may be about 50-60 mm.

Example Cushion 3

Referring to FIGS. 104-131, a mask system 400 according to an embodiment of the present technology comprises a mouth cushion 4100, a cushion clip 4200 and a fascia 4300. The mouth cushion 4100 shares some common features with Example Cushion 2, such as a pocket 4102 adapted to receive a nasal seal portion, and a sealing portion 4106 configured to form a seal with the patient's face. Other common features may be evident from the following description of the mask system 4000. The mouth cushion 4100 may be formed of, for example, silicone. The cushion clip 4200 may be formed of, for example, thermoplastic. The fascia 4300 may be formed of, for example, thermoplastic.

The mouth cushion 4100 may be over-moulded on to the cushion clip 4200. It should be appreciated that the mouth cushion 4100 may be detachably connected to the cushion clip 4200 in a manner described below. The mouth cushion 4100 comprises the pocket 4102, an upper connecting portion 4104 adapted to receive a nasal seal connecting portion 4202 of the cushion clip 4200 and retain the mouth cushion 4100 to the fascia 4300. Referring to, for example, FIG. 117, the upper connecting portion 4104 is tilted or offset away from the sealing portion 4106 so as to allow the nasal seal portion (not shown) to orient toward the patient's nasolabial angle. Referring to, for example, FIGS. 104, 112 and 113, a rear edge 4108 of the pocket 4102 and the upper connecting portion 4104 form an aperture 4110 that receives the nasal seal connecting portion 4202 of the cushion clip 4200. The nasal seal connecting portion 4202 of the cushion clip 4200 fits within the aperture 4110 of the upper connecting portion 4104 and the rear edge 4108 of the pocket 4102.

Referring to, for example, FIGS. 120-124, the mouth cushion 4100 includes a groove 4114 that is configured to receive the cushion clip 4200. The groove 4114 almost completely encloses the cushion clip 4200. A small gap is provided in the groove 4114 to allow tabs 4218 (FIGS. 139-145) of the cushion clip 4200 to extend outwards and engage with and interlock with slots 4310 (FIGS. 134, 135 and 138) of the fascia 4300. The mouth cushion 4100 further comprises a lip seal 4112 to interface with a groove 4302 (FIGS. 104, 109-111 and 138) of the fascia 4300 formed by a tab 4304. As shown, for example, in FIGS. 110 and 111, the lip seal 4112 is shown as overlapping with the tab 4304 of the groove 4302 of the fascia 4300. However it should be appreciated that in the assembled state, the relatively flexible lip seal 4112 will deform and bend into the groove 4302 and be retained by the tab 4304 of the fascia 4300.

Referring to FIGS. 125-131, the cushion clip 4200 comprises a fitting 4204 to receive a ring of the nasal seal portion (not shown). The fitting 4204 includes reliefs 4206 to permit flexing of the fitting 4204 and tabs 4208 to retain the ring of the nasal seal portion. The cushion clip 4200 further comprises supporting regions or portions 4210 on lower corners of the clip 4200 to increase stability and force on the cushion 4100 in the patient's cheek regions to provide a more stable seal on the soft areas of the patient's face. Supporting regions 4210 on lower corners of the clip 4200 may be thicker or stiffer than adjacent portions of the cushion clip 4200. A fascia contacting lip 4212 is provided to engage the groove 4302 of the fascia 4300. A cushion contacting lip 4214 is provided to engage the groove 4114 of the mouth cushion 4100.

Referring to FIGS. 132-145, the fascia 4300 comprises lower headgear connectors 4306 for connecting to the headgear and an elbow connector 4308 for connecting to an elbow adapted to be connected to a gas delivery tube or conduit. The rear surface of the fascia 4300 includes the groove 4302 (FIG. 138) adapted to engage flexible lip seal 4112 of the mouth cushion 4100. The rear surface also includes slots 4310 that are configured to receive and interlock with tabs 4218 of the cushion clip 4200. As shown in FIGS. 138 and 145, the tabs 4218 are rounded to smoothly guide the tabs 4218 into the slots 4310 of the fascia 4300. Tabs 4218 may also be rounded so that the upper tab adjacent fitting 4204 may be connected first and in a first position, then the cushion clip can be rotated to position upper tab in a second position, this second position permitting lower labs adjacent lower headgear connectors 4310 (in use) to engage with fascia 4300.

1.8 Cushion-to-Fascia Interface

Figure 94:
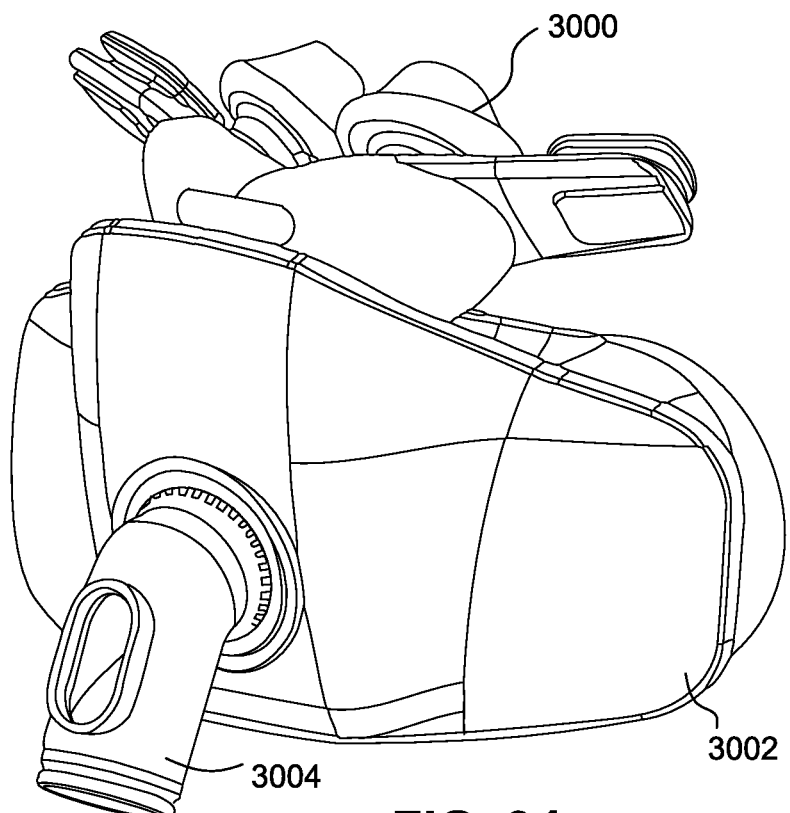
Figure 95:
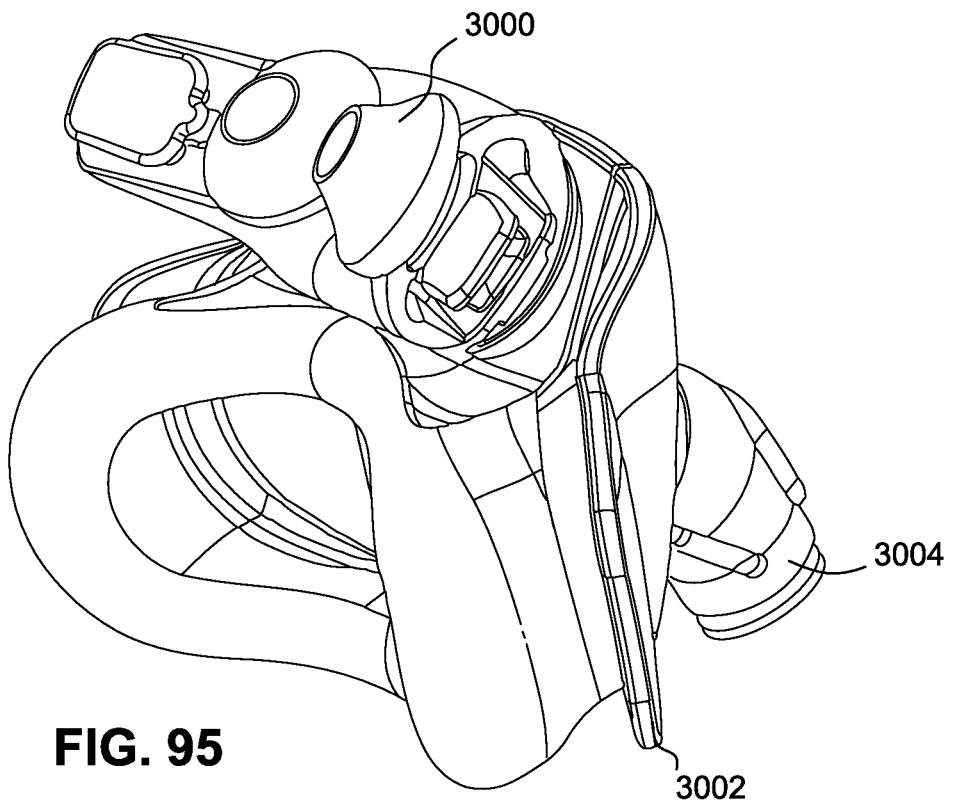
Figure 96:
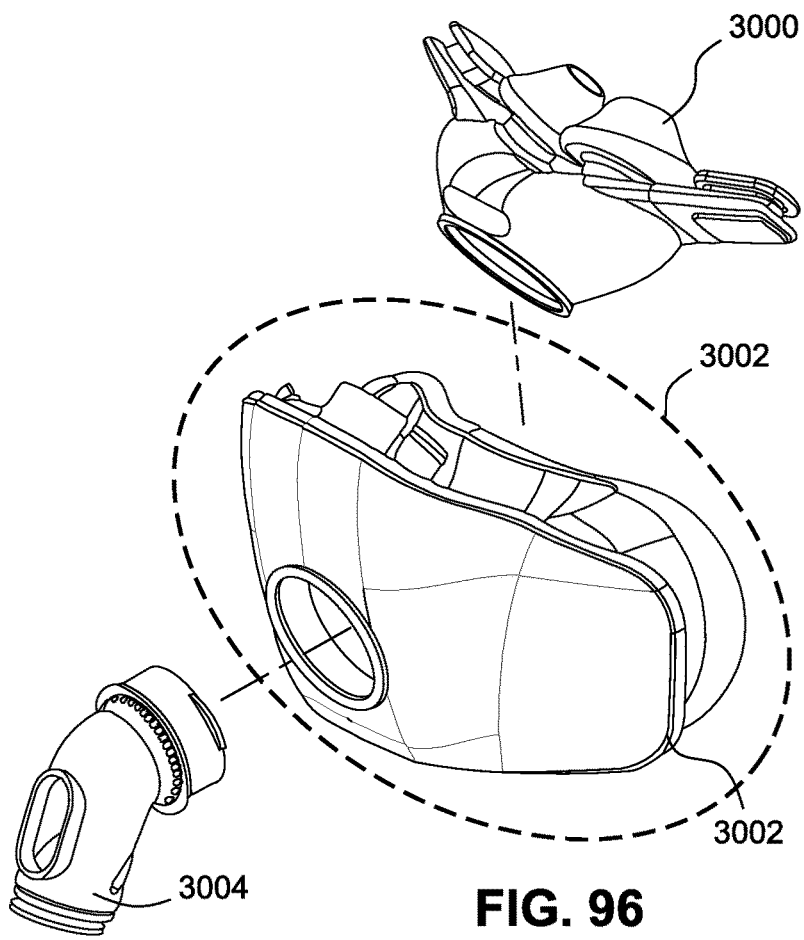

FIGS. 94-102 illustrate an example of a cushion to fascia interface. FIGS. 94 and 95 illustrate the mask assembly in its assembled condition, including pillows 3000, mouth cushion subassembly 3002 and elbow 3004. FIG. 96 illustrates an exploded view thereof.

Figure 97:
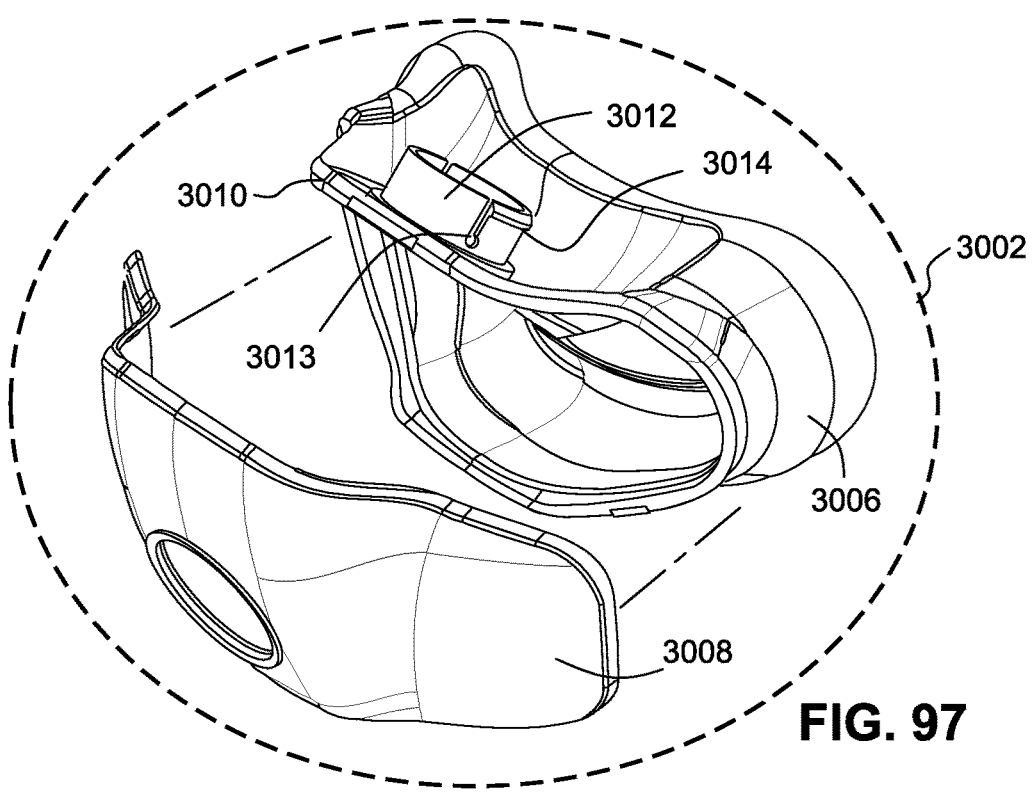

FIG. 97 is an exploded view of subassembly 3002, including cushion 3006 and fascia 3008. Cushion 3006 includes a clip 3010 that may be overmolded on to the cushion. Cushion 3006 may be removably connected to clip 3100.

Clip 3010 may have a fitting 3012 for attachment to the pillows 3000. Fitting 3012 may comprise reliefs 3013 to permit fitting 3012 to flex inwards and thereby accept a nasal seal portion. Fitting 3012 may also comprise tabs 3014 adapted to lock or maintain the position of the nasal seal portion once it is connected. Fitting 3012 may be angled in such a way so as to present the nasal seal portion directly towards the patient's nares. For example, FIGS. 94 and 95 shows the nasal seal portion 3000 oriented to approximate the patient's nasolabial angle.

Clip may be more rigid than cushion, and may be made of Hytrel, polypropylene, nylon, injection molded plastic, etc.

Figure 98A:
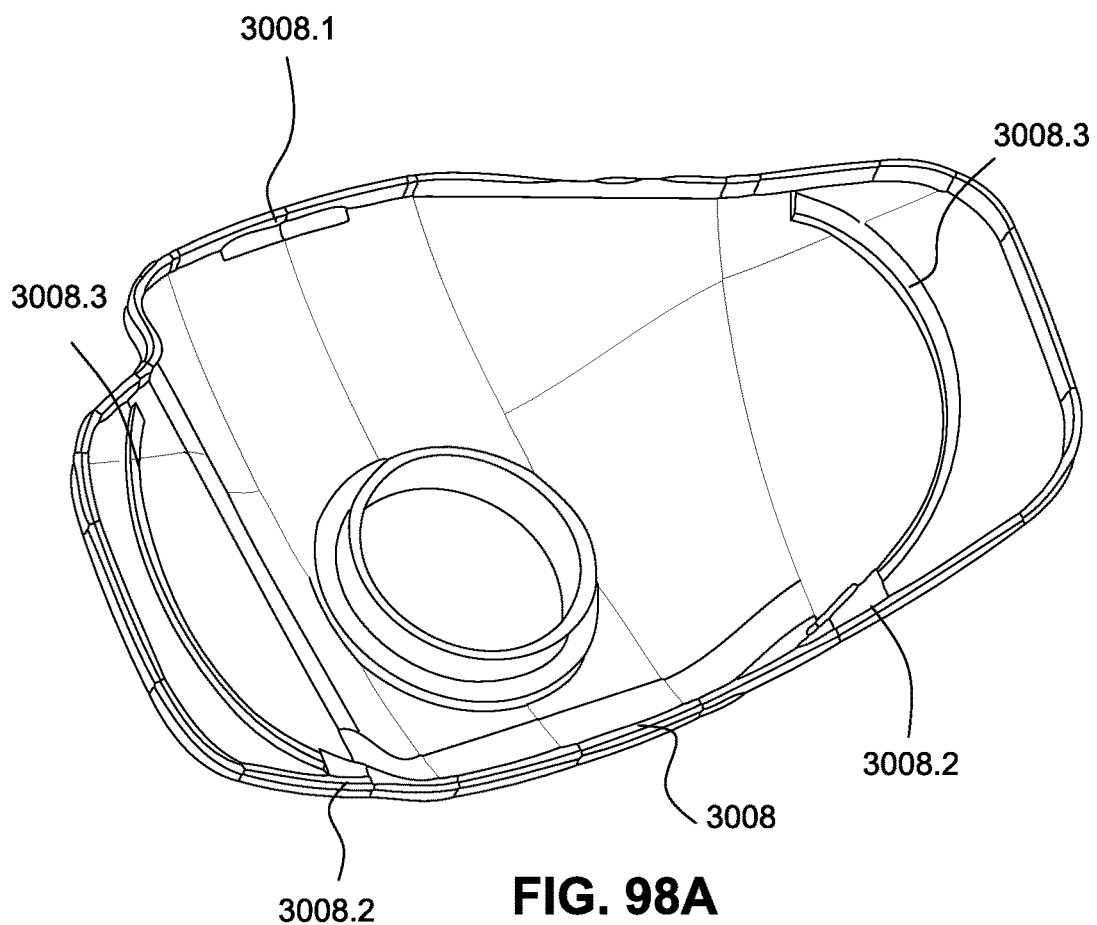

FIG. 98A shows the patient side of the fascia 3008. Fascia 3008 may include recess 3008.1 at the top of the fascia and recesses 3008.2 at the lower side corners of the fascia. Fascia 3008 may further include lugs or ridges 3008.3 adapted to align and/or position the mouth seal portion and/or clip. The outer side or non-patient contacting side of fascia 3008 may be curved or stepped such that the middle portion is raised compared to the side portions. This may aid a patient in picking up the fascia as they can grip on to the curved regions. These curved regions may further include gripping portions (not shown) such as dimples or overmolded buttons to aid the patient in gripping the fascia.

Figure 98B:
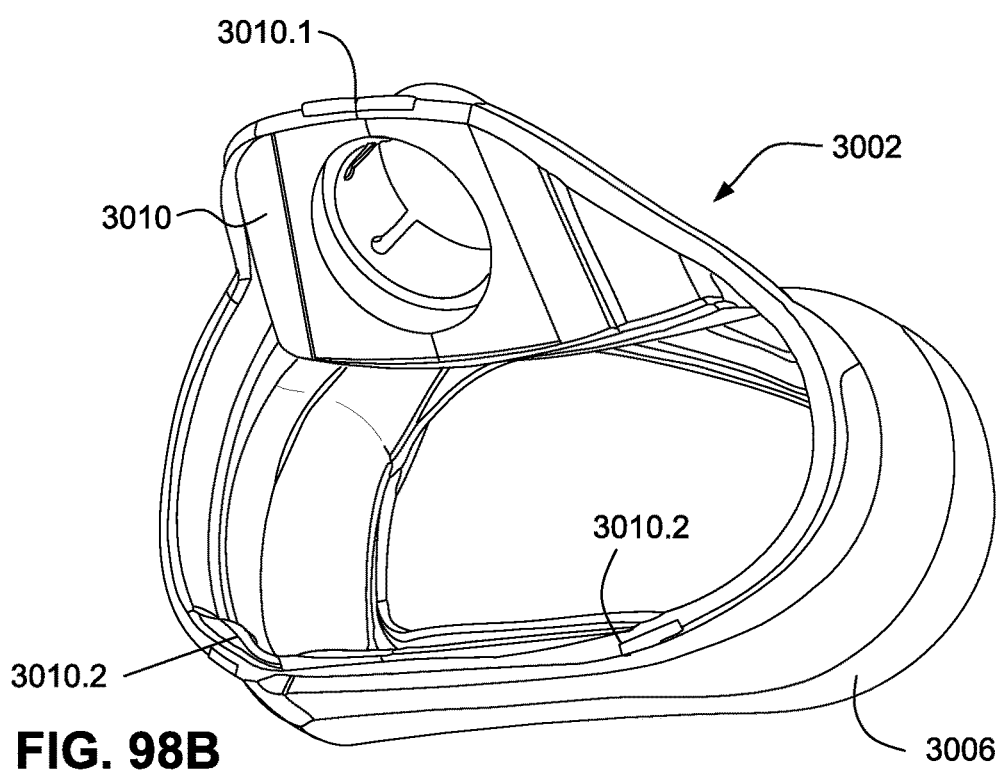
Figure 99:
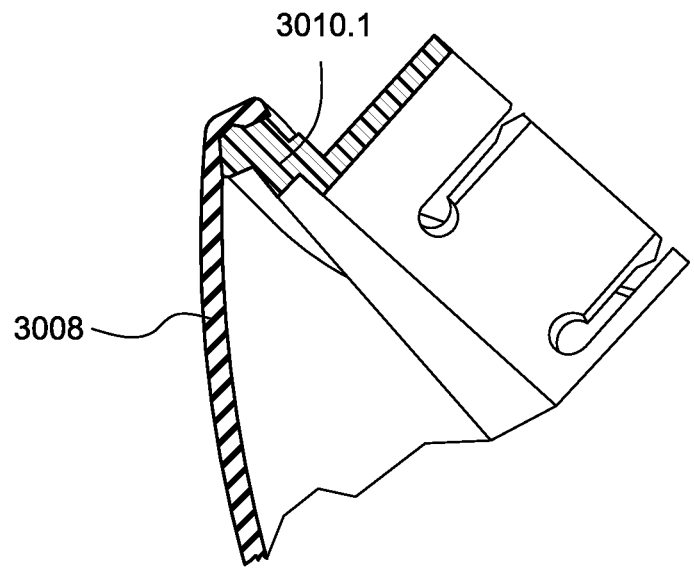
Figure 100:
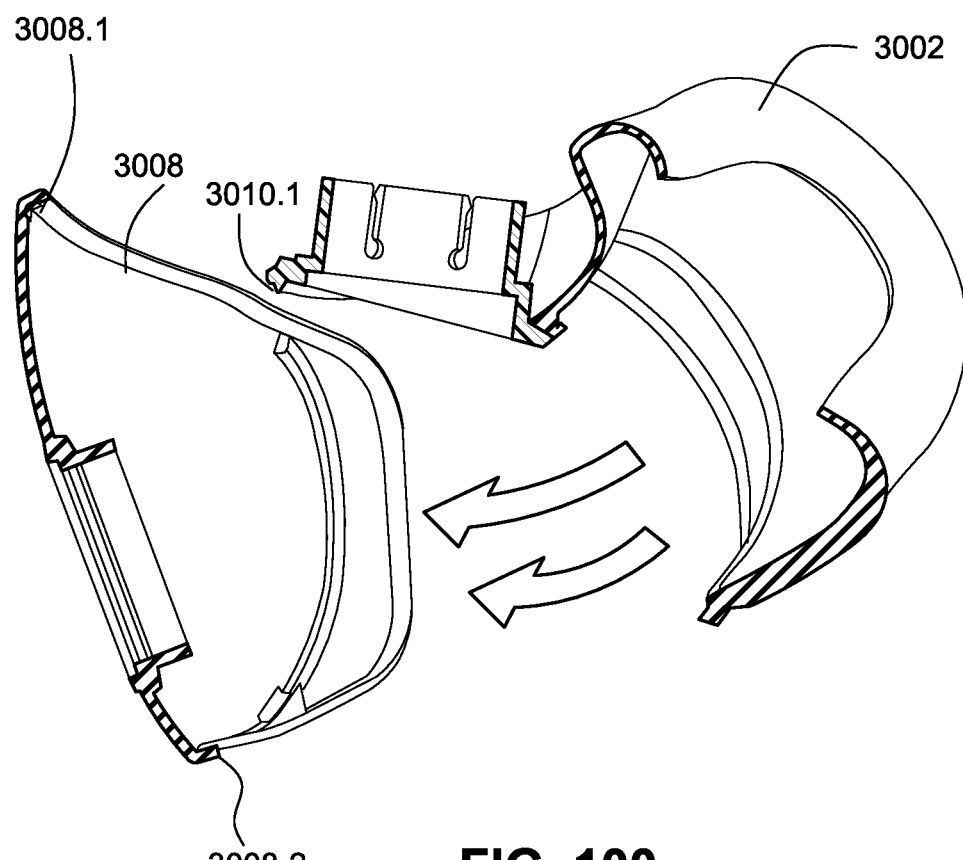

FIG. 97 is a further exploded view showing that the fascia 3008 and set clip 3010 may be clipped together at a number of locations, e.g., two or more, and in this case three locations. As shown in FIGS. 98A, 98B and 99, fascia 3008 may have a recess 3008.1 to receive a projection 3010.1 of clip 3010. FIGS. 100-102 show a sequence of an exemplary fitting assembly between the subassembly 3002. FIG. 100 shows initial engagement between the projection 3010.1 and recess 3008.1 at the top of the mask, after which the mask is pivoted in FIG. 101. Once the lower end of clip readies to the lower part of fascia 3008, the clip snaps home for complete assembly.

The clip may include an integrated (silicone) lip seal to prevent leak between the clip and the fascia 3008. This would make the assembly more robust and less dependent on tolerances to prevent leak. The lip seal may be located in close proximity to the projections 3010.1 or 3010.2. FIG. 103 shows an example of a lip seal 3011 that may be used in such assembly.

1.9 Integrated Mask System

FIGS. 14 and 15 illustrate another mask system 101, which is an integrated mask system. The mask system 101 includes a nares portion 120, a mouth portion 140 and a flexible tube 105 connected to the mouth portion 140 via an elbow 102.

The nares portion 120 may utilize a nares sealing portion 122, which may be in the form of nasal pillows, prongs, a membrane seal such as a nasal cradle, and/or a nasal chamber. The nares sealing portion 122 may be in the form of the nares sealing portion 222 illustrated in FIGS. 19 and 20. The nares portion 120 may further include decoupling portion 125 and headgear connectors 121 adapted to connect to headgear 160.

The mouth portion 140 may include a structural portion 147, a mouth sealing portion 142, decoupling portion 145, headgear connectors 141, and vent 103, which may include one or more vent holes or slots for venting gas exhaled by the patient. A nares portion connector 143 adapted to connect to the nares portion 120 may be utilized when the nares portion 120 and the mouth portion 140 are not formed as a unitary element. The mask system 101 could alternatively be formed as a modular mask system, where the nares portion 120 and the mouth portion 140 are separable and may be used individually, and the nares portion 120 is connectable to the flexible tube 105 via elbow 102.

FIGS. 16-18 illustrate another mask system 201, which includes a nares portion 220 and a mouth portion 240. The nares portion 220 may include a nares sealing portion 222, an orifice 226 for receiving pressurized, breathable gas. The mask system 201 is illustrated with a nares sealing portion 222 such as illustrated in FIGS. 19 and 20, although other nares sealing portions could be utilized, such as pillows, prongs, a nasal chamber, etc.

The mouth portion 240 includes a mouth seal portion 242 which may be in the form of a cushion for sealing with the mouth of the patient, a frame 247, a mouth orifice 246 for receiving the pressurized, breathable air, a decoupling portion 245, and a nares connecting portion 243 for connecting with the nares portion. FIG. 16 is illustrated with the frame 247, the decoupling portion 245 and the connecting portion 243 removed. Although not illustrated, the mouth portion 240 may include connection to a flexible tube for delivery of the pressurized, breathable gas, such as the swivel connector, elbow and flexible tube illustrated in other embodiments.

The mask system 201 could alternatively be formed as a modular mask system, where the nares portion 220 and the mouth portion 240 are separable and may be used individually, and the nares portion 220 is connectable to the flexible tube 105 via elbow 202.

FIG. 23 illustrates a mask system 370, which may include a nares portion 372, a mouth portion 380, and headgear 360. In this embodiment, the mask system 370 may have the nares portion 372 and the mouth portion 380 integrated. The lower headgear strap 379 passes under the patient's ears and provides a normal headgear vector force or sealing force on the patient's face. The headgear strap 360 provides a supporting force to aide positioning and stabilization of the mouth portion 380 on the patient's face. The headgear strap 360 does not connect near the mouth of the patient to aid in keeping obtrusiveness of the mask to a minimum.

The nares portion 372 may include nares sealing portion 374 and mouth sealing portion 375. Decoupling portions may be included.

Figure 27:
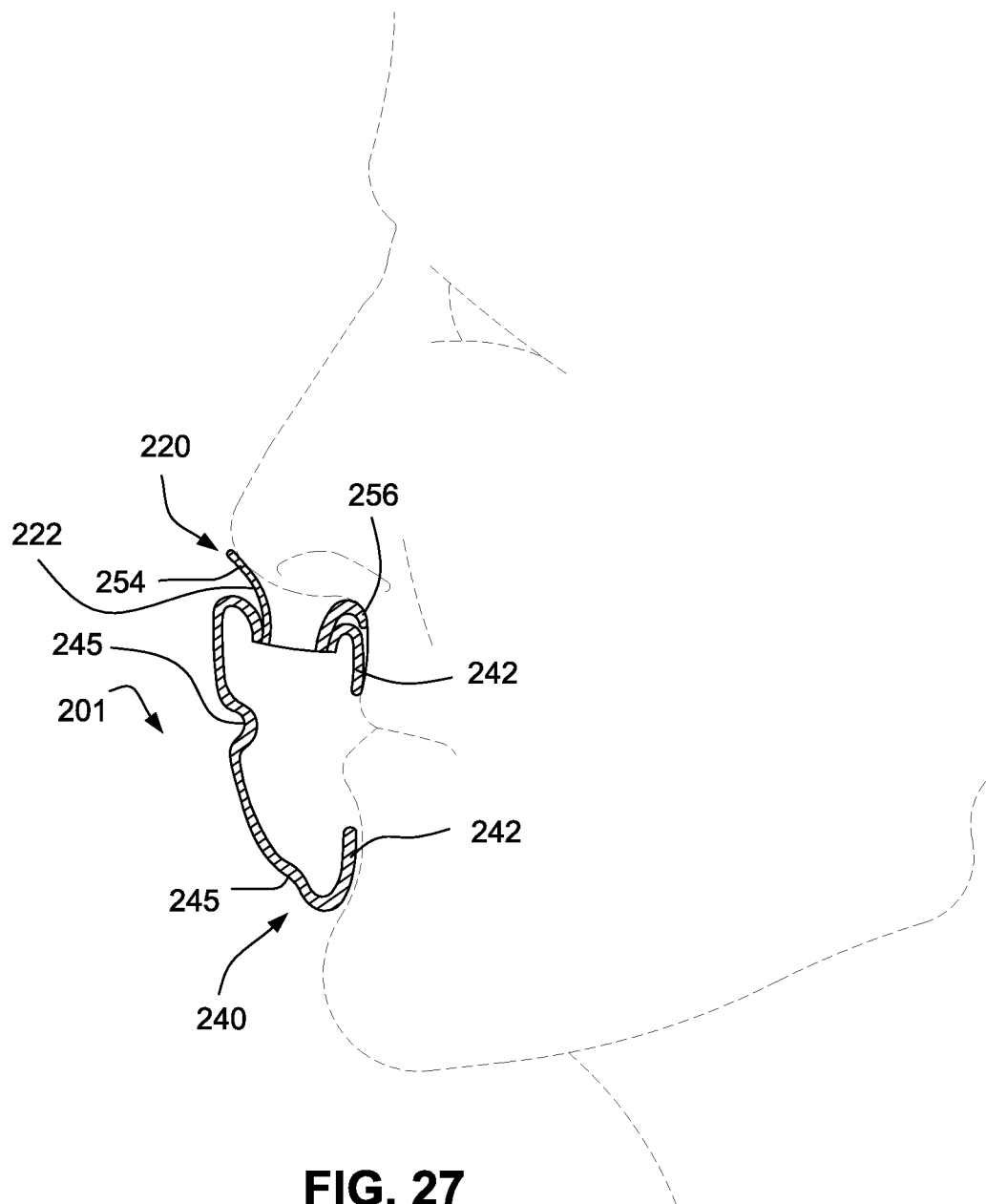
FIG. 27 depicts a schematic cross-sectional view of an integrated mask system on a model patient's head according to an embodiment of the present technology.

FIG. 27 illustrates a schematic cross-section view of an integrated mask system 201 where the nares portion 220 and the mouth portion 240 are formed as a unitary element. The decoupling portion 245 is formed in the mouth portion 240, and may decouple forces applied to the mask system (such as from a flexible supply tube) from the mouth portion 240. The nares sealing portion 222 is a nares sealing portion such as illustrated in FIGS. 19 and 20. The nose tip engagement portion 254 seals with the patients nose tip and the upper lip engagement portion seals with the patient's upper lip. This schematic cross-sectional view omits the connection to the flexible tube.

Figure 28:
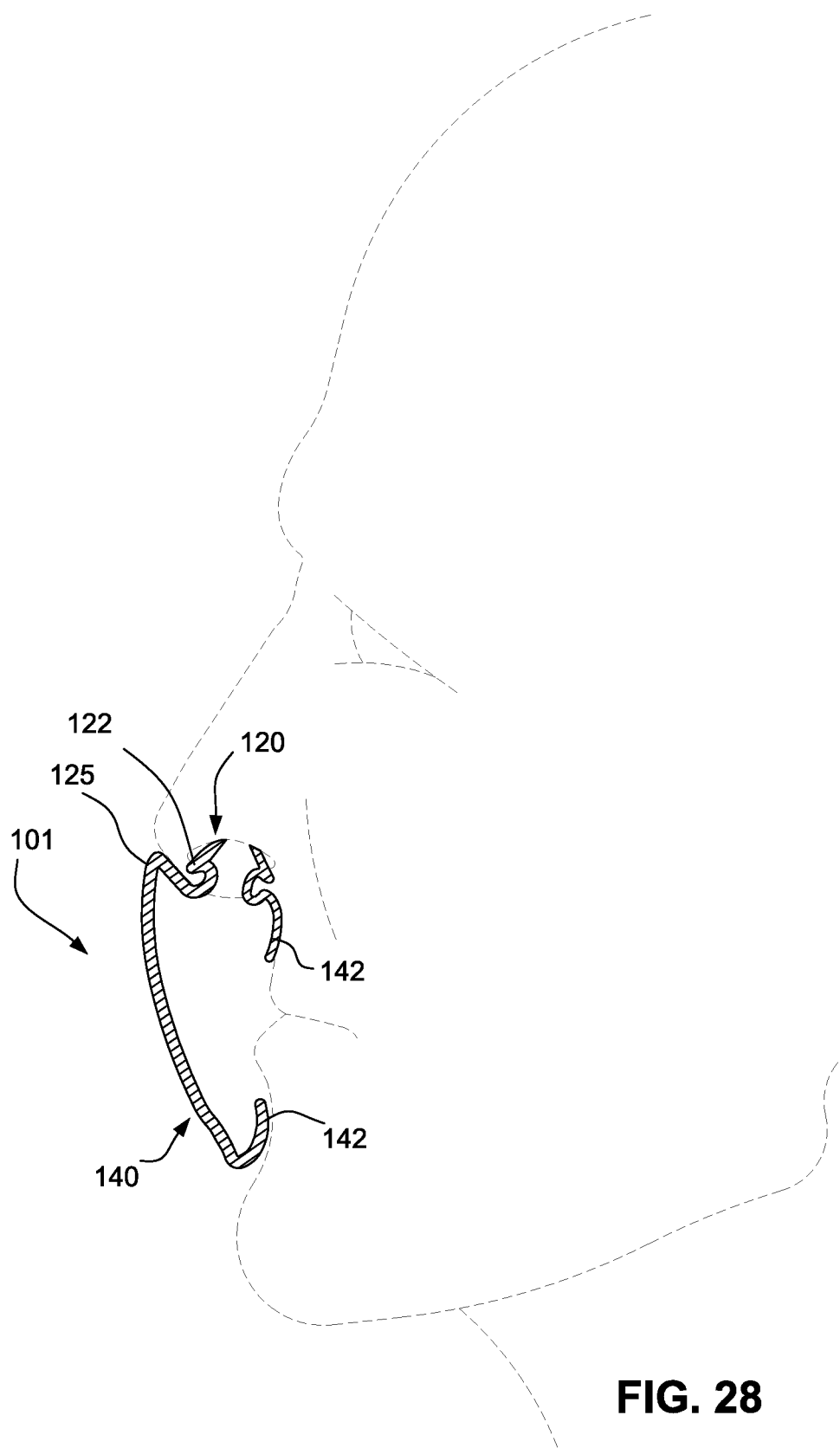
FIG. 28 depicts a schematic cross-sectional view of an integrated mask system on a model patient's head according to an embodiment of the present technology.

FIG. 28 illustrates a schematic cross-sectional view of an integrated mask system 101, where the nares portion 120 and the mouth portion 140 are formed as a unitary element. This schematic cross-sectional view omits the connection to the flexible tube 105. In this embodiment, the mouth sealing portion 142 extends from the mouth portion 140 where the mouth sealing portion 142 seals with the area between the patient's lower lip and the patient's chin, and extends from the nares portion 120 where the mouth sealing portion 142 seals with the patient's upper lip area. A decoupling portion may be formed in the mouth portion 140, and may decouple forces applied to the mask system (such as from a flexible supply tube) from the mouth portion 140.

Figure 31:
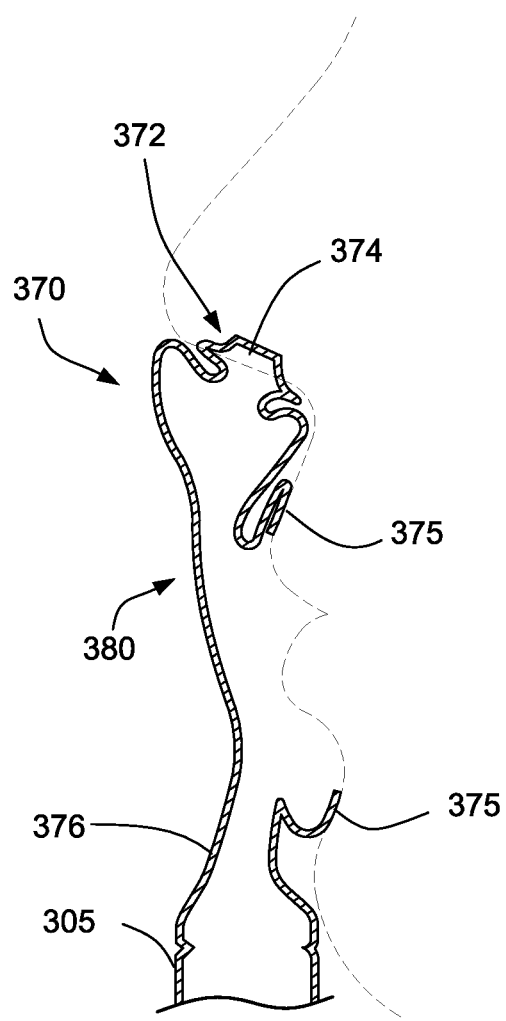
FIG. 31 depicts a cross-sectional view of an integrated mask system on a model patient's head according to an embodiment of the present technology.

FIG. 31 illustrates a schematic cross-sectional view of an integrated mask system 370, where the nares portion 372 and the mouth portion 380 are formed as a unitary element. The nares portion 372 includes a nares sealing portion 374 that forms a seal with the patient's nares, and a mouth sealing portion 375 that forms a seal with the patient's mouth. A gusset 376 may be provided to connect the mouth portion 380 to flexible tube 305. The gusset 376 may function to decouple movement of flexible tube 305 from disrupting the seal of the mouth portion 380 and/or the nares portion 372.

Figure 50:
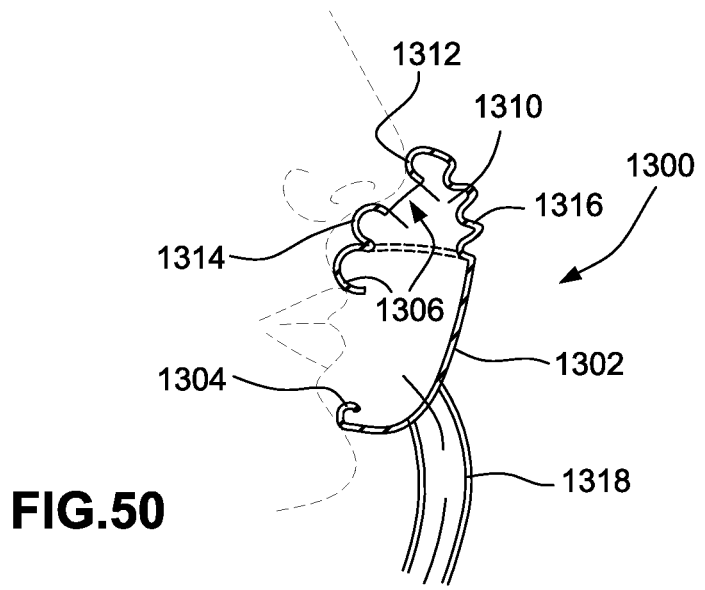
FIG. 50 depicts a schematic cross-sectional view of an integrated (or modular) mask system on a model patient's head according to an embodiment of the present technology.
Figure 51:
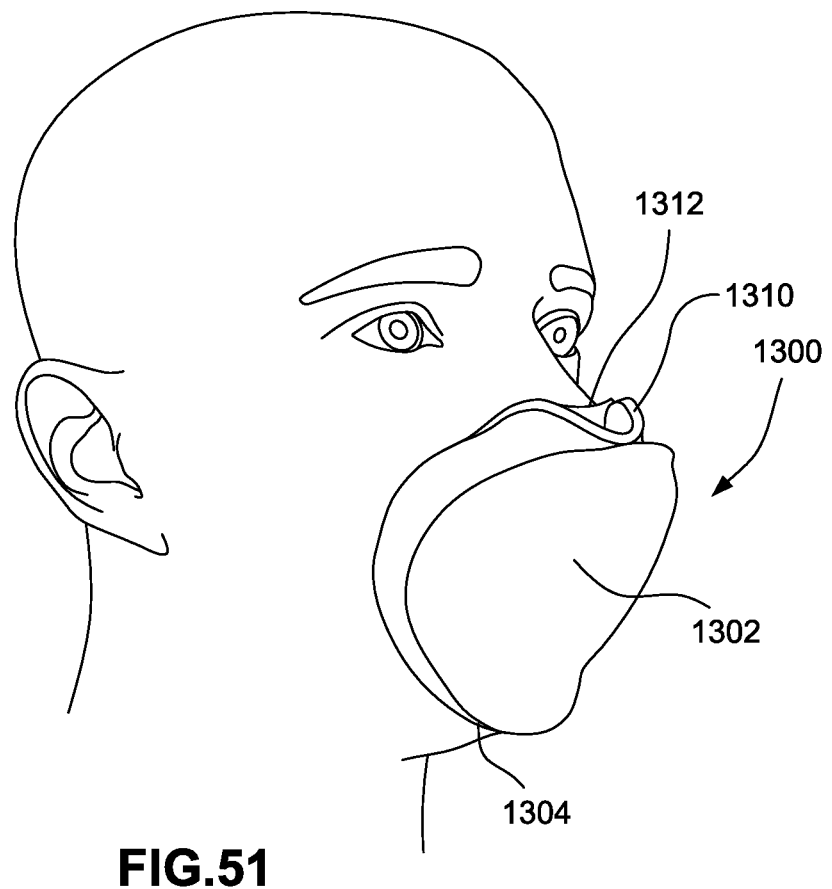
FIG. 51 depicts a perspective view of the integrated (or modular) mask system of FIG. 50 on a model patient's head.
Figure 52:
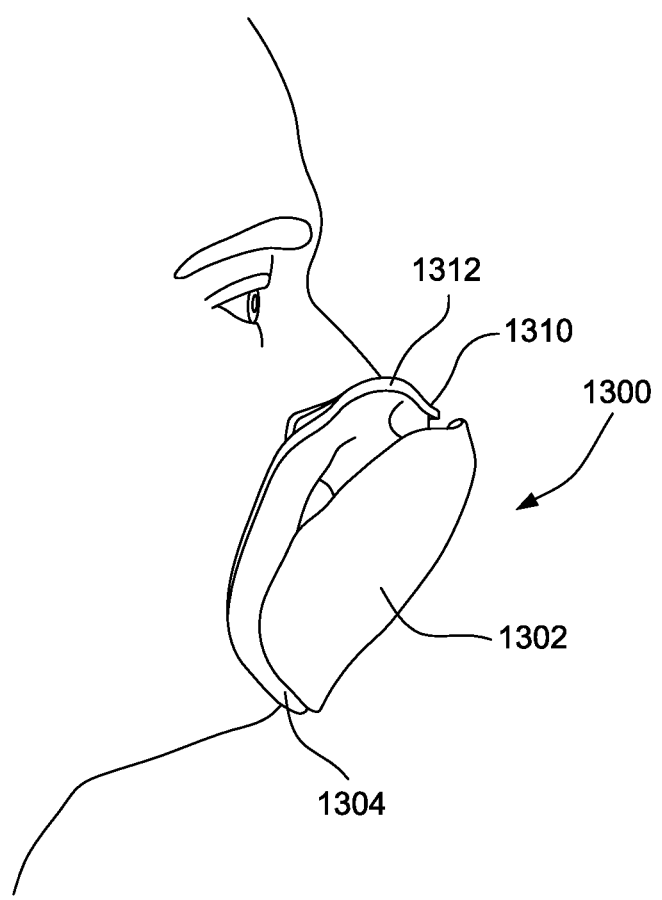
FIG. 52 depicts a side view of the integrated (or modular) mask system of FIG. 51.

FIGS. 50-52 illustrate an integrated mask system 1300. The mask system 1300 includes mouth portion 1302 and nares portion 1310. The mouth seal of the mouth portion 1302 is oriented generally horizontally, while the nares portion 1310 is oriented generally vertically to anatomically match the mouth and nares of the patient. A gas washout vent may also be included.

The mouth portion 1302 includes a lower lip engagement portion 1304 that is adapted to form a seal with a patient's lower lip, an upper lip engagement portion 1306 adapted to form a seal with the patient's upper lip, and an aperture adapted to receive pressurized air from air supply hose 1318. An elbow and/or swivel may be used in conjunction with the air supply hose 1318.

The nares portion 1310 includes a nares engagement portion 1314 adapted to form a seal with the patient's upper lip, a nose tip engagement portion 1312 adapted to form a seal with the patient's nose tip, and a concertina or decoupling portion 1316 (e.g., see FIG. 50). The concertina portion 1316 decouples forces applied to the mouth portion 1302 from being applied to the nares portion 1310. The concertina portion may also fill with air, and utilize air pressure to increase the force and thereby provide a more robust seal.

Figure 53:
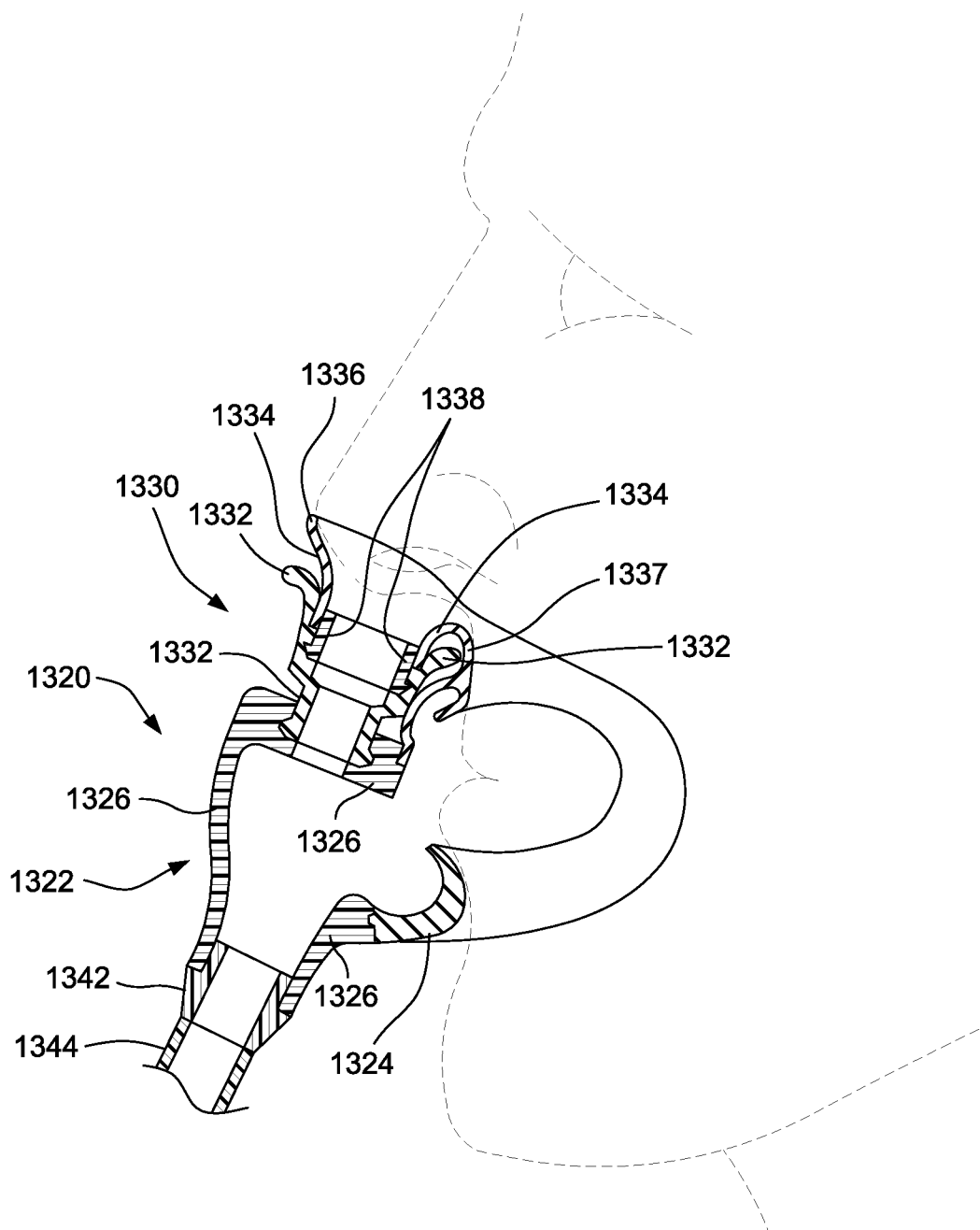
FIG. 53 depicts schematic cross-sectional view of a modular mask system on a model patient's head according to an embodiment of the present technology.

FIG. 53 illustrates an integrated mask system 1320. The mask system 1320 includes a mouth portion 1322 and a nares portion 1330.

The mouth portion 1322 includes a lower lip engagement portion 1324 adapted to form a seal with the patient's lower lip, and a frame 1326. The frame 1326 may be a rigid material, e.g., polycarbonate. The lower lip engagement portion 1324 may be co-molded with the frame 1326.

The nares portion 1330 may include a supporting portion 1332, a sealing portion 1334 and a clip portion 1338 adapted to engage the sealing portion 1334 with the supporting portion 1332. The supporting portion 1332 may be a semi-rigid material, e.g., nylon. The clip portion 1338 may be a semi-rigid material, e.g., nylon or polypropylene.

The sealing portion 1334 includes an upper lip engagement portion 1337 adapted to form a seal with the patient's upper lip, and a nose tip engagement portion 1336 adapted to form a seal with the patient's nose tip. The sealing portion 1334 may be a flexible material, e.g., silicone. The sealing portion 1334 may be co-molded as one piece with the frame 1326.

An air supply hose 1344 may be connected to the mouth portion 1322 by a swivel 1342. The swivel 1342 may be a rigid material, e.g., polycarbonate.

Figure 57:
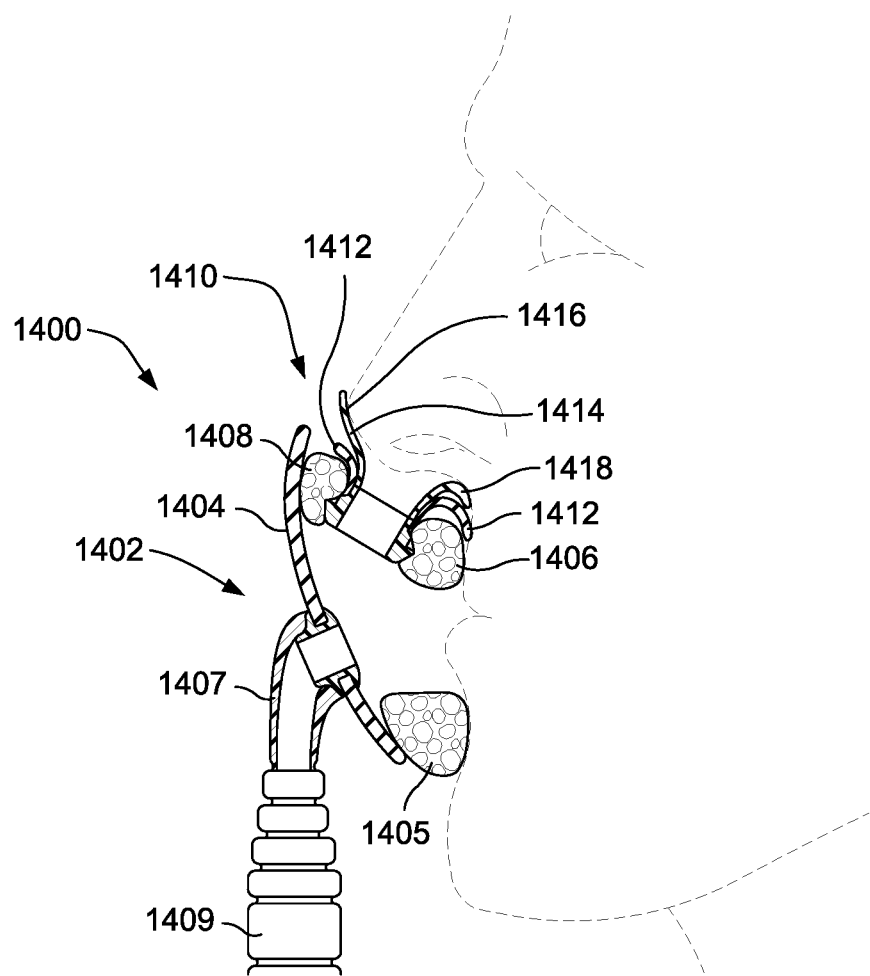
FIG. 57 depicts a schematic cross-sectional view of a modular mask system on a model patient's head according to an embodiment of the present technology.
Figure 58:
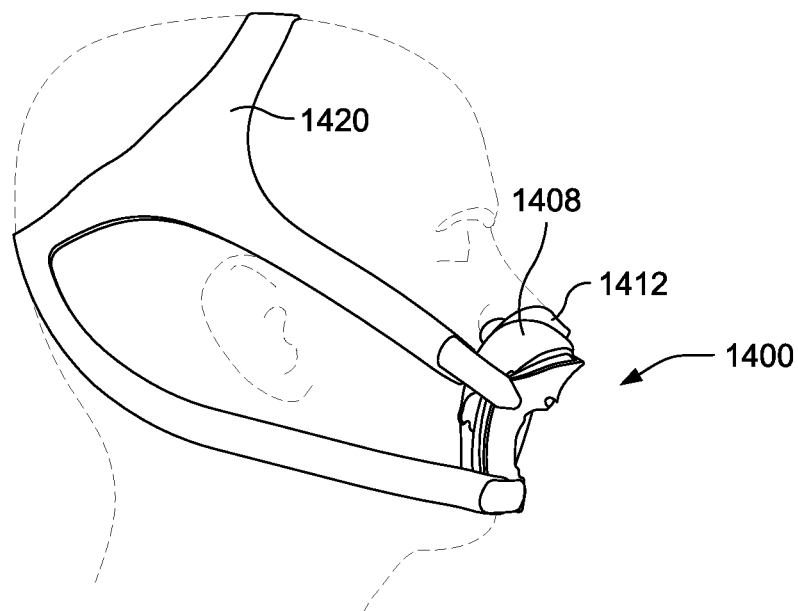
FIG. 58 depicts a side view of an integrated or modular mask system on a model patient's head according to an embodiment of the present technology.
Figure 59:
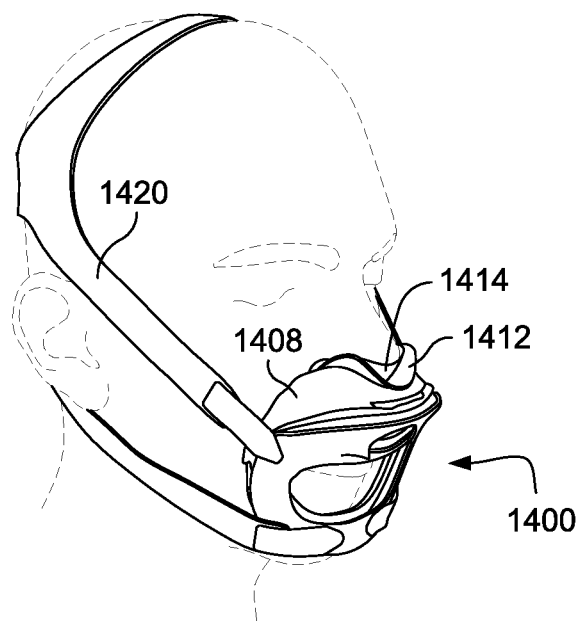
FIG. 59 depicts a perspective view of an integrated or modular mask system on a model patient's head according to an embodiment of the present technology.

FIG. 57 illustrates a modular mask system 1400 and FIGS. 58 and 59 illustrate a related integrated mask system (which could be modular). The mask system 1400 includes mouth portion 1402 and nares portion 1410. An elbow 1407 connects an air supply hose 1409 to the mouth portion 1402 to deliver air to the mask system 1400. Headgear 1420 connects to the mask system 1400 to secure the mask system 1400 to the patient's head.

The mouth portion 1402 includes a front portion 1404 and a lower foam portion 1405. The lower foam portion 1405 is positioned to form a seal between the patient's lower lip/chin and the mouth portion 1402. The front portion 1404 may be a clear portion allowing visibility of the patient's mouth region. The front portion 1404 may be silicone, for example.

The nares portion 1410 may include a supporting portion 1412 and a sealing portion 1414. The sealing portion 1414 may include a nose tip engagement portion 1416 adapted to form a seal with the patient's nose tip, and an upper lip engagement portion 1418 adapted to form a seal with the patient's upper lip. The supporting portion 1412 may also form a seal with the patient's upper lip. An upper foam portion 1406 may be disposed between the nares portion 1410 and the patient's upper lip to provide additional comfort. An outer foam portion 1408 may be disposed between the front portion 1404 and the nares portion 1410. The upper foam portion 1406 and the outer foam portion 1408 may be one foam piece, such as a ring shaped piece of foam, with a hole formed in the foam for insertion of the nares portion 1410.

1.10 Kits

Various components of the disclosed mask systems may be utilized in one or more kits that may be provided. For example, FIG. 33 illustrates a nares only kit 805 that may be provided according to embodiments of the present technology. The nares only kit 805 may include a nares portion 820 adapted to seal with and provide respiratory therapy to a patient's nares, and nares portion headgear 812. The nares only kit may optionally include an elbow or other connector 802 that may connect the nares portion 820 to a supply of pressurized air, although such an elbow or other connector 802 may be provided as part of the nares portion 820. The nares portion 820 may include plug 35 in the embodiment of FIGS. 1-1 to 4. However the nares only kit 805 may be provided with a commercially available mask, e.g., the Swift FX mask. Plug 35 may be removed if utilized with the mouth portion 840.

The nares only kit 805 is adapted to provide a patient with respiratory therapy to a patient's nares. This form of respiratory therapy, provided to the nares only, is preferred because it is less obtrusive to wear, and more comfortable for a patient, and many patients only need nares therapy. However, some patients may need mouth therapy, either mouth only therapy or mouth and nares therapy. For example, some patients who may be mouth breathers need a mouth portion to provide a mouth seal so that effective therapy may be applied to the nares. Other patients may need mouth only therapy or mouth and nares therapy.

Accordingly, mouth kit 810 may be provided to a patient that needs mouth only therapy, or needs mouth and nares therapy but already has a nares only device or nares only kit 805. The mouth kit 810 may include a mouth portion 840 that is adapted to seal with and provide respiratory therapy to a patient's mouth, and mouth portion headgear 850. The mouth portion 840 may be adapted to provide respiratory therapy only to a patient's mouth. The mouth kit 810 may optionally include an elbow or other connector 802 that may connect the mouth portion 840 to a supply of pressurized air, if such a connector is not incorporated in the mouth portion 840.

The mouth portion 840 may optionally be adapted to connect pneumatically to nares portion 820 or another nares only CPAP device. For example, the mouth portion 840 may include the aperture 46 illustrated in FIG. 1-5 adapted to connect to a nares portion, in which case plug 35 may also be provided in the mouth kit 810 for plugging aperture 46. The mouth portion 840 may also optionally include the valve 55 for selectively closing the aperture 46. Further, the mouth kit 810 may be optionally provided with plug 803, which may be used to plug an aperture in the front of the mouth portion 840, and may optionally be provided with double elbow 855, that may be used to connect both the mouth portion 840 and the nares portion 820 to a supply of pressurized air. The mouth portion 840 may function as a docking station, where the mouth portion 840 is adapted to dock with the nares portion 820.

The mouth kit 810 may also be optionally provided with nares and mouth portion headgear 860, which includes a connection region in the back portion, such as connection region 67 illustrated in FIG. 7. The nares and mouth portion headgear 860 may be used instead of the nares portion headgear 812 and the mouth portion headgear 850. Further, the mouth kit 810 may also be optionally provided with connected nares and mouth portion headgear 870, which includes a connector 856 for connecting the nares only headgear and the mouth only headgear at a back portion.

The nares only kit 805 may be utilized as a retrofit kit to a patient having a mouth portion kit 810 or other mouth portion, who wants to convert his mouth only device into a mouth and nares device. In this case, the nares only kit may optionally be provided with the double elbow connector 855, with the plug 803, with the nares and mouth portion headgear 860, or with the connected nares and mouth portion headgear 870. Likewise, the mouth kit 810 may be provided as a retrofit kit to a patient having a nares only kit 805 or other nares portion, who wants to convert his nares only device into a nares and mouth device.

The patient may utilize the nares only kit 805 and/or the mouth kit 810 to convert the nares only CPAP device 805 into a nares and mouth CPAP device in several ways. The patient may remove the elbow or other connector from the nares portion 820, and connect the double elbow connector 855 to both the nares portion 820 and to the mouth portion 840, so that air is delivered through the double elbow connector 855 to both the nares portion 820 and the mouth portion 840. The patient may utilize the original nares portion headgear 812 on the nares portion along with mouth portion headgear 850 on the mouth portion 840. The connector 856 may optionally be utilized to connect the nares portion headgear 812 to the mouth portion headgear 850. Alternatively, nares and mouth portion headgear 860 could be provided to connect to the nares portion 820 to the mouth portion 840. The nares and mouth portion headgear 860 may be connected in a back portion such as through using a connected region 67 or a unified strap as illustrated in FIG. 7. If the nares portion 820 is provided with the structure adapted to connect to a mouth portion, such as the connector 30 illustrated in FIG. 1-5, then the mouth portion 840 provided in the mouth kit 810 may include structure to connect the nares portion 820 to the mouth portion 840, such as opening 46 illustrated in FIG. 5-1. The valve 55 and knob 54 may also be provided.

In embodiments including the structure allowing pneumatic connection between the nares portion 820 and the mouth portion 840, such as the connector 30 and opening 46, the patient may connect the connector 30 to the opening 46, and utilize the elbow or other connector 802 on the nares portion 820 to deliver the air to the patient's nares and to deliver the air to the patient's mouth through the connector 30 and opening 46 to the mouth portion 840. In this embodiment, the plug 803 is connected to the opening on the front of the mouth portion 840. Structure for plugging the connection between the nares portion 820 and the mouth portion 840 could be used, such as a plug 35 or the valve 55, and the mouth portion 840 could then be used as a mouth seal.

Alternatively, in embodiments including the structure allowing pneumatic connection between the nares portion 820 and the mouth portion 840, such as the connector 30 and opening 46, the patient may connect the connector 30 to the opening 46, and utilize the plug 803 to plug the opening in the nares portion 820. The elbow or other connector 802 may then be connected to the opening in the front of the mouth portion 840 to deliver the pressurized air to the mouth portion 840, and through the connector 30 and opening 46 to the nares portion 820. Structure for plugging the connection between the nares portion 820 and the mouth portion 840 could be used, such as a plug 35 or the valve 55, and the nares portion 820 could then be used as a nares seal.

The nares and mouth kit 801 may include the components of the nares only kit 805 and the mouth kit 810. The nares and mouth kit 801 may allow a patient selectively switch between using the nares portion 820 alone, to using the mouth portion 840 alone, or to use the nares portion 820 and the mouth portion 840 together. This allows the patient to periodically change how the devices feel on the patients face. For example, if the patient's nares area becomes irritated (e.g., by air jetting and/or concentrated sealing forces), the patient may switch to using the nares portion 820 and the mouth portion 840, or the mouth portion 840 alone. The patient may switch on a periodic basis, e.g., nightly, weekly, monthly, etc.

Figure 37:
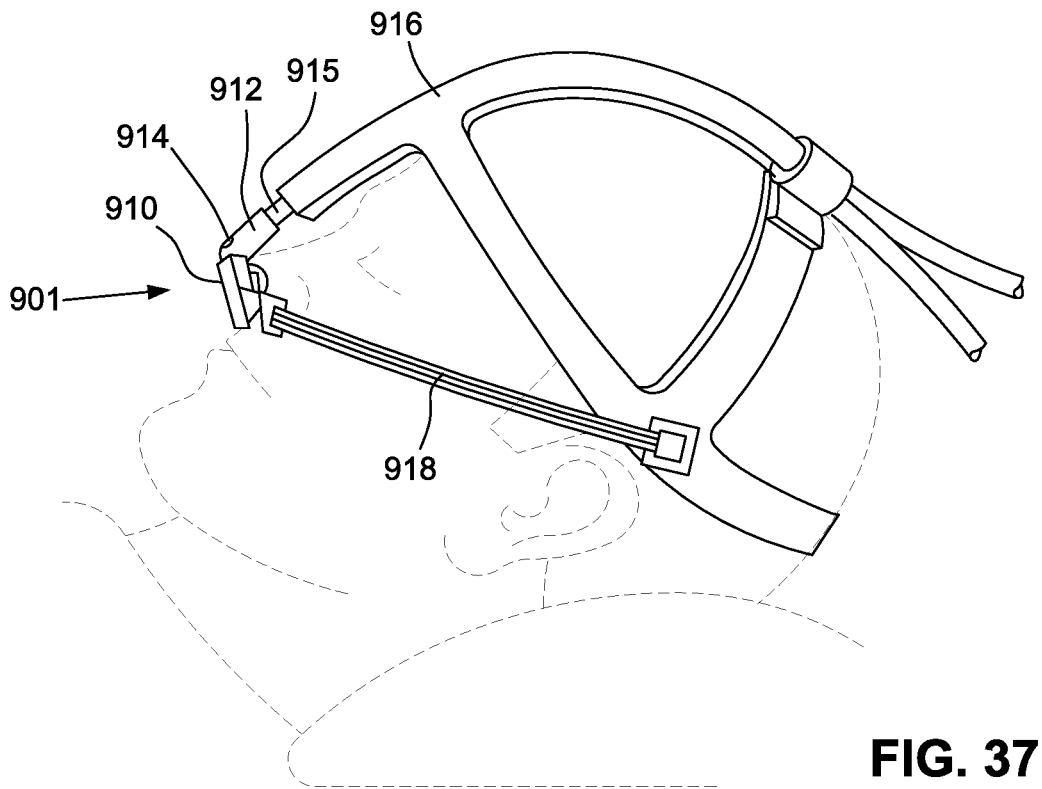
FIG. 37 depicts a prior art nares only CPAP device on a model patient's head.

FIG. 37 illustrates a prior art nares only CPAP device 901 that provides CPAP therapy to a patients nares. The CPAP device 901 may include a nares portion 910 forming a seal with the patient's nares, an elbow connector 912 connecting the nares portion 910 to a tube 915 supplying pressurized gas to the nares portion 910, where the tube extends along the patient's nose, between the patient's eyes and over the patients head, where it is connected to a supply of the pressurized gas. The elbow connector may include a vent 914 for venting gas exhaled by the patient, with the vent having a removable insert. The nares portion 910 may include a nares sealing portion such as nasal pillows, nasal prongs, a nasal membrane, or a nasal chamber. Headgear 918 may secure the nares portion 910 to the patient's head.

Figure 38:
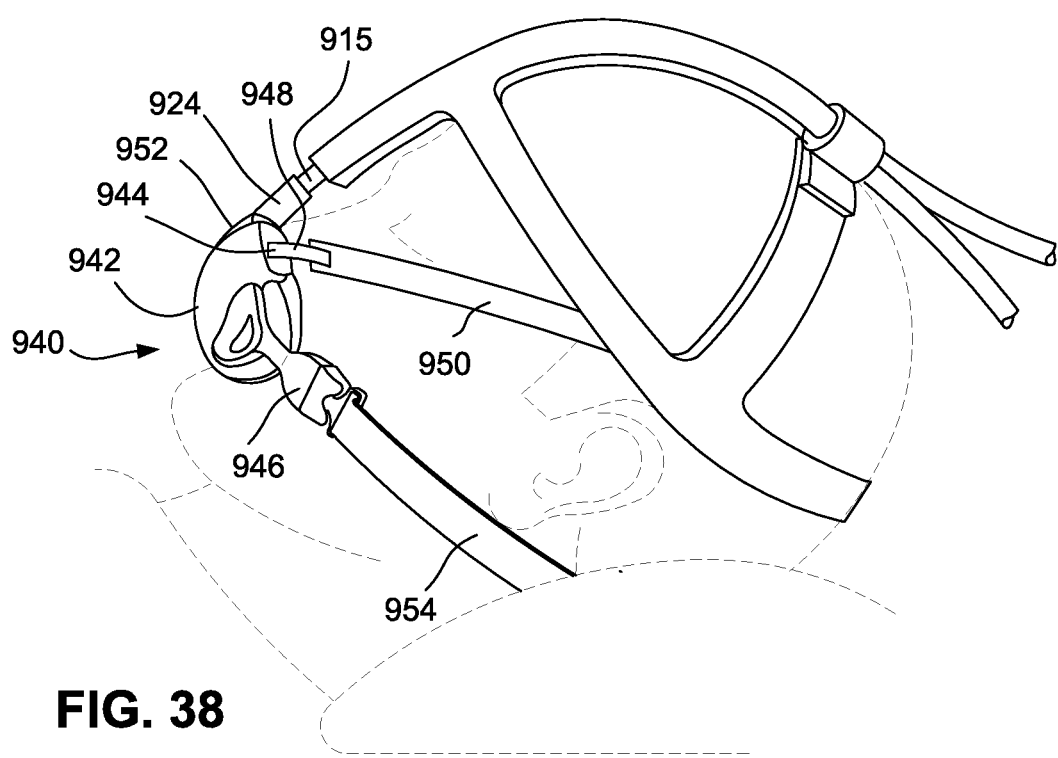
FIG. 38 depicts a retrofit kit used to convert the nares only CPAP device of FIG. 37 into a nares and mouth CPAP device according to an embodiment of the present technology.

FIG. 38 illustrates a side view of how the prior art nasal only device 901 may be converted to a nares and mouth mask system 940 according to an embodiment of the present technology. The nares portion 910 and the elbow 912 may be removed and the mask system 940 including may be connected to the tube 915, such as by a connector 924. The prior art nasal only device may be a "Breeze® Sleepgear®" device, for example.

The mask system 940 may include a mouth portion 942 for forming a seal with the patient's mouth and a nares portion 952 for forming a seal with the patient's nares. The mouth portion 942 may include headgear connectors 946 for connecting to headgear 954, and the nares portion 952 may include headgear connectors 944 for connecting to headgear 950. The mask system 940 may be a modular mask system or an integrated mask system, and is capable of delivering pressurized air to the patient's nares and/or mouth.

The mask system 940 may alternatively utilize the nares portion 910, and add a mouth portion, where the mask system 940 is a mouth portion. In this embodiment, the vent 914 of the elbow 912 is used for connection to the mouth portion 940, where the insert in the vent 914 is removed, and the mouth portion 940 is adapted to connect to the vent pneumatically. In this embodiment, air may flow out of the vent 914 to the mouth portion 940, and any original headgear, such as headgear 918 may be retained.

Figure 39:
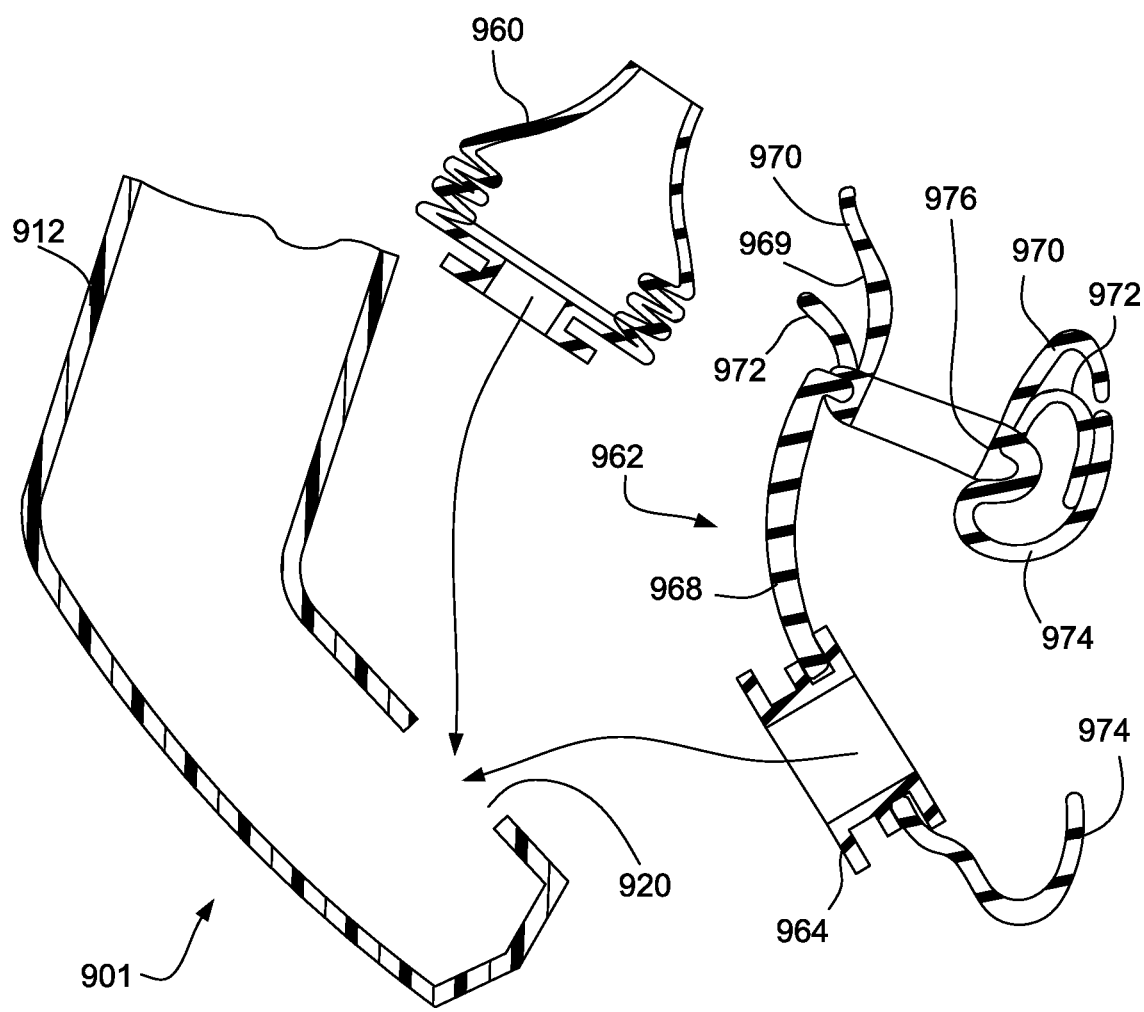
FIG. 39 depicts a retrofit kit used to convert the nares only CPAP device of FIG. 37 into a nares and mouth CPAP device according to an embodiment of the present technology.

FIG. 39 illustrates a schematic side view of another modification of the nares only device 901. In this embodiment, the nasal pillows 960 are removed from the openings 920 in the nares only device 901, and a mask system 962 is connected to the nares only device 901 in place of the nasal pillows 960. The mask system 962 has a pair of connectors 964 adapted to connect to the openings.

The mask system 962 includes a mouth portion 968 and a nares portion 969. The mouth portion 968 forms a seal with a patient's mouth at mouth seal 974 and receives the pressurized air through the connectors 964. The mouth portion 968 is connected to the nares portion 969 with a connector 976. The nares portion 969 may include nares engagement portion 970 adapted to form a seal with the patient's nares and support portion 972. The nares portion 969 may alternatively be another type of nares portion, such as nasal pillows or prongs, or a nasal chamber.

The mask systems 940 and 962 may be used to convert a nares only device for delivering respiratory therapy to a patient into a device for delivering nasal and/or mouth respiratory therapy to a patient.

Figure 40:
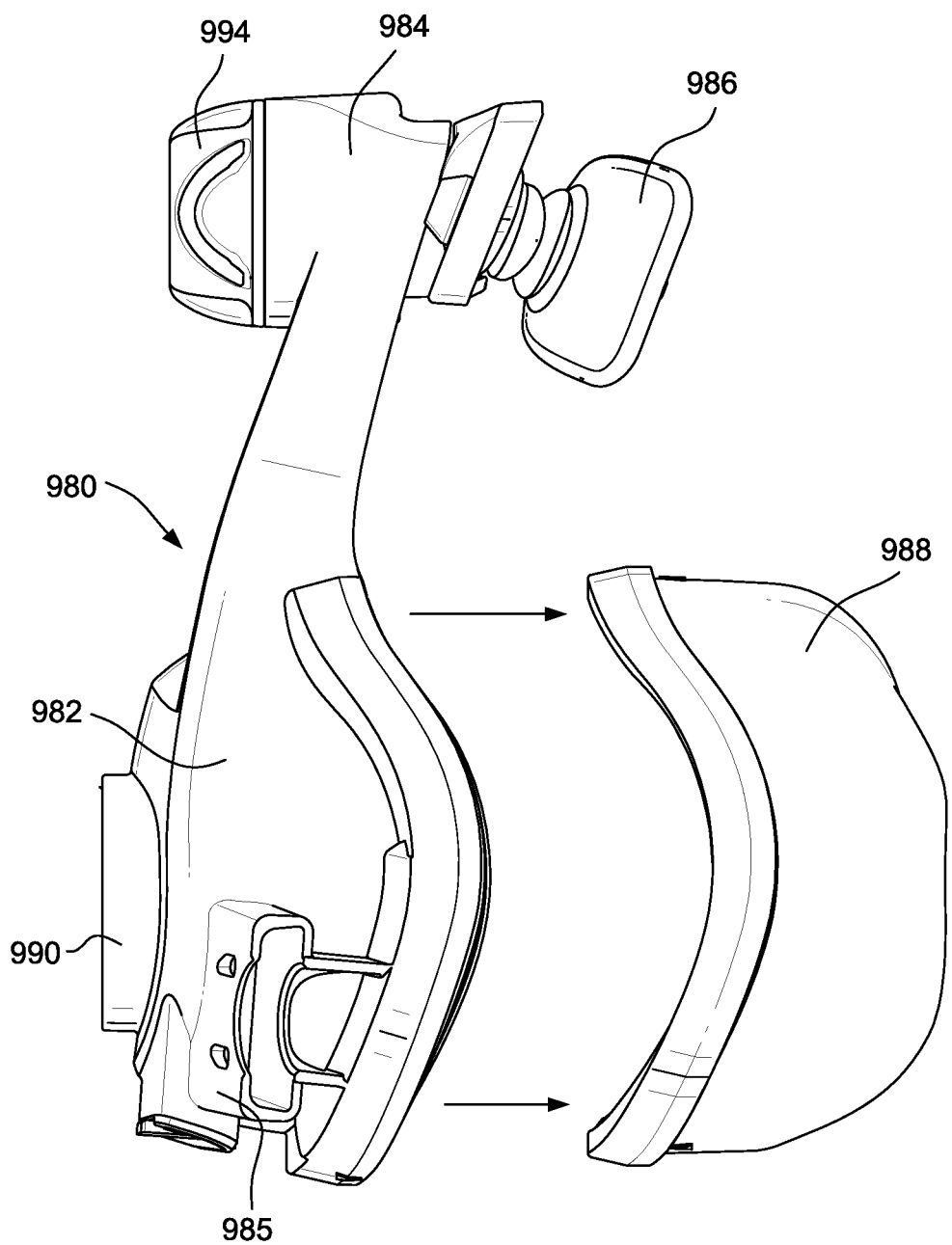
FIG. 40 depicts a prior art nares only CPAP device.

FIG. 40 illustrates a prior art nares only CPAP device 980 that provides CPAP therapy to a patient's nares. The CPAP device 980 may include a nares portion 982 that includes a cushion 988 forming a seal with the patient's nares, a connector 990 for connecting to a source of pressurized gas, headgear connectors 985 for connecting to headgear and a forehead portion 984. The forehead portion 984 includes a forehead support pad 986 and dial 994 for adjusting a position of the forehead support pad 986. The cushion 988 may be removed by pulling it in the direction of the arrows.

Figure 41:
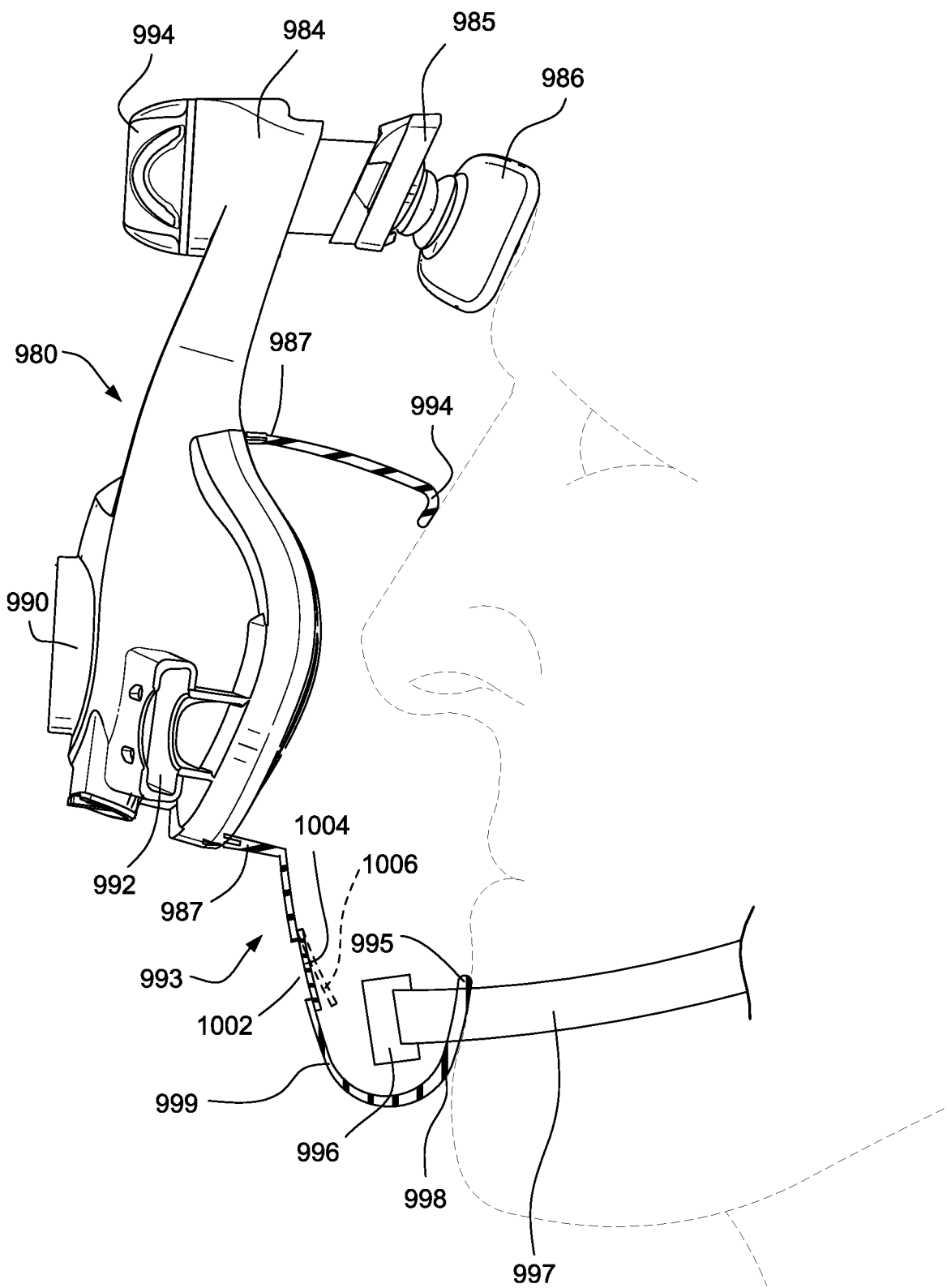
FIG. 41 depicts a retrofit kit to convert the nares only CPAP device of FIG. 40 into a nares and mouth CPAP device illustrated on a model patient's head according to an embodiment of the present technology.

FIG. 41 illustrates a side view of how the prior art nasal only device 980 may be converted to a nares and mouth mask system 993 according to an embodiment of the present technology. The cushion 988 may be removed and the nares and mouth mask system 993 may be connected to the nasal only device in place of the cushion 988.

The nares and mouth mask system 993 may be adapted to connect to the frame of the nasal only device 980 in place of the cushion by being formed with an interface 987 in the same shape as the cushion 988. The nares and mouth mask system 993 includes a cushion 998 adapted to seal with a face of the patient, and may include a nose engagement portion 994 and a lower lip engagement portion 995. A headgear connector 996 may connect to headgear 997. The nares and mouth mask system 993 may thus be utilized to convert the nares only device 980 into a nares and mouth mask system 993. The front portion 999 of the mask system 993 may be formed with a rigidizer to provide additional rigidity.

The nares and mouth mask system 993 may include an AAV (anti-asphyxia valve), which may have and opening 1002 and a flap 1004. When pressure is applied to the mask system 993 such as delivered from an air delivery tube, the flap 1004 is in the closed position. When no pressure is applied, the flap 1004 moves to the open position 1006, allowing a user to breath through the opening 1002. While not shown, the embodiment of FIG. 39 may also include such an AAV.

The mask systems described herein may be used to provide a method of providing respiratory therapy to one of a patient's nares only, a patient's mouth only, or to both a patient's nares and mouth, and periodically changing the respiratory therapy to another of the patient's nares only, the patient's mouth only, or to both the patient's nares and mouth. For example, the respiratory therapy may be initially provided to the patient's nares only, and then periodically changed from being applied to the patient's nares only to being applied to the patient's nares and mouth.

The mask systems described may also be utilized to provide a method of respiratory therapy treatment, where a first mask with a first footprint is applied to a patient for a period of time, then the first mask is removed, and a second mask with a second footprint different from the first footprint is applied to the patient for a second period of time. For example, the first footprint may be one of a nares only mask, a nares and mouth mask, and a mouth only mask, while the second footprint is another one of the nares only mask, the nares and mouth mask, and the mouth only mask.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A patient interface assembly configured to deliver respiratory therapy to a patient's airways, the patient interface assembly comprising:
   a flexible cushion with a nares sealing portion configured to sealingly engage the patient's nose around the nares and a mouth sealing portion configured to seal against the patient's face at or around the patient's mouth, the nares sealing portion being located on a superior side of the mouth sealing portion and comprising a nose tip engaging portion positioned between a pair of lateral nares engagement portions;
   a frame attachment structure that is attached to the flexible cushion and forms at least part of a plenum chamber with the flexible cushion, the frame attachment structure being more rigid than the flexible cushion and comprising a central opening;
   a frame that is more rigid than the flexible cushion and comprises a plurality of headgear attachment points, a superior portion of the frame extending beyond the mouth sealing portion in a superior direction to overlap at least a part of the pair of lateral nares engagement portions of the nares sealing portion; and
   headgear configured to be anchored to the frame at the headgear attachment points,
   wherein the frame attachment structure is attachable to the frame at a rim around the central opening,
   wherein at least a part of the nares sealing portion of the flexible cushion is decoupled from both the frame attachment structure and the superior portion of the frame that overlaps at least a part of the pair of lateral nares engagement portions of the nares sealing portion so that the lateral nares engagement portions of the nares sealing portion are movable independently of the frame and the frame attachment structure,
   wherein the nares sealing portion of the flexible cushion comprises a first aperture configured to communicate with the patient's nasal airways in use, and
   wherein the mouth sealing portion of the flexible cushion comprises a second aperture configured to communicate with the patient's mouth in use, the first and second apertures being separate apertures.

2. The patient interface assembly of claim 1, wherein the frame is in the form of a transparent window.

3. The patient interface assembly of claim 1, wherein the frame and the frame attachment structure are made of thermoplastic and the flexible cushion is made of silicone.

4. The patient interface assembly of claim 1, wherein the headgear comprises:
   a rear panel configured to be positioned at a rear of the patient's head in use, a crown strap connected to the rear panel and configured to cup the crown of the patient's head in use,
   a pair of upper side straps that extend from the crown strap and are configured to extend over the patient's ears in use, and
   a pair of lower side straps that extend from the rear panel and are configured to extend below the patient's ears in use.

5. The patient interface assembly of claim 4, wherein the crown strap is adjustable.

6. The patient interface assembly of claim 4, wherein each of the upper side straps are configured to extend across a respective one of the patient's cheek, under a respective one of the patient's eyes, and over a respective one of the patient's ears.

7. The patient interface assembly of claim 4, wherein the flexible cushion, the frame attachment structure, and the frame form a core body of the patient interface assembly, and wherein the upper side straps are configured to be secured to the core body of the patient interface assembly by way of a push fit tab connection.

8. The patient interface assembly of claim 1, wherein an inferior side of the frame comprises an inlet opening configured to receive a pressurized flow of respiratory gas from an air delivery tube so that the patient interface assembly receives the pressurized flow of respiratory gas from an inferior direction.

9. The patient interface assembly of claim 8, further comprising an anti-asphyxiation valve assembly at the inlet opening.

10. The patient interface assembly of claim 1, wherein the headgear attachment points on the frame are located on opposing lateral sides of the frame.

11. The patient interface assembly of claim 1, wherein an outer side of the frame is convex shaped.

12. The patient interface assembly of claim 1, wherein the flexible cushion is molded to the frame attachment structure.

13. The patient interface assembly of claim 1, wherein a wall thickness of the nares sealing portion is increased at the lateral nares engagement portions.

14. The patient interface assembly of claim 1, further comprising a gas washout vent comprising an array of vent holes that are arranged to vent exhaled gas to atmosphere.

15. The patient interface assembly of claim 1, wherein the flexible cushion is configured to avoid contact with the patient's nasal bridge.

16. The patient interface assembly of claim 1, wherein the flexible cushion has a single wall construction.

17. The patient interface assembly of claim 1, further comprising:
   a gas washout vent comprising an array of vent holes that are arranged to vent exhaled gas to atmosphere; and
   an anti-asphyxiation valve assembly,
   wherein an inferior side of the frame comprises an inlet opening configured to receive a pressurized flow of respiratory gas from an air delivery tube so that the patient interface assembly receives the pressurized flow of respiratory gas from an inferior direction,
   wherein the anti-asphyxiation valve assembly is located at the inlet opening,
   wherein the frame is in the form of a transparent window,
   wherein the headgear comprises:
      a rear panel configured to be positioned at a rear of the patient's head in use,
      a crown strap connected to the rear panel and configured to cup the crown of the patient's head in use,
      a pair of upper side straps that extend from the crown strap and are configured to extend over the patient's ears in use, and
      a pair of lower side straps that extend from the rear panel and are configured to extend below the patient's ears in use,
   wherein the crown strap is adjustable,
   wherein each of the upper side straps are configured to extend across a respective one of the patient's cheek, under a respective one of the patient's eyes, and over a respective one of the patient's ears,
   wherein the headgear attachment points on the frame are located on opposing lateral sides of the frame,
   wherein an outer side of the frame is convex shaped,
   wherein the flexible cushion is configured to avoid contact with the patient's nasal bridge, and
   wherein the flexible cushion has a single wall construction.

18. The patient interface assembly of claim 17, wherein the frame and the frame attachment structure are made of thermoplastic,
   wherein the flexible cushion is molded to the frame attachment structure,
   wherein a wall thickness of the nares sealing portion is increased at the lateral nares engagement portions, and
   wherein the flexible cushion, the frame attachment structure, and the frame form a core body of the patient interface assembly, and wherein the upper side straps are configured to be secured to the core body of the patient interface assembly by way of a push fit tab connection.

19. The patient interface assembly of claim 1, further comprising an air delivery tube configured to be connected to the frame.

20. A patient interface assembly configured to deliver respiratory therapy to a patient's airways, the patient interface assembly comprising:
   a flexible cushion assembly comprising:
      a mouth sealing portion configured to seal against the patient's face at or around the patient's mouth;
      a nares sealing portion located on a superior side of the mouth sealing portion and being configured to sealingly engage the patient's nose around the patient's nares, the nares sealing portion comprising a central engaging portion positioned between a pair of lateral nares engagement portions, a wall thickness of the nares sealing portion being greater at the lateral nares engagement portions than at a central portion of the nares sealing portion; and
      a frame attachment structure that is attached to the mouth sealing portion and forms at least part of a plenum chamber with the mouth sealing portion, the frame attachment structure being more rigid than the mouth sealing portion and comprising a central opening;
   a frame that is more rigid than the flexible cushion assembly and comprises a plurality of headgear attachment points, a superior portion of the frame extending beyond the mouth sealing portion in a superior direction to overlap at least a part of the pair of lateral nares engagement portions of the nares sealing portion; and headgear configured to be anchored to the frame at the headgear attachment points, wherein the frame attachment structure is attachable to the frame at a rim around the central opening, wherein the nares sealing portion of the flexible cushion assembly comprises a pair of nasal apertures configured to communicate with the patient's nasal airways in use, and wherein the mouth sealing portion of the flexible cushion assembly comprises a mouth aperture configured to communicate with the patient's mouth in use, the each of the nasal apertures and the mouth aperture being separate apertures.

21. The patient interface assembly of claim 20, wherein the frame is in the form of a transparent window with a convex outer side and is made of polycarbonate and the flexible cushion assembly is made of silicone.

22. The patient interface assembly of claim 20, wherein the headgear comprises:
 a rear panel configured to be positioned at a rear of the patient's head in use,
 a crown strap connected to the rear panel and configured to cup the crown of the patient's head in use,
 a pair of upper side straps that extend from the crown strap and are configured to extend over the patient's ears in use, and
 a pair of lower side straps that extend from the rear panel and are configured to extend below the patient's ears in use.

23. The patient interface assembly of claim 22, wherein:
 the crown strap is adjustable,
 each of the upper side straps are configured to extend across a respective one of the patient's cheek, under a respective one of the patient's eyes, and over a respective one of the patient's ears, and
 the flexible cushion assembly, the frame attachment structure, and the frame form a core body of the patient interface assembly, and wherein the upper side straps are configured to be secured to the core body of the patient interface assembly by way of a push fit tab connection.

24. The patient interface assembly of claim 20, wherein an inferior side of the frame comprises an inlet opening with an anti-asphyxiation valve assembly, the inlet opening being configured to receive a pressurized flow of respiratory gas from an air delivery tube so that the patient interface assembly receives the pressurized flow of respiratory gas from an inferior direction.

25. The patient interface assembly of claim 20, further comprising a gas washout vent comprising an array of vent holes that are arranged to vent exhaled gas to atmosphere.

26. The patient interface assembly of claim 20, wherein the flexible cushion assembly is configured to avoid contact with the patient's nasal bridge.

27. The patient interface assembly of claim 20, wherein the flexible cushion assembly has a single wall construction.

28. The patient interface assembly of claim 20, further comprising a gas washout vent comprising an array of vent holes that are arranged to vent exhaled gas to atmosphere, wherein the frame is in the form of a transparent window with a convex outer side,
 wherein the headgear comprises:
  a rear panel configured to be positioned at a rear of the patient's head in use,
  a crown strap connected to the rear panel and configured to cup the crown of the patient's head in use,
  a pair of upper side straps that extend from the crown strap and are configured to extend over the patient's ears in use, and
  a pair of lower side straps that extend from the rear panel and are configured to extend below the patient's ears in use,
 wherein the crown strap is adjustable, each of the upper side straps are configured to extend across a respective one of the patient's cheek, under a respective one of the patient's eyes, and over a respective one of the patient's ears,
 wherein an inferior side of the frame comprises an inlet opening with an anti-asphyxiation valve assembly, the inlet opening being configured to receive a pressurized flow of respiratory gas from an air delivery tube so that the patient interface assembly receives the pressurized flow of respiratory gas from an inferior direction,
 wherein the flexible cushion assembly is configured to avoid contact with the patient's nasal bridge, and
 wherein the flexible cushion assembly has a single wall construction.

29. The patient interface assembly of claim 20, further comprising an air delivery tube configured to be connected to the frame.

* * * * *